US012030868B2

(12) United States Patent
Conway et al.

(10) Patent No.: US 12,030,868 B2
(45) Date of Patent: Jul. 9, 2024

(54) PRODRUGS OF CGRP ANTAGONISTS

(71) Applicant: Pfizer Ireland Pharmaceuticals, County Cork (IE)

(72) Inventors: Charles M. Conway, Cheshire, CT (US); Gene M. Dubowchik, Middlefield, CT (US); Jeffrey Claude Pelletier, Lafayette Hill, PA (US); Allen B. Reitz, Lansdale, PA (US)

(73) Assignee: Pfizer Ireland Pharmaceuticals, Ringaskiddy (IE)

( * ) Notice: Subject to any disclaimer, the term of this patent is extended or adjusted under 35 U.S.C. 154(b) by 616 days.

(21) Appl. No.: 17/283,049

(22) PCT Filed: Oct. 10, 2019

(86) PCT No.: PCT/US2019/055525
§ 371 (c)(1),
(2) Date: Apr. 6, 2021

(87) PCT Pub. No.: WO2020/077038
PCT Pub. Date: Apr. 16, 2020

(65) Prior Publication Data
US 2021/0395223 A1 Dec. 23, 2021

Related U.S. Application Data

(60) Provisional application No. 62/745,302, filed on Oct. 13, 2018.

(51) Int. Cl.
*C07D 401/14* (2006.01)
*C07D 498/22* (2006.01)

(52) U.S. Cl.
CPC ......... *C07D 401/14* (2013.01); *C07D 498/22* (2013.01)

(58) Field of Classification Search
CPC .................................................. C07D 401/14
See application file for complete search history.

(56) References Cited

U.S. PATENT DOCUMENTS

| 8,481,546 B2 | 7/2013 | Chaturvedula et al. |
| 2015/0099771 A1 | 4/2015 | Bell et al. |

FOREIGN PATENT DOCUMENTS

| CN | 106478596 A | 3/2017 |
| WO | 2008/070149 A2 | 6/2008 |
| WO | 2009/100090 A1 | 8/2009 |
| WO | 2010/151711 A1 | 12/2010 |
| WO | 2011/084846 A1 | 7/2011 |
| WO | 2011/084850 A1 | 7/2011 |
| WO | 2011/123232 A1 | 10/2011 |
| WO | 2013169563 A1 | 11/2013 |
| WO | 2018178938 A1 | 3/2018 |

OTHER PUBLICATIONS

International Search Report dated Dec. 31, 2019 issued for the corresponding application PCT/US2019/055525 (2 pages).
Written Opinion dated Dec. 31, 2019 issued for the corresponding application PCT/US2019/055525(3 pages).
International Preliminary Report on Patentability dated Dec. 31, 2019 issued for the corresponding application PCT/US2019/055525 (4 pages).
Krise Jeffrey P. et al. "Novel Prodrug Approach for Tertiary Amines: Synthesis and Preliminary Evaluation of N-Phosphonooxymethyl Prodrugs" Journal of Medicinal Chemistry, 1999, 42(16), 3094-3100.
Cann Reginald O. et al. "Selection of an Enantioselective Process for the Preparation of a CGRP Receptor Inhibitor" Organic Process Research & Development, 2012, 16(12), 1953-1966.
Kim Se-Ho et al. "Discovery of a new HIV-1 inhibitor scaffold and synthesis of potential prodrugs of indazoles" Bioorganic & Medicinal Chemistry Letters, 2013, 23(10), 2888-2892.
Chaturvedula Prasad V.et al. "Discovery of (R)-N-(3-(7-methyl-1H-indazol-5-yl)-1-(4-(1-methylpiperidin-4-yl)-1-oxopropan-2-yl)-4-(2-oxo-1,2-dihydroquinolin-3-yl)piperidine-1-carboxamide (BMS-742413): A potent human CGRP antagonist with superior safety profile for the treatment of migraine through intranasal delivery" Bioorganic & Medicinal Chemistry Letters, 2013, 23(11), 3157-3161.
Rautio et al., "The expanding role of prodrugs in contemporary drug design and development", Nature Reviews Drug Discovery, 2018, 17(8), 559-587.

*Primary Examiner* — Samantha L Shterengarts
*Assistant Examiner* — Karen Cheng
(74) *Attorney, Agent, or Firm* — Jessica Zimberlin Eastman

(57) ABSTRACT

Disclosed are prodrugs of CGRP antagonists, methods of treating CGRP related disorders, e.g., migraine, by administering to a patient in need thereof the prodrugs, pharmaceutical compositions comprising prodrugs and kits including the pharmaceutical compositions and instructions for use.

20 Claims, No Drawings

PRODRUGS OF CGRP ANTAGONISTS

CROSS-REFERENCE TO RELATED APPLICATIONS

This application is a national stage application under 35 U.S.C. § 371 of International Application No. PCT/US2019/055625 filed Oct. 10, 2019, which claims priority to and the benefit of U.S. Provisional Application No. 62/745,302 filed on Oct. 13, 2018, the contents of which are hereby incorporated by reference in their entireties.

FIELD OF THE INVENTION

The present invention relates to prodrugs of CGRP antagonists and their use in treating CGRP-related disorders, such as migraine.

BACKGROUND OF THE INVENTION

Prodrugs are molecules with little or no pharmacological activity that are converted to the active parent drug in vivo by enzymatic or chemical reactions or by a combination of the two. Prodrugs are often designed to improve bioavailability when a drug itself is poorly absorbed from the gastrointestinal tract. Since 2008, at least 30 prodrugs have been approved by the U.S. Food and Drug Administration (FDA). See, e.g., Rautio, Jarkko; Meanwell, Nicholas A.; Di, Li; Hageman, Michael J., *Nature Reviews Drug Discovery*, volume 17, pages 559-587 (2018).

Migraine is a chronic and debilitating disorder characterized by recurrent attacks lasting four to 72 hours with multiple symptoms, including typically one-sided, pulsating headaches of moderate to severe pain intensity that are associated with nausea or vomiting, and/or sensitivity to sound (phonophobia) and sensitivity to light (photophobia). Migraines are often preceded by transient neurological warning symptoms, known as auras, which typically involve visual disturbances such as flashing lights, but may also involve numbness or tingling in parts of the body. Migraine is both widespread and disabling. The Migraine Research Foundation ranks migraine as the world's third most prevalent illness, and the Global Burden of Disease Study 2015 ranks migraine as the seventh highest specific cause of disability worldwide. According to the Migraine Research Foundation, in the United States, approximately 36 million individuals suffer from migraine attacks. While most sufferers experience migraine attacks once or twice per month, more than 4 million people have chronic migraine, defined as experiencing at least 15 headache days per month, of which at least eight are migraine, for more than three months. Others have episodic migraine, which is characterized by experiencing less than 15 migraine days per month. People with episodic migraine may progress to chronic migraine over time. Migraine attacks can last four hours or up to three days. More than 90% of individuals suffering from migraine attacks are unable to work or function normally during a migraine attack, with many experiencing comorbid conditions such as depression, anxiety and insomnia. Also, those suffering from migraine often have accompanying nausea and have an aversion to consuming food or liquids during an attack.

CGRP (calcitonin gene-related peptide) is a 37 amino acid neuropeptide, which belongs to a family of peptides that includes calcitonin, adrenomedullin and amylin. In humans, two forms of CGRP (α-CGRP and β-CGRP) exist and have similar activities. They vary by three amino acids and exhibit differential distribution. At least two CGRP receptor subtypes may also account for differential activities. The CGRP receptor is located within pain-signaling pathways, intracranial arteries and mast cells and its activation is thought to play a causal role in migraine pathophysiology. For example, research and clinical studies have shown that serum levels of CGRP are elevated during migraine attacks, that infusion of intravenous CGRP produces persistent pain in migraine sufferers and non-migraine sufferers, and that treatment with anti-migraine drugs normalizes CGRP activity.

Possible CGRP involvement in migraine has been the basis for the development and clinical testing of a number of compounds, including for example, olcegepant (Boehringer Ingelheim, Ridgefield, CT), telcagepant (Merck Sharp & Dohme Corp., Kenilworth, NJ), ubrogepant (Allergan plc, Dublin, Ireland), lasmiditan (Eli Lilly and Company, Indianapolis, IN), rimegepant (Biohaven Pharmaceutical Holding Company Ltd., New Haven, CT), galcanezumab (Eli Lilly and Company, Indianapolis, IN), fremanezumab (Teva Pharmaceutical Industries, Petah Tikva, Israel), eptinezumab (Alder Biopharmaceuticals, Inc., Bothell, WA), and erenumab (Amgen Inc., Thousand Oaks, CA).

Currently, clinicians use a number of pharmacologic agents for the acute treatment of migraine. A study published by the American Headache Society in 2015 concluded that the medications deemed effective for the acute treatment of migraine fell into the following classes: triptans, ergotamine derivatives, non-steroidal anti-inflammatory drugs ("NSAIDs"), opioids and combination medications. The current standard of care for the acute treatment of migraine is prescription of triptans, which are serotonin 5-HT$_{1B/1D}$ receptor agonists. Triptans have been developed and approved for the acute treatment of migraine over the past two decades. The initial introduction of triptans represented a shift toward drugs more selectively targeting the suspected pathophysiology of migraine. While triptans account for almost 80% of anti-migraine therapies prescribed at office visits by healthcare providers, issues such as an incomplete effect or headache recurrence remain important clinical limitations. In fact, only about 30% of patients from clinical trials are pain free at two hours after taking triptans. In addition, triptans are contraindicated in patients with cardiovascular disease, cerebrovascular disease, or significant risk factors for either because of potential systemic or cerebrovascular vasoconstriction from the 5-HT$_{1B}$-mediated effects. Also, according to a January 2017 study published in the journal *Headache*, an estimated 2.6 million migraine sufferers in the United States have a cardiovascular event, condition or procedure that limits the potential of triptans as a treatment option.

Accordingly, there remains a significant unmet medical need for a novel migraine-specific medication that provides enhanced patient benefits compared to existing therapies. In addition, CGRP receptor antagonists may be useful pharmacological agents for illnesses that involve other CGRP-disorders. In addition to migraine, such disorders may include cluster headache (Doods (2001) *Curr. Opin. Invest. Drugs* 2, 1261-1268; Edvinsson et al. (1994) *Cephalalgia* 14, 320-327); chronic tension type headache (Ashina et al. (2000) *Neurology* 14, 1335-1340); pain (Yu et al. (1998) *Eur. J Pharmacol.* 347, 275-282); chronic pain (Hulsebosch et al. (2000) *Pain* 86, 163-175); neurogenic inflammation and inflammatory pain (Holzer (1988) *Neuroscience* 24, 739-768; Delay-Goyet et al. (1992) *Acta Physiol. Scanda.* 146, 537-538; Salmon et al. (2001) *Nature Neurosci.* 4, 357-358); eye pain (May et al. (2002) *Cephalalgia* 22, 195-196), tooth pain (Awawdeh et al. (2002) *Int. Endocrin. J* 35, 30-36), non-insulin dependent diabetes mellitus (Molina et al. (1990) *Diabetes* 39, 260-265); vascular disorders; inflammation (Zhang et al. (2001) *Pain* 89, 265); arthritis, bronchial hyperreactivity, asthma, (Foster et al. (1992) *Ann. NY Acad. Sci.* 657, 397-404; Schini et al. (1994) *Am. J Physiol.* 267, H2483-H2490; Zheng et al. (1993) *J Viral.* 67, 5786-5791); shock, sepsis (Beer et al. (2002) *Crit. Care Med.* 30, 1794-1798); opiate withdrawal syndrome (Salmon et al. (2001) *Nature Neurosci.* 4, 357-358); morphine tolerance (Menard et al. (1996) *J Neurosci.* 16, 2342-2351); hot flashes in men and women (Chen et al. (1993) *Lancet* 342, 49; Spetz et al. (2001) *J Urology* 166, 1720-1723); allergic dermatitis (Wallengren (2000) *Contact Dermatitis* 43, 137-143); psoriasis; encephalitis, brain trauma, ischaemia, stroke, epilepsy, and neurodegenerative diseases (Rohrenbeck et al. (1999) *Neurobiol. Dis.* 6, 15-34); skin diseases (Geppetti and Holzer, Eds., Neurogenic Inflammation, 1996, CRC Press, Boca Raton, FL), neurogenic cutaneous redness, skin rosaceousness and erythema; tinnitus (Herzog et al. (2002) *J Membr. Biol.* 189, 225); obesity (Walker et al. (2010) *Endocrinology* 151, 4257-4269); inflammatory bowel disease, irritable bowel syndrome, (Hoffman et al. (2002) *Scand. J Gastroenterol.* 37, 414-422) and cystitis.

There are several other earlier stage CGRP antagonists in development, such as disclosed, for example, in WO 2003/104236 published Dec. 18, 2003, WO 2011/123232 published Oct. 6, 2011, WO 2017/072721 published May 4, 2017, WO 2017/072722 published May 4, 2017, WO 2017/0727723 published May 4, 2017, and WO 2018/178938 published Oct. 4, 2018.

Certain CGRP antagonists may have bioavailability characteristics that render them challenging to prepare in an oral dosage form. Enhancing the bioavailability of such compounds would be desirable.

SUMMARY OF THE INVENTION

The present invention is directed to the treatment of CGRP-related disorders, e.g., migraine, with prodrugs of CGRP antagonists. By virtue of the present invention, it may now be possible to provide more effective GCRP related treatments to patients. In accordance with the present invention, one or more functionalizable moieties, e.g., —NH groups, present on the parent drug molecule may be substituted with certain lipophilic substituents to enhance the bioavailability of the CGRP antagonists.

In an aspect of the invention, there is provided a compound having General Formula (1), comprising a CGRP Parent Molecule having at least one functionalizable moiety, Z:

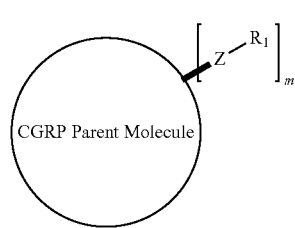

General Formula (1)

wherein:
CGRP Parent Molecule is a moiety derived from a calcitonin gene-related peptide (CGRP) receptor antagonist;

Z is a functionalizable moiety present on the CGRP Parent Molecule;
m is at least 1;
$R_1$ is

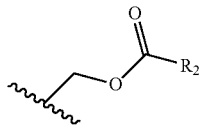

or —$CH_2OP(=O)(OH)_2$;
$R_2$ is —[—$C(R_3)_2$—]$_n$$R_4$, —$NR_3R_4$, or —$OR_4$, wherein each $R_3$ is independently hydrogen or C1-C10 alkyl wherein $R_3$ are optionally connected to form a ring, and $R_4$ is a substituted or unsubstituted C1-C20 alkyl group, a substituted or unsubstituted C2-C20 alkenyl group, a substituted or unsubstituted C2-C20 alkynyl group, a substituted or unsubstituted C1-C20 heteroalkyl group, a substituted or unsubstituted C2-C20 heteroalkenyl group, a substituted or unsubstituted C2-C20 heteroalkynyl group, a substituted or unsubstituted C3-C20 cycloalkyl group, a substituted or unsubstituted C3-C20 heterocycloalkyl group, or a substituted or unsubstituted C6-C20 aryl group, or a substituted or unsubstituted C1-C20 heteroaryl group, and n is 0 or 1, wherein, when m is at least 2, $R_2$ are optionally connected to form a ring.

In an aspect of the invention, there is provided a pharmaceutical composition comprising a therapeutically effective amount of the compound in accordance with the invention described herein.

In an aspect of the invention, there is provided a method of treating migraine in a patient in need thereof, comprising administering to the patient a pharmaceutical composition comprising a therapeutically effective amount of the compound in accordance with the invention described herein.

In an aspect of the invention, there is provided a method of treating a condition associated with aberrant levels of CGRP in a patient in need thereof, comprising administering to the patient a pharmaceutical composition comprising a therapeutically effective amount of the compound in accordance with the invention described herein.

In an aspect of the invention, there is provided a kit for treating a condition associated with aberrant levels of CGRP in a patient, the kit comprising:
(a) a pharmaceutical composition comprising a therapeutically effective amount of a compound in accordance with the invention described herein; and
(b) instructions for administering the pharmaceutical composition.

DETAILED DESCRIPTION OF THE INVENTION

The following detailed description is provided to aid those skilled in the art in practicing the present invention. Those of ordinary skill in the art may make modifications and variations in the embodiments described herein without departing from the spirit or scope of the present disclosure. Unless otherwise defined, all technical and scientific terms used herein have the same meaning as commonly understood by one of ordinary skill in the art to which this disclosure belongs. The terminology used in the description is for describing particular embodiments only and is not intended to be limiting. Terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used in this application, except as otherwise expressly provided herein, each of the following terms shall have the meaning set forth below. Additional definitions are set forth throughout the application. In instances where a term is not specifically defined herein, that term is given an art-recognized meaning by those of ordinary skill applying that term in context to its use in describing the present invention.

As used herein, the term "and/or" includes any and all combinations of one or more of the associated listed items. Expressions such as "at least one of," when preceding a list of elements, modify the entire list of elements and do not modify the individual elements of the list.

The articles "a" and "an" refer to one or to more than one (i.e., to at least one) of the grammatical object of the article unless the context clearly indicates otherwise. By way of example, "an element" means one element or more than one element.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

The term "about" refers to a value or composition that is within an acceptable error range for the particular value or composition as determined by one of ordinary skill in the art, which will depend in part on how the value or composition is measured or determined, i.e., the limitations of the measurement system. For example, "about" can mean within 1 or more than 1 standard deviation per the practice in the art. Alternatively, "about" can mean a range of up to 10% or 20% (i.e., ±10% or ±20%). For example, about 3 mg can include any number between 2.7 mg and 3.3 mg (for 10%) or between 2.4 mg and 3.6 mg (for 20%). Furthermore, particularly with respect to biological systems or processes, the terms can mean up to an order of magnitude or up to 5-fold of a value. When particular values or compositions are provided in the application and claims, unless otherwise stated, the meaning of "about" should be assumed to be within an acceptable error range for that particular value or composition.

The term "administering" refers to the physical introduction of a composition comprising a therapeutic agent to a subject, using any of the various methods and delivery systems known to those skilled in the art. Administering can also be performed, for example, once, a plurality of times, and/or over one or more extended periods and can be a therapeutically effective dose or a subtherapeutic dose.

The term "AUC" (area under the curve) refers to a total amount of drug absorbed or exposed to a subject. Generally, AUC may be obtained from mathematical method in a plot of drug concentration in the subject over time until the concentration is negligible. The term "AUC" (area under the curve) could also refer to partial AUC at specified time intervals.

The term "$C_{max}$" refers to a maximum concentration of a drug in blood, serum, a specified compartment or test area of a subject between administration of a first dose and administration of a second dose. The term $C_{max}$ could also refer to dose normalized ratios if specified.

The term "dosing interval," refers to the amount of time that elapses between multiple doses of a formulation disclosed herein being administered to a subject. Dosing interval can thus be indicated as ranges.

The term "dosing frequency" refers to the frequency of administering doses of a formulation disclosed herein in a given time. Dosing frequency can be indicated as the number of doses per a given time, e.g., once a week or once in two weeks.

The terms "in combination with" and "in conjunction with" refer to administration of one treatment modality in addition to another treatment modality. As such, "in combination with" or "in conjunction with" refers to administration of one treatment modality before, during, or after administration of the other treatment modality to the subject.

The term "pharmaceutically acceptable salt" refers to a salt form of one or more of the compounds or prodrugs described herein which are presented to increase the solubility of the compound in the gastric or gastroenteric juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art.

The terms "subject" and "patient" refer any human or non-human animal. The term "non-human animal" includes, but is not limited to, vertebrates such as non-human primates, sheep, dogs, and rodents such as mice, rats and guinea pigs. In some embodiments, the subject is a human. The terms, "subject" and "patient" are used interchangeably herein.

The terms "effective amount", "therapeutically effective amount", "therapeutically effective dosage" and "therapeutically effective dose" of an agent (also sometimes referred to herein as a "drug") refers to any amount of the agent that, when used alone or in combination with another agent, protects a subject against the onset of a disease or promotes disease regression evidenced by a decrease in severity of disease symptoms, an increase in frequency and duration of disease symptom-free periods, or a prevention of impairment or disability due to the disease affliction. The therapeutically effective amount of an agent can be evaluated using a variety of methods known to the skilled practitioner, such as in human subjects during clinical trials, in animal model systems predictive of efficacy in humans, or by assaying the activity of the agent in in vitro assays.

The term "$T_{max}$" refers to a time or period after administration of a drug when the maximum concentration ($C_{max}$) is reached in blood, serum, a specified compartment or test area of a subject.

The term "treatment" refers to any treatment of a condition or disease in a subject and may include: (i) preventing the disease or condition from occurring in the subject which may be predisposed to the disease but has not yet been diagnosed as having it; (ii) inhibiting the disease or condition, i.e., arresting its development; relieving the disease or condition, i.e., causing regression of the condition; or (iii) ameliorating or relieving the conditions caused by the disease, i.e., symptoms of the disease. Treatment could be used in combination with other standard therapies or alone. Treatment or "therapy" of a subject also includes any type of intervention or process performed on, or the administration of an agent to, the subject with the objective of reversing, alleviating, ameliorating, inhibiting, slowing down or preventing the onset, progression, development, severity or recurrence of a symptom, complication or condition, or biochemical indicia associated with a disease.

With respect to headache, "treatment" is an approach for obtaining beneficial or desired clinical results. For purposes of this invention, beneficial or desired clinical results include, but are not limited to, one or more of the following: improvement in any aspect of a headache including lessening severity, alleviation of pain intensity, and other associated symptoms, reducing frequency of recurrence, increasing the quality of life of those suffering from the headache, and decreasing dose of other medications required to treat the headache. For migraine, other associated symptoms include, but are not limited to, nausea, vomiting, and sensitivity to light, sound, and/or movement. For cluster headache, other associated symptoms include, but are not limited to swelling under or around the eyes, excessive tears, red eye, Rhinorrhea or nasal congestion, and red flushed face.

"Reducing incidence" of headache means any of reducing severity (which can include reducing need for and/or amount of (e.g., exposure to) other drugs and/or therapies generally used for this condition, including, for example, ergotamine, dihydroergotamine, or triptans for migraine), duration, and/or frequency (including, for example, delaying or increasing time to next episodic attack in an individual). As is understood by those skilled in the art, individuals may vary in terms of their response to treatment, and, as such, for example, a "method of reducing incidence of headache in an individual" reflects administering the rimegepant based on a reasonable expectation that such administration may likely cause such a reduction in incidence in that particular individual.

"Ameliorating" headache or one or more symptoms of headache means a lessening or improvement of one or more symptoms of headache as compared to not administering a treatment. "Ameliorating" also includes shortening or reduction in duration of a symptom.

As used herein, "controlling headache" refers to maintaining or reducing severity or duration of one or more symptoms of headache or frequency of headache attacks in an individual (as compared to the level before treatment). For example, the duration or severity of head pain, or frequency of attacks is reduced by at least about any of 10%, 20%, 30%, 40%, 50%, 60%, or 70% in the individual as compared to the level before treatment.

As used therein, "delaying" the development of headache means to defer, hinder, slow, retard, stabilize, and/or postpone progression of the disease. This delay can be of varying lengths of time, depending on the history of the disease and/or individuals being treated. As is evident to one skilled in the art, a sufficient or significant delay can, in effect, encompass prevention, in that the individual does not develop headache (e.g., migraine). A method that "delays" development of the symptom is a method that reduces probability of developing the symptom in a given time frame and/or reduces extent of the symptoms in a given time frame, when compared to not using the method. Such comparisons are typically based on clinical studies, using a statistically significant number of subjects.

"Development" or "progression" of headache means initial manifestations and/or ensuing progression of the disorder. Development of headache can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of headache includes initial onset and/or recurrence.

An "alkyl group" as used herein refers to a linear or branched aliphatic hydrocarbon monovalent group having a specified number of carbon atoms. Non-limiting examples of the "alkyl group" are a methyl group, an ethyl group, a propyl group, an iso-butyl group, a sec-butyl group, a tert-butyl group, a pentyl group, an iso-amyl group, and a hexyl group. An "alkylene group" as used herein refers to a divalent group formed by abstraction of hydrogen from the alkyl group.

An "alkenyl group" as used herein refers to a hydrocarbon monovalent group containing at least one carbon-carbon double bond and having a specified number of carbon atoms. Non-limiting examples thereof are an ethenyl group, a propenyl group, and a butenyl group. An "alkenylene group" as used herein refers to a divalent group formed by abstraction of hydrogen from the alkenyl group.

An "alkynyl group" as used herein refers to a hydrocarbon monovalent group containing at least one carbon-carbon triple bond and having a specified number of carbon atoms. Non-limiting examples thereof are an ethynyl group and a propynyl group. An "alkynylene group" as used herein refers to a divalent group formed by abstraction of hydrogen from the alkynyl group.

A "heteroalkyl group" as used herein refers to an alkyl group as defined above, in which at least one carbon atom is replaced with a heteroatom selected from N, O, P, and S or in which at least one carbon atom is replaced with a group containing at least one of the above heteroatoms. Non-limiting examples thereof are a methoxyethyl group and a dimethylaminoethyl group. A "heteroalkylene group" as used herein refers to a divalent group formed by abstraction of hydrogen from the heteroalkyl group.

A "heteroalkenyl group" as used herein refers to an alkenyl group as defined above, in which at least one carbon atom is replaced with a heteroatom selected from N, O, P, and S. Non-limiting examples thereof are a methoxybutenyl group and a dimethylaminobutenyl group. A "heteroalkenylene group" as used herein refers to a divalent group formed by abstraction of hydrogen from the heteroalkenyl group.

A "heteroalkynyl group" as used herein refers to an alkynyl group as defined above, in which at least one carbon atom is replaced with a heteroatom selected from N, O, P, and S. Non-limiting examples thereof are a methoxybutynyl group and a dimethylaminobutynyl group. A "heteroalkynylene group" as used herein refers to a divalent group formed by abstraction of hydrogen from the heteroalkynyl group.

A "cycloalkyl group" as used herein refers to a monovalent hydrocarbon monocyclic group having a specified number of carbon atoms. Non-limiting examples thereof are a cyclopropyl group, a cyclobutyl group, a cyclopentyl group, a cyclohexyl group, and a cycloheptyl group. A "cycloalkylene group" as used herein refers to a divalent group formed by abstraction of hydrogen from the cycloalkyl group.

A "heterocycloalkyl group" as used herein refers to a monovalent monocyclic group having at least one heteroatom selected from N, O, P, and S as a ring-forming atom and specified number of carbon atoms. Non-limiting examples thereof are a tetrahydrofuranyl group and a tetrahydrothiophenyl group. A "heterocycloalkylene group" as used herein refers to a divalent group formed by abstraction of hydrogen from the heterocycloalkyl group.

An "aryl group" as used herein refers to a monovalent group having a carbocyclic aromatic system having a specified number of carbon atoms. Non-limiting examples of the aryl group are a phenyl group, a naphthyl group, an anthracenyl group, a phenanthrenyl group, a pyrenyl group, and a chrysenyl group. When the aryl group includes two or more rings, the rings may be fused to each other. An "arylene group" as used herein refers to a divalent group formed by abstraction of hydrogen from the aryl group.

A "heteroaryl group" as used herein refers to a monovalent carbocyclic aromatic system having at least one heteroatom selected from N, O, P, and S as a ring-forming atom and a specified number of carbon atoms. Non-limiting examples of the heteroaryl group are a pyridinyl group, a pyrimidinyl group, a pyrazinyl group, a pyridazinyl group, a triazinyl group, a quinolinyl group, and an isoquinolinyl group. When the heteroaryl group includes two or more rings, the rings may be fused to each other. A "heteroarylene group" as used herein refers to a divalent group formed by abstraction of hydrogen from the heteroaryl group.

At least one of substituents of the substituted alkyl group, substituted alkenyl group, substituted alkynyl group, substituted cycloalkyl group, substituted heterocycloalkyl group, substituted aryl group, and substituted heteroaryl group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C1-C10 alkyl group, a C2-C10 alkenyl group, a C2-C10 alkynyl group, and C1-C10 alkoxy group;

a C1-C10 alkyl group, a C2-C10 alkenyl group, a C2-C10 alkynyl group, and C1-C10 alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C3-C10 cycloalkyl group, a C1-C10 heterocycloalkyl group, a C3-C10 cycloalkenyl group, a C1-C10 heterocycloalkenyl group, a C6-C20 aryl group, a C6-C20 aryloxy group, a C6-C20 arylthio group, and a C1-C20 heteroaryl group;

a C3-C10 cycloalkyl group, a C1-C10 heterocycloalkyl group, a C3-C10 cycloalkenyl group, a C1-C10 heterocycloalkenyl group, a C6-C20 aryl group, a C6-C20 aryloxy group, a C6-C20 arylthio group, and a C1-C20 heteroaryl group; and a C3-C10 cycloalkyl group, a C1-C10 heterocycloalkyl group, a C3-C10 cycloalkenyl group, a C1-C10 heterocycloalkenyl group, a C6-C20 aryl group, a C6-C20 aryloxy group, a C6-C20 arylthio group, and a C1-C20 heteroaryl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C1-C10 alkyl group, a C2-C10 alkenyl group, a C2-C10 alkynyl group, and C1-C10 alkoxy group, a C3-C10 cycloalkyl group, a C1-C10 heterocycloalkyl group, a C3-C10 cycloalkenyl group, a C1-C10 heterocycloalkenyl group, a C6-C20 aryl group, a C6-C20 aryloxy group, a C6-C20 arylthio group, and a C1-C20 heteroaryl group.

For example, at least one of substituents of the substituted alkyl group, substituted alkenyl group, substituted alkynyl group, substituted alkoxy group, substituted cycloalkyl group, substituted heterocycloalkyl group, substituted aryl group, and substituted C1-C30 heteroaryl group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C1-C10 alkyl group, a C2-C10 alkenyl group, a C2-C10 alkynyl group, and C1-C10 alkoxy group;

a C1-C10 alkyl group, a C2-C10 alkenyl group, a C2-C10 alkynyl group, and C1-C10 alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C3-C10 cycloalkyl group, a C1-C10 heterocycloalkyl group, a C3-C10 cycloalkenyl group, a C1-C10 heterocycloalkenyl group, a C6-C20 aryl group, a C6-C20 aryloxy group, a C6-C20 arylthio group, and a C1-C20 heteroaryl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group and an imidazopyridinyl group, each substituted with at least one selected from a cyclopentyl group, a cyclohexyl group, a cycloheptyl group, a cyclooctyl group, a cyclopentenyl group, a cyclohexenyl group, a cycloheptenyl group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, each substituted with at least one selected from a cyclopentyl group, a cyclohexyl group, a cycloheptyl group, a cyclooctyl group, a cyclopentenyl group, a cyclohexenyl group, a cycloheptenyl group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C1-C10 alkyl group, a C2-C10 alkenyl group, a C2-C10 alkynyl group, and C1-C10 alkoxy group, a C3-C10 cycloalkyl group, a C1-C10 heterocycloalkyl group, a C3-C10 cycloalkenyl group, a C1-C10 heterocycloalkenyl group, a C6-C20 aryl group, a C6-C20 aryloxy group, a C6-C20 arylthio group, and a C1-C20 heteroaryl group.

When a group containing a specified number of carbon atoms is substituted with any of the groups listed in the preceding paragraph, the number of carbon atoms in the resulting "substituted" group may be defined as the sum of the carbon atoms contained in the original (unsubstituted) group and the carbon atoms (if any) contained in the substituent. For example, when the term "substituted C1-C20 alkyl" refers to a C1-C20 alkyl group substituted with C6-C20 aryl group, the total number of carbon atoms in the resulting aryl substituted alkyl group may be C7-C40.

The starting materials useful for making the compounds and pharmaceutical compositions of the present invention are readily commercially available or can be prepared by those skilled in the art.

The subject compounds are useful as prodrugs in a method of antagonism of CGRP receptors in a patient, such as mammal in need of such antagonism, wherein the method comprises the administration of an effective amount of the compound. Embodiments of the present invention are directed to the use of the compounds disclosed herein as prodrugs of antagonists of CGRP receptors. In addition to primate, especially humans, a variety of other mammals can be treated according to the method of the present invention.

An embodiment of the present invention provides a compound having General Formula (1):

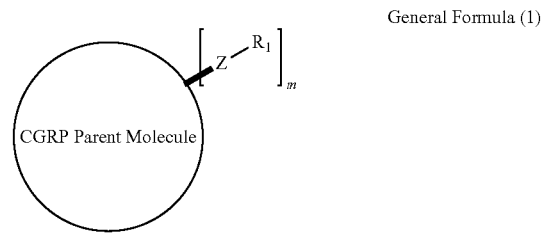

General Formula (1)

In General Formula (1), CGRP Parent Molecule is a moiety derived from a calcitonin gene-related peptide (CGRP) antagonist. The CGRP Parent Molecules suitable for use in accordance with the present invention can be any CGRP antagonist intended for oral administration that may demonstrate an enhancement in bioavailability, e.g., enhancements in AUC, $C_{max}$, or $T_{max}$. Examples of CGRP antagonists are disclosed in WO 2003/104236 published Dec. 18, 2003, WO 2011/123232 published Oct. 6, 2011, WO 2017/072721 published May 4, 2017, WO 2017/072722 published May 4, 2017, WO 2017/0727723 published May 4, 2017, and WO 2018/178938 published Oct. 4, 2018. Other CGRP antagonists include, for example, olcegepant (Boehringer Ingelheim, Ridgefield, CT), telcagepant (Merck Sharp & Dohme Corp., Kenilworth, NJ), ubrogepant (Allergan plc, Dublin, Ireland), lasmiditan (Eli Lilly and Company, Indianapolis, IN), and rimegepant (Biohaven Pharmaceutical Holding Company Ltd., New Haven, CT).

Rimegepant has the chemical formula, $C_{28}H_{28}F_2N_6O_3$ and the IUPAC name [(5S,6S,9R)-5-amino-6-(2,3-difluorophenyl)-6,7,8,9-tetrahydro-5H-cyclohepta[b]pyridin-9-yl] 4-(2-oxo-3H-imidazo[4,5-b]pyridin-1-yl)piperidine-1-carboxylate. Rimegepant is also referred to herein as BHV-3000.

The structure of rimegepant is

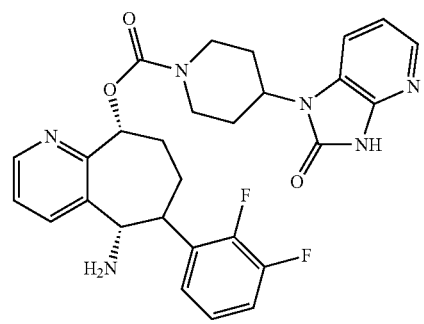 [SMILES: N[C@@H]1c2cccnc2[C@H](OC(=O)N2CCC(n3c(=O)[nH]c4ncccc43)CC2)CCC1c1cccc(F)c1F]

Rimegepant is described, for example in WO 2011/046997 published Apr. 21, 2011. A salt form of rimegepant is described in WO 2013/130402 published Sep. 6, 2013.

The chemical formula of the salt form is $C_{28}H_{28}F_2N_6O_3 \cdot 0.5\ H_2SO_4 \cdot 1.5\ H_2O$ and the structure is as follows:

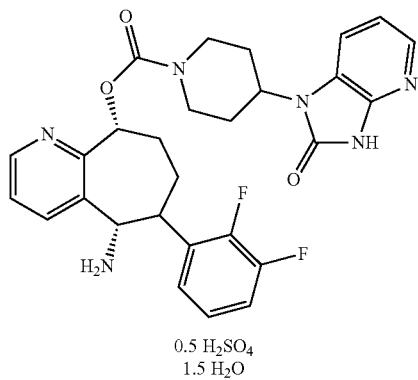 [SMILES: N[C@@H]1c2cccnc2[C@H](OC(=O)N2CCC(n3c(=O)[nH]c4ncccc43)CC2)CCC1c1cccc(F)c1F]

0.5 H$_2$SO$_4$
1.5 H$_2$O

One preferred CGPR Parent Molecule is described in WO 2011/123232 published Oct. 6, 2011, and has the following structure (also referred to herein as BHV-3500):

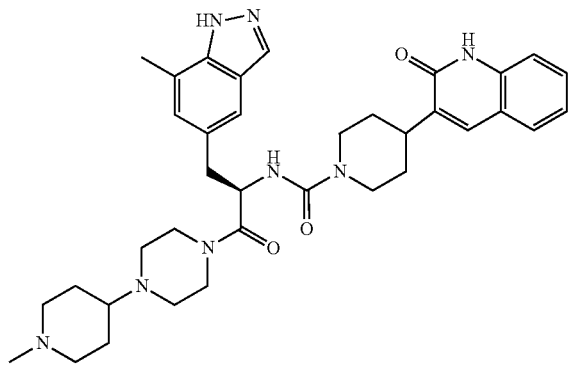 [SMILES: Cc1cc(C[C@@H](NC(=O)N2CCC(c3cc4ccccc4[nH]c3=O)CC2)C(=O)N2CCN(C3CCN(C)CC3)CC2)cc2cn[nH]c12]

The CGPR Parent Molecules of the present invention have at least one functionalizable moiety included in its structure. The functionalizable moiety is referred to as "Z" in General Formula 1. The particular functionalizable moiety is not critical to the present invention. Typically, the functionalizable moiety is one to which a lipophilic prodrug group can be attached. The moiety "—NH" is an example of a functionalizable moiety Z found on many CGRP antagonists. A tertiary amine nitrogen atom is another example of a functionalizable moiety Z found on many CGRP antagonists. A nitrogen atom incorporated in a heterocycle is yet another example of a functionalizable moiety Z found on many CGRP antagonists.

In General Formula 1, $R_1$ may be represented by formula

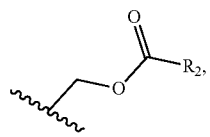

wherein $R_2$ may be —[C(R$_3$)$_2$]$_n$R$_4$, —NR$_3$R$_4$, or —OR$_4$. $R_3$ may independently be hydrogen or a C1-C10 alkyl group. When each $R_3$ is a C1-C10 alkyl group, $R_3$ may be optionally connected with a single bond to form a ring. $R_4$ may be a substituted or unsubstituted C1-C20 alkyl group, a substituted or unsubstituted C2-C20 alkenyl group, a substituted or unsubstituted C2-C20 alkynyl group, a substituted or unsubstituted C1-C20 heteroalkyl group, a substituted or unsubstituted C2-C20 heteroalkenyl group, a substituted or unsubstituted C2-C20 heteroalkynyl group, a substituted or unsubstituted C3-C20 cycloalkyl group, a substituted or unsubstituted C3-C20 heterocycloalkyl group, a substituted or unsubstituted C6-C20 aryl group, or a substituted or unsubstituted C1-C20 heteroaryl group. For example, $R_4$ may be a substituted or unsubstituted C1-C15 alkyl group, a substituted or unsubstituted C2-C15 alkenyl group, a substituted or unsubstituted C2-C15 alkynyl group, a substituted or unsubstituted C1-C15 heteroalkyl group, a substituted or unsubstituted C2-C15 heteroalkenyl group, a substituted or unsubstituted C2-C15 heteroalkynyl group, a substituted or unsubstituted C3-C15 cycloalkyl group, a substituted or unsubstituted C3-C15 heterocycloalkyl group, a substituted or unsubstituted C6-C15 aryl group, or a substituted or unsubstituted C1-C15 heteroaryl group. In another example, $R_4$ may be a substituted or unsubstituted C1-C10 alkyl group, a substituted or unsubstituted C2-C10 alkenyl group, a substituted or unsubstituted C2-C10 alkynyl group, a substituted or unsubstituted C1-C10 heteroalkyl group, a substituted or unsubstituted C2-C10 heteroalkenyl group, a substituted or unsubstituted C2-C10 heteroalkynyl group, a substituted or unsubstituted C3-C10 cycloalkyl group, a substituted or unsubstituted C3-C10 heterocycloalkyl group, a substituted or unsubstituted C6-C10 aryl group, or a substituted or unsubstituted C1-C10 heteroaryl group.

In formula —[C(R$_3$)$_2$]$_n$R$_4$, n may be 0 or 1. When n is 0, moiety [C(R$_3$)$_2$] is absent, and $R_2$ may be the same as $R_4$ described above. When n is 0, examples of $R_1$ groups which may be attached to the functionalizable moiety Z of the CGRP Parent Molecule may include:

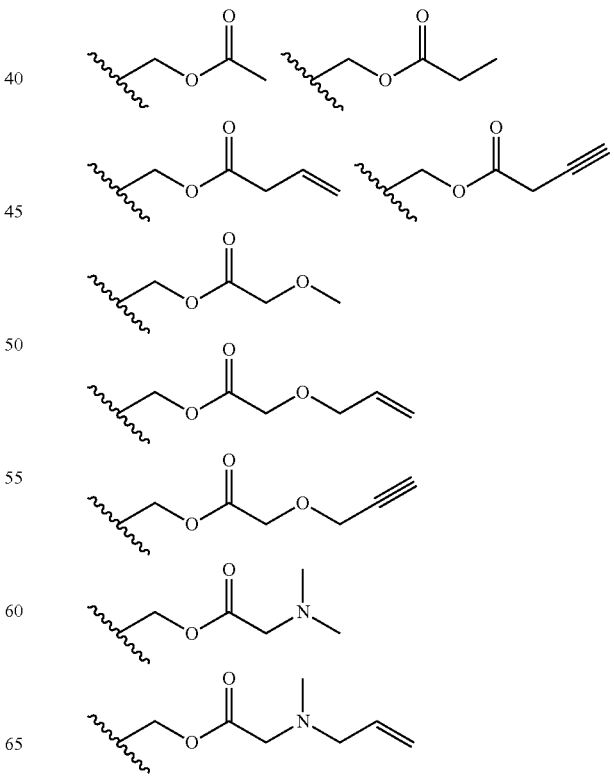

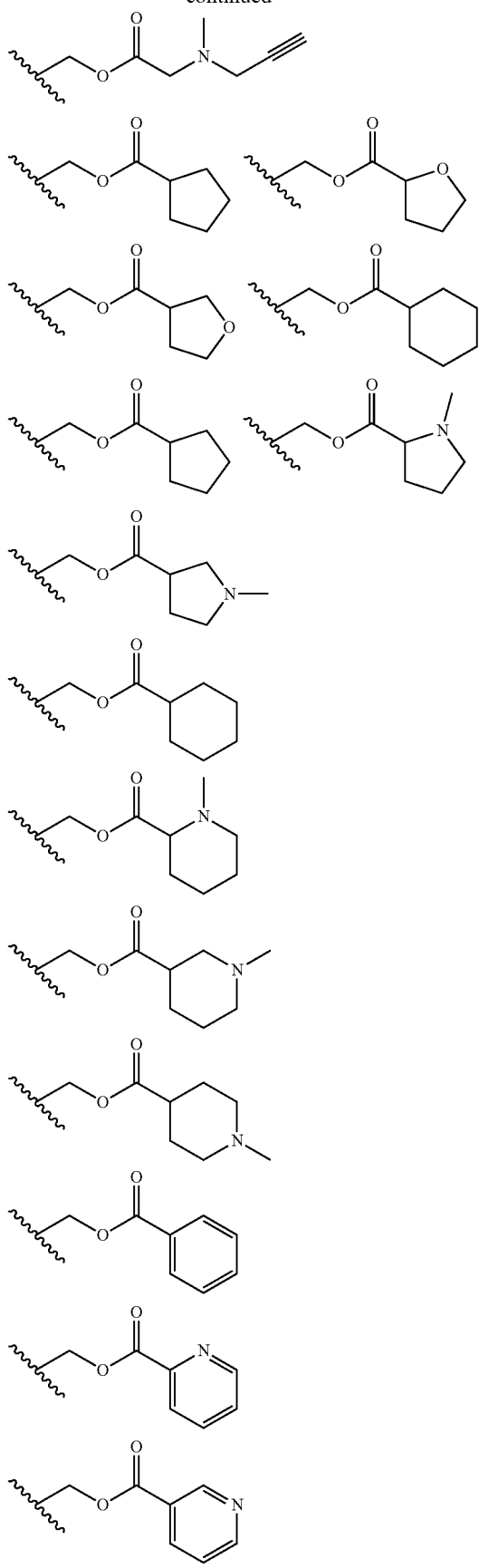
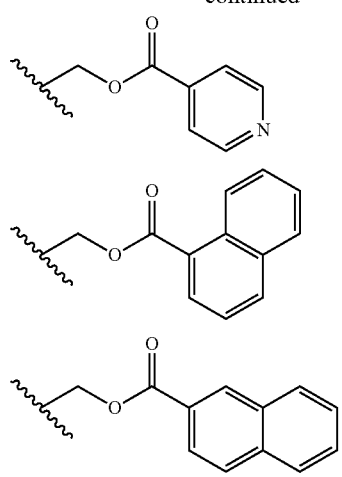

Each of the above groups may be substituted or unsubstituted.

When n in formula —[C(R$_3$)$_2$]$_n$R$_4$ is 1, moiety [C(R$_3$)$_2$] is present. In some embodiments, each R$_3$ in moiety [C(R$_3$)$_2$] may be hydrogen. In other embodiments, one R$_3$ may be hydrogen and the other R$_3$ may be a C1-C10 alkyl group. In some other embodiments, each R$_3$ may be a C1-C10 alkyl group.

When n is 1, examples of R$_1$ groups which can be attached to the functionalizable moiety Z of the CGRP Parent Molecule may include:

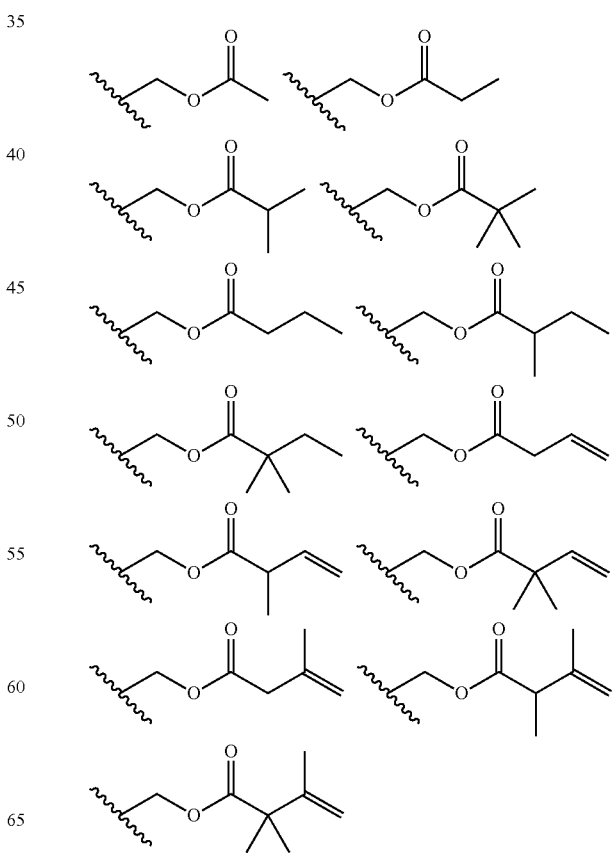

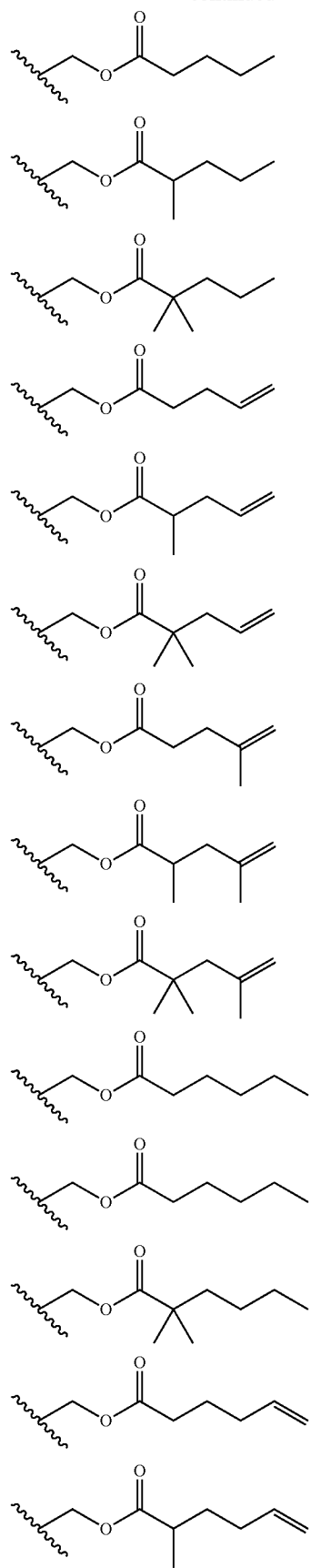
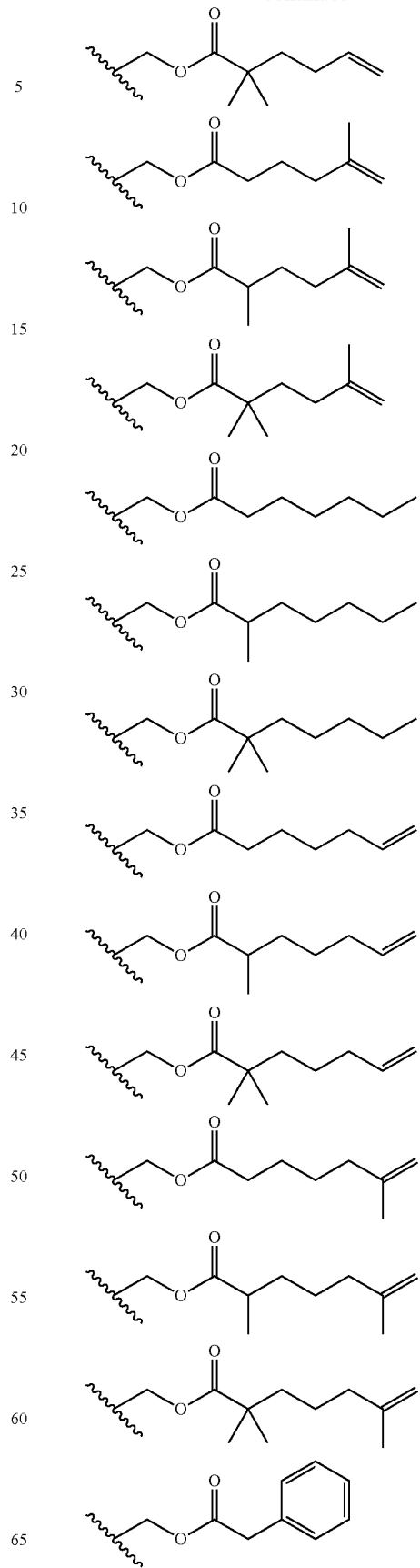

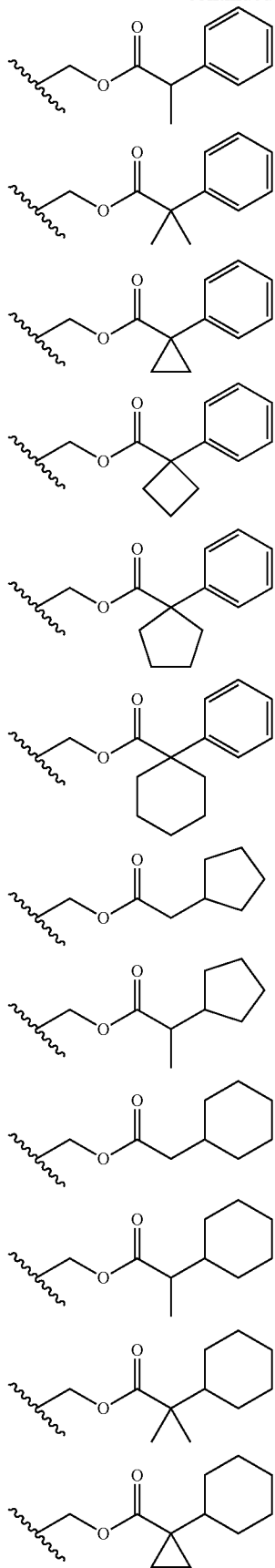

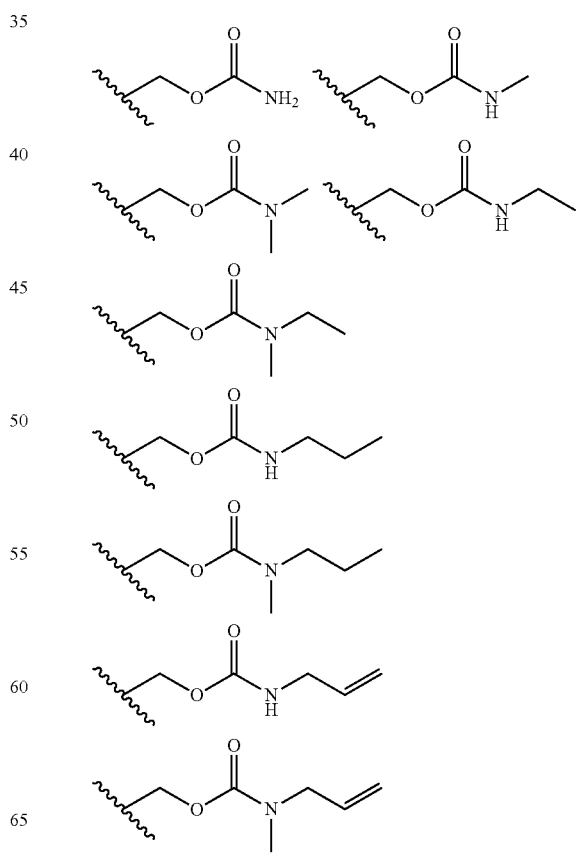

Each of the above groups may be substituted or unsubstituted.

In General Formula (1), $R_2$ may be $-NR_3R_4$, wherein $R_3$ and $R_4$ may be the same as described above. In an embodiment, $R_3$ and $R_4$ may be individual substituents. In another embodiment, $R_3$ and $R_4$ may be connected to form a ring. When $R_2$ is $-NR_3R_4$, examples of $R_1$ groups which can be attached to the functionalizable moiety Z of the CGRP Parent Molecule may include:

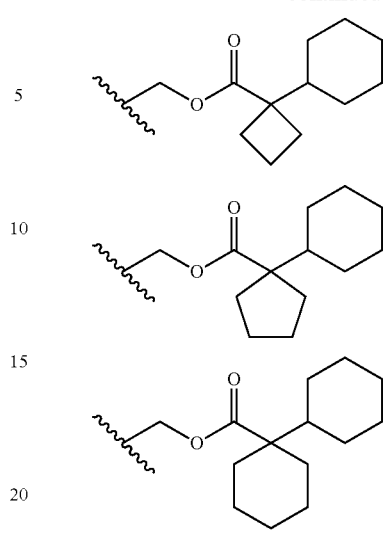

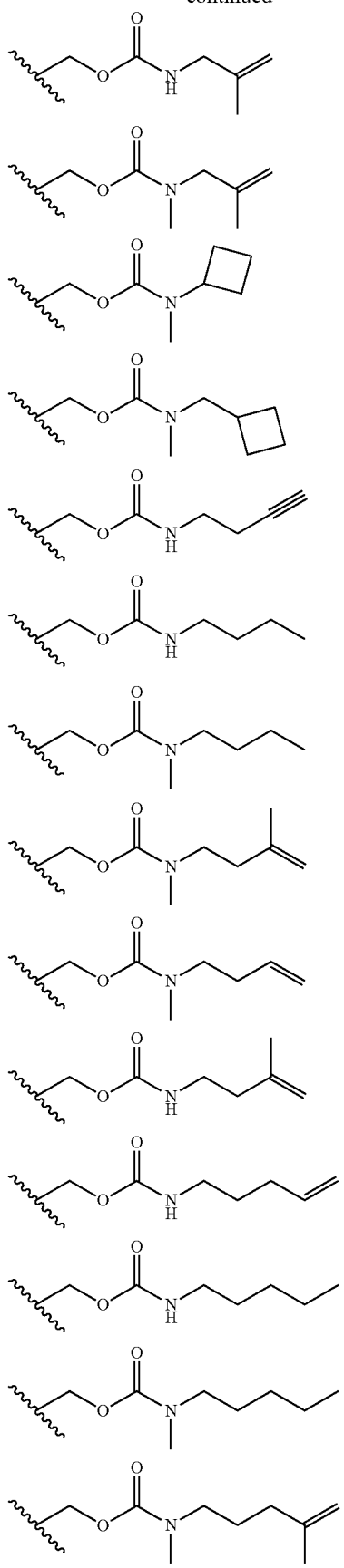
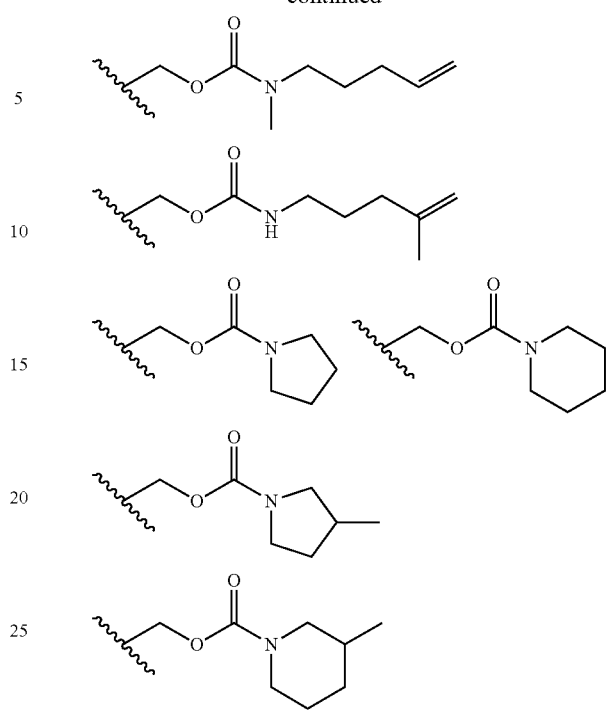
Each of the above groups may be substituted or unsubstituted.
In General Formula (1), $R_2$ may be —$OR_4$, wherein $R_4$ may be the same as described above. When $R_2$ may be —$OR_4$, examples of $R_1$ groups which can be attached to the functionalizable moiety Z of the CGRP Parent Molecule may include:
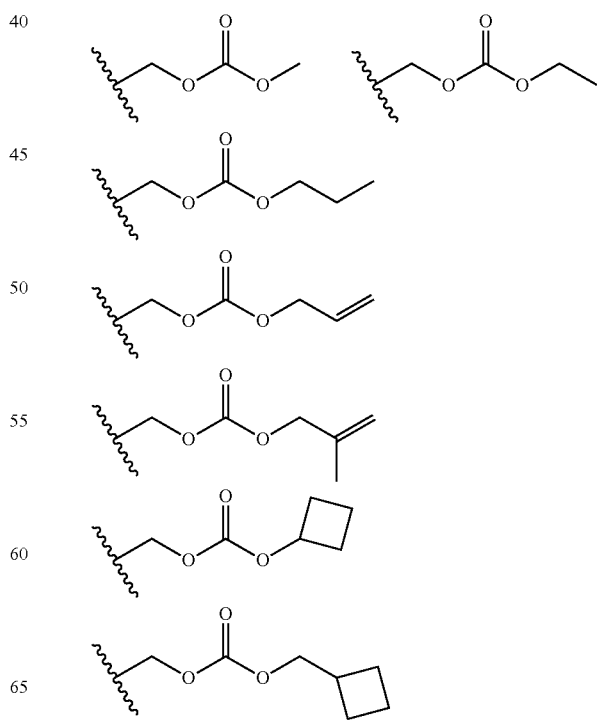

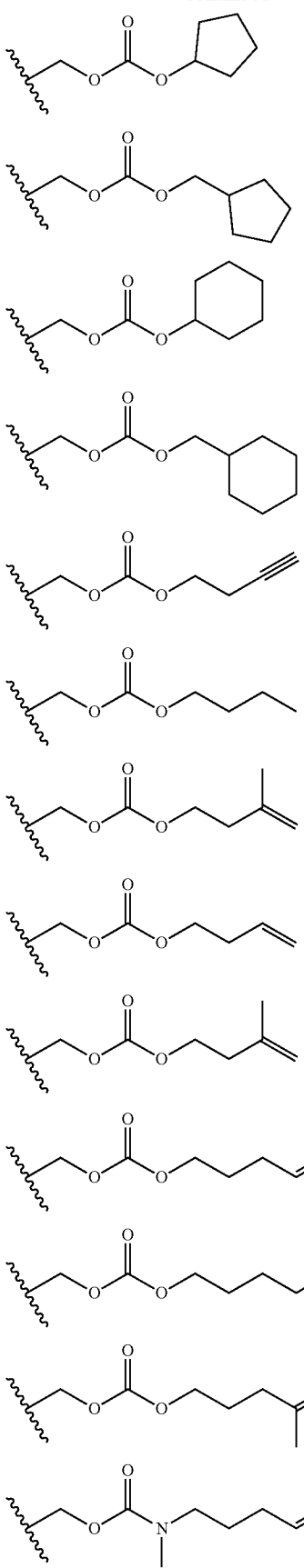

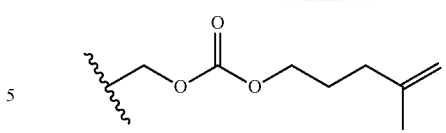

Each of the above groups may be substituted or unsubstituted.

In an embodiment, $R_4$ may be substituted with a natural aminoacid that is linked to $R_4$ through an oxygen atom of a carboxylic acid group. The natural aminoacid may be glycine, alanine, valine, leucine, isoleucine, serine, threonine, cysteine, cystine, methionine, aspartic acid, glutamic acid, asparagine, glutamine, lysine, hydroxylysine, arginine, histidine, phenylalanine, tyrosine, tryptophan, proline, or hydroxyproline. The natural aminoacid may be attached at the terminal or internal carbon atom of the $R_4$ group.

In General Formula 1, $R_1$ may also be —$CH_2OP(=O)(OR^b)_2$, —$CH_2OP(=O)(OR^b)R^a$, —$CH_2OP(=O)R^aR^b$, or —$CH_2OP(=O)(OR^b)$—$OP(=O)(OR^b)_2$. In these formulae, $R^a$ and $R^b$ may be independently selected from hydrogen, a substituted or unsubstituted C1-C20 alkyl group, a substituted or unsubstituted C3-C20 cycloalkyl group, a substituted or unsubstituted C6-C20 aryl group, a substituted or unsubstituted C1-C20 heteroaryl group. In an embodiment, $R_1$ may be —$CH_2OP(=O)(OH)_2$.

In General Formula 1, "m" may be an integer of at least one, for example, an integer of at least two, or an integer of at least three. In other words, General Formula 1 requires the presence of at least one group —[Z—$R_1$]. When at least two functionalizable moieties Z are present, $R_1$ in neighboring groups —[Z—$R_1$] may be optionally connected to form a ring.

In an embodiment, —Z—$R_1$ may be represented by General Formula 2:

General Formula (2)

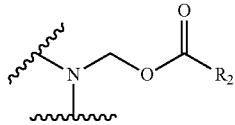

wherein, in General Formula (2), $R_2$ is the same as that described above in connection with General Formula (1).

Non-limiting examples of the moieties containing the functionalizable group Z may found on pages 28-30 of WO 2003/104236 published Dec. 18, 2003. However, the functionalizable group Z is not limited thereto, and any moiety of the CGRP antagonist capable of being functionalized with group $R_1$ as indicated above may serve as the functionalizable group Z.

In an embodiment, at least two functionalizable groups Z may be present, and one group —Z—$R_1$ may be represented by General Formula (3) or (4):

General Formula (3)

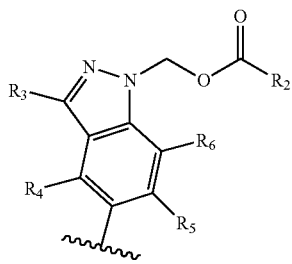

General Formula (4)

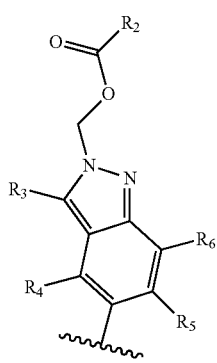

In General Formulae (3) and (4), $R_3$, $R_4$, $R_5$, and $R_6$ may each independently be hydrogen, a halogen, a hydroxyl group, a nitro group, a cyano group, a C1-C3 alkyl group optionally substituted with fluorine, or a C1-C3 alkoxy group optionally substituted with fluorine.

For example, group —Z—$R_1$ may be represented by General Formulae (5) or (6):

General Formula (5)

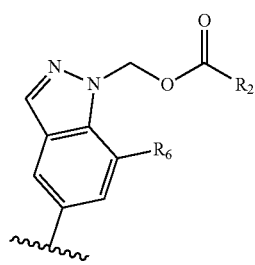

General Formula (6)

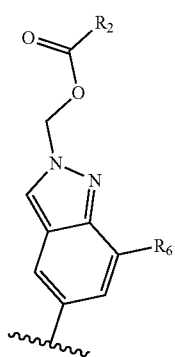

In General Formulae (5) and (6), $R_6$ may be hydrogen or a methyl group ($CH_3$) optionally substituted with fluorine ($CH_2F$, $CHF_2$, and $CF_3$), and $R_2$ may be the same as that described above in connection with General Formula (1).

In another embodiment, group —Z—$R_1$ may be represented by General Formula (7), (8), or (9):

General Formual (7)

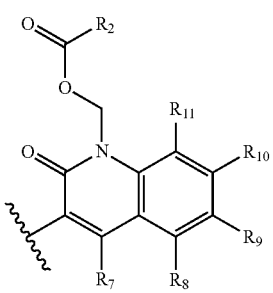

General Formula (8)

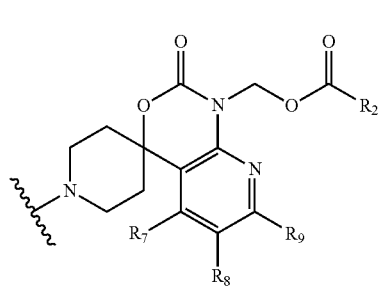

General Formula (9)

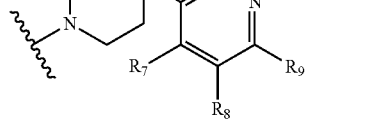

In General Formulae (7), (8), and (9), $R_7$, $R_8$, $R_9$, $R_{10}$, and $R_{11}$ may each independently be hydrogen, halogen, a hydroxyl group, a nitro group, a cyano group, a C1-C3 alkyl group optionally substituted with fluorine, or a C1-C3 alkoxy group optionally substituted with fluorine, and $R_2$ may be the same as in General Formula (1) above.

For example, group —Z—$R_1$ may be represented by General Formula (10), (11), or (12):

General Formula (10)

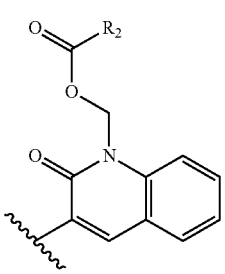

General Formula (11)

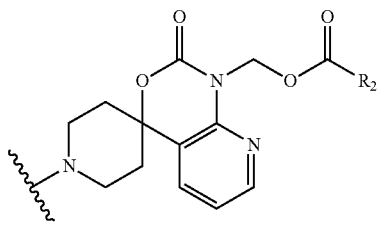

General Formula (12)

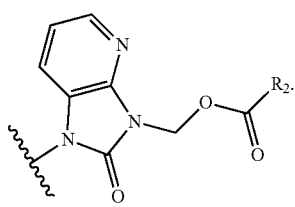

In General Formulae (10), (11), and (12), $R_2$ may be the same as that described above in connection with General Formula (1).

In an embodiment, when at least one functionalizable group Z is present, one group —Z—$R_1$ may be represented by one of General Formulae (3) and (4) and another group Z—$R_1$ may be represented by one of General Formulae (7), (8), and (9). For example, one group —Z—$R_1$ may be represented by one of General Formulae (5) and (6) and another group Z—$R_1$ may be represented by one of General Formulae (10), (11), and (12).

In yet another embodiment, group —Z—$R_1$ may be represented by General Formula (13):

General Formula (13)

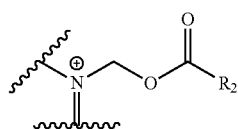

In General Formula (13), the positively charged nitrogen may constitute a part of the heterocyclic ring, and $R_2$ may be the same as that described above in connection with General Formula (1).

In an embodiment, when a group represented by General Formula (13) is present, an additional group represented by one of General Formulae (3) and (4) may be present. In another embodiment, when a group represented by General Formula (13) is present, an additional group represented by one of General Formulae (7), (8), and (9) may be present. In yet another embodiment, a group represented by General Formula (13) is present, one of the groups represented by one of General Formulae (3) and (4) may be present, and one of the groups represented by one of General Formulae (7), (8), and (9) may also be present.

In an embodiment, a group represented by the General Formula (4) may be present together with one of the groups represented by General Formulae (7), (8), and (9). In that embodiment, group $R_2$ of General Formula 4 and group $R_2$ of one of General Formulae (7), (8), and (9) may be connected with a single bond to form a linking group L having the constitution —$R_2$—$R_2$—. For example, a group represented by the General Formula (6) may be present together with one of the groups represented by General Formulae (10), (11), and (12). In that embodiment, group $R_2$ of General Formula (6) and group $R_2$ of one of General Formulae (10), (11), and (12) may be connected with a single bond to form a linking group L having the structure —$R_2$—$R_2$—. The described connection forms an additional ring in the compound.

The number of $R_1$ substituents attached to functionalizable moieties Z on the CGRP Parent Molecule depend on factors which can be determined by one skilled in the art, e.g., the desired degree of bioavailability. Also, not all functionalizable moieties Z need to be substituted with an $R_1$ group. If more than one functionalizable moiety Z is substituted with an $R_1$ group, the $R_1$ groups may be the same or different.

In some embodiments, the CGRP parent molecule may be BHV-3500, which has at least four functionalizable moieties Z: three NH moieties and a nitrogen atom of the terminal N-methylpiperidine group. With regard to BHV-3500, the compound having General Formula (I) may be represented by one of Formula (I) to (IV):

(I)

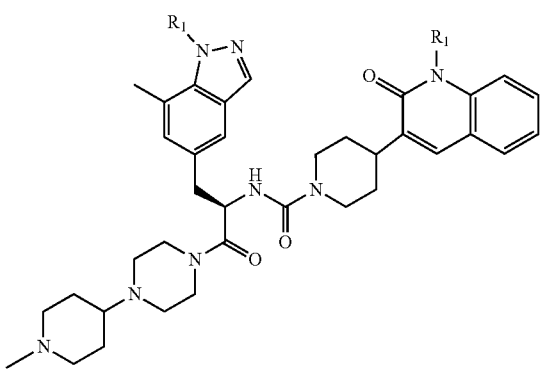

(II)

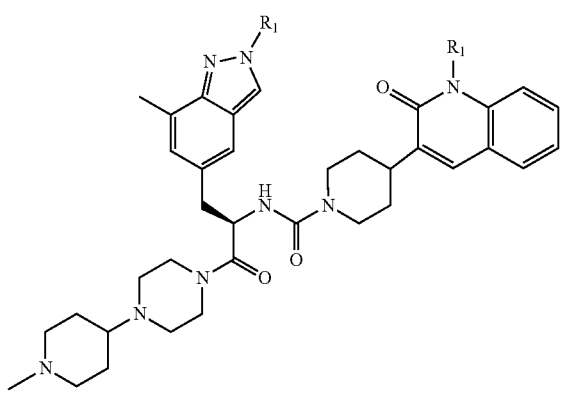

-continued

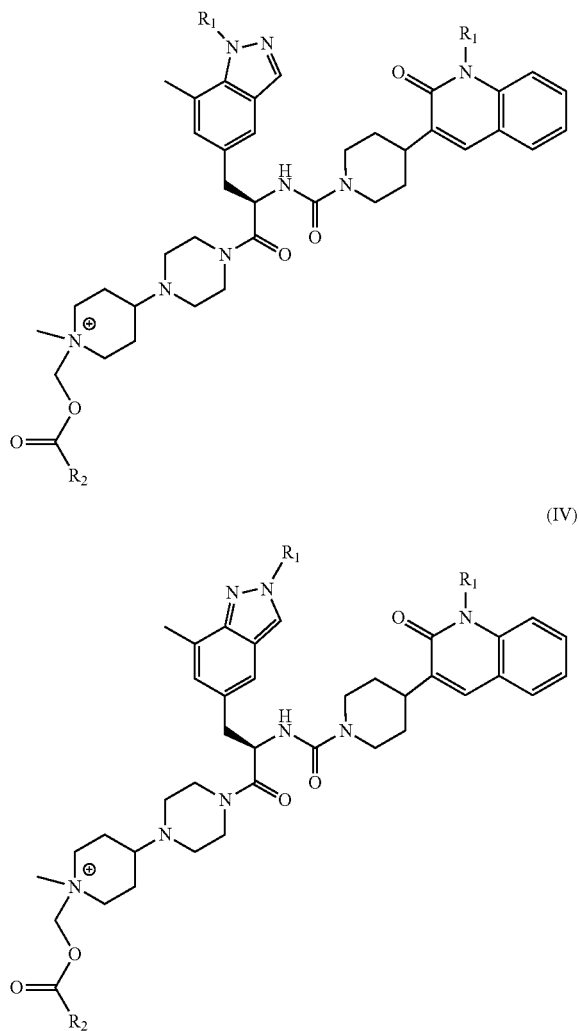

In Formulae (I) to (IV),
each $R_1$ may independently be H,

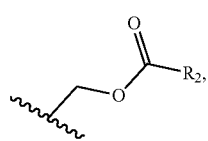

or —$CH_2OP(=O)(OH)_2$, provided that at least one $R_1$ is

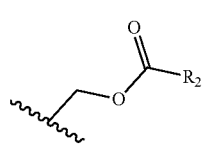

or —$CH_2OP(=O)(OH)_2$. Thus, Formulae (I) to (IV) require the presence of at least one group that is other than hydrogen. In Formulae (I) to (II), each $R_1$ may be

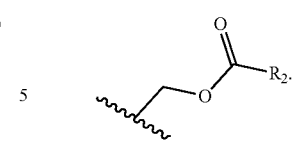

In Formulae (I) to (IV), $R_2$ may be —$[C(R_3)_2]_nR_4$, —$NR_3R_4$, or —$OR_4$, wherein each $R_3$ may independently be hydrogen or C1-C10 alkyl, and $R_4$ may be a substituted or unsubstituted C1-C20 alkyl group, a substituted or unsubstituted C2-C20 alkenyl group, a substituted or unsubstituted C2-C20 alkynyl group, a substituted or unsubstituted C1-C20 heteroalkyl group, a substituted or unsubstituted C2-C20 heteroalkenyl group, a substituted or unsubstituted C2-C20 heteroalkynyl group, a substituted or unsubstituted C3-C20 cycloalkyl group, a substituted or unsubstituted C3-C20 heterocycloalkyl group, or a substituted or unsubstituted C6-C20 aryl group, or a substituted or unsubstituted C1-C20 heteroaryl group. n may be 0 or 1. $R_3$ may be optionally connected to form a ring, which can be, for example, a substituted or unsubstituted cyclopropyl ring, a substituted or unsubstituted cyclobutyl ring, a substituted or unsubstituted cyclopentyl ring, or a substituted or unsubstituted cyclohexyl ring.

In Formulae (I) to (IV), at least one $R_3$ may not be hydrogen, or each $R_3$ may not be hydrogen. For example, at least one $R_3$ may be a methyl group or each $R_3$ may be a methyl group. In these embodiments, $R_2$ may independently be —$C(H)(CH_3)R_4$ or —$C(CH_3)_2R_4$, wherein $R_4$ may be the same as that described above. In an embodiment, $R_4$ may each independently be a substituted or unsubstituted C1-C15 alkyl group, a substituted or unsubstituted C2-C15 alkenyl group, a substituted or unsubstituted C2-C15 alkynyl group, a substituted or unsubstituted C1-C15 heteroalkyl group, a substituted or unsubstituted C2-C15 heteroalkenyl group, a substituted or unsubstituted C2-C15 heteroalkynyl group, a substituted or unsubstituted C3-C15 cycloalkyl group, a substituted or unsubstituted C3-C15 heterocycloalkyl group, a substituted or unsubstituted C6-C15 aryl group, or a substituted or unsubstituted C1-C15 heteroaryl group. In another embodiment, $R_4$ may each independently be a substituted or unsubstituted C1-C10 alkyl group, a substituted or unsubstituted C2-C10 alkenyl group, a substituted or unsubstituted C2-C10 alkynyl group, a substituted or unsubstituted C1-C10 heteroalkyl group, a substituted or unsubstituted C2-C10 heteroalkenyl group, a substituted or unsubstituted C2-C10 heteroalkynyl group, a substituted or unsubstituted C3-C10 cycloalkyl group, a substituted or unsubstituted C3-C10 heterocycloalkyl group, a substituted or unsubstituted C6-C10 aryl group, or a substituted or unsubstituted C1-C10 heteroaryl group.

In Formulae (II) and (IV), when each $R_1$ is

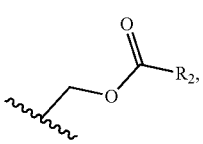

$R_2$ may be connected to form a ring.

When the compound has Formula (I), the compound may be represented by one of Formulae (Ia), (Ib), and (Ic):
When the compound has Formula (II), the compound may be represented by one of Formulae (IIa) and (IIb):
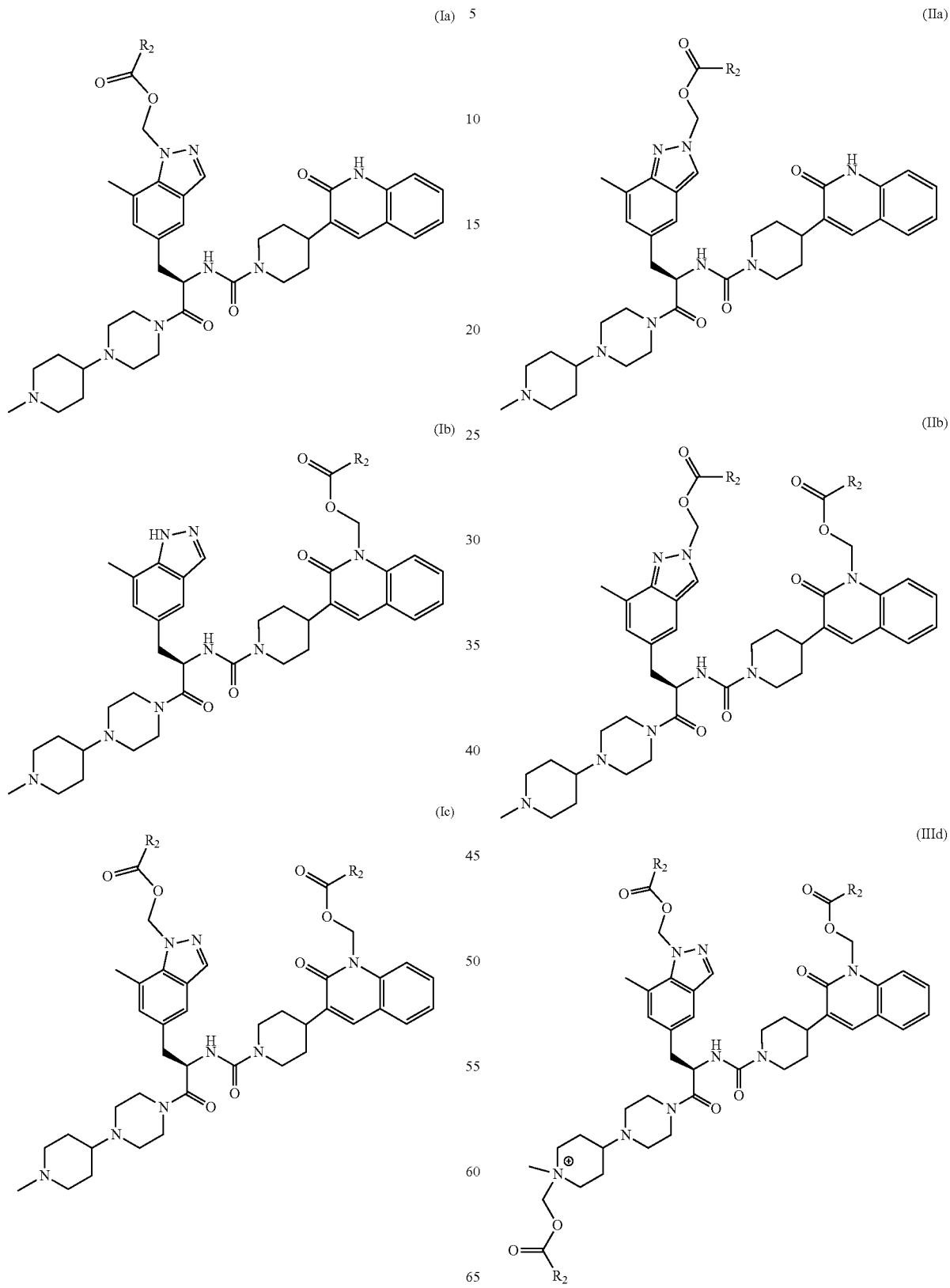
In Formulae (Ia), (Ib), and (Ic), R₂ may be the same as those described in connection with Formula (I).

In Formulae (IIa) and (IIb), R₂ may be the same as those described in connection with Formula (II).

When the compound is represented by Formula (Ic), R₂ may be connected with a single bond to form a linking group L, as in Formula (Id):

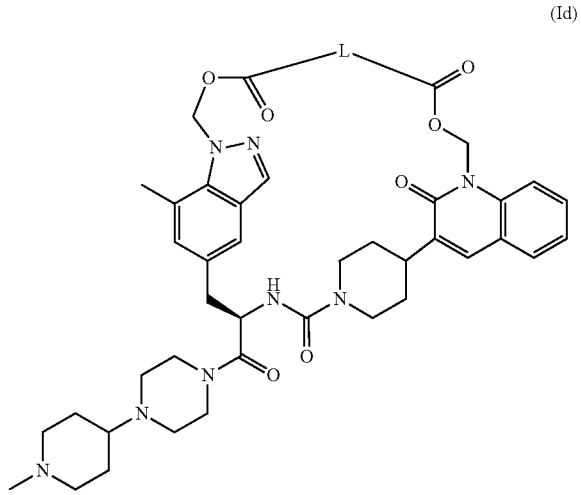

(Id)

When the compound is represented by Formula (IIb), R₂ may be connected with a single bond to form a linking group L, as in Formula (IIc):

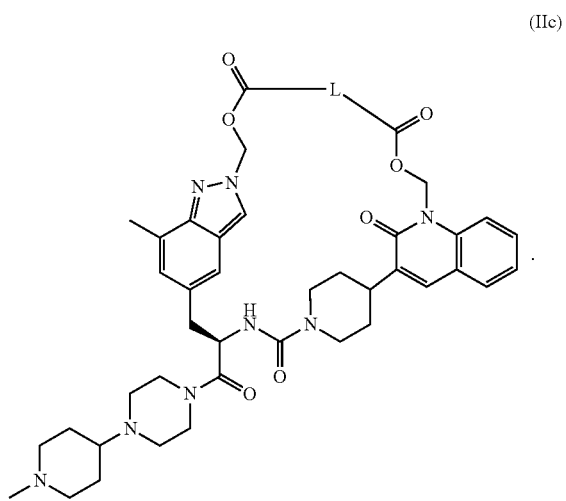

(IIc)

In the Formulae (Ic) and (IIb), the linking group L may be a substituted or unsubstituted C1-C10 alkylene group, a substituted or unsubstituted C2-C10 alkenylene group, a substituted or unsubstituted C2-C10 alkynylene group, a substituted or unsubstituted C1-C10 heteroalkylene group, a substituted or unsubstituted C2-C10 heteroalkenylene group, a substituted or unsubstituted C2-C10 heteroalkynylene group, a substituted or unsubstituted C3-C10 cycloalkylene group, a substituted or unsubstituted C3-C10 heterocycloalkylene group, a substituted or unsubstituted C6-C10 arylene group, or a substituted or unsubstituted C1-C10 heteroarylene group, or any combination thereof.

In the Formulae (Ic) and (IIb), the linking group L may be composed of two groups R₂ and may have the structure —R₂—R₂—. For example, the linking group may have Formula (L-1):

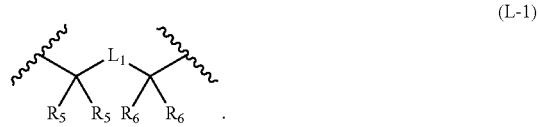

(L-1)

In Formula (L-1), L₁ may be a substituted or unsubstituted C1-C10 alkylene group, a substituted or unsubstituted C2-C10 alkenylene group, a substituted or unsubstituted C2-C10 alkynylene group, a substituted or unsubstituted C1-C10 heteroalkylene group, a substituted or unsubstituted C2-C10 heteroalkenylene group, a substituted or unsubstituted C2-C10 heteroalkynylene group, a substituted or unsubstituted C3-C10 cycloalkylene group, a substituted or unsubstituted C3-C10 heterocycloalkylene group, a substituted or unsubstituted C6-C10 arylene group, or a substituted or unsubstituted C1-C10 heteroarylene group. For example, L₁ may be a substituted or unsubstituted C1-C10 alkylene group or a substituted or unsubstituted C2-C10 alkenylene group. R₅ and R₆ may each independently be hydrogen or a C1-C10 alkyl group, for example, a C1-C5 alkyl group, or a C1-C3 alkyl group.

In Formula (L-1), at least one R₅ may not hydrogen and at least one R₆ may not hydrogen. For example, at least one R₅ may be a methyl group and at least one R₆ may be a methyl group. Two geminal groups R₅ may be optionally connected with a single bond to form a ring. Also, two geminal groups R₆ may be optionally connected with a single bond to form a ring. The ring may be a cyclopropyl ring, a cyclobutyl ring, a cyclopentyl ring, or a cyclohexyl ring, each of which may be substituted or unsubstituted. In some embodiments, the linking group L may have one of Formulae (L-11), (L-12), (L-13), (L-14), and (L-15):

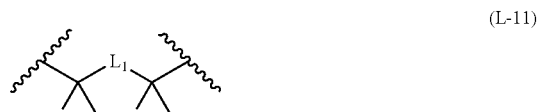

(L-11)

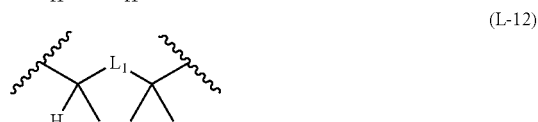

(L-12)

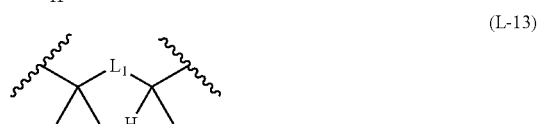

(L-13)

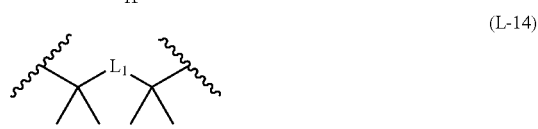

(L-14)

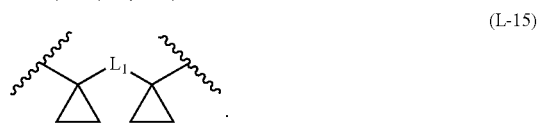

(L-15)

In Formulae (L-11) to (L-15) above, $L_1$ may be the same as that described in connection with Formula (L-1).
When the compound has Formula (III), the compound may be represented by one of Formulae (IIIa), (IIIb), (IIIc), and (IIId):
(IIIa)
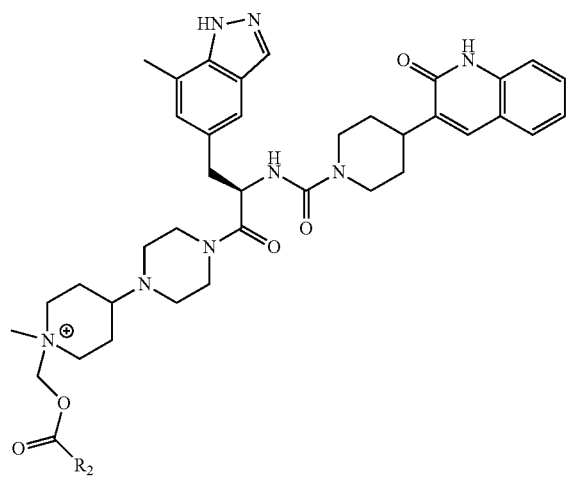
(IIIb)
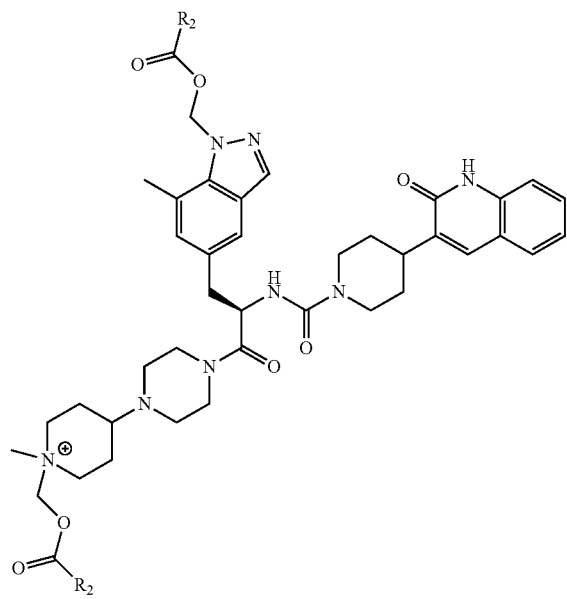
(IIIc)
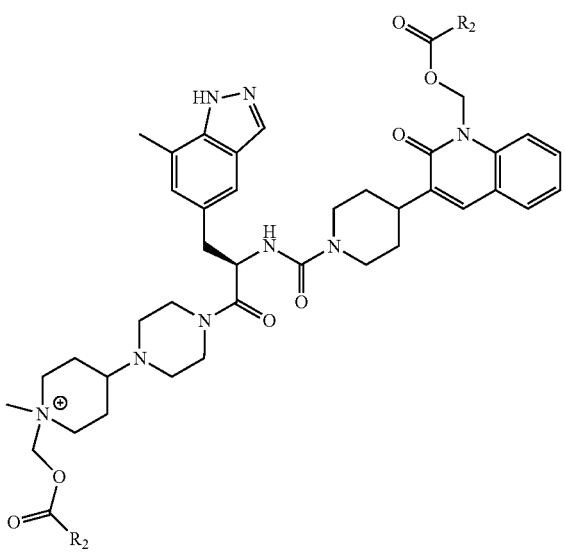
(IIId)
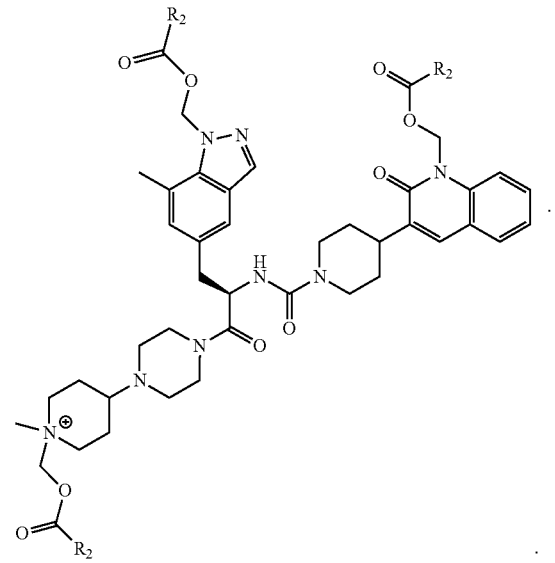
In Formulae (IIIa), (IIIb), (IIIc), and (IIId), $R_2$ may be the same as that described in connection with Formula (III).

When the compound has Formula (IV), the compound may be represented by one of Formulae (IVa) and (IVb):

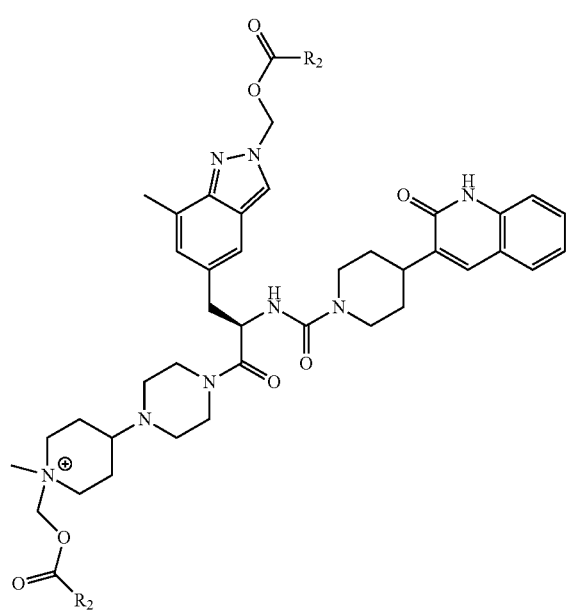

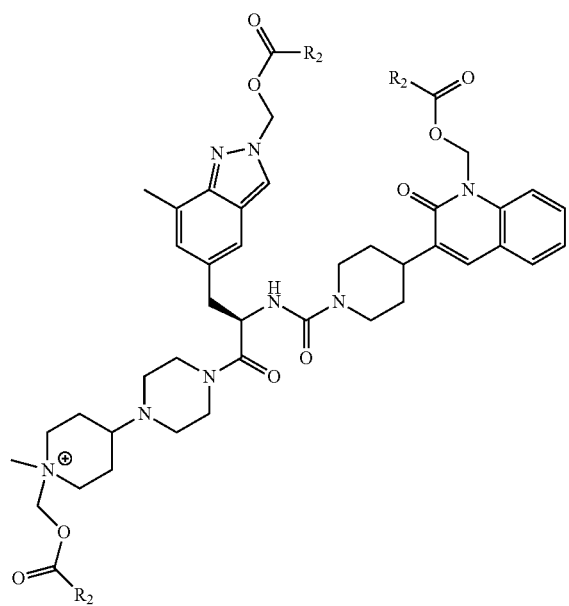

In Formulae (IVa) and (IVb), $R_2$ may be the same as that described in connection with Formula (III).

When the compound is represented by Formula (IIId) and (IVb), $R_2$ may be connected with a single bond to form a linking group L, as in Formulae (IIIe) and (IVc), respectively:

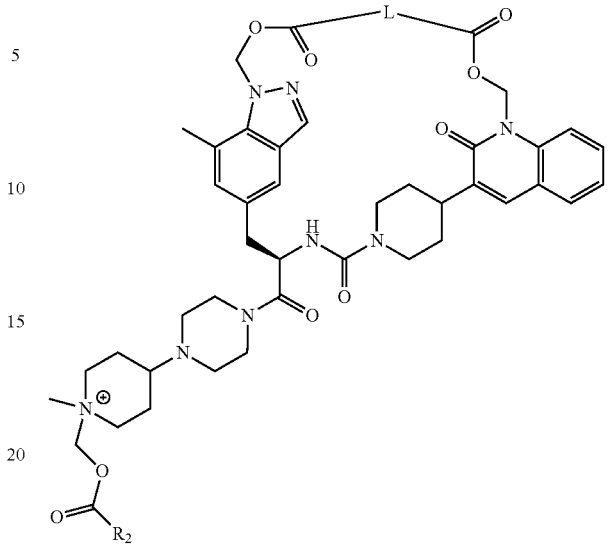

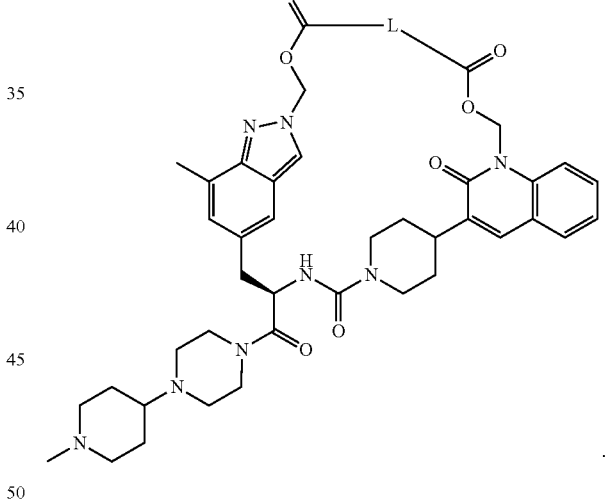

In the Formulae (IIIe) and (IVc), the linking group L may be a substituted or unsubstituted C1-C10 alkylene group, a substituted or unsubstituted C2-C10 alkenylene group, a substituted or unsubstituted C2-C10 alkynylene group, a substituted or unsubstituted C1-C10 heteroalkylene group, a substituted or unsubstituted C2-C10 heteroalkenylene group, a substituted or unsubstituted C2-C10 heteroalkynylene group, a substituted or unsubstituted C3-C10 cycloalkylene group, a substituted or unsubstituted C3-C10 heterocycloalkylene group, a substituted or unsubstituted C6-C10 arylene group, or a substituted or unsubstituted C1-C10 heteroarylene group, or any combination thereof.

In the Formulae (IIIe) and (IVc), the linking group L may be composed of two groups $R_2$ and may have the structure —$R_2$—$R_2$—. For example, the linking group may have Formula (L-1):

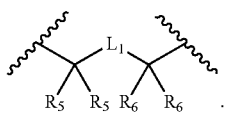
(L-1)

In Formula (L-1), $L_1$ may be a substituted or unsubstituted C1-C10 alkylene group, a substituted or unsubstituted C2-C10 alkenylene group, a substituted or unsubstituted C2-C10 alkynylene group, a substituted or unsubstituted C1-C10 heteroalkylene group, a substituted or unsubstituted C2-C10 heteroalkenylene group, a substituted or unsubstituted C2-C10 heteroalkynylene group, a substituted or unsubstituted C3-C10 cycloalkylene group, a substituted or unsubstituted C3-C10 heterocycloalkylene group, a substituted or unsubstituted C6-C10 arylene group, or a substituted or unsubstituted C1-C10 heteroarylene group. For example, $L_1$ may be a substituted or unsubstituted C1-C10 alkylene group or a substituted or unsubstituted C2-C10 alkenylene group.

$R_5$ and $R_6$ may each independently be hydrogen or a C1-C10 alkyl group, for example, a C1-C5 alkyl group, or a C1-C3 alkyl group.

In Formula (L-1), at least one $R_5$ may not hydrogen and at least one $R_6$ may not hydrogen. For example, at least one $R_5$ may be a methyl group and at least one $R_6$ may be a methyl group. Two geminal groups $R_5$ may be optionally connected with a single bond to form a ring. Also, two geminal groups $R_5$ may be optionally connected with a single bond to form a ring. The ring may be a cyclopropyl ring, a cyclobutyl ring, a cyclopentyl ring, or a cyclohexyl ring, each of which may be substituted or unsubstituted. Thus, in some embodiments, the linking group L may have one of Formulae (L-11), (L-12), (L-13), (L-14), and (L-15):

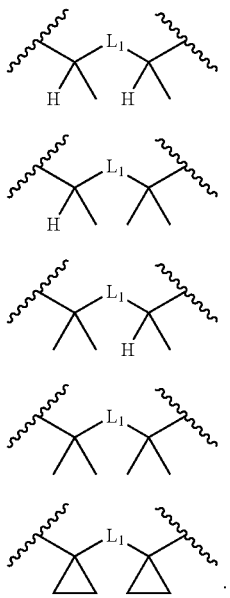

In Formulae (L-11) to (L-15) above, $L_1$ may be the same as that described in connection with Formula (L-1).

A person of ordinary skill in the art would be able to apply the above inventive concepts to conveniently functionalize any CGRP antagonist known in the art without undue experimentation. For example, the following CGRP antagonist (V):

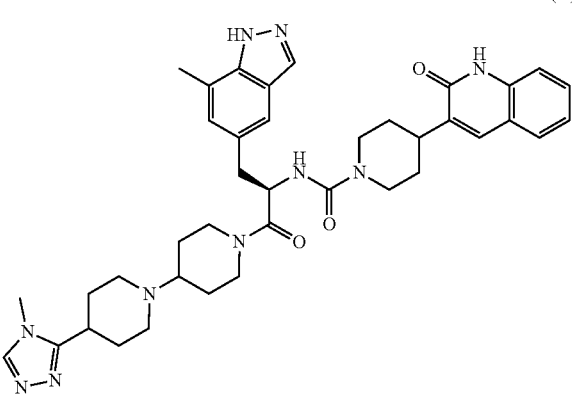
(V)

may be used as a CGRP Parent Molecule to prepare prodrug compounds represented, for example, by Formulae (VI) to (IX):

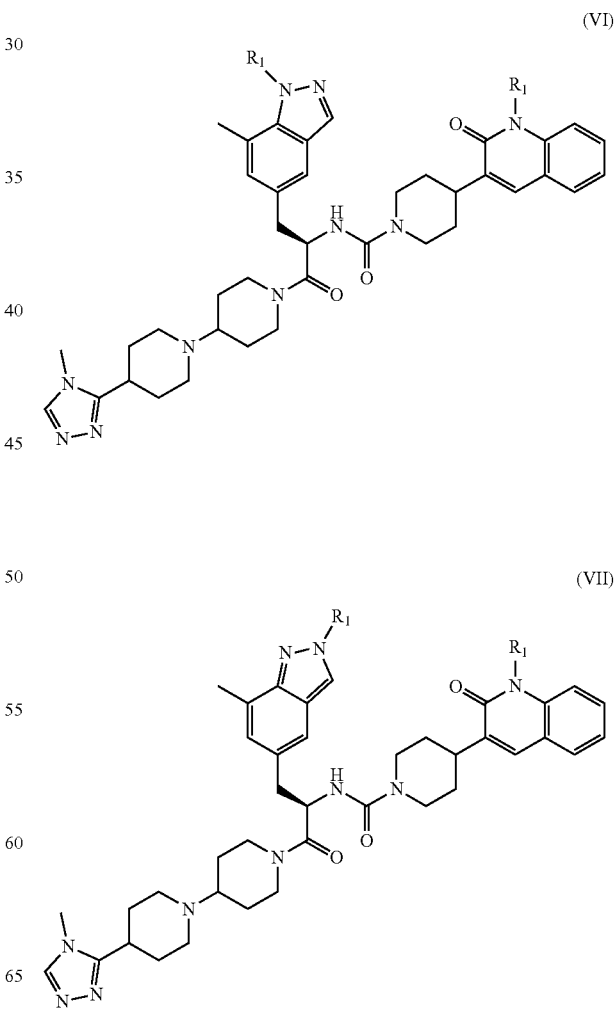

-continued (VIII)

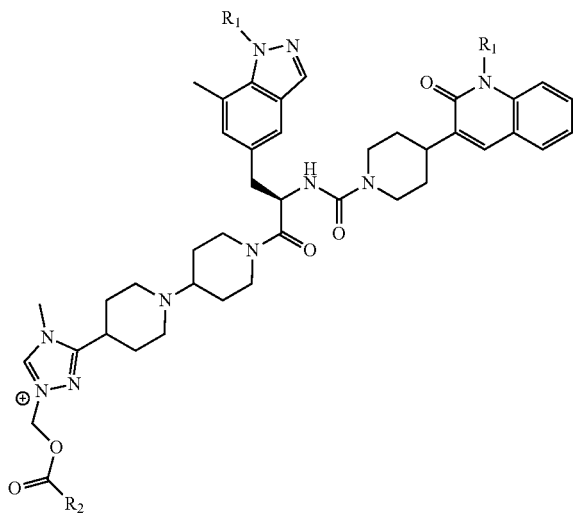

(IX)

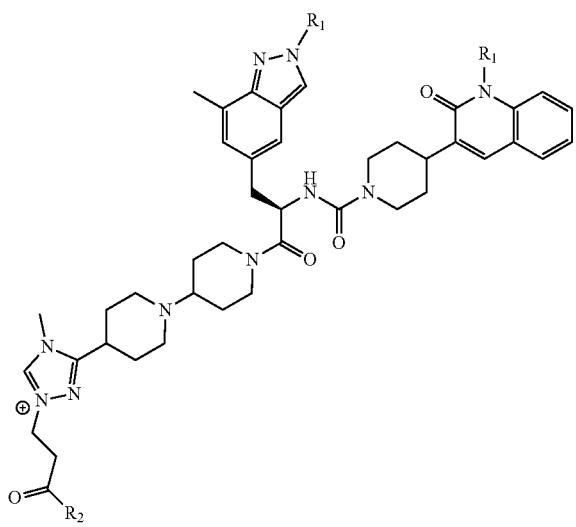

In Formulae (VI) to (IX), R₁ may be the same as that described in connection with Formulae (I) to (IV) above.

In another example, the following CGRP antagonist (X)

(X)

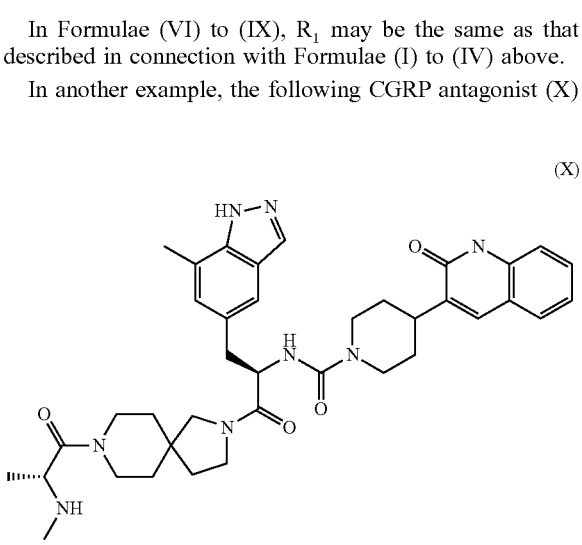

may be used to prepare prodrug compounds represented, for example, by Formulae (XI) and (XII):

(XI)

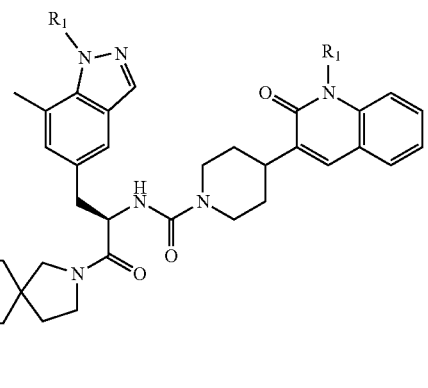

(XII)

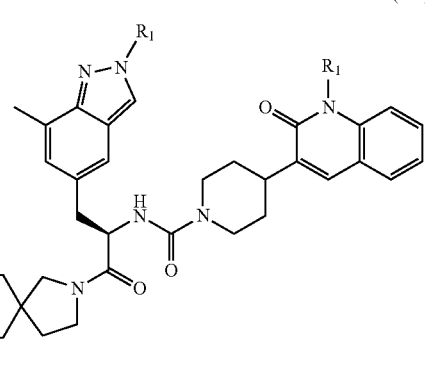

In Formulae (XI) to (XII), R₁ may be the same as that described in connection with Formulae (I) to (IV) above.

In another example, the following CGRP antagonist (XIII)

(XIII)

may be used to prepare prodrug compounds represented, for example, by Formulae (XI) and (XII):

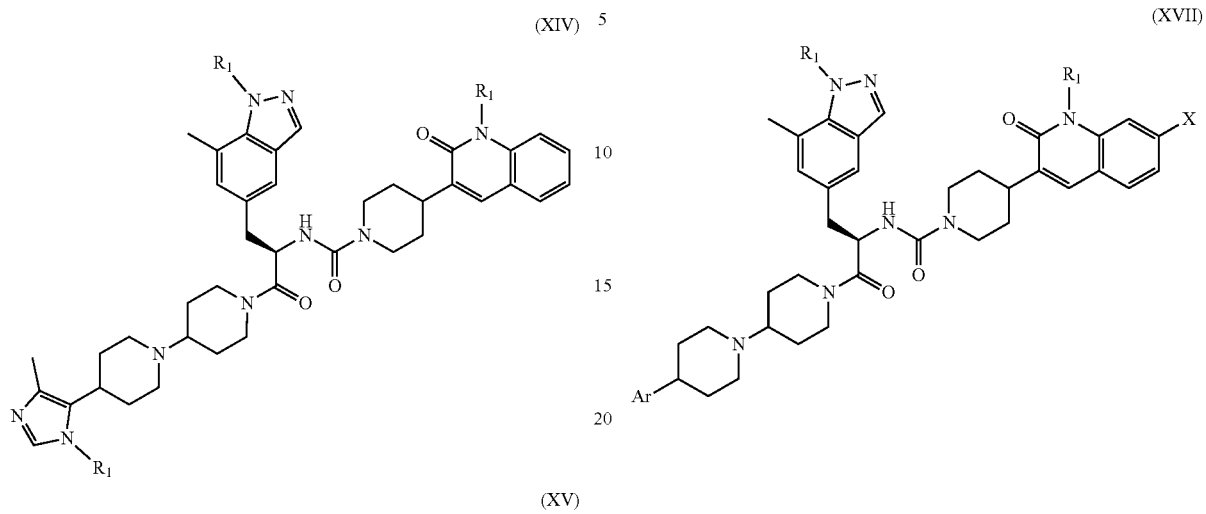

In Formulae (XIV) and (XV), $R_1$ may be the same as that described in connection with Formulae (I) to (IV) above.

In another example, the following CGRP antagonist (XVI)

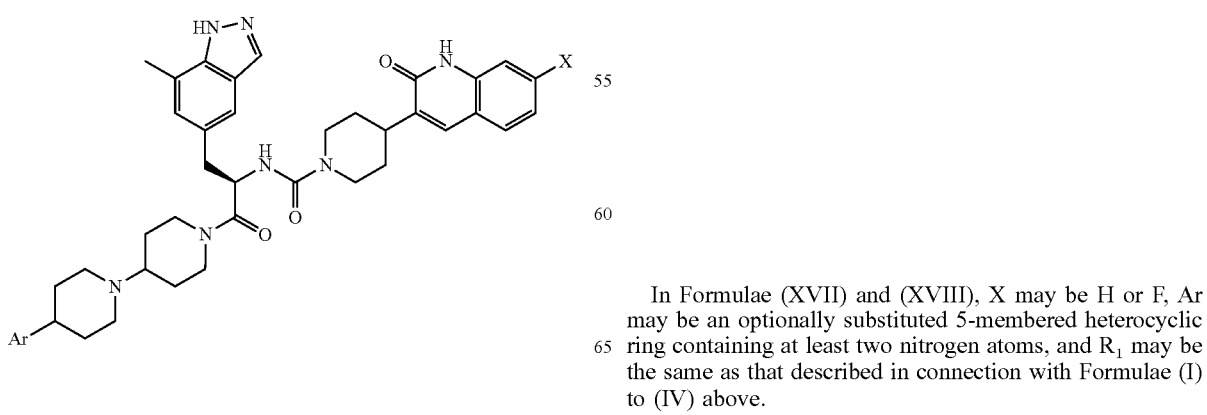

may be used to prepare prodrug compounds represented, for example, by Formulae (XVII) and (XVIII):

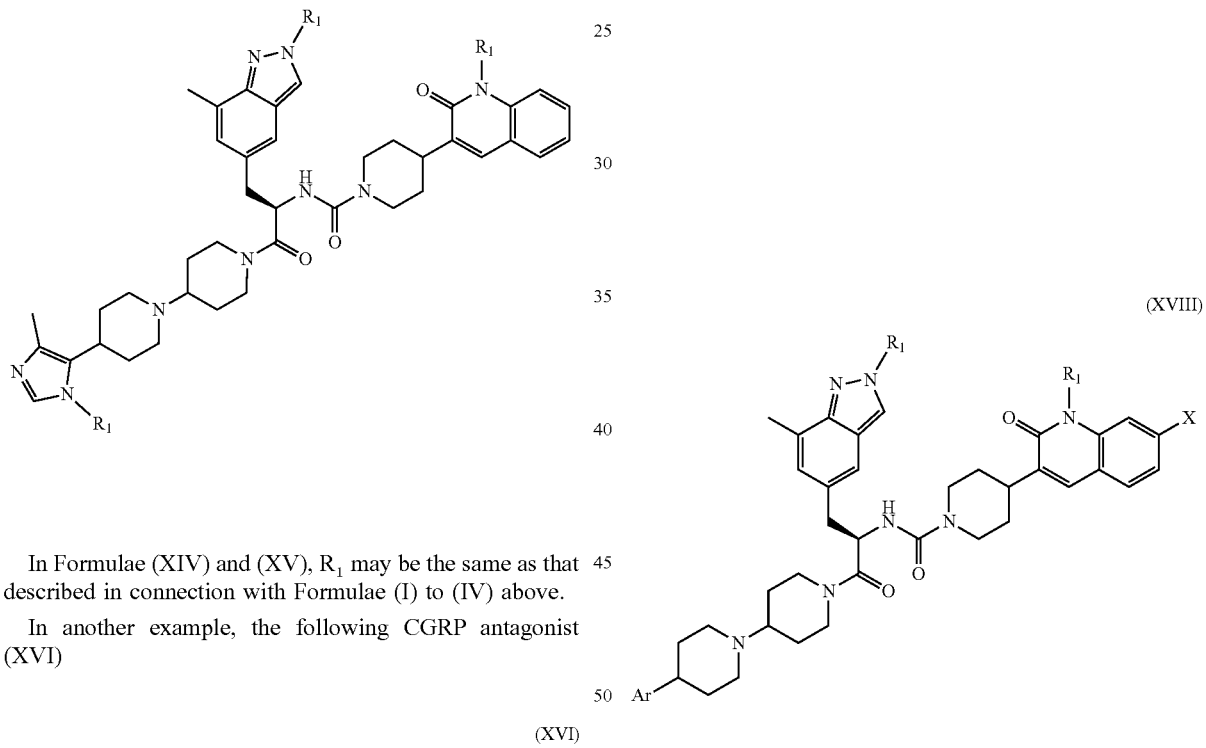

In Formulae (XVII) and (XVIII), X may be H or F, Ar may be an optionally substituted 5-membered heterocyclic ring containing at least two nitrogen atoms, and $R_1$ may be the same as that described in connection with Formulae (I) to (IV) above.

In another example, the following CGRP antagonist (XIX)
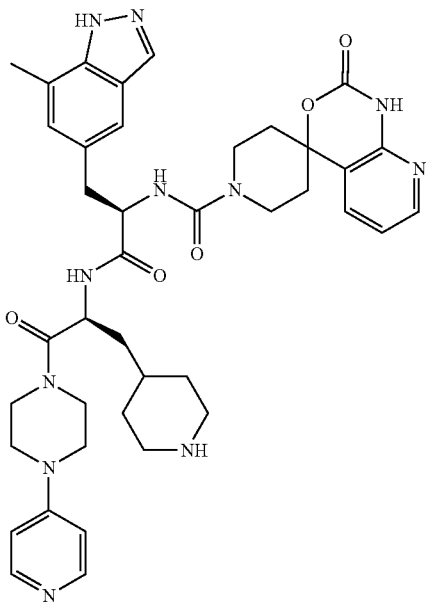 (XIX)
may be used to prepare prodrug compounds represented by Formulae (XI) and (XII):
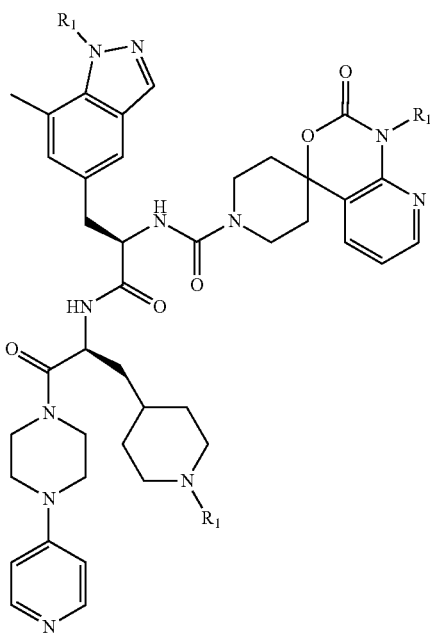 (XX)
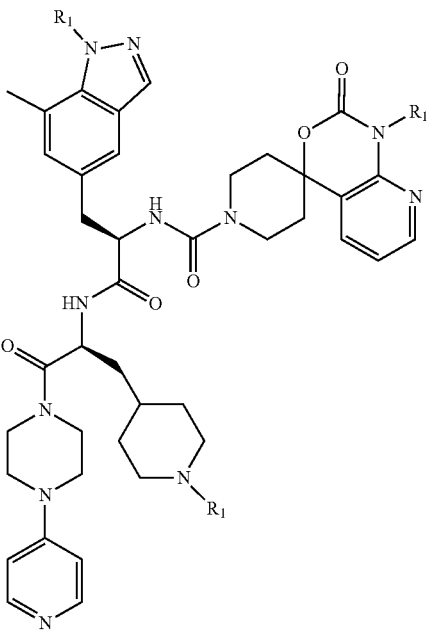 (XXI)
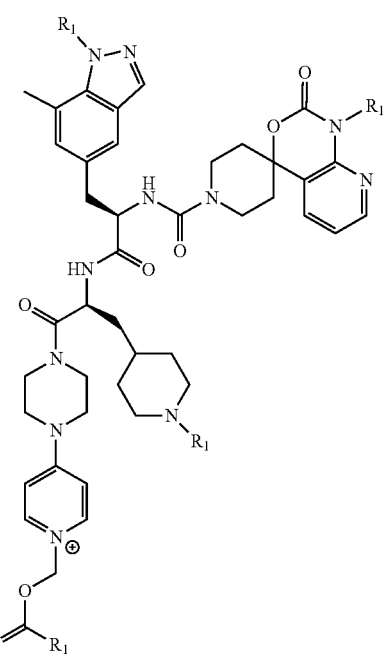 (XXII)

-continued

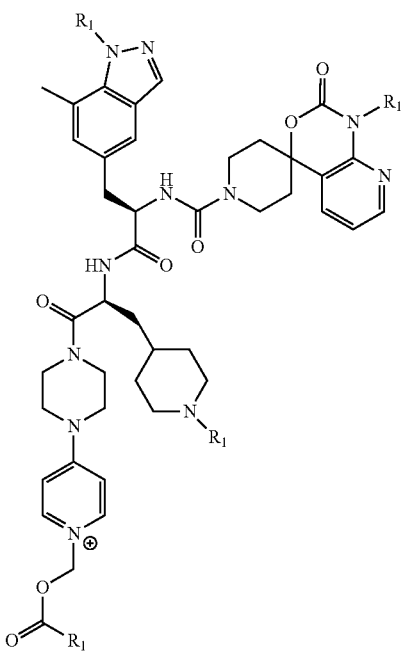

(XXIII)

In Formulae (XX) and (XXIII), $R_1$ may be the same as that described in connection with Formulae (I) to (IV) above.

In another example, the following CGRP antagonist (XXIV)

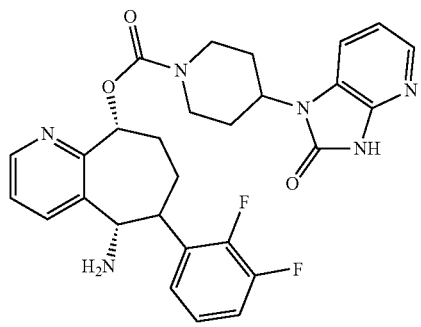

(XXIV)

may be used to prepare prodrug compounds represented by Formula (XXV):

(XXV)

In Formula (XXV), $R_1$ may be the same as that described in connection with Formulae (I) to (IV) above.

The compounds of the invention may be made in the form of pharmaceutically acceptable salts.

The present invention is further directed to a pharmaceutical composition comprising a therapeutically effective amount of a compound. The pharmaceutical compositions of the present invention can be prepared in any suitable dosage form, but are typically prepared as tablets, capsules, powders, granules, or solutions.

The pharmaceutical compositions of the present invention comprising the compounds of the invention typically also include other pharmaceutically acceptable carriers and/or excipients such as, for example, binders, lubricants, diluents, coatings, disintegrants, barrier layer components, glidants, coloring agents, solubility enhancers, gelling agents, fillers, proteins, co-factors, emulsifiers, solubilizing agents, suspending agents, flavorants, preservatives and mixtures thereof. A skilled artisan in the art would know what other pharmaceutically acceptable carriers and/or excipients could be included in the formulations according to the invention. The choice of excipients would depend on the characteristics of the compositions and on the nature of other pharmacologically active compounds in the formulation. Appropriate excipients are known to those skilled in the art (see *Handbook of Pharmaceutical Excipients,* fifth edition, 2005 edited by Rowe et al., McGraw Hill) and have been utilized to yield a novel formulation with unexpected properties.

Examples of pharmaceutically acceptable carriers that may be used in preparing the pharmaceutical compositions of the present invention may include, but are not limited to, fillers such as sugars, including lactose, sucrose, mannitol, or sorbitol; cellulose preparations such as maize starch, wheat starch, rice starch, potato starch, gelatin, gum tragacanth, methyl cellulose, hydroxypropyl methyl-cellulose, sodium carboxymethylcellulose, polyvinyl-pyrrolidone (PVP), talc, calcium sulphate, vegetable oils, synthetic oils, polyols, alginic acid, phosphate buffered solutions, emulsifiers, isotonic saline, pyrogen-free water and combinations thereof. If desired, disintegrating agents may be combined as well, and exemplary disintegrating agents may be, but not limited to, cross-linked polyvinyl pyrrolidone, agar, or alginic acid or a salt thereof such as sodium alginate. In an embodiment, the flavoring agent may be selected from mint, peppermint, berries, cherries, menthol and sodium chloride flavoring agents, and combinations thereof. In an embodiment, the sweetener may be selected from sugar, sucralose, aspartame, acesulfame, neotame, and combinations thereof.

Typical routes of administering the pharmaceutical compositions of the invention include, without limitation, oral administration. The compositions may also be administered by parenteral (e.g., intramuscular, intraperitoneal, intravenous, intracerebroventricular, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000).

The present invention is further directed to a method for the manufacture of a medicament for antagonism of CGRP receptors activity in humans and animals comprising combining a prodrug compound of the present invention with a pharmaceutical carrier or diluent. In general, the pharmaceutical compositions of the present invention may be manufactured in conventional methods known in the art, for example, by means of conventional mixing, dissolving, granulating, dragee-making, levigating, emulsifying, encapsulating, entrapping, lyophilizing processes and the like.

All methods include the step of bringing the active ingredient (or prodrug thereof) into association with the carrier which constitutes one or more accessory ingredients. In general, the pharmaceutical compositions are prepared by uniformly and intimately bringing the active ingredient (or prodrug thereof) into association with a liquid carrier or a finely divided solid carrier or both, and then, if necessary, shaping the product into the desired formulation. In the pharmaceutical composition the active compound (or prodrug thereof) is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the prodrug of the invention, and the inert ingredient(s) that make up the carrier, as well as any product which results, directly or indirectly, from combination, complexation or aggregation of any two or more ingredients, or from dissociation of one or more ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

Preferably, the pharmaceutical compositions containing the active ingredient (or prodrug thereof) may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. No. 4,256,108 published Mar. 17, 1981; U.S. Pat. No. 4,160,452 published Jul. 10, 1979; and U.S. Pat. No. 4,265,874 published May 5, 1981; to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient (or prodrug thereof) is mixed with an inert solid diluent, for example, calcium carbonate, calcium phosphate or kaolin, or as soft gelatin capsules wherein the active ingredient (or prodrug thereof) is mixed with water or an oil medium, for example peanut oil, liquid paraffin, or olive oil.

Aqueous suspensions contain the active materials (or prodrugs thereof) in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient (or prodrug thereof) in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient (or prodrug thereof) in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are used. Similarly, transdermal patches may also be used for topical administration.

The pharmaceutical composition and method of the present invention may further include other therapeutically active compounds (or prodrug thereof) as noted herein which are usually applied in the treatment of the above mentioned pathological conditions.

In another embodiment, the invention is directed to a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The invention is also directed to a therapeutically effective intravenous formulation of the compounds of the invention, which is solution stable and isotonic with human blood. The intravenous formulation preferably can be packaged in plastic or glass, and meets government and compendial (USP in the US) particulate standards, and can be used as effective therapeutic agents.

The intravenous formulation may contain a buffer which can maintain the pH of the intravenous formulation within a desirable range. The buffering agent may maintain the intravenous formulation in an acceptable particulate profile for storage and subsequent use.

Pharmaceutical injectable formulations (such as subcutaneous formulations) will generally include a therapeutically effective amount of a compound of the invention, in addition to one or more pharmaceutically acceptable excipients. The compositions are advantageously prepared together with liquid inert carriers, such as water. Suitable liquid excipients/carriers are Water for Injection (US Pharmocoepia) and saline solution. The solution should be pyrogen-free, and also should be absent of particulate matter. Limits for the amount of particulate matter (i.e., extraneous, mobile undissolved substances, other than gas bubbles) which may be found in IV fluids are defined in the US Pharmacoepia.

Other suitable excipients and other additives include solvents such as ethanol, glycerol, propylene glycol, and mixtures thereof; stabilizers such as EDTA (ethylene diamine tetraacetic acid), citric acid, and mixtures thereof; antimicrobial preservatives, such as benzyl alcohol, methyl paraben, propyl paraben, and mixtures thereof; buffering agents, such as citric acid/sodium citrate, potassium hydrogen tartrate, sodium hydrogen tartrate, acetic acid/sodium acetate, maleic acid/sodium maleate, sodium hydrogen phthalate, phosphoric acid/potassium dihydrogen phosphate, phosphoric acid/disodium hydrogen phosphate, and mixtures thereof; tonicity modifiers, such as sodium chloride, mannitol, dextrose, and mixtures thereof; fluid and nutrient replenishes such as synthetic amino acids, dextrose, sodium chloride, sodium lactate, Ringer's solution, and other electrolyte solutions.

The buffer system is generally a mixture of a weak acid and a soluble salt thereof, e.g., sodium citrate/citric acid; or the monocation or dication salt of a dibasic acid, e.g., potassium hydrogen tartrate; sodium hydrogen tartrate, phosphoric acid/potassium dihydrogen phosphate, and phosphoric acid/disodium hydrogen phosphate. The amount of buffer system used is dependent on the desired pH and the amount of the compound of the invention. The choice of appropriate buffer and pH of a formulation, depending on solubility of the drug to be administered, is readily made by a person having ordinary skill in the art.

In an embodiment, the injectable formulation may be suitable for use with a needle-free injection device. Solid compositions are normally formulated in dosage units providing from about 1 to about 1000 mg of the active ingredient per dose. Some examples of solid dosage units are 0.1 mg, 1 mg, 10 mg, 37.5 mg, 75 mg, 100 mg, 150 mg, 300 mg, 500 mg, 600 mg and 1000 mg. Typical dose ranges in accordance with the present invention include from about 10-600 mg, 25-300 mg, 25-150 mg, 50-100 mg, 60-90 mg, and 70-80 mg. Liquid compositions are generally in a unit dosage range of 1-100 mg/mL. Some examples of liquid dosage units are 0.1 mg/mL, 1 mg/mL, 10 mg/mL, 25 mg/mL, 50 mg/mL, and 100 mg/mL.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In some embodiments, a method may comprise administering to a subject one or more additional agent(s) simultaneously or sequentially with the compounds of the invention. In some embodiments, an additional agent may be an anti-headache medication such as an example anti-headache medication (e.g., 5-HT$_{1B/1D}$ agonist, for example sumatriptan, naratriptan, zolmitriptan, eletriptan, almotriptan, frovatriptan, donitriptan, a 5-HT$_{1D}$ agonist such as PNU-142633 and a 5HT$_{1F}$ agonist such as LY334370, a cyclooxygenase inhibitor, such as a selective cycloosygenase-2 inhibitor, for example, rofecoxib, etoricoxib, celecoxib, valdecoxib or parecoxib, ergot alkaloids, opiates, adrenergic antagonists, a non-steroidal anti-inflammatory agent (NSAID), a cytokine-suppressing anti-inflammatory agent, for example, with a compound such as ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; glucocorticoids, or antibodies) known in the art. Similarly, the instant compounds may be administered with an analgesic such as aspirin, acetaminophen, phenacetin, fentanyl, sufentanil, methadone, acetyl methadol, buprenorphine or morphine.

Additionally, the present compounds may be used in conjunction with an interleukin inhibitor, such as an interleukin-1 inhibitor; an NK-I receptor antagonist, for example aprepitant; an NMDA antagonist; an NR2B antagonist; a bradykinin-1 receptor antagonist; an adenosine AI receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrine precursor; anti-anxiety agents such as diazepam, alprazolam, chlordiazepoxide and chlorazepate; serotonin 5HT$_2$ receptor antagonists; opioid agonists such as codeine, hydrocodone, tramadol, dextropropoxyphene and fentanyl; an mGluR$_5$ agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipraraine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors, neuronal calcium channel blockers such as civamide, AMPA/KA antagonists such as LY293558, sigma receptor agonists, and vitamin B2. Also, the present compounds may be used in conjunction with ergot alkaloids other than ergotamine and dihydroergotamine, for example ergonovine, methylergonovine, metergoline, ergoloid mesylates, dihydroergocoraine, dihydroergocristine, dihydroergocryptine, dihydro-α-ergocryptine, dihydro-β-ergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor such as phenelzine; a calcium channel blocker such as flunarizine, diltiazem, amlodipine, felodipine, nisolipine, isradipine, nimodipine, lomerizine, verapamil, nifedipine, or prochlorperazine; a neuroleptic such as olanzapine, droperidol, prochlorperazine, chlorpromazine and quetiapine; an anticonvulsant such as topiramate, zonisamide, tonabersat, carabersat, levetiracetam, lamotrigine, tiagabine, gabapentin, pregabalin or divalproex sodium, an anti-hypertensive such as an angiotensin II antagonist such as losartan, irbesartin, valsartan, eprosartan, telmisartan, olmesartan, medoxomil, candesartan, or candesartan cilexetil; an angiotensin I antagonist, an angiotensin converting enzyme inhibitor such as Hsinopril, enalapril, captopril, benazepril, quinapril, perindopril, ramipril, or trandolapril; or botulinum toxin type A or B. The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics. In a particularly preferred embodiment the present compounds are used in conjunction with an anti-migraine agent such as ergotamine or dihydroergotamine; a 5-HT$_1$ agonist, especially a 5-HT$_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib, or paracoxib.

The above combinations include combinations of a compound of the present invention not only with one other active compound (or prodrug thereof), but also with two or more other active compounds (or prodrugs thereof). Likewise, compounds of the present invention may be used in combination with other drugs (or prodrugs thereof) that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients (or prodrug thereof), in addition to a compound of the present invention. The weight ratio of the compound of the compound of the present invention to the other active ingredient(s) (or prodrugs thereof) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients (or prodrugs thereof) will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s), via the same or different routes of administration.

In some embodiments, a therapeutic effect may be greater as compared to use of a compound of the invention or one or more additional agent(s) alone. Accordingly, a synergistic effect between a compound of the invention and the one or more additional agents may be achieved. In some embodiments, the one or more additional agent(s) may be taken by a subject prophylactically.

In addition to migraine, other CGRP-related disorders that may be treated by the pharmaceutical compositions and methods of the present invention include, for example, cluster headache, chronic tension type headache, chronic pain, neurogenic inflammation and inflammatory pain, eye pain, tooth pain, non-insulin dependent diabetes mellitus, vascular disorders, inflammation, arthritis, bronchial hyperreactivity, asthma, shock, sepsis, opiate withdrawal syndrome, morphine tolerance, hot flashes in men and women, allergic dermatitis, psoriasis, encephalitis, brain trauma, ischaemia, stroke, epilepsy, and neurodegenerative diseases, skin diseases, neurogenic cutaneous redness, skin rosaceousness and erythema, tinnitus, obesity, inflammatory bowel disease, irritable bowel syndrome, and cystitis.

In an aspect, the invention also provides kits for use in the instant methods. Kits can include one or more containers comprising a pharmaceutical composition described herein and instructions for use in accordance with any of the methods described herein. Generally, these instructions comprise a description of administration of the pharmaceutical composition to treat, ameliorate or prevent headache (such as migraine), or other CRGP disorder, according to any of the methods described herein. The kit may, for example, comprise a description of selecting an individual suitable for treatment based on identifying whether that individual has headache or whether the individual is at risk of having headache. The instructions are typically provided in the form of a package insert, or label, in accordance with the requirements of the regulatory having authority over the jurisdiction where the pharmaceutical composition is to be provided to patients.

EXAMPLES

The following examples illustrate the invention and are not intended to limit the scope of the invention. In some examples, abbreviations are used which are known to those skilled in the art or are readily accessible from the documents cited in the examples.

General Experimental

1. Analytical Methods

Method A: LC/MS data were determined with a Waters Alliance 2695 HPLC/MS (Waters Symmetry C18, 4.6× 75 mm, 3.5 µm) with a 2996 diode array detector from 210-400 nm. The solvent system was 5-95% acetonitrile in water (with 0.1% TFA) over nine minutes using a linear gradient, and retention times are in minutes. Mass spectrometry was performed on a Waters ZQ using electrospray in positive mode.

Method B: Preparative reversed phase HPLC was performed on a Phenomenex LUNA column (19×100 mm, C18, 5 µm) with a 10 min mobile phase gradient of 10% acetonitrile/water to 90% acetonitrile/water with 0.1% TFA as buffer using 214 and 254 nm as detection wavelengths. Injection and fraction collection were performed with a Gilson 215 liquid handling apparatus using Trilution LC software.

Method C: Preparative reversed phase HPLC was performed on a Waters Sunfire column (19×50 mm, C18, 5 µm) with a 10 min mobile phase gradient of 10% acetonitrile/water to 90% acetonitrile/water with 0.1% TFA as buffer using 214 and 254 nm as detection wavelengths. Injection and fraction collection were performed with a Gilson 215 liquid handling apparatus using Trilution LC software.

Method D: Preparative reversed phase HPLC was performed on a Waters Sunfire column (30×150 mm, C18, 10 µm) with a 15 min mobile phase gradient of with 0.1% TFA as buffer using 214 and 254 nm as detection wavelengths. Injection and fraction collection were performed with a Gilson 215 liquid handling apparatus using Trilution LC software.

$^1$H-NMR spectra were taken on a Varian 300 MHz NMR using tetramethylsilane (TMS) as internal standard (d=0.00) with peaks reported downfield from TMS.

2. General Synthetic Schemes

SCHEME 1: Monoalkylation of BHV-3500

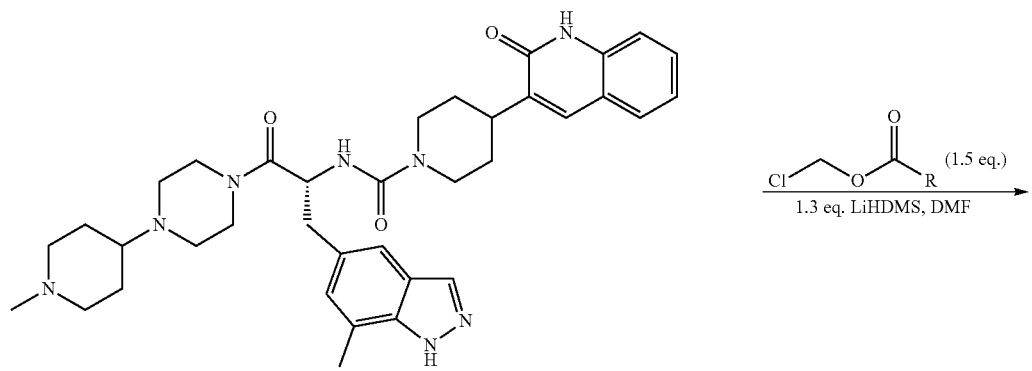

-continued
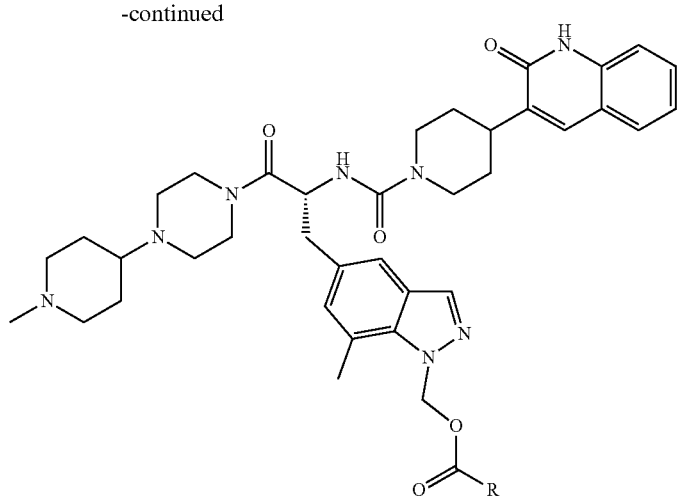
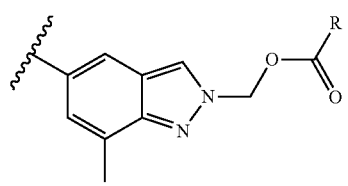
1:1
In Scheme 1, BHV-3500 is deprotonated with 1.3 equivalents of lithium bis(trimethylsilyl)amide (LiHMDS) and selectively alkylated with 1.5 equivalents of a chloromethyl ester to provide a mixture of monoalkylated isomeric indazoles without affecting the quinolone moiety.
-continued
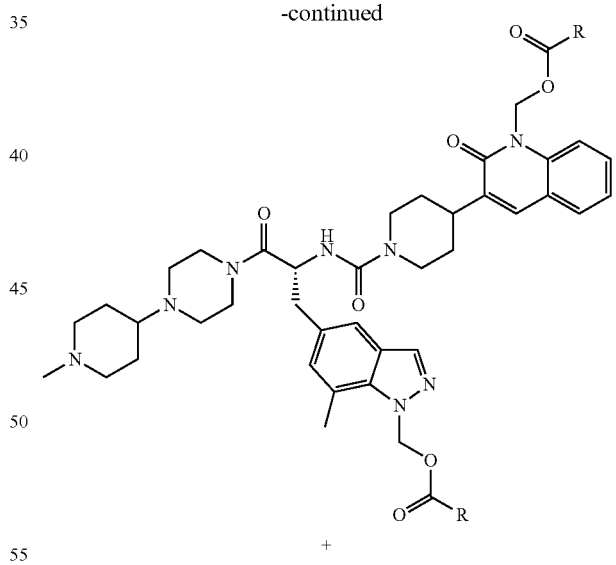
+
SCHEME 2: Bisalkylation of BHV-3500
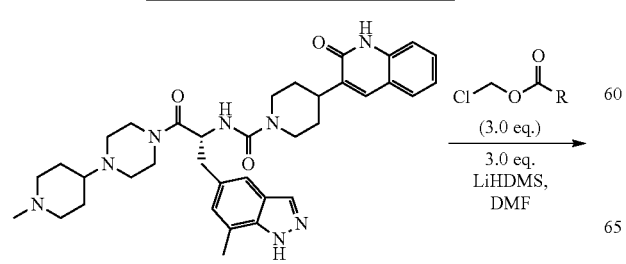
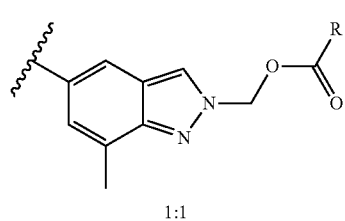
1:1

In Scheme 2, BHV-3500 is deprotonated with 3.0 equivalents of lithium bis(trimethylsilyl)amide (LiHMDS) and alkylated with 3.0 equivalents of a chloromethyl ester to provide a mixture of dialkylated isomeric indazoles with the alkylated quinolone moiety.
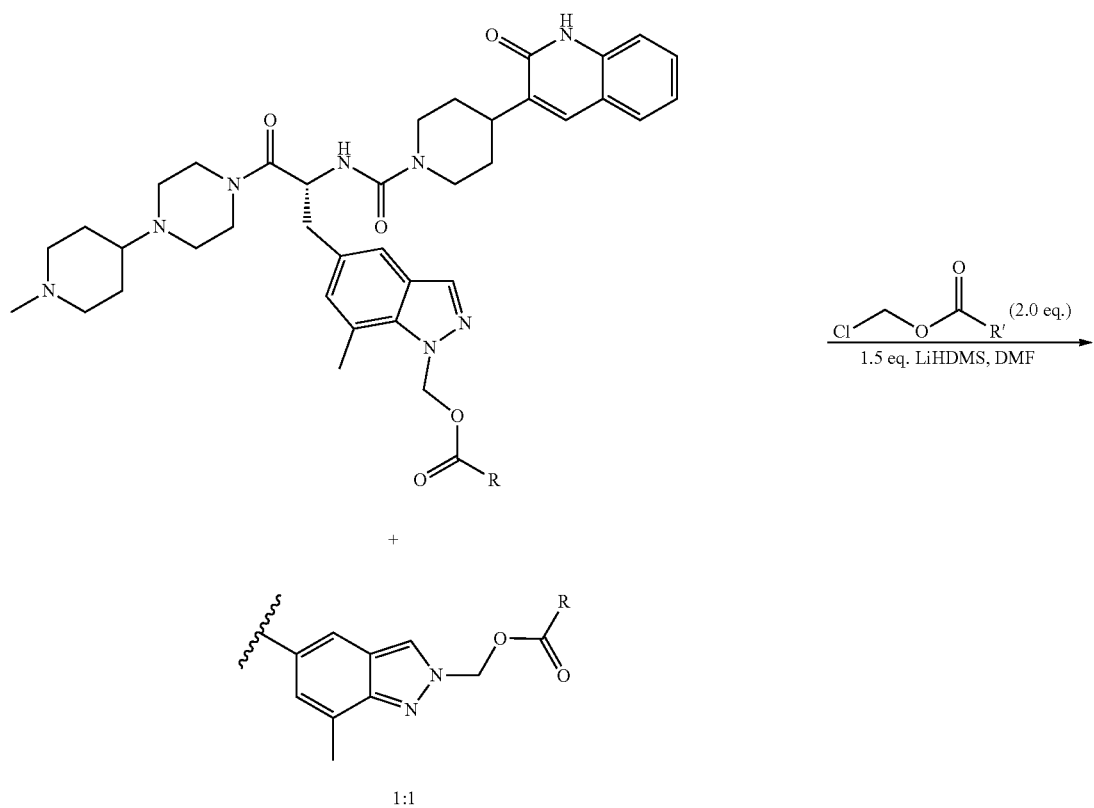
SCHEME 3: Quinolone alkylation of monoalkylated BHV-3500

-continued
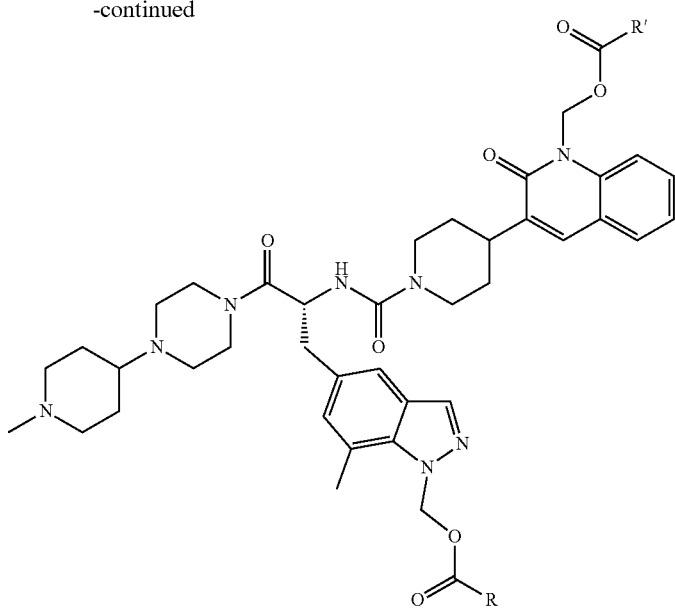
1:1
In Scheme 3, a mixture of monoalkylated BHV-3500 was deprotonated with 1.5 equivalents of lithium bis(trimethylsilyl)amide (LiHMDS) and was further alkylated with 2.0 equivalents of a chloromethyl ester on the quinolone moiety to provide a mixture of dialkylated products.
-continued
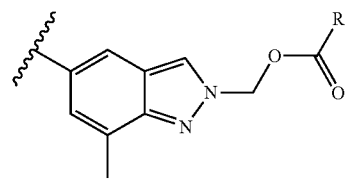
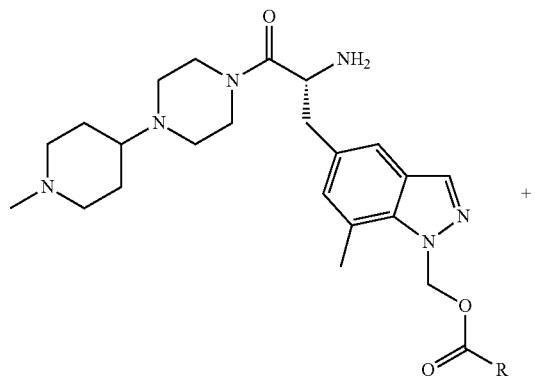
1:1
SCHEME 4: Alternative preparation of dialkylated BHV-3500
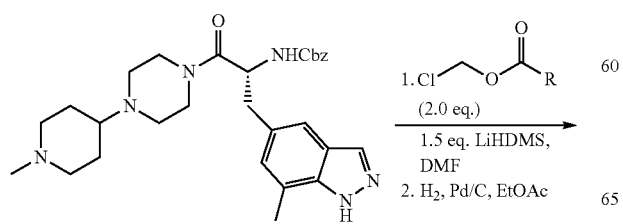
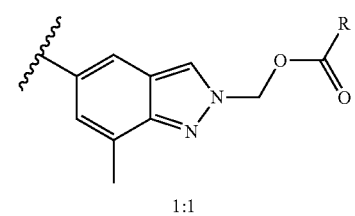

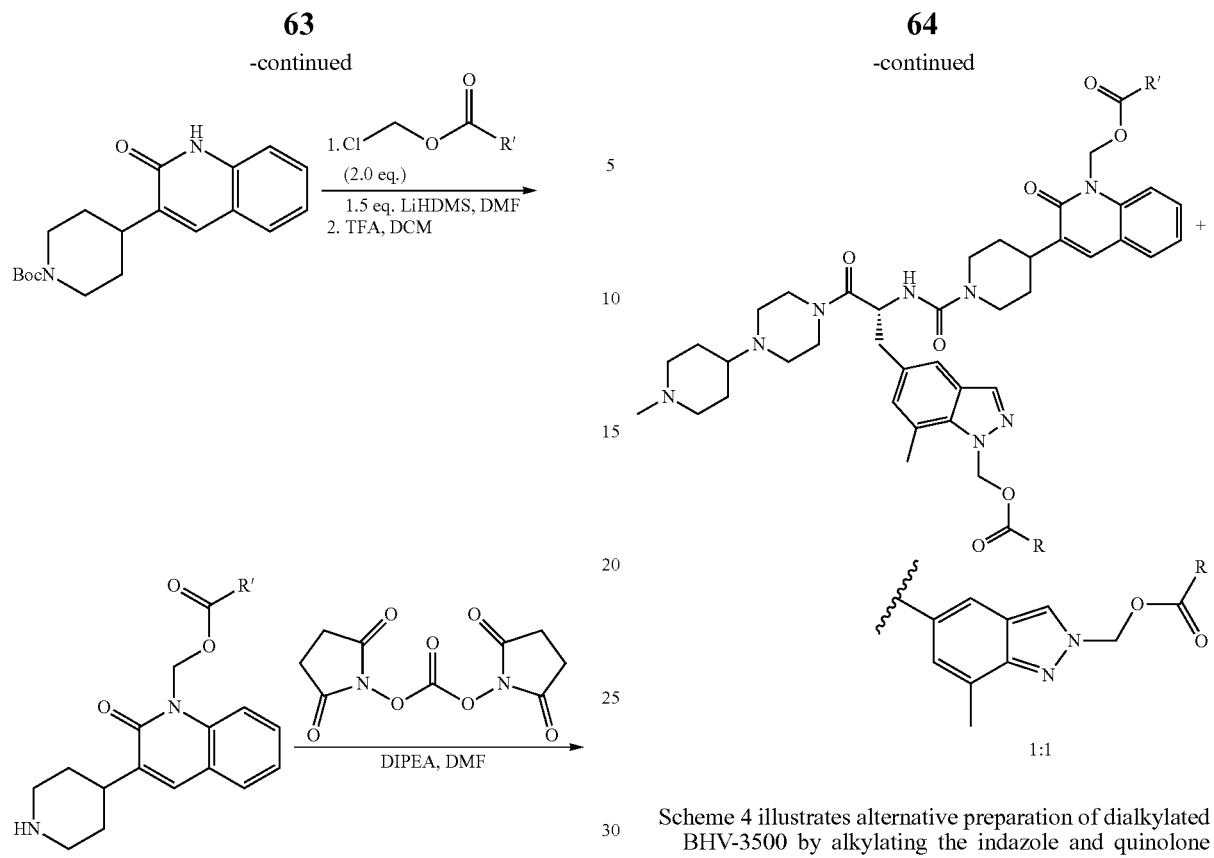
Scheme 4 illustrates alternative preparation of dialkylated BHV-3500 by alkylating the indazole and quinolone intermediates followed by coupling of the alkylated intermediates.
SCHEME 5: Preparation of quarternary ammonium salts
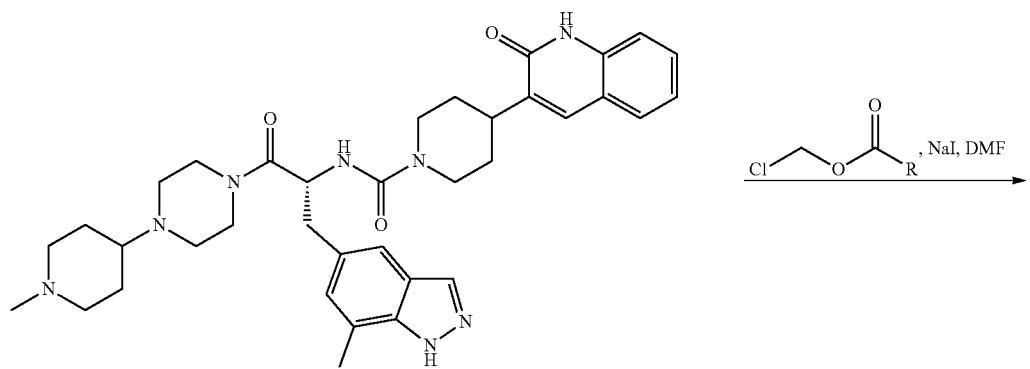

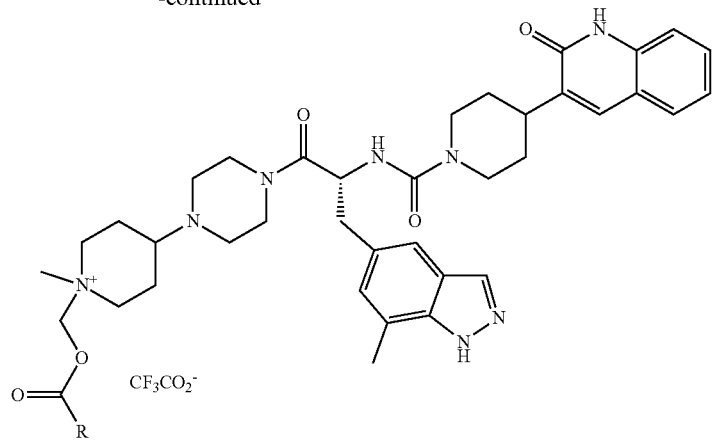

Scheme 5 illustrates selective alkylation of the piperidine moiety with a chloromethyl ester in the presence of sodium iodide in DMF. Under these mild conditions, no alkylation of indazole and quinazolinone moieties takes place.

SCHEME 6: Preparation of chloromethyl esters

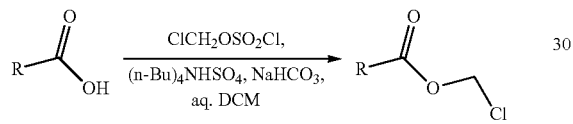

Scheme 6 illustrates preparation of chloromethyl esters from carboxylic acids by treating the carboxylic acid with chloromethyl sulfurochloridate in the presence of tetra-n-butylammonium hydrosulfate and sodium hydrocarbonate in aqueous dichloromethane (N. Harada et al., *Synthetic Commun.*, 1994, 24, 767-772).

SCHEME 7: Preparation of iodomethyl esters

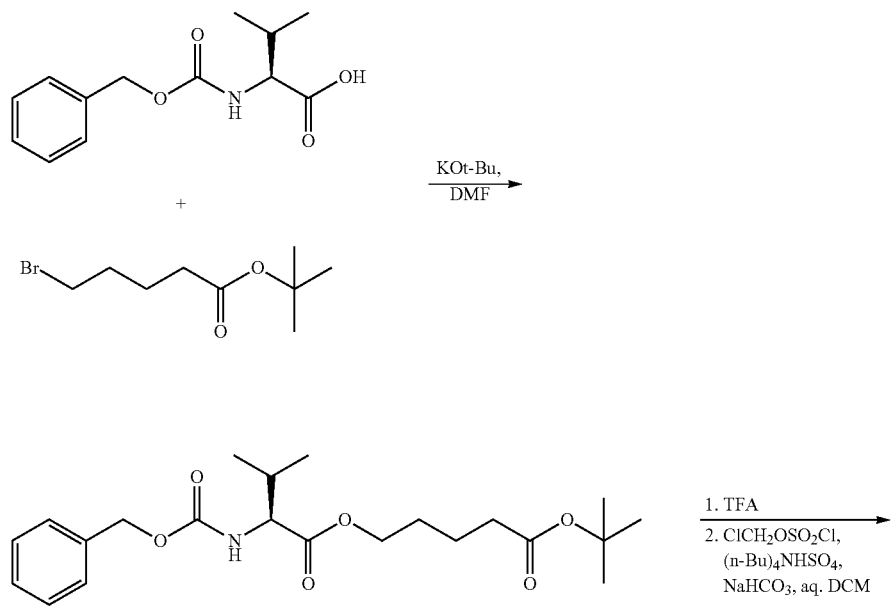

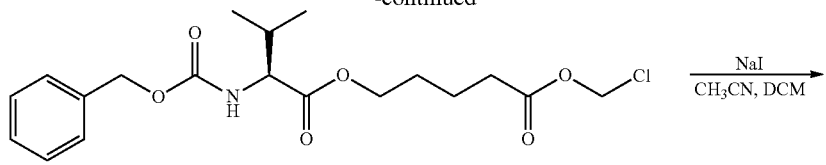

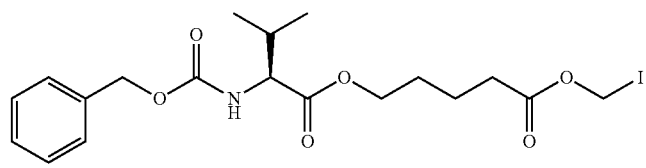

Scheme 7 illustrates preparation of iodomethylcarboxylic esters by alkylation of a carboxylic acid with potassium t-butoxide in DMF, cleavage of the t-butyl ester with chloromethyl sulfurochloridate in the presence of tetra-n-butylammonium hydrosulfate and sodium hydrocarbonate in aqueous dichloromethane (N. Harada et al., Synthetic Commun., 1994, 24, 767-772), and displacement of the chlorine with iodine by a reaction of the chloromethyl ester with sodium iodide in acetonitrile-dichloromethane solvent mixture.

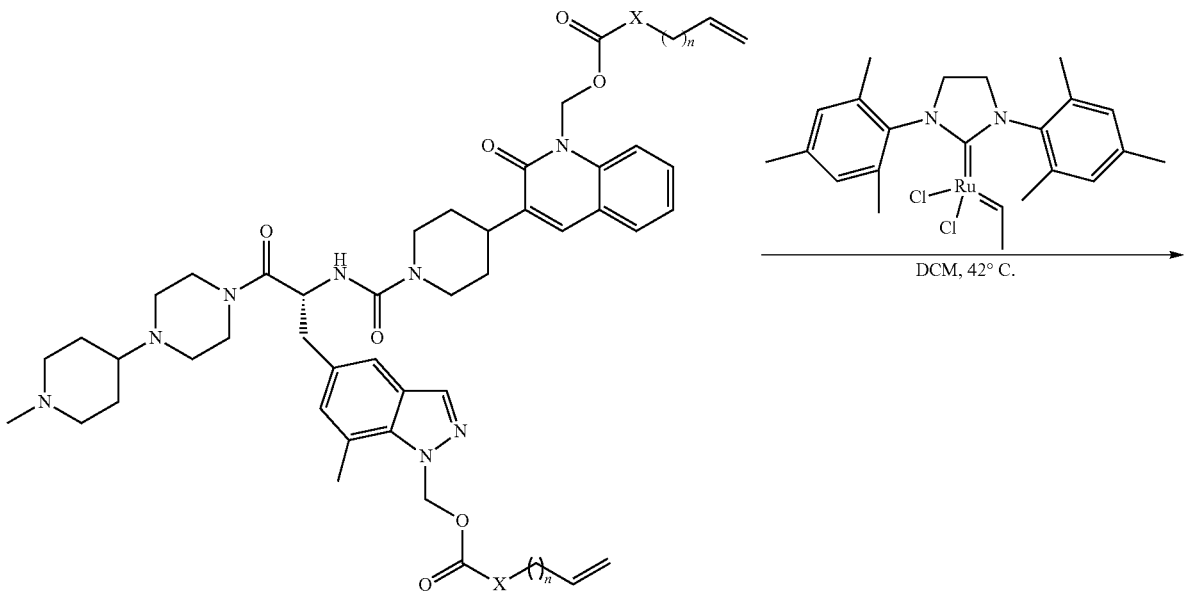

SCHEME 8: Macrocycle preparation

-continued
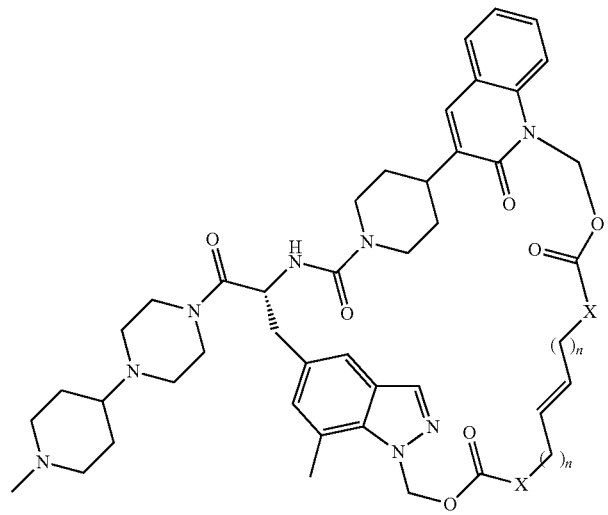
X = CH₂, N
n = 1-4
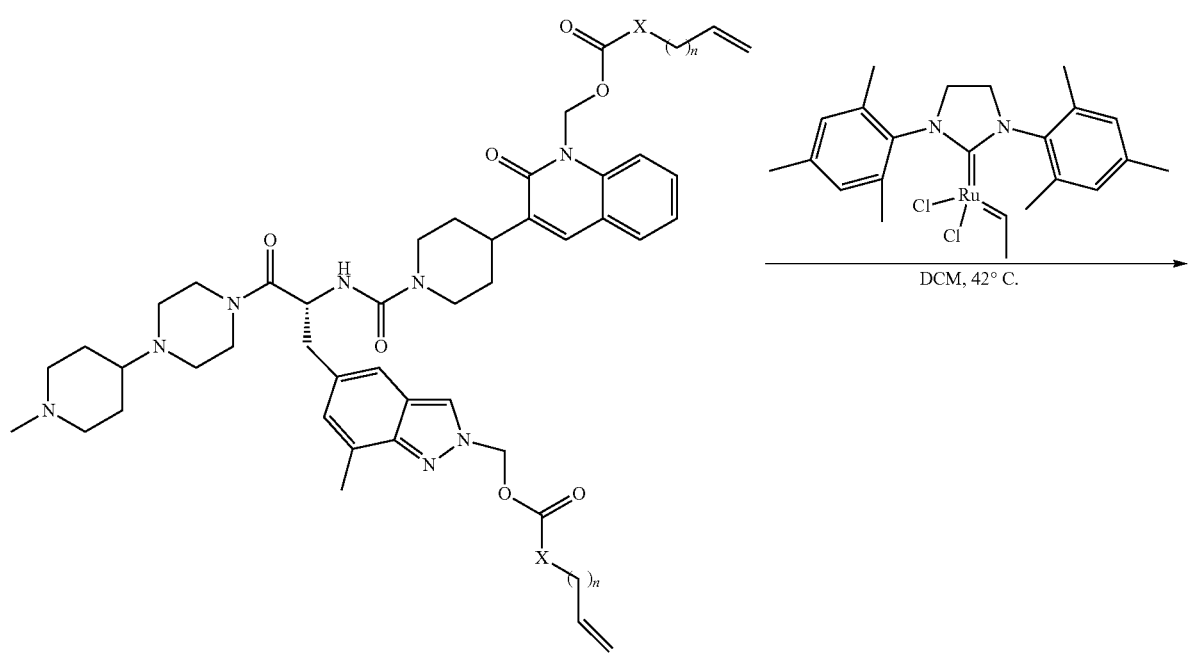

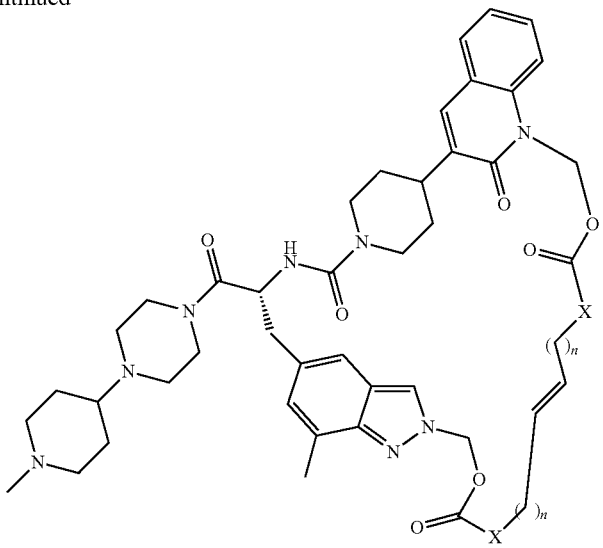

X = CH₂, N
n = 1-4

Scheme 8 illustrates preparation of macrocycles by olefin metathesis of dialkylated bis-unsaturated molecules in the presence of a Grubbs $2^{nd}$ generation catalyst.

The above schemes are provided only to illustrate embodiments of the present invention. In some cases, the final product may be further modified, for example, by manipulation of substituents. These manipulations may include, but are not limited to, reduction, oxidation, alkylation, acylation, and hydrolysis reactions which are commonly known to those of ordinary skill in the art.

In some cases, the order of carrying out the reactions in the foregoing schemes may be varied to facilitate the reaction or to avoid unwanted reaction products. Additionally, various protecting group strategies may be employed to facilitate the reaction or to avoid unwanted reaction products. The following examples are provided so that the invention might be more fully understood. These examples are illustrative only and should not be construed as limiting the invention in any way.

Compound Synthesis and Characterization

Exemplary Procedures for the Preparation of Chloromethyl Esters

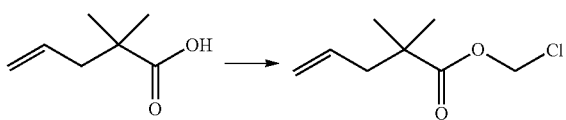

2,2-Dimethyl-pent-4-enoic acid chloromethyl ester. To a solution of 2,2-dimethyl-pent-4-enoic acid (3.9 mmol, 0.536 mL) in DCM:H₂O (36:24 mL) at room temperature was added NaHCO₃ (5.24 g, 62.4 mmol) and tetrabutylammonium hydrogen sulfate (0.39 mmol, 0.132 g). The reaction mixture was cooled to 0° C. and allowed to stir for 15 minutes. Chloromethyl chlorosulfate (5.07 mmol, 0.513 mL) was added, and the reaction mixture was allowed to warm slowly to room temperature. After 3 days, the reaction was partitioned reaction between CH₂Cl₂ and H₂O. The organic and aqueous layers were separated, and the aqueous layer was washed with 2×20 mL of CH₂Cl₂. The combined organic layers were washed with brine, dried over MgSO₄, filtered, and concentrated in vacuo. The residue was purified on an 80 g siliasep column, eluting with 0-40% EtOAc/hexanes. The fractions containing the desired product were concentrated in vacuo to yield 0.77 g of product (28%). ¹H NMR (CDCl₃) δ: 5.71 (s, 2H), 5.08-5.12 (m, 1H), 5.02-5.08 (m, 1H), 2.32 (t, J=1.2 Hz, 1H), 2.28-2.30 (m, 1H), 1.20 (s, 6H).

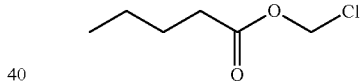

Pentanoic acid chloromethyl ester. To a solution of pentanoic acid (1 g, 9.8 mmol) in dichloromethane (10 mL) and water (10 mL) was added sodium bicarbonate (3.13 g, 37.3 mmol) and Bu₄HSO₄ (333 mg, 0.98 mmol) followed by dropwise addition of chloromethyl chlorosulfonate (1.85 g, 11.2 mmol). The mixture was stirred for 20 h, diluted with water (50 mL), and extracted with dichloromethane (50 mL). The organic layer was separated and washed with water (25 mL), dried (MgSO₄), and evaporated. The product mixture was purified by silica chromatography eluted with hexanes to obtain the product as a colorless oil (944 mg, 64%). ¹H NMR (CDCl₃) δ: 5.70 (s, 2H), 2.39 (t, J=7.3 Hz, 2H), 1.53-1.69 (m, 2H), 1.25-1.38 (m, 2H), 0.92 (t, J=7.3 Hz, 3H).

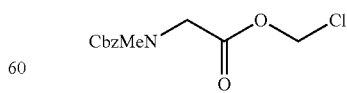

(Benzyloxycarbonyl-methyl-amino)-acetic acid chloromethyl ester. Prepared in similar fashion to the esters above. ¹H NMR (CDCl₃) δ: 7.29-7.38 (m, 5H), 5.74 (s, 1H), 5.67 (s, 1H), 5.15 (d, J=10.5 Hz, 2H), 4.10 (d, J=18.8 Hz, 2H), 3.03 (s, 3H).

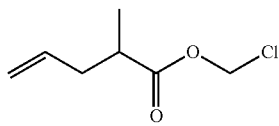

2-Methyl-pent-4-enoic acid chloromethyl ester. To a solution of 2-methyl-pent-4-enoic acid (43.8 mmol, 5.27 mL) in DCM:H$_2$O (36:24 mL) at room temperature was added NaHCO$_3$ (14.7 g, 175 mmol), followed by tetrabutylammonium hydrogen sulfate (1.48, g 4.38 mmol). The mixture was cooled to 0° C. and allowed to stir for 15 minutes. Chloromethyl chlorosulfate (5.76 mL, 56.9 mmol) was added and the reaction mixture was allowed to stir for 18 hours. The reaction mixture was diluted with H$_2$O and CH$_2$Cl$_2$. The organic and aqueous layers were separated, and the aqueous layer was washed with 2×20 mL of CH$_2$Cl$_2$. The combined organic layers were washed with brine and dried over Na$_2$SO$_4$, filtered, and concentrated in vacuo. The residue was purified on the ISCO using an 80 g siliasep column, eluting with 0-30% EtOAc/hexanes. The fractions containing the desired product were concentrated in vacuo to yield 3.09 g (19.0 mmol, 43%) of 2-methyl-pent-4-enoic acid chloromethyl ester. $^1$H NMR (CHLOROFORM-d) δ: 5.70 (br d, J=3.2 Hz, 2H), 4.99-5.14 (m, 2H), 2.53-2.67 (m, 1H), 2.34-2.51 (m, 1H), 2.17-2.18 (m, 1H), 2.10-2.32 (m, 1H), 1.18 (dd, J=6.8, 3.1 Hz, 3H).

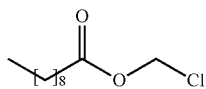

Chloromethyl decanoate. A 250 mL rounded bottom flask was charged with 1250 mg (7.27 mmol) of decanoic acid, 20 mL water, 20 mL DCM and 446 mg (1.45 mmol) of tetrabutylammonium hydrogensulfate. After stirring for five minutes, 3660 mg (43.6 mmol) of sodium hydrogen carbonate was added over several minutes. After ten minutes of stirring, the reaction was cooled in an ice water bath, 2400 mg (14.5 mmol, 1.47 mL) of chloromethyl chlorosulfate was added dropwise over ten minutes, and the reaction was allowed to stir for 18 h at room temperature. The reaction was diluted with 20 mL of DCM and 20 mL water. The aqueous phase was extracted with 20 mL DCM. The combined organic extracts were dried and concentrated under vacuum. The concentrate was chromatographed on a 20 gram silica column with an ethyl acetate/hexane gradient from 0 to 30%. Similar fractions were combined and concentrated under vacuum to yield 820 mg of an oil with NMR consistent with assigned structure. $^1$H NMR (CDCl$_3$) δ 5.70 (s, 2H), 2.13-2.58 (m, 2H), 1.65 (br t, J=7.2 Hz, 2H), 1.13-1.39 (m, 12H), 0.74-1.00 (m, 3H).

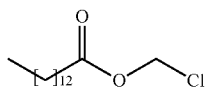

Chloromethylmyristate. Prepared in similar fashion to the chloromethyl decanoate above from myristic acid (1280 mg) to yield 1040 mg of product. $^1$H NMR (CDCl$_3$) δ 5.70 (s, 2H), 2.38 (t, J=7.5 Hz, 2H), 1.43-1.78 (m, 5H), 1.16-1.33 (m, 18H), 0.73-0.98 (m, 3H).

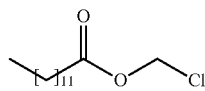

Chloromethyldodecanoate. Prepared in similar fashion to the chloromethyl decanoate above from dodecanoic acid (1440 mg) to yield 1200 mg of product. $^1$H NMR (CDCl$_3$) δ 5.70 (s, 2H), 2.38 (t, J=7.5 Hz, 2H), 1.45-1.74 (m, 2H), 1.25 (d, J=1.5 Hz, 12H), 0.81-0.93 (m, 3H).

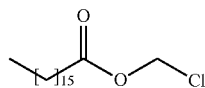

Heptadecanoic acid chloromethyl ester. To a solution of heptadecanoic acid (3.69 mmol, 1.00 g) in DCM:H$_2$O (18:12 mL) at room temperature was added NaHCO$_3$ (1.24 g, 14.7 mmol), followed by tetrabutylammonium hydrogen sulfate (0.370 mmol, 0.125 g). The mixture was cooled to 0° C. and allowed to stir for 15 minutes, followed by the addition of chloromethyl chlorosulfate (4.81 mmol, 0.486 mL). Slow gas evolution was observed. After 18 hours, the reaction mixture was diluted with H$_2$O and CH$_2$Cl$_2$. The organic and aqueous layers were separated, and the aqueous layer was washed with CH$_2$Cl$_2$ (2×20 mL). The combined organic layers were washed with brine, dried over Na$_2$SO$_4$, filtered, and concentrated in vacuo. The residue was purified on a 40 g silicel silica gel column, eluting with 0-25% ethyl acetate in hexanes. The fractions containing the desired product were concentrated in vacuo to yield heptadecanoic acid chloromethyl ester 0.734 g (63%). $^1$H NMR (CHLOROFORM-d) δ: 5.68 (s, 2H), 2.36 (m, 2H), 1.55-1.70 (m, 2H), 1.24 (s, 26H), 0.79-0.93 (m, 3H).

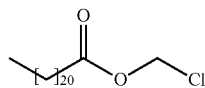

Docosanoic acid chloromethyl ester. To a solution of behinic acid (2.93 mmol, 1.00 g) in DCM:H$_2$O (18:12 mL) at room temperature was added NaHCO$_3$ (0.99 g, 11.8 mmol), followed by tetrabutylammonium hydrogen sulfate (0.293 mmol, 0.098 g). The mixture was cooled to 0° C. and allowed to stir for 15 minutes, followed by the addition of chloromethyl chlorosulfate (3.82 mmol, 0.386 mL). Slow gas evolution was observed. After 18 hours, the reaction mixture was diluted with H$_2$O and CH$_2$Cl$_2$. The organic and aqueous layers were separated, and the aqueous layer was washed with CH$_2$Cl$_2$ (2×20 mL). The combined organic layers were washed with brine, dried over Na$_2$SO$_4$, filtered, and concentrated in vacuo. The residue was purified on a 40 g silicel column eluting with 0-25% EtOAc in hexanes. The fractions containing the desired product were concentrated in vacuo to yield docosanoic acid chloromethyl ester 1.054 g (92%). $^1$H NMR (CHLOROFORM-d) δ: 5.72 (br d, J=10.4 Hz, 2H), 2.37 (br t, J=7.7 Hz, 2H), 1.53-1.81 (m, 2H), 1.25 (s, 36H), 0.87 (br t, J=6.3 Hz, 3H).

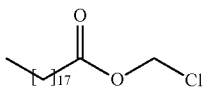

Nonadecanoic acid chloromethyl ester. Prepared using the same procedure as above for docosanoic acid chloromethyl ester. Nonadecanoic acid chloromethyl ester 0.902 g (77%). $^1$H NMR (CHLOROFORM-d) δ: 5.69 (s, 2H), 2.37 (t, J=7.5 Hz, 2H), 1.64 (br t, J=7.2 Hz, 2H), 1.17-1.38 (m, 30H), 0.82-0.94 (m, 3H).

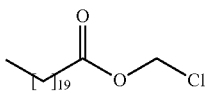

Henicosanoic acid chloromethyl ester. Prepared using the same procedure as above to yield henicosanoic acid chloromethyl ester, 0.958 g (84%). $^1$H NMR (CHLOROFORM-d) δ: 5.70 (s, 2H), 2.38 (t, J=7.5 Hz, 2H), 1.57-1.73 (m, 2H), 1.25 (s, 34H), 0.82-0.93 (m, 3H).

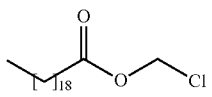

Icosanoic acid chloromethyl ester. Prepared using a similar procedure as above to yield icosanoic acid chloromethyl ester, 0.771 g (67%). $^1$H NMR (CHLOROFORM-d) δ: 5.70 (s, 2H), 2.38 (t, J=7.5 Hz, 2H), 1.57-1.73 (m, 2H), 1.25 (s, 32H), 0.82-0.93 (m, 3H).

Octadecanoic acid chloromethyl ester. Prepared in a similar manner to products above to yield octadecanoic acid chloromethyl ester, 0.734 g (63%). $^1$H NMR (CHLOROFORM-d) δ: 5.60-5.78 (m, 2H), 2.38 (t, J=7.5 Hz, 2H), 1.57-1.72 (m, 2H), 1.25 (s, 28H), 0.83-0.92 (m, 3H).

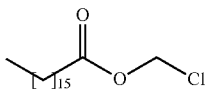

Heptadecanoic acid chloromethyl ester. Prepared in a manner similar to products above to yield heptadecanoic acid chloromethyl ester, 0.734 g (63%). $^1$H NMR (CHLOROFORM-d) δ: 5.68 (s, 2H), 2.36 (m, 2H), 1.55-1.70 (m, 2H), 1.24 (s, 19H), 0.79-0.93 (m, 3H).

Octadec-9-enoic acid chloromethyl ester. Prepared in a manner similar to products above to yield octadec-9-enoic acid chloromethyl ester, 0.37 g (64%). $^1$H NMR (CHLOROFORM-d) δ: 5.70 (s, 2H), 5.26-5.44 (m, 2H), 2.38 (t, J=7.5 Hz, 2H), 1.91-2.09 (m, 4H), 1.65 (br t, J=7.1 Hz, 2H), 1.20-1.41 (m, 20H), 0.77-0.97 (m, 3H). No LC/MS data was obtained.

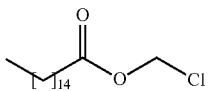

Hexadecanoic acid chloromethyl ester. Prepared in a manner similar to products above to yield hexadecanoic acid chloromethyl ester, 1.15 g (97%). $^1$H NMR (CHLOROFORM-d) δ: 5.68 (s, 2H), 2.36 (t, J=7.5 Hz, 2H), 1.53-1.76 (m, 2H), 1.24 (s, 24H), 0.77-0.92 (m, 3H).

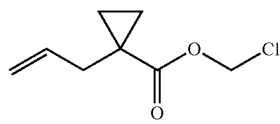

1-Allyl-cyclopropanecarboxylic acid chloromethyl ester. Prepared in a manner similar to products above to yield 0.49 g (26%) of product. $^1$H NMR (CHLOROFORM-d) δ: 5.75-5.96 (m, 1H), 5.66-5.74 (m, 2H), 4.97-5.12 (m, 2H), 2.27-2.42 (m, 2H), 1.21-1.36 (m, 2H), 0.76-0.94 (m, 2H).

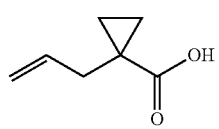

1-Allyl-cyclopropanecarboxylic acid. To a 0° C. solution of 1-allyl-cyclopropanecarboxylic acid tert-butyl ester (2.48 g, 13.6 mmol) in 10 mL CH$_2$Cl$_2$ was added 3.12 mL (40.84 mmol) of TFA. After 18 hours, 1.0 mL TFA was added. After 2 hours, additional 0.5 mL of TFA was added. After 1 hour, the reaction mixture was concentrated in vacuo to yield 1-allyl-cyclopropanecarboxylic acid, 1.51 g (88%). $^1$H NMR (CHLOROFORM-d) δ: 11.53-12.20 (m, 1H), 5.48-6.06 (m, 1H), 4.90-5.22 (m, 2H), 2.07-2.40 (m, 2H), 1.18-1.34 (m, 2H), 0.63-0.93 (m, 2H).

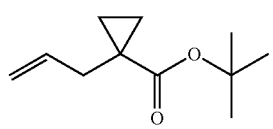

1-Allyl-cyclopropanecarboxylic acid tert-butyl ester. To a solution of 1M LDA (42.1 mmol, 42.1 mL) at −78° C. was added dropwise t-butylcyclopropane carboxylate (5.0 g, 35.1 mmol) in 70 mL THF. After 1.5 hours, a solution of allyl bromide (3.03 mL, 35.1 mmol) in 10 mL THF was added. The reaction mixture was allowed to warm slowly to room temperature. After 18 hours, the reaction was quenched with saturated NH$_4$Cl (aq), and partitioned between EtOAc and H$_2$O. The organic and aqueous layers were separated, and the aqueous layer was washed with 2×20 mL ethyl acetate. The combined organic layers were washed with brine, dried over Na$_2$SO$_4$, filtered, and concentrated in vacuo. The residue was purified on an 80 g silacel column, eluting with 0-15% EtOAc/hexanes. The product fractions were concentrated in vacuo to yield 1-allyl-cyclopropanecarboxylic acid tert-butyl ester, 2.48 g (38% yield). $^1$H NMR (CHLOROFORM-d) δ: 5.73-6.01 (m, 1H), 4.91-5.13 (m, 2H), 2.27 (dt, J=6.6, 1.3 Hz, 2H), 1.42 (s, 9H), 0.99-1.20 (m, 2H), 0.49-0.73 (m, 2H).

Chloromethyl hexanoate. Prepared in similar fashion to the chloromethyl decanoate above from hexanoic acid (1240 mg) to yield 560 mg of product. $^1$H NMR (CDCl$_3$) δ 5.71 (s, 2H), 2.21-2.55 (m, 2H), 1.57-1.80 (m, 2H), 1.25-1.39 (m, 2H), 0.90 (s, 3H).

Chloromethyl octanoate. Prepared in similar fashion to the chloromethyl decanoate above from octanoic acid (12 g) to yield 12.7 g of product. $^1$H NMR (CDCl$_3$) δ 5.70 (s, 2H), 2.38 (t, J=7.4 Hz, 2H), 1.59-1.76 (m, 2H), 1.19-1.41 (m, 10H), 0.79-0.98 (m, 3H).

Chloromethyl heptanoate. Prepared in similar fashion to the chloromethyl decanoate above from heptanoic acid (13 g) to yield 10.6 g of product. $^1$H NMR (CDCl$_3$) δ 5.72 (d, J=11.5 Hz, 2H), 2.38 (t, J=7.5 Hz, 31H), 1.58 (s, 31H), 1.20-1.38 (m, 98H), 0.88 (s, 3H).

Chloromethyl-(2-methyl)hexanoate. Prepared in similar fashion to the chloromethyl decanoate above from 2-methylhexanoic acid (13 g) to yield 10.6 g of product. $^1$H NMR (CDCl$_3$) δ: 5.65-5.77 (m, 2H), 2.38-2.64 (m, 2H), 1.61-1.81 (m, 2H), 1.58 (s, 1H), 1.37-1.51 (m, 1H), 1.11-1.35 (m, 6H), 0.89 (s, 3H).

Chloromethyl cyclohexanoic acid. Prepared in similar fashion to the chloromethyl decanoate above from cyclohexanoic acid (1.0 g) to yield 460 mg of product. $^1$H NMR (CDCl$_3$) δ: 5.70 (s, 2H), 2.37 (tt, J=11.0, 3.6 Hz, 1H), 1.83-1.98 (m, 2H), 1.59-1.82 (m, 3H), 1.37-1.53 (m, 2H), 1.13-1.35 (m, 3H).

Chloromethyl-2,2-dimethylhexanoate. Prepared in similar fashion to the chloromethyl decanoate above from 2,2-dimethylhexanoic acid (1.0 g) to yield 760 mg of product. $^1$H NMR (CDCl$_3$) δ: 5.71 (s, 2H), 1.46-1.63 (m, 4H), 1.19 (s, 6H), 0.83-0.94 (m, 3H).

Chloromethyl nonanoate. Prepared in similar fashion to the chloromethyl decanoate above from nonanoic acid (1.5 g) to yield 1.45 g of product. $^1$H NMR (CDCl$_3$) δ: 5.70 (s, 2H), 2.38 (t, J=7.5 Hz, 2H), 1.65 (br t, J=7.3 Hz, 2H), 1.57 (s, 2H), 1.14-1.37 (m, 8H), 0.78-0.93 (m, 3H).

Chloromethyl-2,2-dimethylpentanoate. Prepared in similar fashion to the chloromethyl decanoate above from 2,2-dimethylpentanoic acid (1.45 g) to yield 0.28 g of product. $^1$H NMR (CDCl$_3$) δ: 5.71 (s, 2H), 1.46-1.63 (m, 2H), 1.22 (s, 6H), 0.80-0.96 (m, 3H).

Chloromethyl-(2,2-dimethyl)butanoate. Prepared in similar fashion to the chloromethyl decanoate above from 2,2-dimethylbutanoic acid (1.8 g) to yield 0.96 g of product. $^1$H NMR (CDCl$_3$) δ: 5.71 (s, 2H), 1.42-1.67 (m, 2H), 1.19 (s, 6H), 0.83-0.94 (m, 3H).

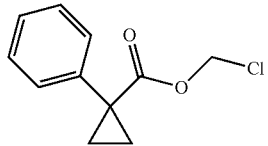 [SMILES: O=C(OCCl)C1(c2ccccc2)CC1]

Chloromethyl 1-phenylcyclopropane-1-carboxylate. A 250 mL round bottom flask was charged with 1-phenylcyclopropane carboxylic acid (1.1 g, 6.75 mmol), water (14.2 mL), dichloromethane (14.2 mL), tetrabutylammonium hydrogen sulfate (229.2 mg, 675 μmop, and sodium hydrogen carbonate (2.27 g, 27 mmol). Chloromethyl chlorosulfonate (817 μL, 8.17 mmol) was added via syringe, and the reaction was stirred overnight at room temperature. The organic and aqueous layers were separated, and the aqueous layer was extracted with dichloromethane (14 mL). The combined organic extracts were dried and concentrated under vacuum, and the residues was chromatographed using an ISCO silica column (40 g) eluting with ethyl acetate/hexane gradient from 0 to 5%. Similar fractions were combined and concentrated under vacuum to provide the titled compound as a pale oil (1.16 g, 81.6%). $^1$H NMR (DMSO-d$_6$) δ: 7.26-7.43 (m, 5H), 5.78 (s, 2H), 1.55 (q, J=4.0 Hz, 2H), 1.30 (q, J=4.2 Hz, 2H).

Chloromethyl 2-methyl-2-phenylpropanoate. Prepared from 2-methyl-2-phenylpropionic acid using the method above to provide the titled compound, a clear solid (1.09 g, 76.0%). $^1$H NMR (CHLOROFORM-d) δ: 7.31-7.33 (m, 5H), 5.67 (s, 2H), 1.61 (s, 6H).

Chloromethyl 1-phenylcyclopentane-1-carboxylate. Prepared from phenylcyclopentane carboxylic acid using the method above to provide the titled compound as crystalline solid (1.28 g, 79.4%). $^1$H NMR (DMSO-d$_6$) δ: 7.31-7.33 (m, 5H), 5.79 (s, 2H), 2.52-2.40-2.52 (m, 2H), 1.85-1.91 (m, 2H), 1.63-1.70 (m, 4H).

Chloromethyl 1-phenylcyclohexane-1-carboxylate. Prepared from phenylcyclohexane carboxylic acid using the method above to provide the titled compound as clear oil (1.52 g, 89%). $^1$H NMR (DMSO-d$_6$) δ: 7.32-7.34 (m, 2H), 7.23-7.26 (m, 3H), 5.83 (s, 2H), 2.32-2.39 (m, 2H), 1.60-1.72 (m, 4H), 1.22-1.44 (m, 4H).

Chloromethyl 3-ethenylbenzoate. Prepared from 3-vinyl benzoic acid using half scale (3.375 mmol) according to the method described above to provide the title compound (440 mg, 66.4%). $^1$H NMR (DMSO-d$_6$) δ: 8.03 (br s, 1H), 7.83-7.92 (m, 2H), 7.55 (t, J=7.70 Hz, 1H), 6.74-6.93 (m, 1H), 6.10 (s, 2H), 5.94 (dd, J=17.61, 2.92 Hz, 1H), 5.37 (br d, J=10.65 Hz, 1H).

Chloromethyl 4-ethenylbenzoate. Prepared from 4-vinyl benzoic acid according to the method described above to provide the title compound as a pale oil (1.10 g, 82.9%). $^1$H NMR (DMSO-d$_6$) δ: 7.95-7.98 (m, 2H), 7.64-7.67 (m, 2H), 6.78-6.85 (dd, 1H), 6.09 (s, 2H), 6.00-6.06 (dd, 1H), 5.44-5.48 (dd, 1H).

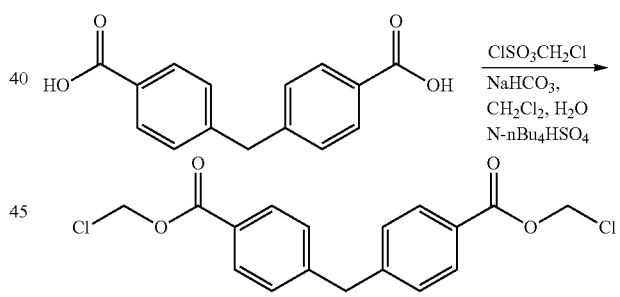

Chloromethyl 4-({4-[(chloromethoxy)carbonyl]phenyl}methyl)benzoate. A 250 mL round bottom flask was charged with diphenylmethane-4, 4' dicarboxylic acid (1 g, 3.9 mmol), water (16.4 mL), dichloromethane (16.4 mL), tetrabutylammonium hydrogen sulfate (265 mg, 78.1 μmop, and sodium hydrogen carbonate (2.62 g, 31.2 mmol). Chloromethyl chlorosulfonate (943 μL, 9.43 mmol) was added via syringe, and the reaction was stirred overnight at room temperature. The reaction was separated and the aqueous phase was extracted with dichloromethane (16 mL). The combined organic extracts were dried and concentrated under vacuum, and the residue was chromatographed on silica column (40 g) eluting with dichloromethane. Similar fractions were combined and concentrated under vacuum to provide the titled compound as a white solid (530 mg, 38.5%). $^1$H NMR (DMSO-d$_6$) δ: 7.94 (d, J=12.31, Hz 4H), 7.44 (d, J=8.79 Hz, 4H), 6.07 (s, 4H), 4.15 (s, 2H).

Examples 1-4
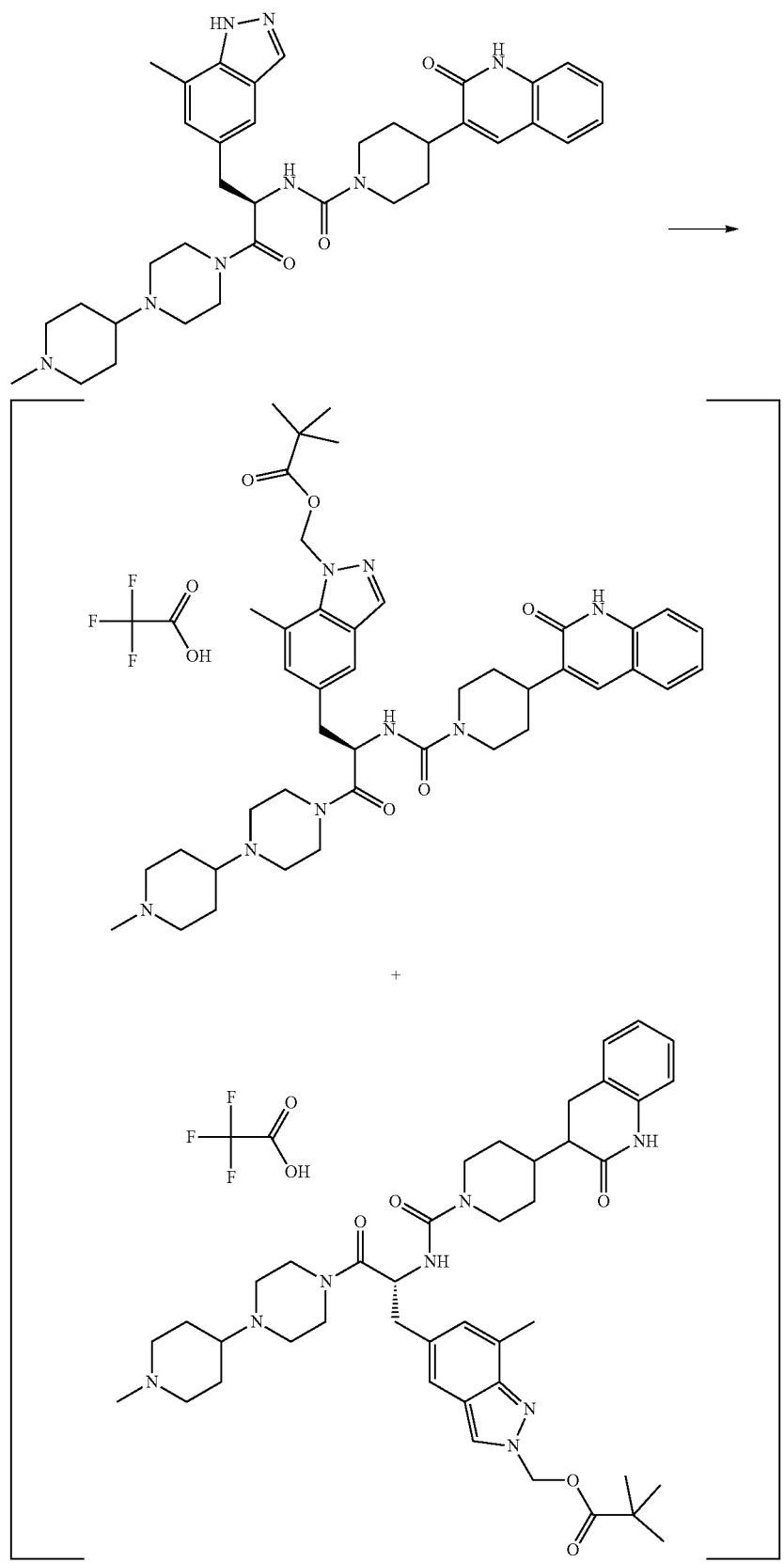

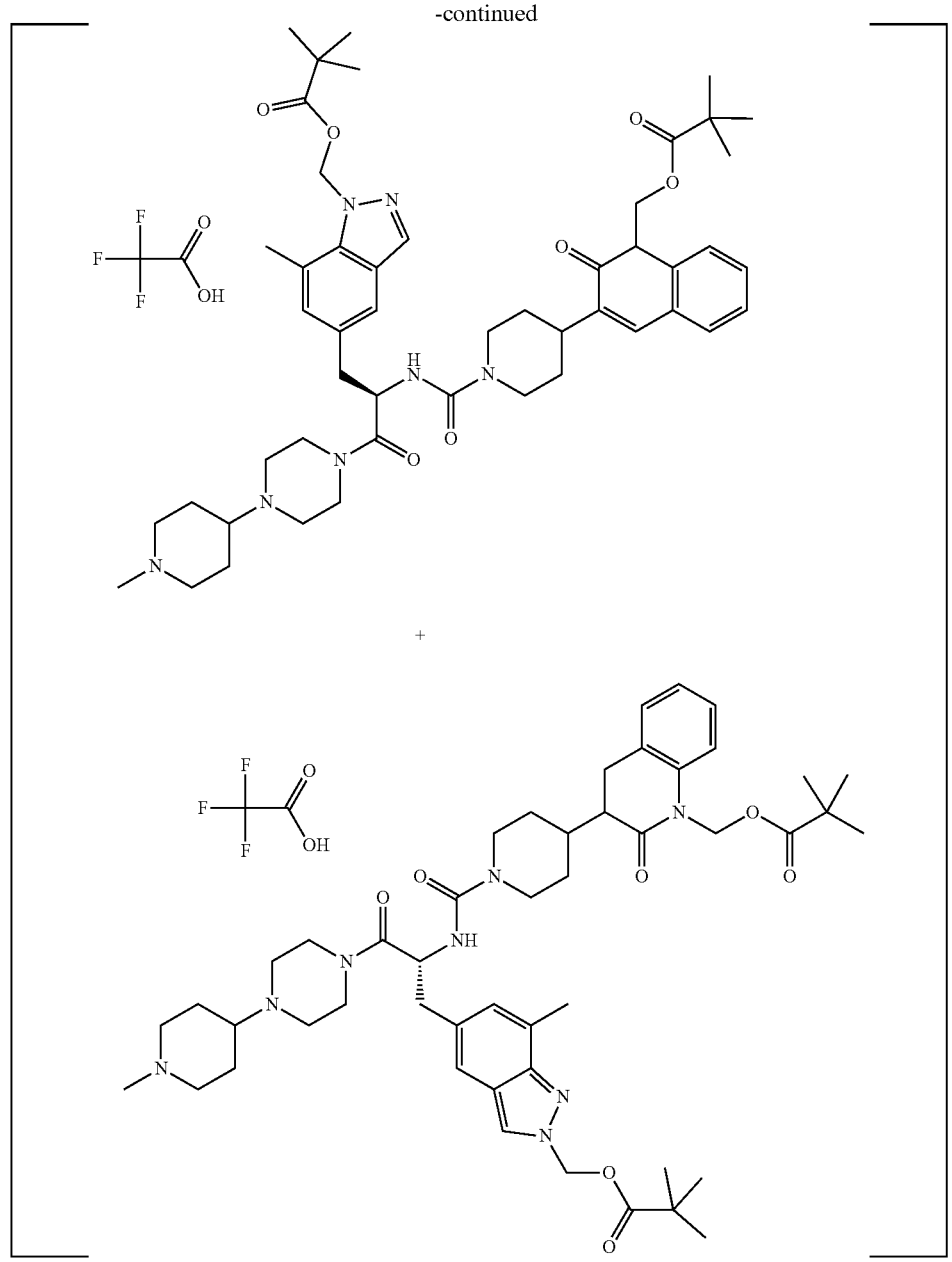

{7-methyl-5-[(2R)-3-[4-(1-methylpiperidin-4-yl)piperazin-1-yl]-3-oxo-2-{[4-(2-oxo-1,2-dihydroquinolin-3-yl)piperidine-1-carbonyl]amino}propyl]-1H-indazol-1-yl}methyl 2,2-dimethylpropanoate trifluoroacetate and {7-methyl-5-[(2R)-3-[4-(1-methylpiperidin-4-yl)piperazin-1-yl]-3-oxo-2-{[4-(2-oxo-1,2-dihydroquinolin-3-yl)piperidine-1-carbonyl]amino}propyl]-2H-indazol-2-yl}methyl 2,2-dimethylpropanoate trifluoroacetate and {5-[(2R)-2-{[4-(1-{[(2,2-dimethylpropanoyl)oxy]methyl}-2-oxo-1,2-dihydroquinolin-3-yl)piperidine-1-carbonyl]amino}-3-[4-(1-methylpiperidin-4-yl)piperazin-1-yl]-3-oxopropyl]-7-methyl-1H-indazol-1-yl}methyl 2,2-dimethylpropanoate trifluoroacetate and {5-[(2R)-2-{[4-(1-{[(2,2-dimethylpropanoyl)oxy]methyl}-2-oxo-1,2-dihydroquinolin-3-yl)piperidine-1-carbonyl]amino}-3-[4-(1-methylpiperidin-4-yl)piperazin-1-yl]-3-oxopropyl]-7-methyl-2H-indazol-2-yl}methyl 2,2-dimethylpropanoate trifluoroacetate. A solution of N-[(2R)-3-(7-methyl-1H-indazol-5-yl)-1-[4-(1-methylpiperidin-4-yl)piperazin-1-yl]-1-oxopropan-2-yl]-4-(2-oxo-1,2-dihydroquinolin-3-yl)piperidine-1-carboxamide (162 mg, 254 µmop in DMF (3.9 mL) was treated with lithium hexamethyldisilylamide (1.0 M in THF, 762 µL, 762 µmop and stirred for 20 minutes. Chloromethyl pivalate (146 µL, 1,016 µmop was added via syringe and the mixture was stirred for 2 h. The reaction was quenched by the addition of saturated aqueous ammonium chloride (200 µL), filtered with a syringe filter (45 urn), and the crude product mixture was purified by RP-HPLC (method D), where the product fractions were combined and lyophilized to provide the pure product as a white solid consisting of a mixture of mono 1-alkylated and 2-alkylated indazole isomers (63.1 mg, 28.7%) and bis 1-alkylated and 2-alkylated indazole isomers (103.9 mg, 41.7%). The mixed fractions of both mono and bis targets were purified two additional times (method D) to provide the four title compounds as individual indazole isomers characterized below.

{7-methyl-5-[(2R)-3-[4-(1-methylpiperidin-4-yl)piperazin-1-yl]-3-oxo-2-{[4-(2-oxo-1,2-dihydroquinolin-3-yl)piperidine-1-carbonyl]amino}propyl]-1H-indazol-1-yl}methyl 2,2-dimethylpropanoate trifluoroacetate (1): (3 mg, 1.4%), $^1$H NMR (300 MHz, DMSO-$d_6$) δ=11.76 (s, 1H), 8.10 (s, 1H), 7.85-7.51 (m, 2H), 7.51-7.34 (m, 2H), 7.33-7.04 (m, 3H), 6.81 (m, 1H), 6.54 (br d, J=7.0 Hz, 4H), 6.39 (s, 2H), 4.76 (br d, J=6.4 Hz, 1H), 4.25-3.96 (m, 2H), 3.02-2.81 (m, 6H), 2.78-2.60 (m, 8H), 2.45-2.32 (m, 3H), 2.31-2.16 (m, 2H), 2.07-1.89 (m, 4H), 1.75-1.49 (m, 3H), 1.45-1.03 (m, 5H), 1.00 (s, 9H). LC/MS method A: $R_t$=3.55 mins., (M+H)$^+$=753, purity=91%.

{7-methyl-5-[(2R)-3-[4-(1-methylpiperidin-4-yl)piperazin-1-yl]-3-oxo-2-{[4-(2-oxo-1,2-dihydroquinolin-3-yl)piperidine-1-carbonyl]amino}propyl]-2H-indazol-2-yl}methyl 2,2-dimethylpropanoate trifluoroacetate (2): (12 mg, 5.5%), $^1$H NMR (300 MHz, DMSO-$d_6$) δ=11.75 (s, 1H), 8.39 (s, 1H), 7.64 (d, J=6.4 Hz, 1H), 7.54 (s, 1H), 7.43 (t, J=7.7 Hz, 1H), 7.39-7.37 (m, 1H), 7.26 (d, J=8.2 Hz, 1H), 7.20-7.12 (m, 1H), 7.01 (s, 1H), 6.81 (br d, J=5.9 Hz, 1H), 6.35-6.25 (m, 2H), 4.78 (br dd, J=2.3, 5.3 Hz, 1H), 4.35-4.01 (m, 2H), 2.98-2.62 (m, 15H), 2.47-2.38 (m, 4H), 2.32-2.16 (m, 1H), 2.07 (m, 1H), 2.03-1.84 (m, 2H), 1.83-1.48 (m, 4H), 1.45-1.15 (m, 4H), 1.08-1.03 (m, 1H), 1.06 (s, 9H). LC/MS method A: $R_t$=3.48 mins., (M+H)$^+$=753, purity=96%.

{5-[(2R)-2-{[4-(1-{[(2,2-dimethylpropanoyl)oxy]methyl}-2-oxo-1,2-dihydroquinolin-3-yl)piperidine-1-carbonyl]amino}-3-[4-(1-methylpiperidin-4-yl)piperazin-1-yl]-3-oxopropyl]-7-methyl-1H-indazol-1-yl}methyl 2,2-dimethylpropanoate trifluoroacetate (3): (6 mg, 2.4%), $^1$H NMR (300 MHz, DMSO-$d_6$) δ=8.11 (s, 1H), 7.72 (dd, J=1.5, 7.9 Hz, 2H), 7.66-7.41 (m, 3H), 7.34-7.27 (m, 1H), 7.20 (s, 1H), 6.86 (br d, J=6.4 Hz, 1H), 6.38 (s, 2H), 6.26 (br s, 2H), 4.77 (br d, J=7.5 Hz, 1H), 4.32-3.97 (m, 2H), 3.46 (m, 4H), 3.02-2.83 (m, 7H), 2.80-2.66 (m, 7H), 2.46-2.12 (m, 3H), 2.11-1.84 (m, 1H), 1.83-1.52 (m, 4H), 1.51-1.16 (m, 6H), 1.09 (s, 9H), 0.98 (s, 9H). LC/MS method A: $R_t$=4.27 mins., (M+H)$^+$=867, purity=95%.

{5-[(2R)-2-{[4-(1-{[(2,2-dimethylpropanoyl)oxy]methyl}-2-oxo-1,2-dihydroquinolin-3-yl)piperidine-1-carbonyl]amino}-3-[4-(1-methylpiperidin-4-yl)piperazin-1-yl]-3-oxopropyl]-7-methyl-2H-indazol-2-yl}methyl 2,2-dimethylpropanoate trifluoroacetate (4): (38 mg, 15.2%), $^1$H NMR (300 MHz, DMSO-$d_6$) δ=8.40 (s, 1H), 7.75 (dd, J=1.2, 7.6 Hz, 1H), 7.64-7.55 (m, 2H), 7.43 (d, J=8.6 Hz, 1H), 7.38 (s, 1H), 7.30 (t, J=7.0 Hz, 1H), 7.02 (s, 1H), 6.86-6.82 (m, 1H), 6.31-6.23 (m, 4H), 4.77 (br d, J=7.0 Hz, 1H), 4.07 (br dd, J=5.9, 7.6 Hz, 2H), 3.58-3.47 (m, 4H), 2.98-2.62 (m, 14H), 2.47-2.37 (m, 4H), 2.47-2.37 (m, 1H), 2.25 (br dd, J=1.8, 4.1 Hz, 2H), 1.97 (br d, J=1.2 Hz, 1H), 1.78-1.60 (m, 4H), 1.30-1.20 (m, 2H), 1.09 (s, 9H), 1.04 (s, 9H). LC/MS method A: $R_t$=4.25 mins., (M+H)$^+$=867, purity=98%.

Example 5

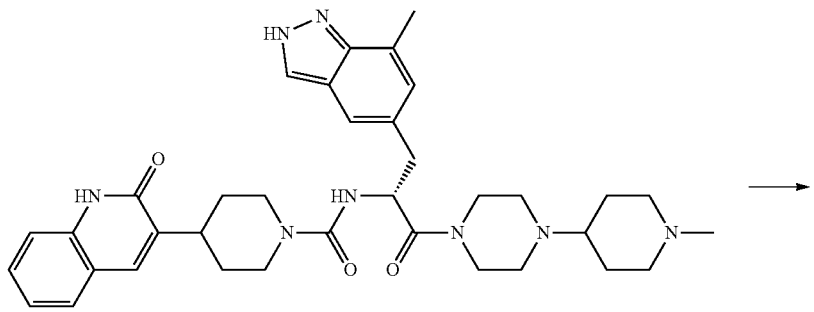

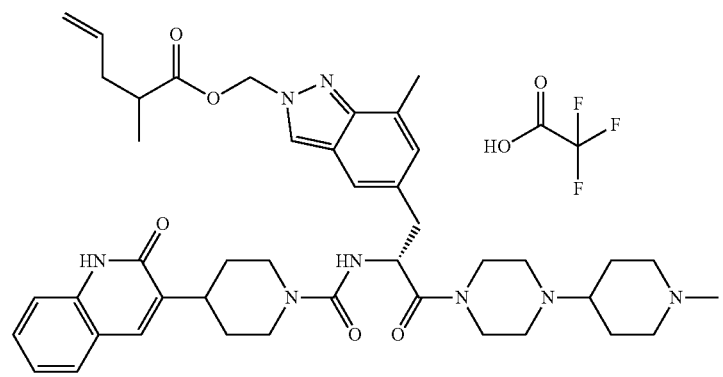

2-Methyl-pent-4-enoic acid 7-methyl-5-{2-({4-[1-(2-methyl-pent-4-enoyloxymethyl)-2-oxo-1,2-dihydro-quinolin-3-yl]-piperidine-1-carbonyl}-amino)-3-[4-(1-methyl-piperidin-4-yl)-piperazin-1-yl]-3-oxo-propyl}-indazol-2-ylmethyl ester trifluoroacetate (5). Added NaH (0.0226 g, 0.94 mmol) to a solution of 2-(7-methyl-2H-indazol-5-ylmethyl)-1-[4-(1-methyl-piperidin-4-yl)-piperazin-1-yl]-4-[4-(2-oxo-1,2-dihydro-quinolin-3-yl)-piperidin-1-yl]-butane-1,4-dione (0.200 g, 0.313 mmol) at room temperature under N₂, and the reaction mixture was magnetically stirred in 5 mL of DMF. The reaction was stirred until gas evolution ceased (2.5 hours), followed by the addition of 2-methyl-pent-4-enoic acid chloromethyl ester (0.164 g, 0.94 mmol). After 72 hours, the reaction was quenched with saturated NH₄Cl (aq), and partitioned between CHCl₃ with 10% IPA and H₂O. The organic and aqueous layers were separated, and the aqueous layer was washed with 10% IPA, 90% CHCl₃. The combined the organic layers were washed with brine, dried over Na₂SO₄, and concentrated in vacuo. The residue was purified on a 40 g silasep column, eluting with 0-10% MeOH (containing 3.5 N NH₃)/CH₂Cl₂ to yield 60 mg of a mix of isomers and mono and di alkylated products. Further purification was conducted by RP-HPLC, eluting with 45 to 95% ACN with 0.1% TFA. The product fractions were combined and lyophilized to yield the desired product (52 mg, 16.5%). ¹H NMR (METHANOL-d₄) δ: 8.31 (s, 1H), 8.05 (s, 1H), 7.72 (dd, J=7.8, 1.5 Hz, 2H), 7.62 (br d, J=4.4 Hz, 1H), 7.55-7.60 (m, 1H), 7.46-7.52 (m, 2H), 7.41 (s, 1H), 7.34 (t, J=7.0 Hz, 1H), 7.06 (d, J=1.7 Hz, 1H), 6.44 (br dd, J=2.5, 1.3 Hz, 2H), 6.29 (t, J=5.0 Hz, 2H), 5.51-5.80 (m, 2H), 4.92-5.05 (m, 3H), 4.78-4.87 (m, 2H), 4.16 (br t, J=13.9 Hz, 3H), 3.85-4.06 (m, 2H), 3.64 (s, 2H), 3.16-3.28 (m, 3H), 2.92-3.15 (m, 7H), 2.89 (s, 4H), 2.71 (s, 1H), 2.57 (s, 3H), 2.06-2.40 (m, 5H), 1.78-2.05 (m, 4H), 1.32-1.60 (m, 3H), 1.13 (d, J=6.9 Hz, 3H), 1.08 (d, J=7.0 Hz, 3H), 1.04 (dd, J=7.0, 2.3 Hz, 1H). LC/MS R_t=4.13 min, (M+H)⁺=891 (94%).

Example 6

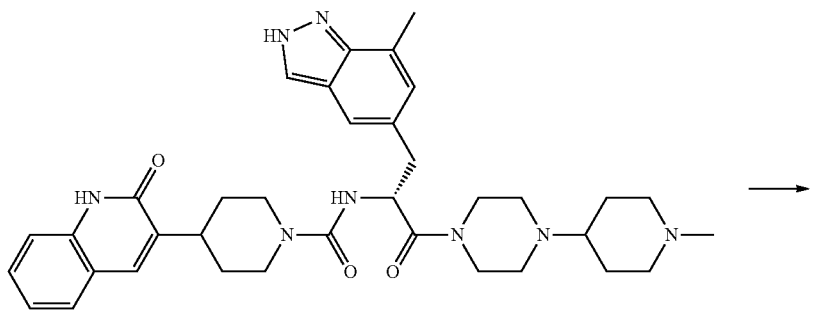

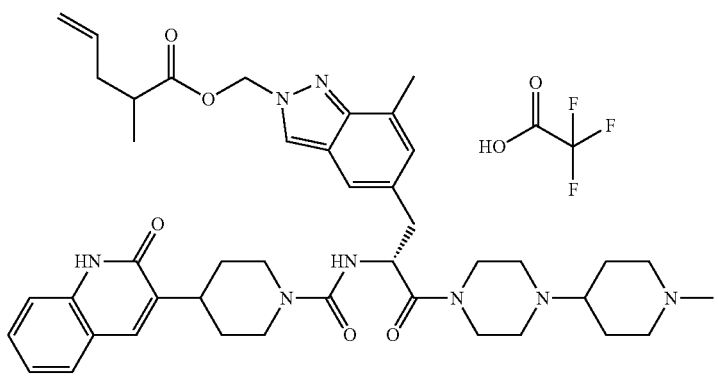

2-Methyl-pent-4-enoic acid 7-methyl-5-(3-[4-(1-methyl-piperidin-4-yl)-piperazin-1-yl]-3-oxo-2-{[4-(2-oxo-1,2-di-hydro-quinolin-3-yl)-piperidine-1-carbonyl]-amino}-propyl)-indazol-2-ylmethyl ester trifluoroacetate (6). A by-product of the preparation of Example 5. Yielded desired product (66 mg, 24%). $^1$H NMR (METHANOL-$d_4$) δ: 8.31 (s, 1H), 8.06 (s, 1H), 7.63-7.73 (m, 3H), 7.46-7.57 (m, 2H), 7.41 (s, 1H), 7.32 (d, J=8.3 Hz, 1H), 7.21-7.28 (m, 2H), 7.06 (d, J=1.4 Hz, 1H), 6.45 (t, J=2.1 Hz, 1H), 6.29 (t, J=5.3 Hz, 2H), 5.52-5.71 (m, 1H), 4.89-5.01 (m, 2H), 4.78-4.87 (m, 3H), 4.17 (br t, J=13.6 Hz, 2H), 3.82-4.07 (m, 1H), 3.58-3.74 (m, 3H), 3.34-3.56 (m, 2H), 2.96-3.26 (m, 8H), 2.92 (br d, J=13.0 Hz, 1H), 2.41-2.76 (m, 6H), 2.26-2.36 (m, 1H), 2.05-2.25 (m, 4H), 1.79-1.98 (m, 5H), 1.28-1.61 (m, 3H), 1.09 (d, J=6.9 Hz, 3H), 1.05 (dd, J=7.0, 2.0 Hz, 1H). LC/MS $R_t$=3.43 min, (M+H)$^+$=765 (95%).

Example 7 loxymethyl)-2-oxo-1,2-dihydro-quinolin-3-yl]-piperidine-1-carbonyl}-amino)-3-[4-(1-methyl-piperidin-4-yl)-piperazin-1-yl]-3-oxo-propyl}-indazol-2-ylmethyl ester trifluoroacetate (1.83 g, 1.99 mmol). Grubbs 2nd generation catalyst (0.845 g, 1.0 mmol) was subsequently added. A balloon of $N_2$ with a condenser was placed on the flask, and the reaction mixture was warmed to 40° C. and stirred for 4 hours. The mixture was then cooled to room temperature and allowed to stir for another 72 hours. The reaction mixture was concentrated reaction in vacuo, and then purified via RP-HPLC eluting with 35-95% ACN in $H_2O$ with 0.1% TFA. The product fractions were lyophilized to yield (16Z,31S)-14,19,27-trimethyl-31-[4-(1-methylpiperidin-4-yl)piperazine-1-carbonyl]-12,21-dioxa-10,23,32,34,40-pentaazahexacyclo[32.2.2.1$^{2,10}$.1$^{23,26}$.1$^{25,29}$.0$^{4,9}$]hentetraconta-2,4(9),5,7,16,24,26(40),27,29(39)-nonaene-13,20,33,41-tetrone trifluoroacetate. $^1$H NMR (METHANOL-$d_4$) δ: 8.38 (dd, J=10.2, 4.5 Hz, 1H), 8.14-8.24 (m, 1H), 7.98-8.14 (m, 1H), 7.54-7.74 (m, 3H), 7.50 (d, J=3.2 Hz, 1H), 7.23-7.46

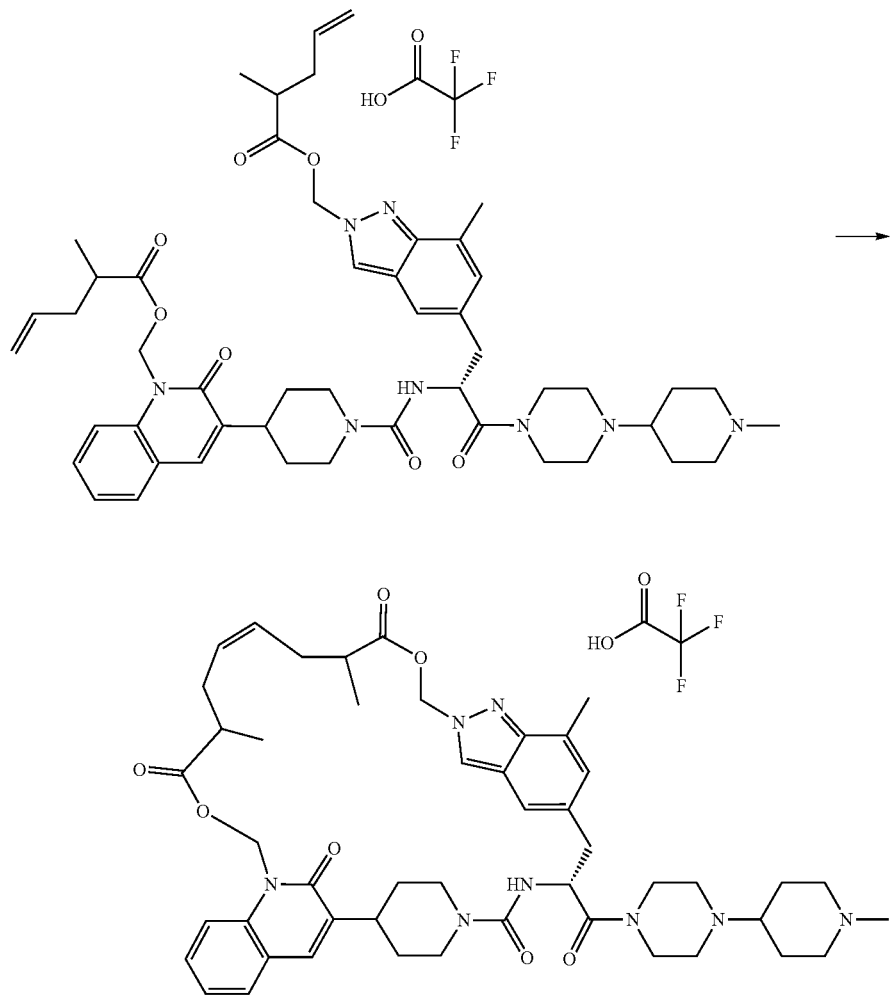

(16Z,31Z)-14,19,27-trimethyl-31-[4-(1-methylpiperidin-4-yl)piperazine-1-carbonyl]-12,21-dioxa-10,23,32,34,40-pentaazahexacyclo[32.2.2.1$^{2,10}$.1$^{23,26}$.1$^{25,29}$.0$^{4,9}$]hentetraconta-2,4(9),5,7,16,24,26(40),27,29(39)-nonaene-13,20,33,41-tetrone trifluoroacetate (7). To a magnetically stirred deoxygenated DCM (100 mL) was added 2-methyl-pent-4-enoic acid 7-methyl-5-{2-({4-[1-(2-methyl-pent-4-enoy- (m, 2H), 7.00-7.16 (m, 2H), 5.89-6.52 (m, 4H), 4.94-5.13 (m, 3H), 4.69-4.86 (m, 2H), 3.92-4.38 (m, 4H), 3.71 (br d, J=13.0 Hz, 5H), 3.34-3.57 (m, 4H), 2.94-3.21 (m, 5H), 2.91 (s, 3H), 2.60-2.68 (m, 3H), 2.40-2.59 (m, 3H), 1.95-2.25 (m, 6H), 1.64 (s, 4H), 1.25-1.48 (m, 2H), 1.09-1.25 (m, 5H), 0.70-0.93 (m, 2H), 0.51-0.68 (m, 4H). LC/MS, $R_t$=3.70 95% purity, (M+H)$^+$=863 (95%).

Examples 8 and 9

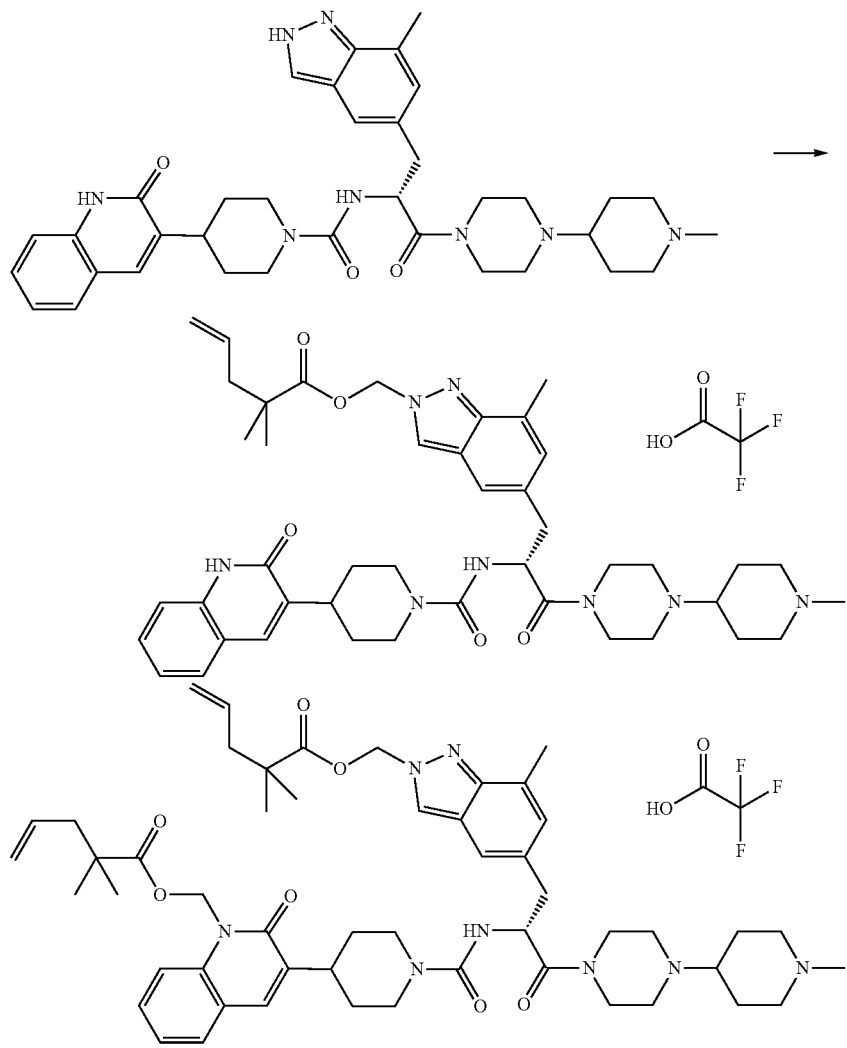

{7-methyl-5-[(2R)-3-[4-(1-methylpiperidin-4-yl)piperazin-1-yl]-3-oxo-2-{[4-(2-oxo-1,2-dihydroquinolin-3-yl)piperidine-1-carbonyl]amino}propyl]-1H-indazol-1-yl}methyl 2,2-dimethylpent-4-enoate (8) and {5-[(2R)-2-{[4-(1-{[(2,2-dimethylpent-4-enoyl)oxy]methyl}-2-oxo-1,2-dihydroquinolin-3-yl)piperidine-1-carbonyl]amino}-3-[4-(1-methylpiperidin-4-yl)piperazin-1-yl]-3-oxopropyl]-7-methyl-2H-indazol-2-yl}methyl 2,2-dimethylpent-4-enoate (9). A suspension of N-[(2S)-3-(7-methyl-1H-indazol-5-yl)-1-[4-(1-methylpiperidin-4-yl)piperazin-1-yl]-1-oxopropan-2-yl]-4-(2-oxo-1,2-dihydroquinolin-3-yl)piperidine-1-carboxamide (100 mg, 0.16 mmol) in THF (3 mL) was treated with lithium hexamethyldisilylamide (1.0 M in THF, 0.47 mL, 0.47 mmol), and the reaction mixture was stirred for 30 minutes at ambient temperature. 2,2-Dimethyl-pent-4-enoic acid chloromethyl ester (83 mg, 0.47 mmol) was added via pipette and the mixture stirred 72 h. The product mixture was purified directly by RP-HPLC (method B, 30-70% acetonitrile/water with 0.1% TFA), and the product fractions were combined and lyophilized to provide the pure product as a white solid consisting of mono alkylated 2:1 mixture of (1-alkylated indazole and 2-alkylated indazole regioisomers with the 2-alkylated isomer in 2:1 excess (42 mg, 29%)) and di alkylated 2:1 mixture of (1-alkylated indazole and 2-alkylated indazole regioisomers with the 2-alkylated isomer in 2:1 excess (30 mg, 18%)).

{7-methyl-5-[(2R)-3-[4-(1-methylpiperidin-4-yl)piperazin-1-yl]-3-oxo-2-{[4-(2-oxo-1,2-dihydroquinolin-3-yl)piperidine-1-carbonyl]amino}propyl]-1H-indazol-1-yl}methyl 2,2-dimethylpent-4-enoate (8). $^1$H NMR (CD$_3$OD) δ: 8.31 and 8.05 (s, 1H), 7.63-7.72 (m, 2H), 7.49-7.55 (m, 1H), 7.39-7.48 (m, 1H), 7.32 (d, J=8.2 Hz, 1H), 7.20-7.29 (m, 1H), 7.06 and 6.45 (s, 1H), 6.23-6.35 (m, 1H), 5.43-5.64 (m, 1H), 4.90-5.03 (m, 2H), 4.70-4.86 (m, 2H), 4.16 (br t, J=14.2 Hz, 2H), 3.77-4.05 (m, 1H), 3.34-3.76 (m, 3H), 2.92-3.26 (m, 7H), 2.88 (s, 3H), 2.53-2.78 (m, 4H), 2.04-2.28 (m, 3H), 1.89 (s, 3H), 1.27-1.64 (m, 2H), 0.95-1.17 (m, 5H). LC/MS method A (regioisomers coelute): R$_t$=3.55 mins., (M+H)$^+$=779, purity>95%.

{5-[(2R)-2-{[4-(1-{[(2,2-dimethylpent-4-enoyl)oxy]methyl}-2-oxo-1,2-dihydroquinolin-3-yl)piperidine-1-carbonyl]amino}-3-[4-(1-methylpiperidin-4-yl)piperazin-1-yl]-3-oxopropyl]-7-methyl-2H-indazol-2-yl}methyl 2,2-dimethylpent-4-enoate (9). $^1$H NMR (CD$_3$OD) δ: 8.31 and 8.35 (s, 1H), 7.68-7.77 (m, 1H), 7.61-7.68 (m, 1H), 7.45-7.56 (m, 2H), 7.42 (s, 1H), 7.30-7.39 (m, 1H), 7.22 and 7.06 (s, 1H), 6.41 (br d, J=16.6 Hz, 3H), 6.24-6.34 (m, 2H), 5.43-5.82 (m, 2H), 5.01-5.11 (m, 1H), 4.91-4.99 (m, 2H), 4.72-4.85 (m, 3H), 3.81-4.25 (m, 3H), 3.64 (s, 2H), 3.14-3.28 (m, 3H), 2.93-3.14 (m, 8H), 2.88 (s, 5H), 2.55-2.76 (m, 4H), 2.07-2.31 (m, 8H), 1.09-1.15 (m, 12H), 1.06 (d, J=1.1 Hz, 2H.). LC/MS method A (regioisomers coelute): $R_f$=4.45 mins., (M+H)$^+$=919, purity >95%.

Example 10

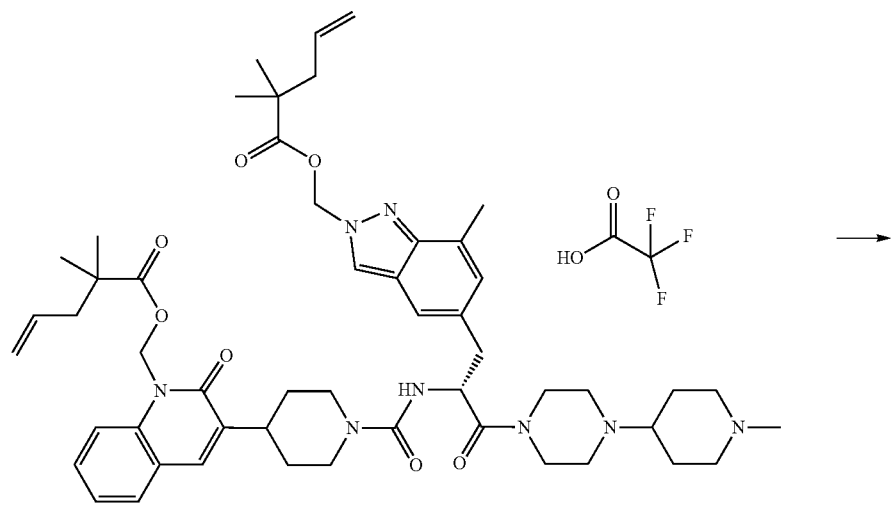

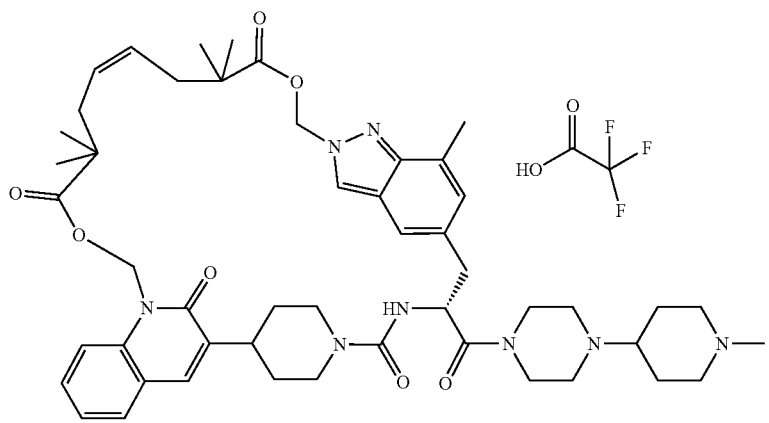

{(16Z,31R)-14,14,19,19,27-pentamethyl-31-[4-(1-methylpiperidin-4-yl)piperazine-1-carbonyl]-12,21-dioxa-10,23,32,34,40-pentaazahexacyclo[32.2.2.1$^{2,10}$.1$^{23,26}$.1$^{25,29}$.0$^{4,9}$]hentetraconta-2,4(9),5,7,16,24,26(40),27,29(39)-nonaene-13,20,33,41-tetrone (10). Grubbs 2nd generation catalyst (12.3 g, 0.0145 mmol) was added to a degassed solution of {5-[(2R)-2-{[4-(1-{[(2,2-dimethylpent-4-enoyl)oxy]methyl}-2-oxo-1,2-dihydroquinolin-3-yl)piperidine-1-carbonyl]amino}-3-[4-(1-methylpiperidin-4-yl)piperazin-1-yl]-3-oxopropyl]-7-methyl-2H-indazol-2-yl}methyl 2,2-dimethylpent-4-enoate (25 mg, 0.024 mmol) in 100 mL DCM. The reaction mixture was placed under an N$_2$ atmosphere and monitored by LCMS. After 24 hours, more Grubbs 2nd generation catalyst (10 mg, 0.012 mmol) was added. After 3 days, the reaction mixture was concentrated in vacuo, and the product mixture was purified directly by RP-HPLC on a Waters Sunfire column (30×150 mm, C18, 5 μm) with a 10 min mobile phase gradient of 20-85% acetonitrile/water with 0.1% TFA as buffer using 214 and 254 nm as detection wavelengths. Injection and fraction collection were performed with a Gilson 215 liquid handling apparatus using Trilution LC software. The product fractions were combined and lyophilized to yield the pure product as a white solid of 5.2 mg (18%). $^1$H NMR (DMSO-d$_6$) δ: 9.80-10.06 (m, 1H), 8.44 (s, 1H), 8.09-8.25 (m, 1H), 7.46-7.66 (m, 3H), 7.20-7.44 (m, 2H), 6.95-7.14 (m, 1H), 6.75 (br d, J=9.1 Hz, 1H), 6.15-6.56 (m, 3H), 4.55-5.11 (m, 4H), 3.23-3.78 (m, 7H), 2.76 (s, 3H), 2.20-2.44 (m, 3H), 1.71-2.08 (m, 6H), 1.22-1.70 (m, 7H), 1.01-1.17 (m, 6H), 0.42-0.80 (m, 6H). LC/MS method A (regioisomers coelute): $R_f$=3.97 mins., (M+H)$^+$=891, purity >95%.

Examples 11-12
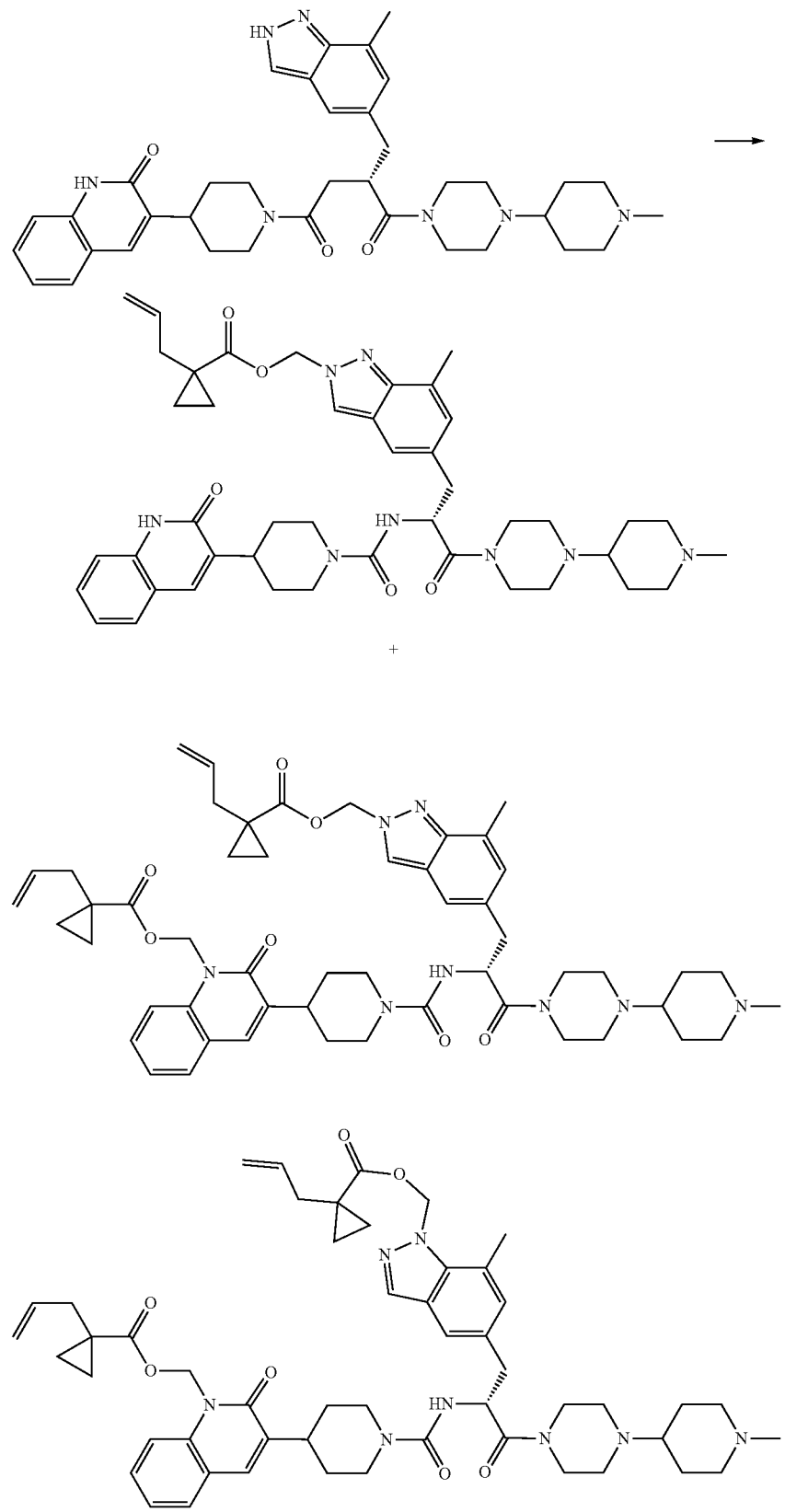

[3-(1-{[(2S)-3-(7-methyl-2-{[1-(prop-2-en-1-yl)cyclopropanecarbonyloxy]methyl}-2H-indazol-5-yl)-1-[4-(1-methylpiperidin-4-yl)piperazin-1-yl]-1-oxopropan-2-yl]carbamoyl}piperidin-4-yl)-2-oxo-1,2-dihydroquinolin-1-yl] methyl 1-(prop-2-en-1-yl)cyclopropane-1-carboxylate (11) and 1-Allyl-cyclopropanecarboxylic acid 7-methyl-5-(3-[4-(1-methyl-piperidin-4-yl)-piperazin-1-yl]-3-oxo-2-{[4-(2-oxo-1,2-dihydro-quinolin-3-yl)-piperidine-1-carbonyl]-amino}-propyl)-indazol-2-ylmethyl ester (12). NaH (0.022 g, 0.94 mmol) was added to a solution of N-[(2R)-3-(7-methyl-1H-indazol-5-yl)-1-[4-(1-methylpiperidin-4-yl)piperazin-1-yl]-1-oxopropan-2-yl]-4-(2-oxo-1,2-dihydroquinolin-3-yl)piperidine-1-carboxamide (0.200 g, 0.313 mmol) at room temperature under $N_2$, and the reaction mixture was magnetically stirred in 5 mL of DMF. After 2.5 hours, 1-allyl-cyclopropanecarboxylic acid chloromethyl ester (0.16 g, 0.94 mmol) was added. After 72 hours, the reaction was quenched with saturated $NH_4Cl$ (aq) and partitioned between $CHCl_3$ with 10% IPA, and $H_2O$. The organic and aqueous layers were separated, and the aqueous layer was washed with a solvent containing 10% IPA and 90% $CHCl_3$. The organic layers were combined, washed with brine, dried over $Na_2SO_4$, and concentrated in vacuo. The residue was purified on an 80 g silacel column, eluting with 0-10% MeOH (containing 3.5 N $NH_3$)/$CH_2Cl_2$ to yield [3-(1-{[(2S)-3-(7-methyl-2-{[1-(prop-2-en-1-yl)cyclopropanecarbonyloxy]methyl}-2H-indazol-5-yl)-1-[4-(1-methylpiperidin-4-yl)piperazin-1-yl]-1-oxopropan-2-yl]carbamoyl}piperidin-4-yl)-2-oxo-1,2-dihydroquinolin-1-yl] methyl 1-(prop-2-en-1-yl)cyclopropane-1-carboxylate, 84.1 mg, (29%) and 1-allyl-cyclopropanecarboxylic acid 7-methyl-5-(3-[4-(1-methyl-piperidin-4-yl)-piperazin-1-yl]-3-oxo-2-{[4-(2-oxo-1,2-dihydro-quinolin-3-yl)-piperidine-1-carbonyl]-amino}-propyl)-indazol-2-ylmethyl ester 77 mg (31%).

$^1$H NMR (METHANOL-$d_4$) δ: 8.27-8.31 (m, 1H), 7.76-7.87 (m, 2H), 7.66-7.76 (m, 1H), 7.55-7.65 (m, 1H), 7.42-7.50 (m, 1H), 7.39 (s, 1H), 7.28-7.36 (m, 1H), 6.99-7.10 (m, 1H), 6.30-6.47 (m, 2H), 6.20-6.30 (m, 2H), 5.66-5.88 (m, 2H), 4.90-5.08 (m, 3H), 4.77-4.88 (m, 1H), 4.18 (br dd, J=11.8, 6.4 Hz, 2H), 3.63 (s, 1H), 3.32-3.45 (m, 2H), 2.97-3.12 (m, 4H), 2.82-2.96 (m, 4H), 2.56 (s, 3H), 2.47 (s, 1H), 2.31-2.42 (m, 1H), 2.21-2.31 (m, 8H), 1.81-2.17 (m, 7H), 1.48-1.70 (m, 4H), 1.23-1.46 (m, 2H), 1.13-1.22 (m, 4H), 0.75-0.84 (m, 4H). LC/MS $R_t$=4.1 and 4.45 min., (M+H)$^+$=915.

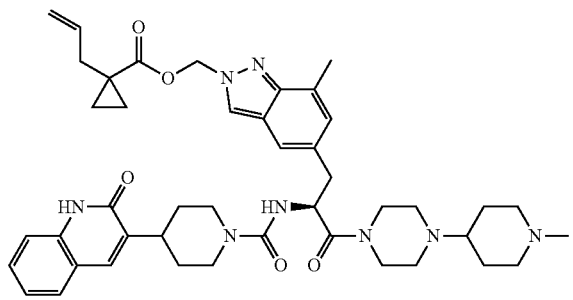

1-Allyl-cyclopropanecarboxylic acid 7-methyl-5-(3-[4-(1-methyl-piperidin-4-yl)-piperazin-1-yl]-3-oxo-2-{[4-(2-oxo-1,2-dihydro-quinolin-3-yl)-piperidine-1-carbonyl]-amino}-propyl)-indazol-2-ylmethyl ester (12). $^1$H NMR (METHANOL-$d_4$) δ: 8.30 (s, 1H), 7.67 (br d, J=1.4 Hz, 2H), 7.45-7.55 (m, 1H), 7.39 (s, 1H), 7.29-7.35 (m, 1H), 7.18-7.28 (m, 1H), 7.03 (t, J=1.4 Hz, 1H), 6.20-6.35 (m, 2H), 5.66-5.87 (m, 1H), 4.94-5.06 (m, 2H), 4.92 (d, J=1.9 Hz, 1H), 4.79-4.87 (m, 1H), 4.11-4.25 (m, 2H), 3.63 (s, 1H),

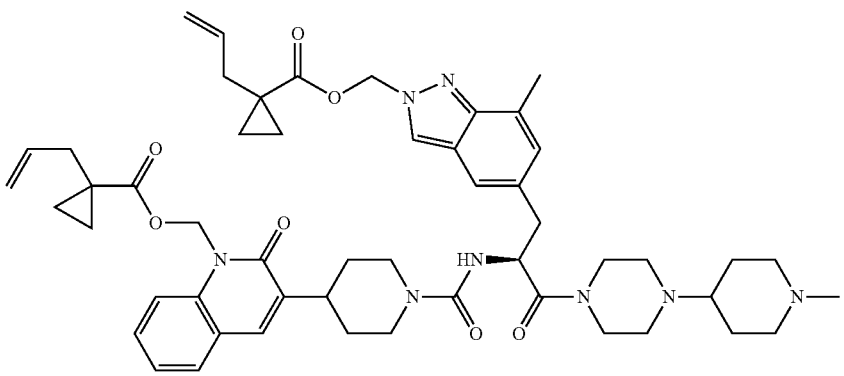 [SMILES: C=CCC1(C(=O)OCn2cc3cc(C[C@H](NC(=O)N4CCC(c5cc6ccccc6n(COC(=O)C6(CC=C)CC6)c5=O)CC4)C(=O)N4CCN(C5CCN(C)CC5)CC4)cc(C)c3n2)CC1]

[3-(1-{[(2S)-3-(7-methyl-2-{[1-(prop-2-en-1-yl)cyclopropanecarbonyloxy]methyl}-2H-indazol-5-yl)-1-[4-(1-methylpiperidin-4-yl)piperazin-1-yl]-1-oxopropan-2-yl]carbamoyl}piperidin-4-yl)-2-oxo-1,2-dihydroquinolin-1-yl] methyl 1-(prop-2-en-1-yl)cyclopropane-1-carboxylate (11).

3.33-3.47 (m, 2H), 2.83-3.13 (m, 6H), 2.56 (s, 3H), 2.42-2.53 (m, 1H), 2.34 (s, 1H), 2.28 (s, 4H), 2.17-2.23 (m, 1H), 1.81-2.16 (m, 6H), 1.23-1.69 (m, 7H), 1.14-1.21 (m, 2H), 1.05-1.13 (m, 1H), 0.83-0.94 (m, 2H), 0.79 (d, J=2.9 Hz, 2H). LC/MS RT=3.4 min., (M+H)$^+$=777.

Examples 13-14
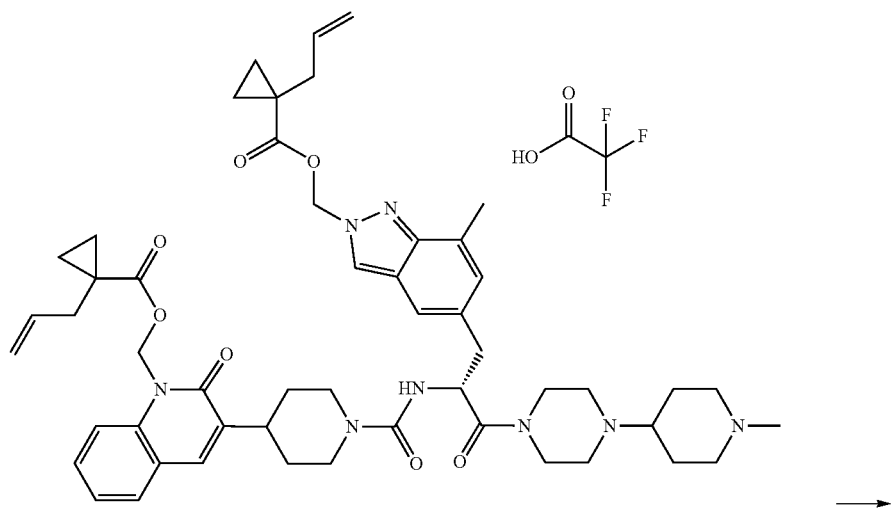
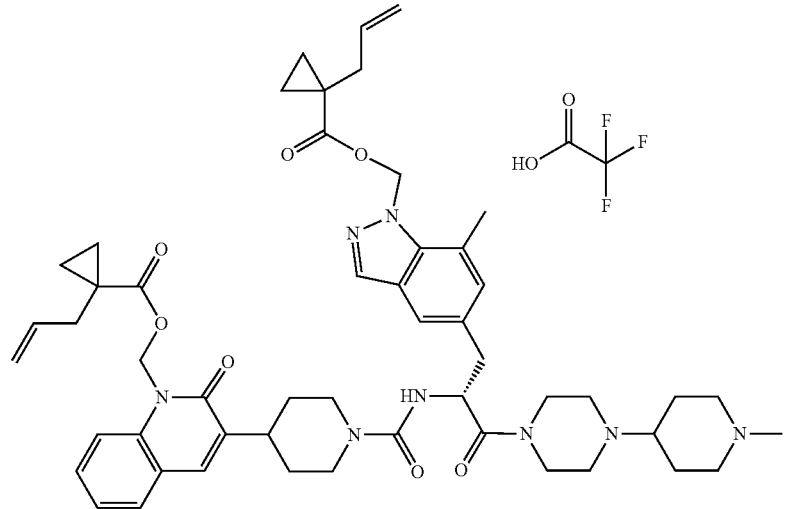
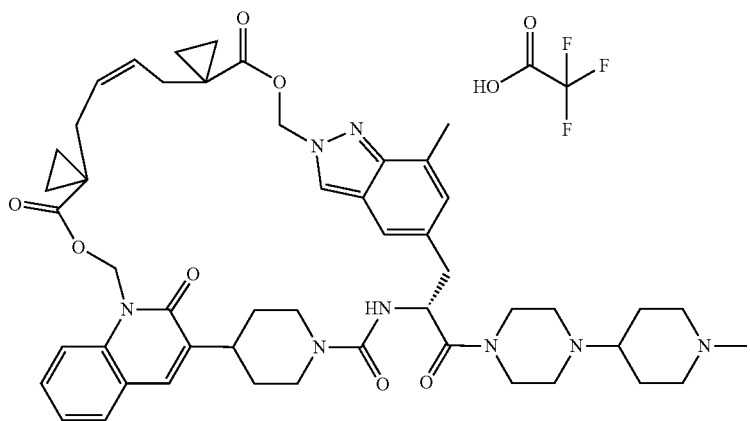

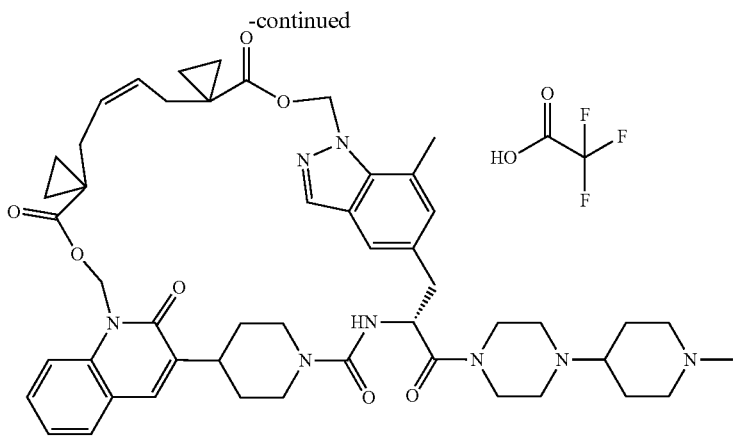

Examples 15-19

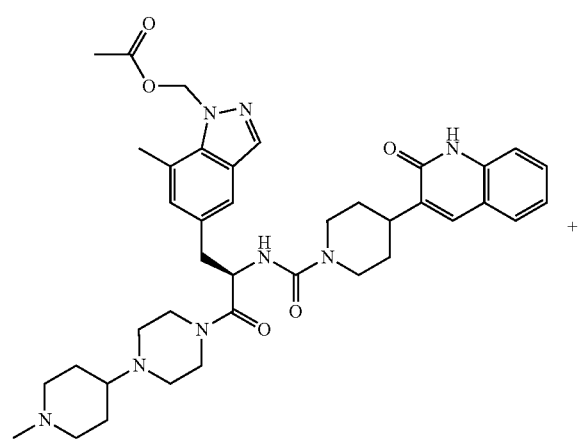

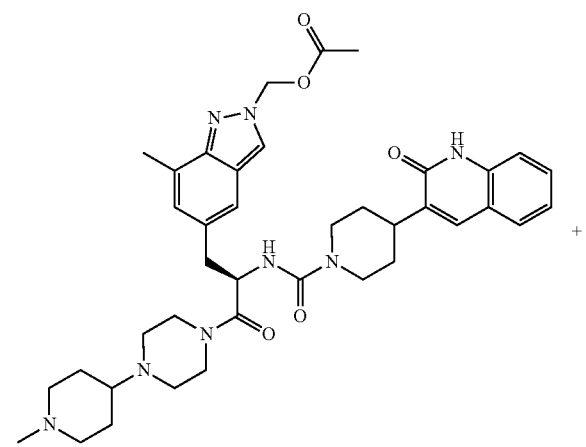

(16'Z,31'S)-27'-methyl-31'-[4-(1-methylpiperidin-4-yl)piperazine-1-carbonyl]dispiro[cyclopropane-1,14'-[12,21]dioxa-[10,23,32,34,40]pentaazahexacyclo[32.2.2.1$^{2,10}$.1$^{23,26}$.1$^{25,29}$.0$^{4,9}$]hentetracontane-19',1''-cyclopropane]-2',4'(9'),5',7',16',24',26'(40'),27',29'(39')-nonaene-13',20',33',41'-tetrone trifluoroacetate (13). Prepared in a similar manner to Example 10 above to yield (16'Z,31'S)-27'-methyl-31'-[4-(1-methylpiperidin-4-yl)piperazine-1-carbonyl]dispiro[cyclopropane-1,14'-[12,21]dioxa-[10,23,32,34,40]pentaazahexacyclo[32.2.2.1$^{2,10}$.1$^{23,26}$.1$^{25,29}$.0$^{4,9}$]hentetracontane-19',1''-cyclopropane]-2',4'(9'),5',7',16',24',26'(40'),27',29'(39')-nonaene-13',20',33',41'-tetrone trifluoroacetate, 16.5 mg 19.5%. $^1$H NMR (METHANOL-d$_4$) δ: 8.33 (s, 1H), 8.16 (br d, J=8.5 Hz, 1H), 7.56-7.70 (m, 2H), 7.47-7.54 (m, 2H), 7.38-7.45 (m, 1H), 7.22-7.36 (m, 1H), 7.07-7.16 (m, 1H), 6.22-6.57 (m, 4H), 6.10 (d, J=10.5 Hz, 1H), 4.96 (s, 2H), 4.67-4.86 (m, 2H), 4.13-4.41 (m, 2H), 3.90-4.09 (m, 3H), 3.64-3.82 (m, 3H), 3.34-3.59 (m, 5H), 3.24 (s, 1H), 3.05-3.20 (m, 4H), 2.91 (s, 4H), 2.55-2.71 (m, 4H), 2.30-2.53 (m, 3H), 1.88-2.23 (m, 5H), 1.72-1.85 (m, 1H), 1.53-1.71 (m, 3H), 1.10-1.33 (m, 3H), 0.85 (br d, J=3.4 Hz, 2H), 0.67-0.81 (m, 4H), 0.40 (s, 2H). LC/MS-R$_t$=3.68, (M+H)$^+$=887, (93%).

(16'Z,32'S)-28'-methyl-32'-[4-(1-methylpiperidin-4-yl)piperazine-1-carbonyl]dispiro[cyclopropane-1,14'-[12,21]dioxa-[10,23,24,33,35]pentaazahexacyclo[33.2.2.1$^{2,10}$.1$^{26,30}$.0$^{4,9}$.0$^{23,27}$]hentetracontane-19',1''-cyclopropane]-2',4'(9'),5',7',16',24',26'(40'),27',29'-nonaene-13',20',34',41'-tetronetrifluoroacetate (14). Yield 12.6 mg, (15%). Example 14: $^1$H NMR (METHANOL-d$_4$) δ: 8.40 (s, 2H), 8.20-8.29 (m, 1H), 7.90-8.14 (m, 1H), 7.74-7.84 (m, 2H), 7.58-7.74 (m, 2H), 7.27-7.54 (m, 3H), 7.01-7.22 (m, 1H), 5.93-6.48 (m, 5H), 4.94-5.31 (m, 2H), 4.53-4.87 (m, 1H), 3.54-3.81 (m, 3H), 3.40-4.42 (m, 8H), 2.77-3.21 (m, 10H), 2.27-2.75 (m, 7H), 1.53-2.20 (m, 7H), 1.03-1.45 (m, 5H), 0.59-1.03 (m, 5H), 0.04-0.58 (m, 3H). LC/MS-R$_t$=3.94 (M+H)$^+$=887, (>95%).

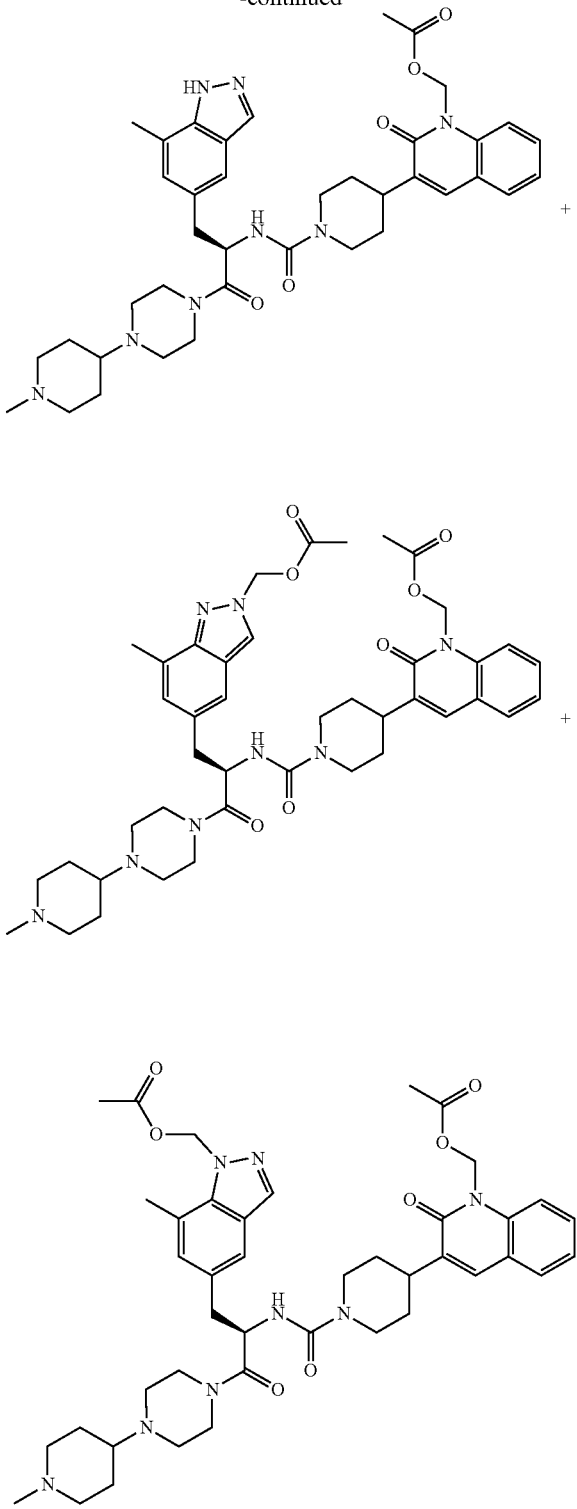

Acetic acid 7-methyl-5-(3-[4-(1-methyl-piperidin-4-yl)-piperazin-1-yl]-3-oxo-2-{[4-(2-oxo-1,2-dihydro-quinolin-3-yl)-piperidine-1-carbonyl]-amino}-propyl)-indazol-1-ylmethyl ester (15). A suspension of (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl) piperidine-1-carboxamide, (100 mg, 0.157 mmol) in DMF (3 mL) was treated with lithium hexamethyldisilylamide (1.0 M in THF, 0.24 mL, 0.24 mmol) under $N_2$ and stirred for 30 minutes. Chloromethyl acetate (39 mg, 0.31 mmol) in DMF (0.5 mL) was added via syringe and the mixture was stirred for 18 h. The reaction was quenched with a few drops of saturated $NH_4Cl$ and purified directly by RP-HPLC twice (Method B) to get the pure product separated from isomers as a white solid (5 mg, 5% yield). $^1H$ NMR (DMSO-$d_6$) δ: 11.75 (s, 1H), 8.40 (s, 1H), 7.61-7.64 (m, 1H), 7.54 (s, 1H), 7.37-7.43 (m, 2H), 7.23-7.27 (m, 1H), 7.14-7.18 (m, 1H), 7.01 (s, 1H), 6.83 (br d, J=7.6 Hz, 1H), 6.26 (s, 2H), 4.71-4.78 (m, 1H), 4.06-4.14 (m, 2H), 3.24-3.95 (m, 15H), 2.79-2.99 (m, 4H), 2.66-2.79 (m, 4H), 2.22 (s, 3H), 2.04 (s, 3H), 1.66-1.78 (m, 4H), 1.25-1.31 (m, 2H). $(M+H)^+=711$, purity >95%.

Acetic acid 7-methyl-5-(3-[4-(1-methyl-piperidin-4-yl)-piperazin-1-yl]-3-oxo-2-{[4-(2-oxo-1,2-dihydro-quinolin-3-yl)-piperidine-1-carbonyl]-amino}-propyl)-indazol-2-ylmethyl ester (16). The target compound was purified twice from the above reaction mixture by RP-HPLC (Method B) as a white solid (5 mg, 5% yield). $^1H$ NMR (DMSO-$d_6$) δ: 11.75 (s, 1H), 8.11 (s, 1H), 7.51-7.74 (m, 2H), 7.32-7.51 (m, 2H), 7.02-7.32 (m, 3H), 6.82 (br d, J=7.6 Hz, 1H), 6.38 (s, 2H), 4.72-4.80 (m, 1H), 3.98-4.24 (m, 2H), 3.13-3.71 (m, 12H), 2.80-3.03 (m, 4H), 2.56-2.80 (m, 4H), 2.56 (s, 3H), 2.25 (s, 3H), 1.97 (s, 3H), 1.62-1.87 (m, 4H), 1.19-1.38 (m, 2H). $(M+H)^+=711$, purity >95%.

Acetic acid 3-(1-{1-(7-methyl-1H-indazol-5-ylmethyl)-2-[4-(1-methyl-piperidin-4-yl)-piperazin-1-yl]-2-oxo-ethyl-carbamoyl}-piperidin-4-yl)-2-oxo-2H-quinolin-1-ylmethyl ester (17). The target compound was purified twice from the reaction mixture by RP-HPLC (Method B) as a white solid (5 mg, 5% yield). $^1H$ NMR (DMSO-$d_6$) δ: 13.05 (s, 1H), 7.98 (s, 1H), 7.65-7.83 (m, 2H), 7.45-7.64 (m, 2H), 7.40 (s, 1H), 7.17-7.36 (m, 1H), 7.07 (s, 1H), 6.68-7.00 (m, 1H), 6.25 (s, 2H), 4.71-4.80 (m, 1H), 3.98-4.20 (m, 2H), 3.56-3.91 (m, 16H), 2.81-3.10 (m, 4H), 2.60-2.81 (m, 5H), 2.53 (s, 3H), 2.03 (s, 3H), 1.45-1.85 (m, 2H), 1.13-1.45 (m, 2H). $(M+H)^+=711$, purity >95%.

Acetic acid 5-{2-{[4-(1-acetoxymethyl-2-oxo-1,2-dihydro-quinolin-3-yl)-piperidine-1-carbonyl]-amino}-3-[4-(1-methyl-piperidin-4-yl)-piperazin-1-yl]-3-oxo-propyl}-7-methyl-indazol-2-ylmethyl ester (18). The target compound was purified twice from above reaction mixture by RP-HPLC (Method B) as a white solid (4 mg, 4% yield). $^1H$ NMR (DMSO-$d_6$) δ: 8.40 (s, 1H), 7.73 (dd, J=7.6, 1.8 Hz, 1H), 7.66 (s, 1H), 7.52-7.62 (m, 1H), 7.48 (d, J=8.2 Hz, 1H), 7.18-7.42 (m, 2H), 7.01 (s, 1H), 6.84 (br d, J=7.6 Hz, 1H), 6.26 (s, 4H), 4.71-4.81 (m, 1H), 3.94-4.24 (m, 2H), 3.31-3.62 (m, 15H), 2.81-3.02 (m, 4H), 2.61-2.80 (m, 4H), 2.25 (m, 3H), 2.08 (s, 3H), 2.04 (s, 3H), 1.54-1.82 (m, 4H), 1.20-1.38 (m, 2H). $(M+H)^+=783$, purity >95%.

Acetic acid 5-{2-{[4-(1-acetoxymethyl-2-oxo-1,2-dihydro-quinolin-3-yl)-piperidine-1-carbonyl]-amino}-3-[4-(1-methyl-piperidin-4-yl)-piperazin-1-yl]-3-oxo-propyl}-7-methyl-indazol-1-ylmethyl ester (19). The target compound was purified twice from the above reaction mixture by RP-HPLC (Method B) as a white solid (3 mg, 3% yield). $^1H$ NMR (DMSO-$d_6$) δ: 8.11 (s, 1H), 7.65-7.78 (m, 2H), 7.52-7.65 (m, 1H), 7.42-7.52 (m, 2H), 7.23-7.26 (m, 1H), 7.19 (s, 1H), 6.84 (br d, J=7.6 Hz, 1H), 6.38 (s, 2H), 6.25 (s, 2H), 4.65-4.84 (m, 1H), 3.97-4.24 (m, 4H), 3.53-3.80 (m, 10H), 2.81-3.05 (m, 4H), 2.65-2.90 (m, 4H), 2.65 (s, 3H), 2.26 (s, 3H), 2.05 (s, 3H), 1.98 (m, 3H), 1.72-1.81 (m, 4H), 1.21-1.41 (m, 2H). $(M+H)^+=783$, purity >95%.

Examples 20-22

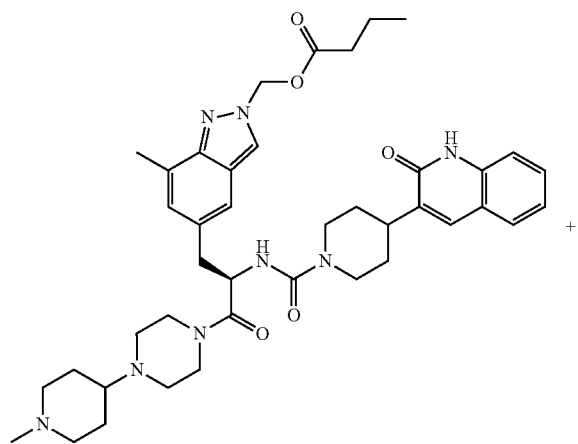

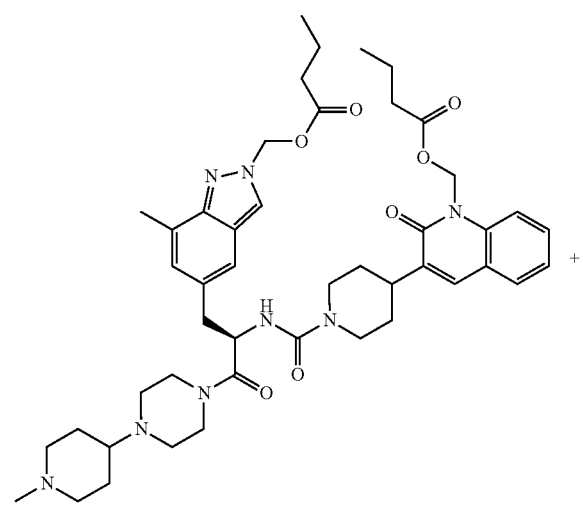

Butyric acid 7-methyl-5-(3-[4-(1-methyl-piperidin-4-yl)-piperazin-1-yl]-3-oxo-2-{[4-(2-oxo-1,2-dihydro-quinolin-3-yl)-piperidine-1-carbonyl]-amino}-propyl)-indazol-2-ylmethyl ester (20) was prepared from (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide, by the same procedure as the Examples 15-19 above on a 90 mg scale (15 mg, 15% yield). $^1$H NMR (DMSO-$d_6$) δ: 11.75 (s, 1H), 8.41 (s, 1H), 7.57-7.73 (m, 1H), 7.52 (s, 1H), 7.32-7.48 (m, 2H), 7.25 (d, J=8.2 Hz, 1H), 7.07-7.21 (m, 1H), 7.01 (s, 1H), 6.90 (br d, J=7.6 Hz, 1H), 6.25 (s, 2H), 4.72-4.83 (m, 1H), 3.91-4.22 (m, 2H), 3.35-3.65 (m, 15H), 2.82-3.05 (m, 4H), 2.58-2.82 (m, 4H), 2.25 (s, 3H), 2.20-2.30 (m, 2H), 1.57-1.87 (m, 4H), 1.38-1.57 (m, 2H), 1.18-1.30 (m, 2H), 0.80 (t, J=7.2 Hz, 3H). (M+H)$^+$=739, purity >95%.

Butyric acid 5-{2-{[4-(1-butyryloxymethyl-2-oxo-1,2-dihydro-quinolin-3-yl)-piperidine-1-carbonyl]-amino}-3-[4-(1-methyl-piperidin-4-yl)-piperazin-1-yl]-3-oxo-propyl}-7-methyl-indazol-2-ylmethyl ester (21). The target compound was purified twice from the reaction mixture by RP-HPLC (Method B) as a white solid (17 mg, 14% yield). $^1$H NMR (DMSO-$d_6$) δ: 8.41 (s, 1H), 7.74 (dd, J=7.9, 1.5 Hz, 1H), 7.62 (s, 1H), 7.51-7.61 (m, 1H), 7.42-7.51 (m, 1H), 7.37 (s, 1H), 7.25-7.31 (m, 1H), 7.01 (s, 1H), 6.84 (br d, J=7.6 Hz, 1H), 6.28 (s, 4H), 4.71-4.81 (m, 1H), 4.02-4.27 (m, 2H), 3.23-3.60 (m, 15H), 2.81-3.01 (m, 4H), 2.60-2.81 (m, 4H), 2.42 (s, 3H), 2.17-2.36 (m, 4H), 1.59-1.86 (m, 4H), 1.33-1.59 (m, 4H), 1.21-1.33 (m, 2H), 0.64-0.94 (m, 6H). (M+H)$^+$=839, purity >95%.

Butyric acid 5-{2-{[4-(1-butyryloxymethyl-2-oxo-1,2-dihydro-quinolin-3-yl)-piperidine-1-carbonyl]-amino}-3-[4-(1-methyl-piperidin-4-yl)-piperazin-1-yl]-3-oxo-propyl}-7-methyl-indazol-1-ylmethyl ester (22). The target compound was purified twice from the reaction mixture by RP-HPLC (Method B) as a white solid (23 mg, 19% yield). $^1$H NMR (DMSO-$d_6$) δ: 8.11 (s, 1H), 7.63-7.74 (m, 2H), 7.54-7.60 (m, 1H), 7.44-7.50 (m, 2H), 7.29 (t, J=7.3 Hz, 1H), 7.18 (s, 1H), 6.84 (br d, J=7.6 Hz, 1H), 6.40 (s, 2H), 6.27 (br s, 2H), 4.72-4.80 (m, 1H), 4.04-4.17 (m, 2H), 3.27-3.73 (m, 15H), 2.82-3.05 (m, 4H), 2.65-2.82 (m, 4H), 2.61 (s, 3H), 2.11-2.35 (m, 4H), 1.59-1.87 (m, 4H), 1.36-1.59 (m, 4H), 1.09-1.38 (m, 2H), 0.65-0.95 (m, 6H). (M+H)$^+$=840, purity >95%.

Examples 22-25

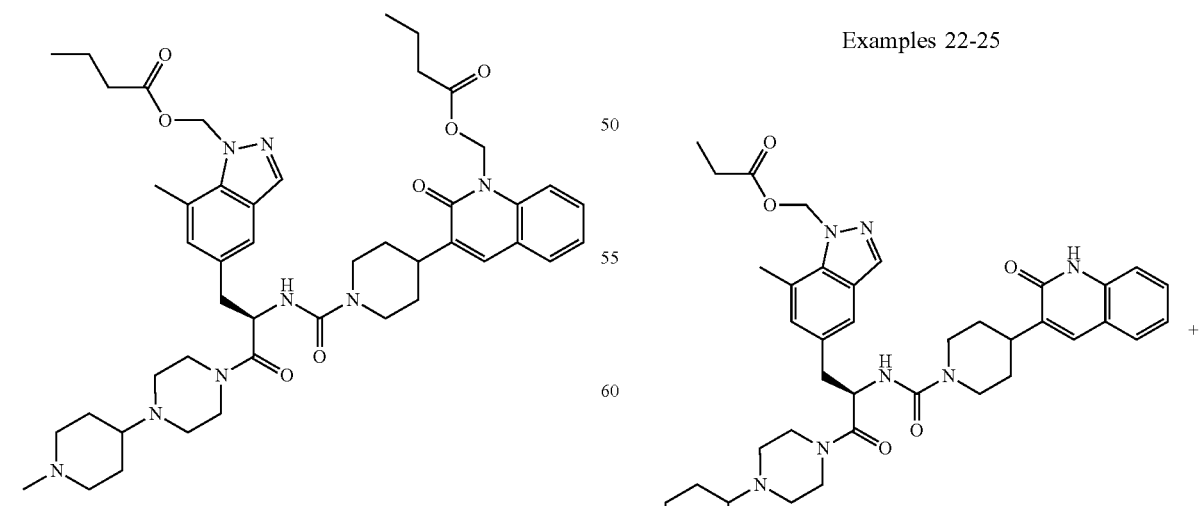

-continued

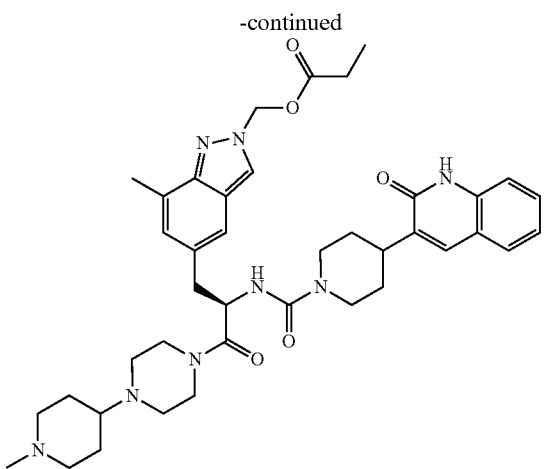

+

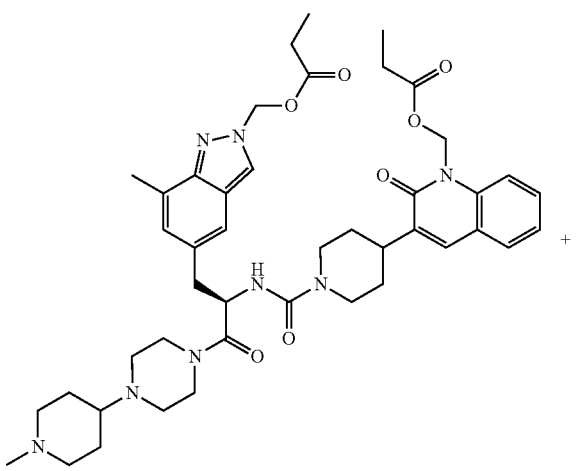

+

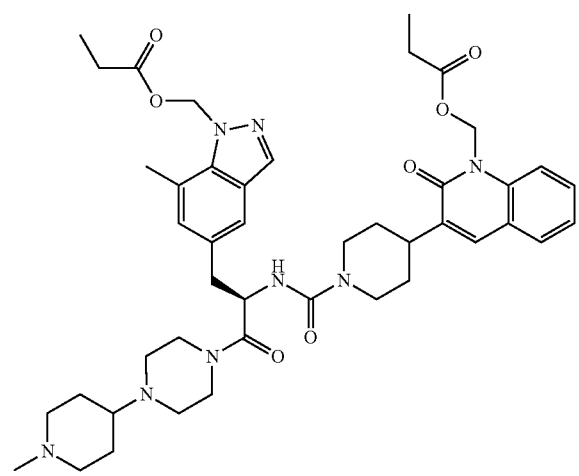

Propionic acid 7-methyl-5-(3-[4-(1-methyl-piperidin-4-yl)-piperazin-1-yl]-3-oxo-2-{[4-(2-oxo-1,2-dihydro-quinolin-3-yl)-piperidine-1-carbonyl]-amino}-propyl)-indazol-1-ylmethyl ester (22) was prepared from (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide, by the same procedure as above on 60 mg scale purified by Method B to yield a white solid (21 mg, 31% yield). $^1$H NMR (DMSO-$d_6$) δ: 11.76 (s, 1H), 8.41 (s, 1H), 7.63 (dd, J=7.9, 1.5 Hz, 1H), 7.53 (s, 1H), 7.36-7.45 (m, 2H), 7.25 (d, J=7.6 Hz, 1H), 7.08-7.20 (m, 1H), 7.01 (s, 1H), 6.70-6.93 (m, 1H), 6.27 (s, 2H), 4.70-4.82 (m, 1H), 4.05-4.15 (m, 2H), 3.28-3.62 (m, 15H), 2.80-3.01 (m, 4H), 2.58-2.78 (m, 4H), 2.51 (s, 3H), 2.22-2.34 (m, 2H), 1.60-1.79 (m, 4H), 1.20-1.31 (m, 2H), 0.96 (t, J=7.3 Hz, 3H). (M+H)$^+$=725, purity >95%.

Propionic acid 7-methyl-5-(3-[4-(1-methyl-piperidin-4-yl)-piperazin-1-yl]-3-oxo-2-{[4-(2-oxo-1,2-dihydro-quinolin-3-yl)-piperidine-1-carbonyl]-amino}-propyl)-indazol-2-ylmethyl ester (23). The target compound was purified twice from the reaction mixture by RP-HPLC (Method B) as a white solid (13 mg, 19% yield). $^1$H NMR (DMSO-$d_6$) δ: 11.76 (s, 1H), 8.11 (s, 1H), 7.60 (dd, J=8.2, 1.2 Hz, 1H), 7.54 (s, 1H), 7.33-7.52 (m, 2H), 7.25 (d, J=8.2 Hz, 1H), 7.05-7.22 (m, 2H), 6.74-6.94 (m, 1H), 6.40 (s, 2H), 4.60-4.91 (m, 1H), 3.99-4.21 (m, 2H), 3.35-3.65 (m, 15H), 2.82-3.05 (m, 6H), 2.65-2.82 (m, 4H), 2.61 (s, 3H), 1.60-1.79 (m, 4H), 1.20-1.41 (m, 2H), 0.96 (t, J=7.3 Hz, 3H). (M+H)$^+$=726, purity >95%.

Propionic acid 7-methyl-5-(3-[4-(1-methyl-piperidin-4-yl)-piperazin-1-yl]-3-oxo-2-{[4-(2-oxo-1-propionyloxymethyl-1,2-dihydro-quinolin-3-yl)-piperidine-1-carbonyl]-amino}-propyl)-indazol-2-ylmethyl ester (24). The target compound was purified twice from the reaction mixture by RP-HPLC (Method B) as a white solid (16 mg, 21% yield). $^1$H NMR (DMSO-$d_6$) δ: 8.41 (s, 1H), 7.73 (dd, J=7.9, 1.5 Hz, 1H), 7.65 (s, 1H), 7.54-7.60 (m, 1H), 7.47 (d, J=8.2 Hz, 1H), 7.37 (s, 1H), 7.30 (t, J=7.0 Hz, 1H), 7.00 (s, 1H), 6.73-6.94 (m, 1H), 6.27 (s, 4H), 4.63-4.89 (m, 1H), 4.01-4.23 (m, 2H), 3.28-3.58 (m, 11H), 2.81-3.09 (m, 6H), 2.58-2.81 (m, 6H), 2.47 (s, 3H), 2.18-2.39 (m, 4H), 1.55-1.85 (m, 4H), 1.11-1.44 (m, 2H), 0.84-1.10 (m, 6H). (M+H)$^+$=811, purity >95%.

Propionic acid 7-methyl-5-(3-[4-(1-methyl-piperidin-4-yl)-piperazin-1-yl]-3-oxo-2-{[4-(2-oxo-1-propionyloxymethyl-1,2-dihydro-quinolin-3-yl)-piperidine-1-carbonyl]-amino}-propyl)-indazol-1-ylmethyl ester (25). The target compound was purified twice from the reaction mixture by RP-HPLC (Method B) as a white solid (22 mg, 19% yield). $^1$H NMR (DMSO-$d_6$) δ: 8.11 (s, 1H), 7.71 (d, J=7.5 Hz, 1H), 7.66 (s, 1H), 7.52-7.62 (m, 1H), 7.41-7.52 (m, 2H), 7.22-7.38 (m, 1H), 7.18 (s, 1H), 6.85 (br d, J=6.4 Hz, 1H), 6.40 (s, 2H), 6.27 (s, 2H), 4.85-4.91 (m, 1H), 4.05-4.18 (m, 2H), 3.30-3.45 (m, 11H), 2.83-3.01 (m, 6H), 2.66-2.83 (m, 6H), 2.61 (s, 3H), 2.21-2.38 (m, 4H), 1.60-1.81 (m, 4H), 1.11-1.38 (m, 2H), 0.80-1.09 (m, 6H). (M+H)$^+$=812, purity >95%.

Examples 26-27

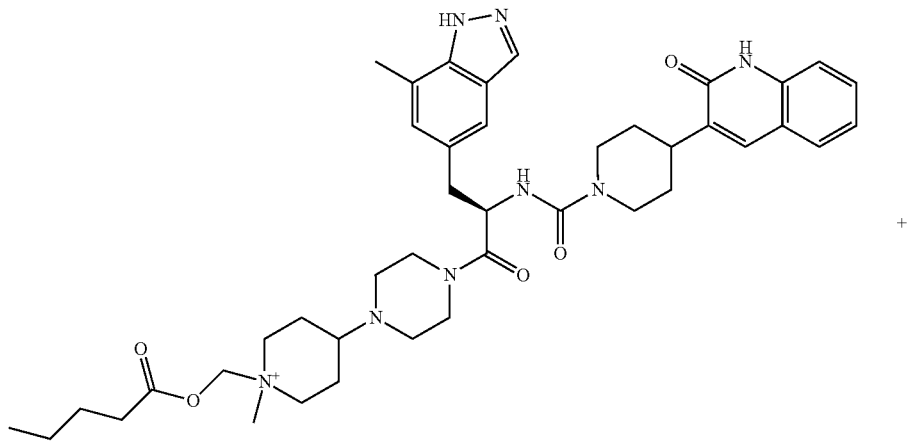

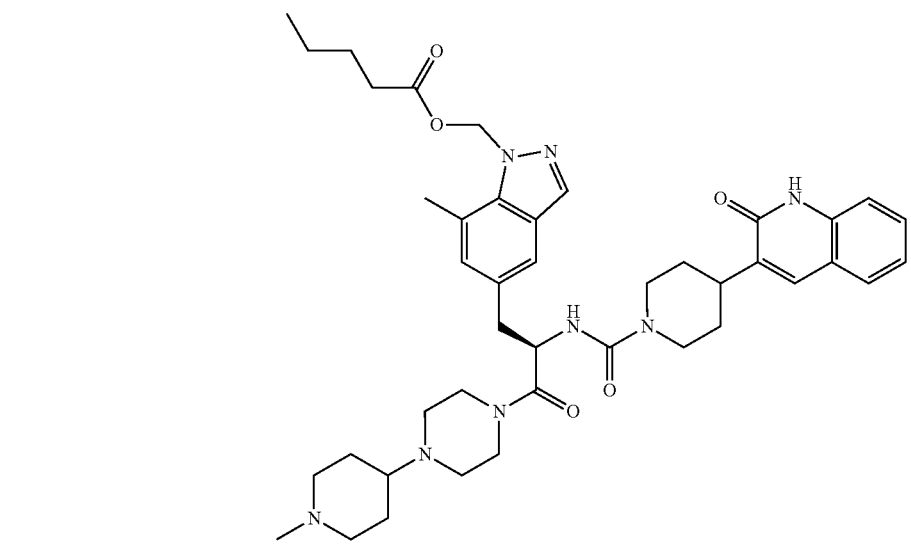

1-Methyl-4-[4-(3-(7-methyl-1H-indazol-5-yl)-2-{[4-(2-oxo-1,2-dihydro-quinolin-3-yl)-piperidine-1-carbonyl]-amino}-propionyl)-piperazin-1-yl]-1-pentanoyloxymethyl-piperidinium (26) was prepared from (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl) piperidine-1-carboxamide, by the same procedure as above at 60 mg scale and purified by Method B to yield a white solid (5 mg, 7% yield). $^1$H NMR (DMSO-d$_6$) δ: 13.06 (br d, J=1.8 Hz, 1H), 11.76 (s, 1H), 7.98 (d, J=2.9 Hz, 1H), 7.49-7.78 (m, 2H), 7.33-7.49 (m, 2H), 7.20-7.33 (m, 1H), 6.98-7.20 (m, 2H), 6.64-6.98 (m, 1H), 5.35 (s, 1H), 5.29 (s, 1H), 4.64-4.86 (m, 1H), 4.03-4.23 (m, 2H), 3.25-3.62 (m, 11H), 3.02 (s, 3H), 2.80-2.95 (m, 4H), 2.60-2.80 (m, 3H), 2.45-2.60 (m, 7H), 1.69-2.08 (m, 4H), 1.48-1.63 (m, 2H), 1.11-1.41 (m, 4H), 0.87 (t, J=7.3 Hz, 3H). (M+H)$^+$=753, purity >95%.

Pentanoic acid 7-methyl-5-(3-[4-(1-methyl-piperidin-4-yl)-piperazin-1-yl]-3-oxo-2-{[4-(2-oxo-1,2-dihydro-quinolin-3-yl)-piperidine-1-carbonyl]-amino}-propyl)-indazol-1-ylmethyl ester (27). The target compound was purified twice from the reaction mixture by RP-HPLC (Method B) as a white solid (7 mg, 10% yield). $^1$H NMR (DMSO-d$_6$) δ: 11.75 (s, 1H), 8.11 (s, 1H), 7.61 (d, J=6.4 Hz, 1H), 7.35-7.56 (m, 3H), 7.25 (d, J=8.8 Hz, 1H), 7.09-7.21 (m, 2H), 6.70-6.99 (m, 1H), 6.40 (s, 2H), 4.61-4.86 (m, 1H), 3.89-4.24 (m, 2H), 3.25-3.63 (m, 17H), 2.79-3.02 (m, 4H), 2.65-2.79 (m, 4H), 2.61 (s, 3H), 2.11-2.22 (t, J=7.3 Hz, 2H), 1.62-1.87 (m, 2H), 1.35-1.45 (m, 2H), 1.12-1.32 (m, 4H), 0.87 (t, J=7.3 Hz, 3H). (M+H)$^+$=754, purity >95%.

Example 28-30

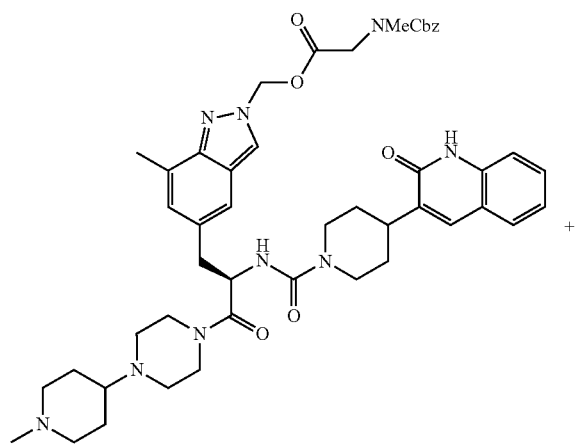

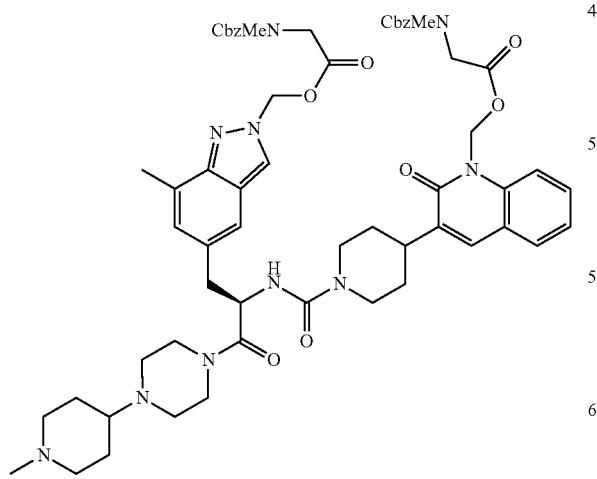

(Benzyloxycarbonyl-methyl-amino)-acetic acid 7-methyl-5-(3-[4-(1-methyl-piperidin-4-yl)-piperazin-1-yl]-3-oxo-2-{[4-(2-oxo-1,2-dihydro-quinolin-3-yl)-piperidine-1-carbonyl]-amino}-propyl)-indazol-2-ylmethyl ester (28) was prepared from (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide, by the same procedure as the example above at 120 mg scale and purified by Method B as a white solid (4 mg, 2% yield). $^1$H NMR (DMSO-d$_6$) δ: 11.75 (s, 1H), 8.39 (d, J=14.1 Hz, 1H), 7.55-7.65 (m, 2H), 7.22-7.48 (m, 7H), 7.10-7.20 (m, 2H), 7.00 (s, 1H), 6.75-6.85 (m, 1H), 6.25 (s, 2H), 5.05 (s, 1H), 4.95 (s, 1H), 4.70-4.80 (m, 1H), 4.03-4.38 (m, 4H), 3.05-3.60 (m, 13H), 2.79-3.02 (m, 8H), 2.65-2.79 (m, 6H), 2.45 (s, 3H), 1.63-1.80 (m, 2H), 1.19-1.38 (m, 2H). (M+H)$^+$=874, purity >95%.

(Benzyloxycarbonyl-methyl-amino)-acetic acid 3-(1-{1-(7-methyl-1H-indazol-5-ylmethyl)-2-[4-(1-methyl-piperidin-4-yl)-piperazin-1-yl]-2-oxo-ethylcarbamoyl}-piperidin-4-yl)-2-oxo-2H-quinolin-1-ylmethyl ester (29). The target compound was purified twice from the reaction mixture by RP-HPLC (Method B) to yield a white solid (4 mg, 2% yield). $^1$H NMR (DMSO-d$_6$) δ: 13.02 (br s, 1H), 7.98 (s, 1H), 7.61-7.81 (m, 2H), 7.56-7.61 (m, 1H), 7.40-7.50 (m, 1H), 7.21-7.40 (m, 7H), 7.05 (s, 1H), 6.78-6.85 (m, 1H), 6.34 (s, 2H), 5.00 (d, J=14.1 Hz, 2H), 4.68-4.80 (m, 1H), 4.03-4.38 (m, 4H), 3.05-3.43 (m, 13H), 2.82-2.99 (m, 8H), 2.60-2.79 (m, 6H), 2.45 (s, 3H), 1.68-1.80 (m, 2H), 1.21-1.38 (m, 2H). (M+H)$^+$=874, purity >95%.

{5-[(2R)-2-{[4-(1-{[(2-{[(benzyloxy)carbonyl](methyl)amino}acetyl)oxy]methyl}-2-oxo-1,2-dihydroquinolin-3-yl)piperidine-1-carbonyl]amino}-3-[4-(1-methylpiperidin-4-yl)piperazin-1-yl]-3-oxopropyl]-7-methyl-2H-indazol-2-yl}methyl 2-{[(benzyloxy)carbonyl](methyl)amino}acetate (30). The target compound was purified twice from the reaction mixture by RP-HPLC (Method B) as a white solid (18 mg, 9% yield). $^1$H NMR (DMSO-d$_6$) δ: 8.40 (d, J=14.1 Hz, 1H), 7.60-7.82 (m, 2H), 7.42-7.60 (m, 2H), 7.11-7.42 (m, 7H), 7.02 (s, 1H), 6.86 (br d, J=7.0 Hz, 1H), 6.20-6.46 (m, 4H), 5.05 (s, 2H), 4.96 (d, J=13.5 Hz, 2H), 4.81-4.72 (m, 1H), 3.88-4.46 (m, 16H), 3.54 (br d, J=11.1 Hz, 4H), 2.81-3.41 (m, 12H), 3.04 (br s, 3H), 2.05-2.20 (m, 2H), 1.54-1.83 (m, 4H), 1.20-1.41 (m, 2H). (M+H)$^+$=1110, purity >95%.

Example 31

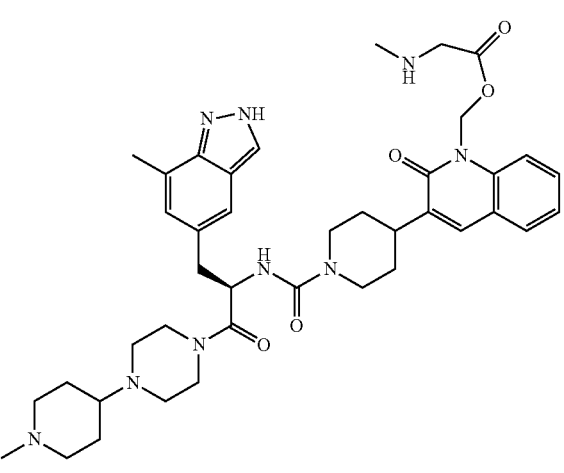 [SMILES: CNCC(=O)OCn1c(=O)c(C2CCN(C(=O)N[C@H](Cc3cc(C)c4n[nH]cc4c3)C(=O)N3CCN(C4CCN(C)CC4)CC3)CC2)cc2ccccc21]

Methylamino-acetic acid 3-(1-{1-(7-methyl-2H-indazol-5-ylmethyl)-2-[4-(1-methyl-piperidin-4-yl)-piperazin-1-yl]-2-oxo-ethylcarbamoyl}-piperidin-4-yl)-2-oxo-2H-quinolin-1-ylmethyl ester (31). To a solution of {5-[(2R)-2-{[4-(1-{[(2-{[(benzyloxy)carbonyl](methyl)amino}acetyl)oxy]methyl}-2-oxo-1,2-dihydroquinolin-3-yl)piperidine-1-carbonyl]amino}-3-[4-(1-methylpiperidin-4-yl)piperazin-1-yl]-3-oxopropyl}-7-methyl-2H-indazol-2-yl}methyl 2-{[(benzyloxy)carbonyl](methyl)amino}acetate, (24 mg, 0.022 mmol) in EtOAc (0.5 mL) and MeOH (0.5 mL) protected under $N_2$ was added 10% Pd—C (5 mg). Replacing the nitrogen by hydrogen balloon, the reaction mixture was degassed for 10 minutes and kept stirring under H2 and was monitored by LC-MS. The reaction was complete in 1 hour, filtered through celite and the filtrate was concentrated and the residue was purified by RP-HPLC (Method B) to yield a white solid (4 mg, 25%). $^1$H NMR (DMSO-$d_6$) δ: 13.02 (br s, 1H), 7.98 (s, 1H), 7.61-7.81 (m, 2H), 7.56-7.61 (m, 2H), 7.25-7.50 (m, 2H), 7.05 (s, 1H), 6.78-6.85 (m, 1H), 6.34 (s, 2H), 4.68-4.80 (m, 1H), 4.03-4.38 (m, 4H), 3.05-3.63 (m, 18H), 2.82-2.99 (m, 4H), 2.60-2.79 (m, 7H), 2.45 (s, 3H), 1.68-1.80 (m, 2H), 1.21-1.38 (m, 2H). $(M+H)^+$=740, purity >95%.

Example 32

Heptadecanoic acid 5-{2-{[4-(1-heptadecanoyloxymethyl-2-oxo-1,2-dihydro-quinolin-3-yl)-piperidine-1-carbonyl]-amino}-3-[4-(1-methyl-piperidin-4-yl)-piperazin-1-yl]-3-oxo-propyl}-7-methyl-indazol-2-ylmethyl ester (32). Added NaH (0.022 g, 0.705 mmol) to a solution of 2-(7-methyl-2H-indazol-5-ylmethyl)-1-[4-(1-methyl-piperidin-4-yl)-piperazin-1-yl]-4-[4-(2-oxo-1,2-dihydro-quinolin-3-yl)-piperidin-1-yl]-butane-1,4-dione (0.15 g, 0.235 mmol) at room temperature, under $N_2$ and magnetically stirred in 5 mL of DMF. Let stir until gas evolution ceased (2.5 hours) then added heptadecanoic acid chloromethyl ester (0.224 g, 0.705 mmol). Warmed to 70° C. for 3 hours, then cooled to room temperature and let stir for 72 hours. Concentrated reaction in vacuo. Purified with a 40 g silicel column, eluting with 0-10% MeOH (containing 3.5 N $NH_3$) in $CH_2Cl_2$. Re-purified using RP-HPLC eluting with 75-100% acetonitrile with 0.1% TFA. The product was lyophilized to yield 8 mg (2.6%). $^1$H NMR (METHANOL-$d_4$) δ: 8.30 (d, J=17.4 Hz, 1H), 7.45-7.86 (m, 5H), 7.29-7.44 (m, 2H), 7.01-7.10 (m, 1H), 6.20-6.47 (m, 4H), 4.53-4.64 (m, 1H), 3.95-4.27 (m, 2H), 3.70-3.93 (m, 1H), 3.48-3.68 (m, 3H), 3.36-3.42 (m, 1H), 3.16-3.28 (m, 2H), 2.92-3.13 (m, 6H), 2.62-2.84 (m, 4H), 2.55 (d, J=8.2 Hz, 2H), 2.00-2.43 (m, 6H), 1.66-1.96 (m, 5H), 1.40-1.65 (m, 7H), 1.27 (br s, 55H), 0.83-0.96 (m, 6H). LC/MS $(M+H)^+$=1203, purity=91%.

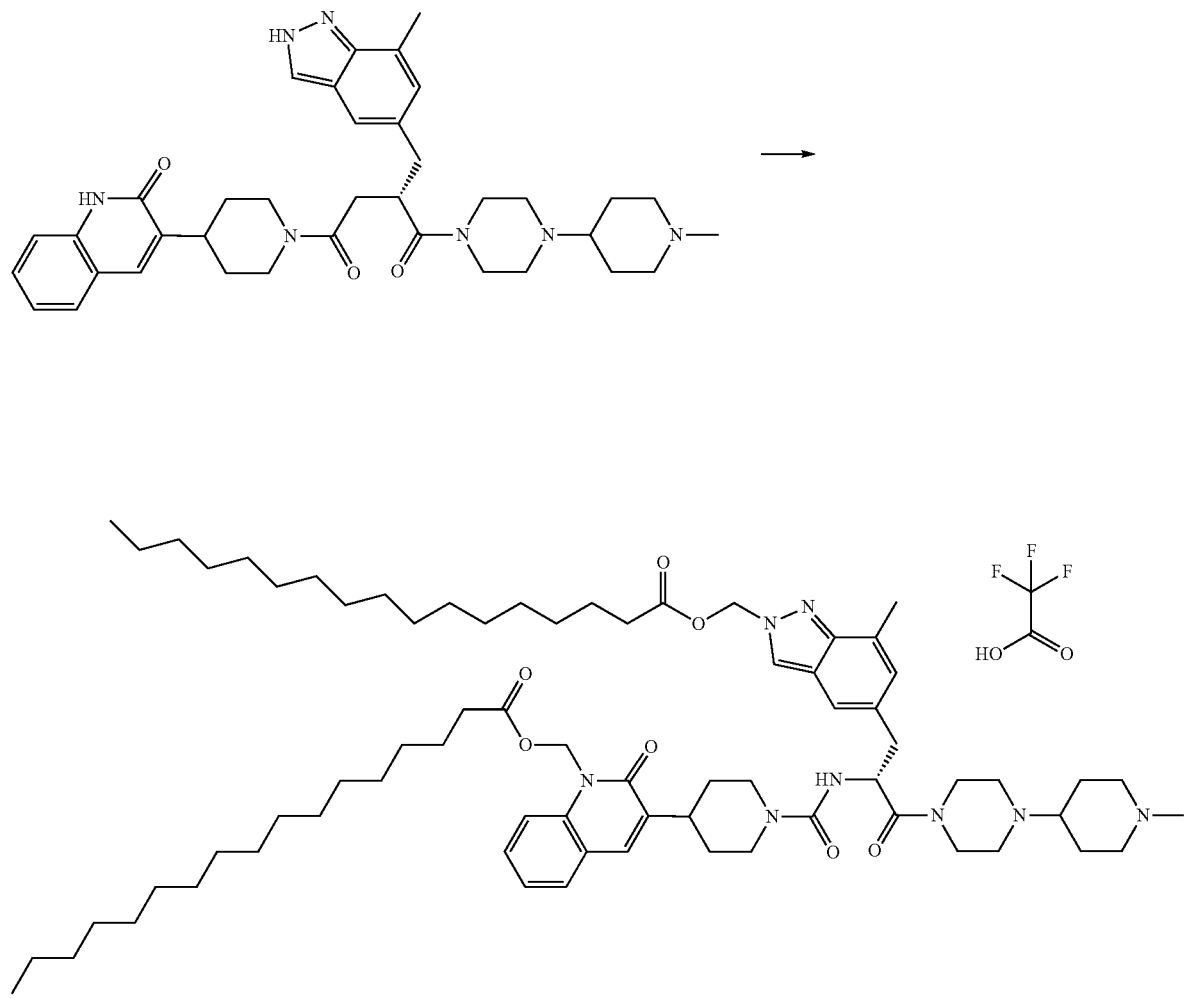

Example 33

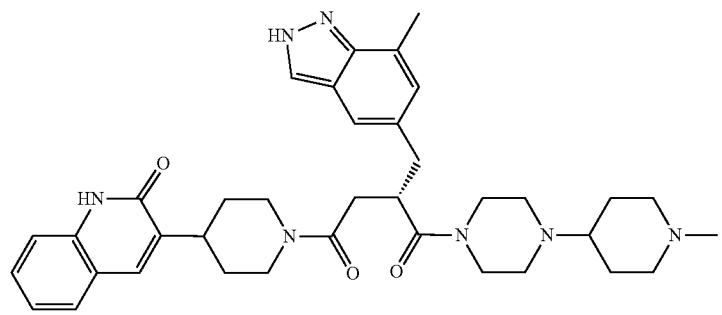

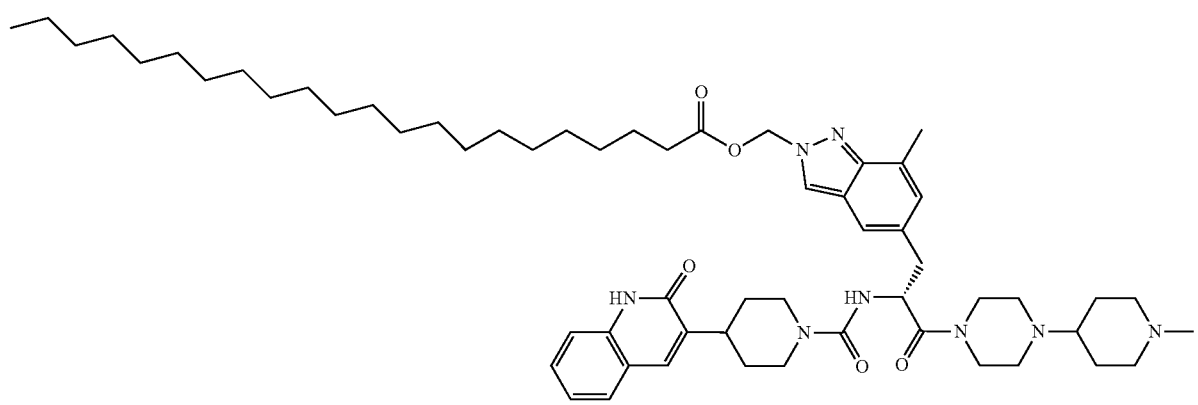

Docosanoic acid 7-methyl-5-(3-[4-(1-methyl-piperidin-4-yl)-piperazin-1-yl]-3-oxo-2-{[4-(2-oxo-1,2-dihydro-quinolin-3-yl)-piperidine-1-carbonyl]-amino}-propyl)-indazol-2-ylmethyl ester (33). NaH (0.008 g, 0.35 mmol) was added to a solution of 2-(7-methyl-2H-indazol-5-ylmethyl)-1-[4-(1-methyl-piperidin-4-yl)-piperazin-1-yl]-4-[4-(2-oxo-1,2-dihydro-quinolin-3-yl)-piperidin-1-yl]-butane-1,4-dione (0.15 g, 0.235 mmol) at room temperature, under $N_2$ and the reaction mixture was magnetically stirred in 5 mL of DMF. The reaction was allowed to stir for another 2.5 hours, until gas evolution ceased. Docosanoic acid chloromethyl ester (0.233 g, 0.235 mmol) was added, and the reaction was magnetically stirred for 72 hours at room temperature under $N_2$. The reaction was quenched with saturated $NH_4Cl$ (aq) and partitioned between $CHCl_3$ with 10% IPA and $H_2O$. The organic and aqueous layers were separated, and the aqueous layer was washed with 10% IPA, 90% $CHCl_3$. The combined organic layers were washed with brine, dried over $Na_2SO_4$, and concentrated in vacuo. The residue was purified on a 40 g column, eluting with 0-10% MeOH (containing 3.5 N $NH_3$)/$CH_2Cl_2$. The fractions containing the desired product were concentrated in vacuo. The residue was re-purified using RP-HPLC eluting with 45-95% ACN in $H_2O$ with 0.1% TFA holding at 95% ACN in $H_2O$ with 0.1% TFA. The product fractions were collected and concentrated in vacuo. The residue was re-dissolved in 30 mL of $CHCl_3$ and 10% IPA, and washed with saturated $NaHCO_3$ (aq) solution. The basic layer was then washed with IPA/$CHCl_3$ solution 2×20 mL. The organic layer was dried over $Na_2SO_4$, filtered, and concentrated in vacuo. The product was purified on a 12 g ISCO column eluting with 0-10% MeOH (containing 3.5 N $NH_3$)/$CH_2Cl_2$. The product fractions were concentrated in vacuo to yield the desired product. 49.3 mg (21%). $^1$H NMR (METHANOL-$d_4$) δ: 8.32 (s, 1H), 7.63-7.74 (m, 3H), 7.45-7.54 (m, 2H), 7.38 (s, 1H), 7.32 (d, J=8.2 Hz, 1H), 7.22-7.28 (m, 1H), 7.19-7.22 (m, 1H), 7.03 (s, 1H), 6.29 (dd, J=15.2, 10.6 Hz, 2H), 4.99 (t, J=7.7 Hz, 1H), 4.16 (s, 2H), 3.62-3.76 (m, 1H), 3.35-3.43 (m, 2H), 3.21-3.28 (m, 1H), 2.96-3.11 (m, 4H), 2.79-2.96 (m, 5H), 2.56 (s, 3H), 2.43-2.53 (m, 1H), 2.27-2.39 (m, 3H), 2.23 (s, 3H), 1.82-2.13 (m, 7H), 1.45-1.62 (m, 8H), 1.32-1.45 (m, 3H), 1.27 (s, 29H), 0.85-0.93 (m, 3H). LC/MS $R_t$=6.38 min/9 min. (M+H)$^+$=991 (97%).

Example 34

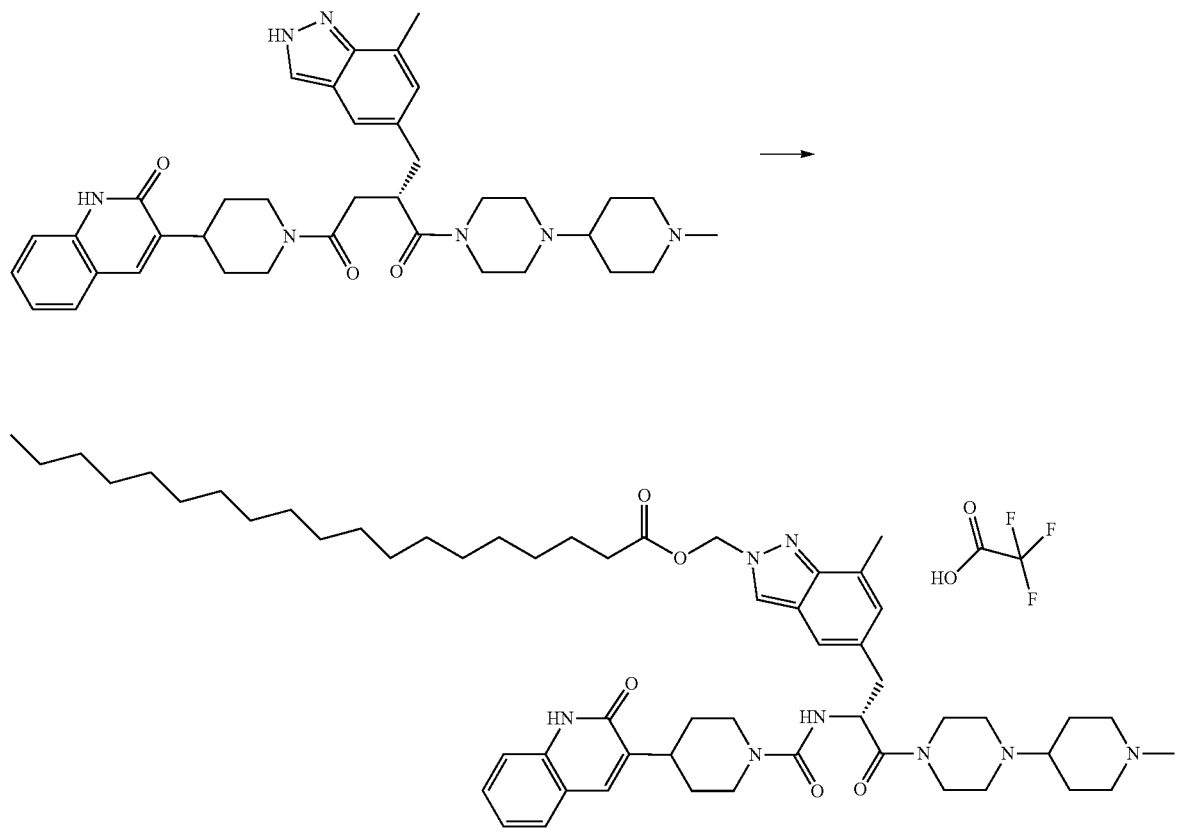

Nonadecanoic acid 7-methyl-5-(3-[4-(1-methyl-piperidin-4-yl)-piperazin-1-yl]-3-oxo-2-{[4-(2-oxo-1,2-dihydro-quinolin-3-yl)-piperidine-1-carbonyl]-amino}-propyl)-indazol-2-ylmethyl ester trifluoroacetate (34). Prepared in a similar manner as above to yield 77.4 mg (31%). $^1$H NMR (METHANOL-$d_4$) δ: 8.33 (s, 1H), 7.62-7.73 (m, 3H), 7.45-7.58 (m, 2H), 7.42 (s, 1H), 7.29-7.35 (m, 1H), 7.20-7.28 (m, 2H), 7.06 (s, 1H), 6.24-6.35 (m, 2H), 3.83-4.28 (m, 4H), 3.35-3.76 (m, 5H), 2.81-3.27 (m, 17H), 2.72 (s, 1H), 2.57 (s, 3H), 2.03-2.37 (m, 5H), 1.67-2.00 (m, 5H), 1.38-1.64 (m, 5H), 1.27 (s, 25H), 0.82-0.96 (m, 3H). LC/MS $R_t$=5.88, (M+H)$^+$=949 (>95%).

Example 35

Henicosanoic acid 7-methyl-5-(3-[4-(1-methyl-piperidin-4-yl)-piperazin-1-yl]-3-oxo-2-{[4-(2-oxo-1,2-dihydro-quinolin-3-yl)-piperidine-1-carbonyl]-amino}-propyl)-indazol-2-ylmethyl ester trifluoroacetate (35). Prepared by a similar procedure as above to yield 40.5 mg (16%). $^1$H NMR (METHANOL-$d_4$) δ: 8.26-8.37 (m, 1H), 7.65-7.73 (m, 2H), 7.55 (s, 1H), 7.45-7.53 (m, 1H), 7.37-7.44 (m, 1H), 7.29-7.35 (m, 1H), 7.24-7.28 (m, 1H), 7.03-7.08 (m, 1H), 6.24-6.35 (m, 2H), 6.22 (s, 1H), 4.93 (br d, J=9.1 Hz, 2H), 3.80-4.26 (m, 6H), 3.50-3.73 (m, 4H), 3.19-3.27 (m, 4H), 2.93-3.18 (m, 9H), 2.80-2.91 (m, 6H), 2.72 (s, 2H), 2.51-2.60 (m, 6H), 2.05-2.37 (m, 3H), 1.68-2.00 (m, 3H), 1.39-1.63 (m, 3H), 1.27 (s, 32H), 0.89 (s, 3H). LC/MS $R_t$=6.45 min, (M+H$^+$)=977 (99.1%).

Example 36

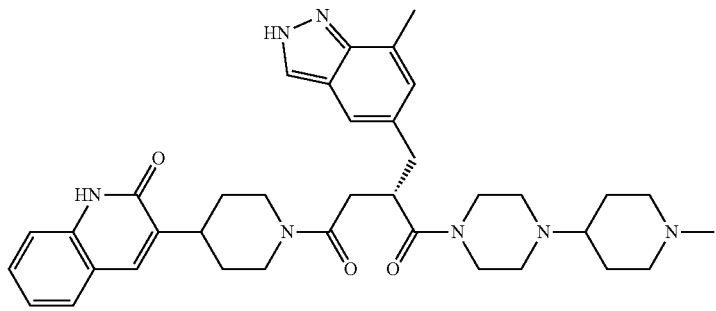

-continued
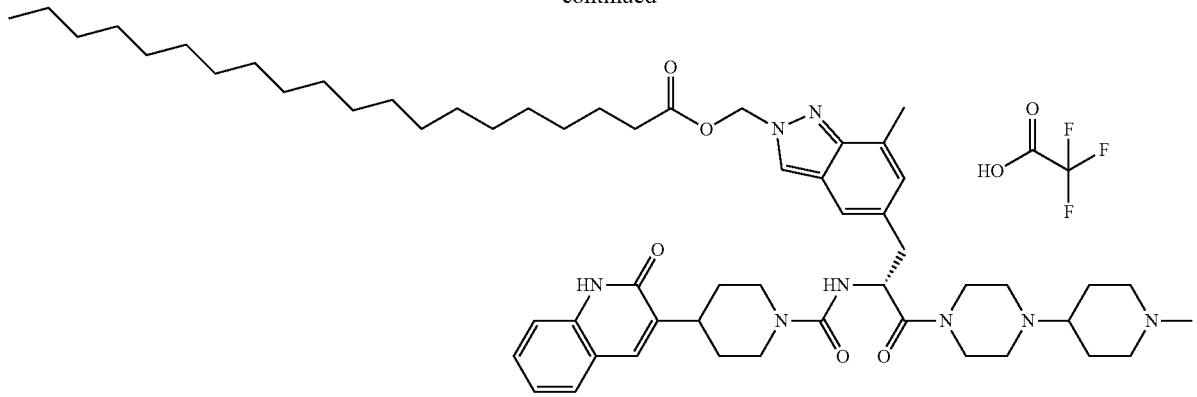
Icosanoic acid 7-methyl-5-(3-[4-(1-methyl-piperidin-4-yl)-piperazin-1-yl]-3-oxo-2-{[4-(2-oxo-1,2-dihydro-quinolin-3-yl)-piperidine-1-carbonyl]-amino}-propyl)-indazol-2-ylmethyl ester (36). Prepared in a similar way to the above products to yield 18.1 mg (18%). $^1$H NMR (METHANOL-$d_4$) δ: 7.66 (s, 1H), 7.45-7.54 (m, 1H), 7.41 (s, 1H), 7.32 (d, J=8.2 Hz, 1H), 7.20-7.28 (m, 1H), 7.06 (s, 1H), 6.29 (d, J=4.9 Hz, 2H), 4.94 (br d, J=8.0 Hz, 1H), 4.17 (br s, 2H), 3.74-4.00 (m, 1H), 3.56-3.70 (m, 2H), 3.35-3.56 (m, 1H), 2.92-3.17 (m, 6H), 2.82-2.91 (m, 4H), 2.57 (s, 3H), 2.32 (t, J=7.3 Hz, 2H), 2.05-2.21 (m, 1H), 1.88 (br s, 3H), 1.36-1.62 (m, 2H), 1.27 (s, 30H), 1.18 (s, 8H), 0.83-0.94 (m, 3H). LC/MS $R_t$=6.3 min, (M+H)$^+$=963 (93%).
Example 37
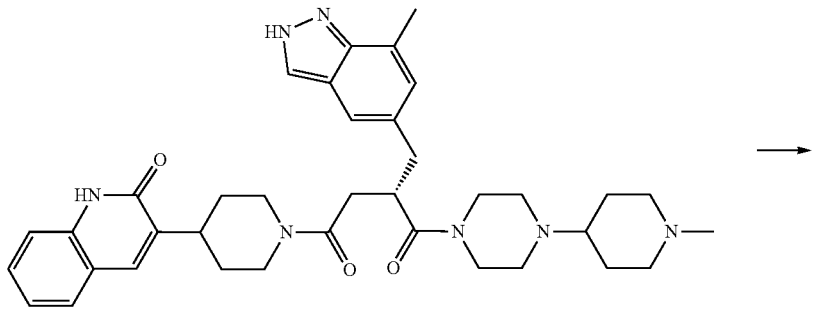
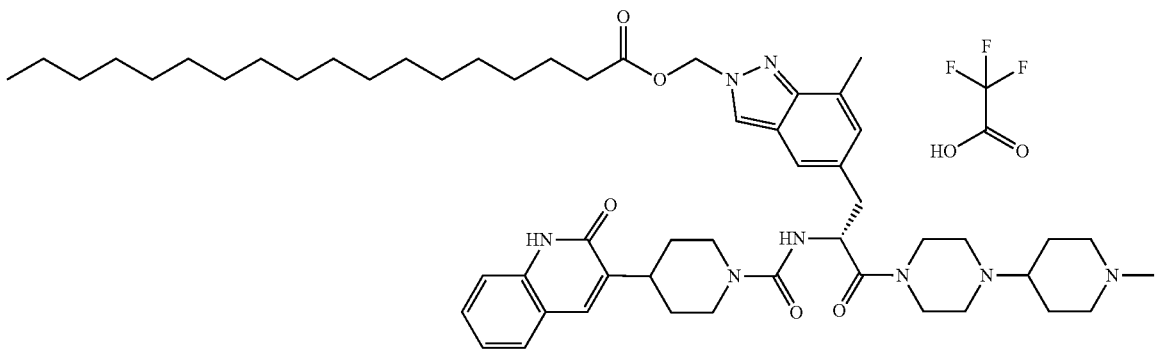

Octadecanoic acid 7-methyl-5-(3-[4-(1-methyl-piperidin-4-yl)-piperazin-1-yl]-3-oxo-2-{[4-(2-oxo-1,2-dihydro-quinolin-3-yl)-piperidine-1-carbonyl]-amino}-propyl)-indazol-2-ylmethyl ester; trifluoro-acetic acid (37). Prepare in a similar way to products above to yield 23.3 mg (9%). $^1$H NMR (METHANOL-$d_4$) δ: 8.33 (s, 1H), 8.06 (s, 1H), 7.62-7.74 (m, 2H), 7.44-7.59 (m, 1H), 7.32 (d, J=8.2 Hz, 1H), 7.18-7.29 (m, 1H), 7.06 (s, 1H), 6.24-6.35 (m, 2H), 4.94 (br d, J=12.8 Hz, 3H), 4.52-4.65 (m, 1H), 4.17 (br t, J=14.2 Hz, 2H), 3.87 (s, 2H), 3.47-3.72 (m, 4H), 3.33-3.42 (m, 1H), 3.16-3.27 (m, 2H), 2.96-3.13 (m, 6H), 2.88 (s, 3H), 2.72 (s, 3H), 2.57 (s, 3H), 2.05-2.39 (m, 3H), 1.68-1.98 (m, 3H), 1.37-1.66 (m, 3H), 1.27 (bs, 30H), 0.84-0.97 (m, 3H). LC/MS $R_t$=5.7 min, (M+H)$^+$=935 (>95%).

Example 38

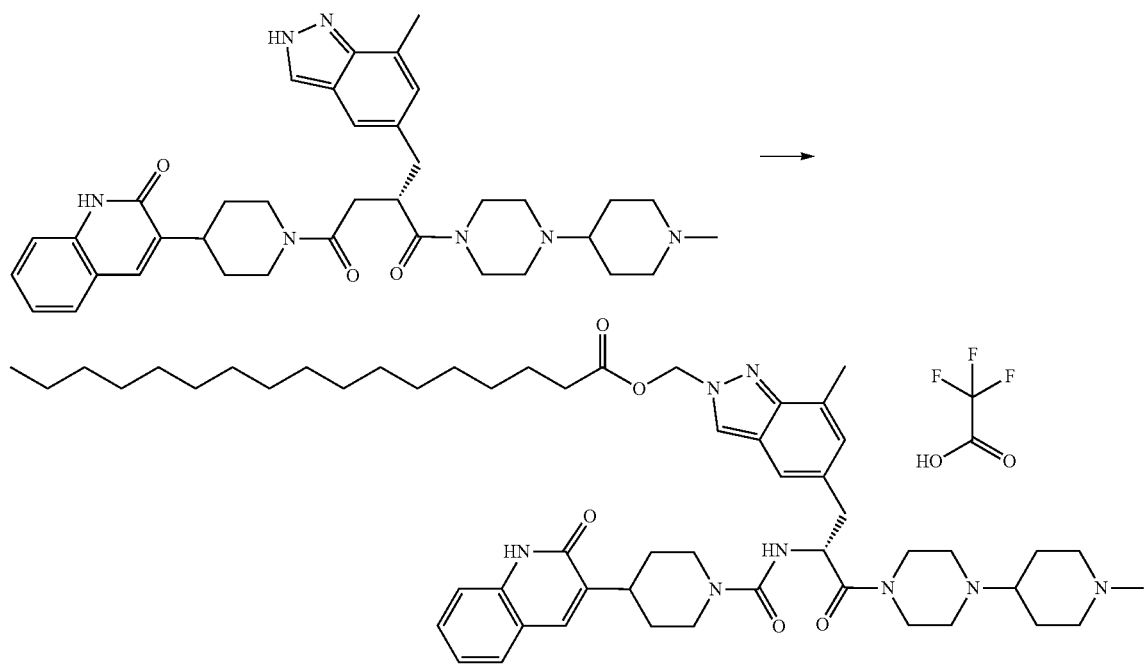

Heptadecanoic acid 7-methyl-5-(3-[4-(1-methyl-piperidin-4-yl)-piperazin-1-yl]-3-oxo-2-{[4-(2-oxo-1,2-dihydroquinolin-3-yl)-piperidine-1-carbonyl]-amino}-propyl)-indazol-2-ylmethyl ester trifluoroacetate (38). Prepared in a similar manner to products above to yield 30.7 mg (13%). $^1$H NMR (METHANOL-$d_4$) δ: 8.33 (s, 1H), 7.62-7.75 (m, 2H), 7.45-7.55 (m, 1H), 7.41 (s, 1H), 7.32 (d, J=8.2 Hz, 1H), 7.20-7.28 (m, 1H), 7.06 (t, J=1.4 Hz, 1H), 6.24-6.35 (m, 2H), 4.91-4.99 (m, 1H), 4.17 (br t, 2H), 3.73-4.02 (m, 2H), 3.46-3.71 (m, 2H), 3.35-3.43 (m, 4H) 3.20-3.27 (m, 4H), 2.88 (s, 6H), 2.57 (s, 3H), 2.22-2.38 (m, 3H), 2.13 (br d, J=11.9 Hz, 1H), 1.70-2.02 (m, 4H), 1.41-1.65 (m, 3H), 1.08-1.37 (m, 38H), 0.81-0.98 (m, 3H). LC/MS $R_t$=5.4 min., (M+H)$^+$=935 (>95%).

Example 39

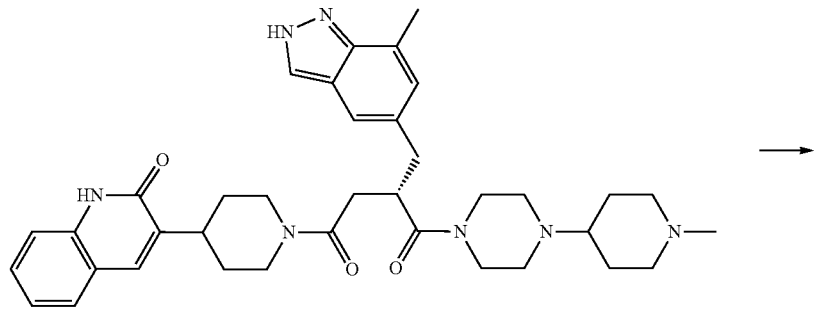

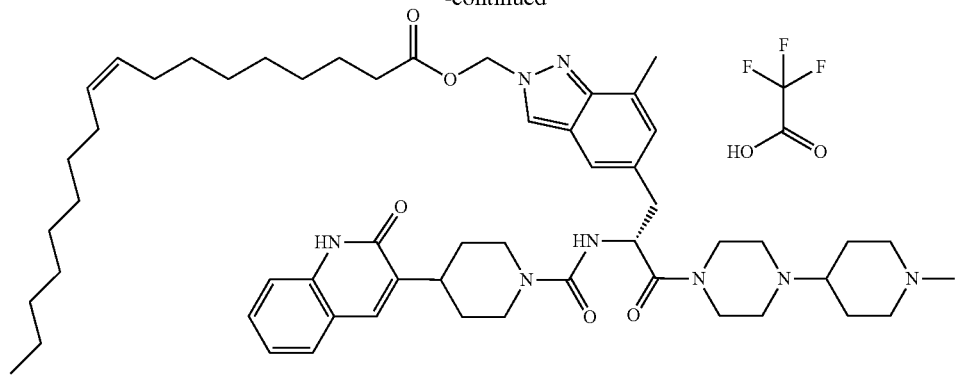

Octadec-9-enoic acid 7-methyl-5-(3-[4-(1-methyl-piperidin-4-yl)-piperazin-1-yl]-3-oxo-2-{[4-(2-oxo-1,2-dihydroquinolin-3-yl)-piperidine-1-carbonyl]-amino}-propyl)-indazol-2-ylmethyl ester trifluoroacetate (39). Prepared in a manner similar to products above to yield 13.1 mg (5.2%). $^1$H NMR (METHANOL-$d_4$) δ: 8.33 (s) and 8.06 (d, J=1.9 Hz) (1H), 7.64-7.72 (m, 2H), 7.46-7.53 (m, 1H), 7.41 (s, 1H), 7.32 (d, J=8.2 Hz, 1H), 7.20-7.29 (m, 1H), 7.06 (s, 1H), 6.24-6.37 (m, 2H), 5.26-5.38 (m, 2H), 4.92-5.04 (m, 2H), 4.17 (br t, J=13.5 Hz, 2H), 3.69-3.93 (m, 2H), 3.48-3.68 (m, 3H), 3.18-3.26 (m, 2H), 2.91-3.14 (m, 15H), 2.87 (s, 3H), 2.51-2.77 (m, 2H), 2.21-2.36 (m, 2H), 1.83-2.16 (m, 6H), 1.63-1.83 (m, 2H), 1.41-1.62 (m, 4H), 1.12-1.38 (m, 20H), 0.82-0.94 (m, 3H). LC/MS $R_t$=5.3 mins., (M+H)$^+$=935 (>95%).

Example 40

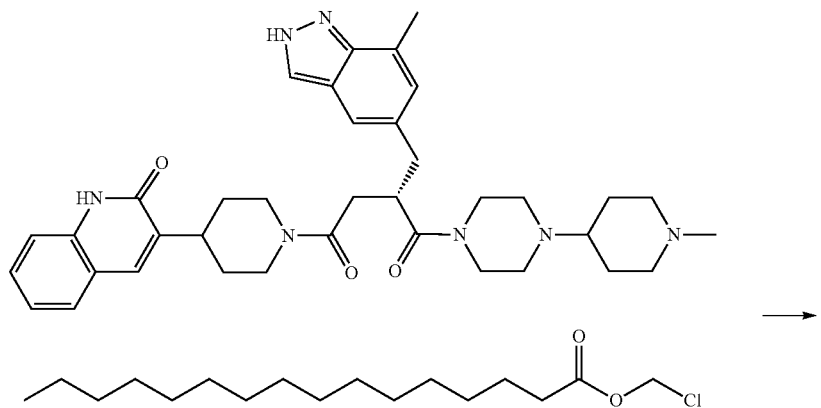

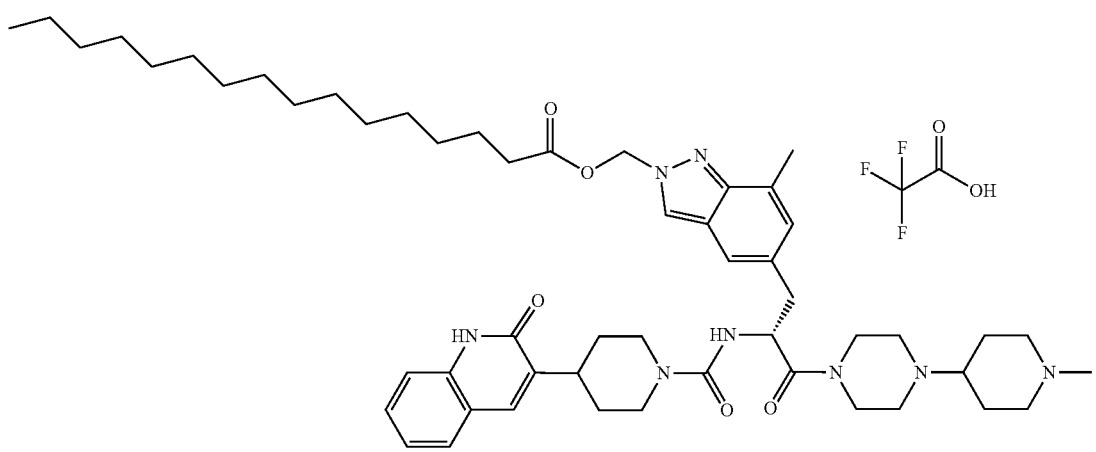

Hexadecanoic acid 7-methyl-5-(3-[4-(1-methyl-piperidin-4-yl)-piperazin-1-yl]-3-oxo-2-{[4-(2-oxo-1,2-dihydroquinolin-3-yl)-piperidine-1-carbonyl]-amino}-propyl)-indazol-2-ylmethyl ester trifluoroacetate (40). Prepared in a manner similar to products above to yield 17.3 mg (16%). $^{1}$H NMR (METHANOL-$d_4$) δ: 8.34 (s, 1H), 7.69 (dd, J=8.0, 1.4 Hz, 1H), 7.66 (s, 1H), 7.45-7.55 (m, 1H), 7.41 (s, 1H), 7.32 (d, J=8.2 Hz, 1H), 7.21-7.29 (m, 1H), 7.06 (s, 1H), 6.23-6.37 (m, 2H), 4.17 (br t, J=13.7 Hz, 2H), 3.71-3.97 (m, 2H), 3.48-3.70 (m, 3H), 3.36 (dd, J=10.2, 3.2 Hz, 1H), 2.94-3.18 (m, 8H), 2.90 (br d, J=2.6 Hz, 1H), 2.57 (s, 3H), 2.32 (t, J=7.3 Hz, 2H), 2.10 (br d, J=12.2 Hz, 1H), 1.69-1.98 (m, 4H), 1.38-1.62 (m, 4H), 1.09-1.36 (m, 25H), 0.83-0.95 (m, 3H). LC/MS $R_f$=5.2 min., (M+H)$^+$=907 (>95%).

Examples 41-42

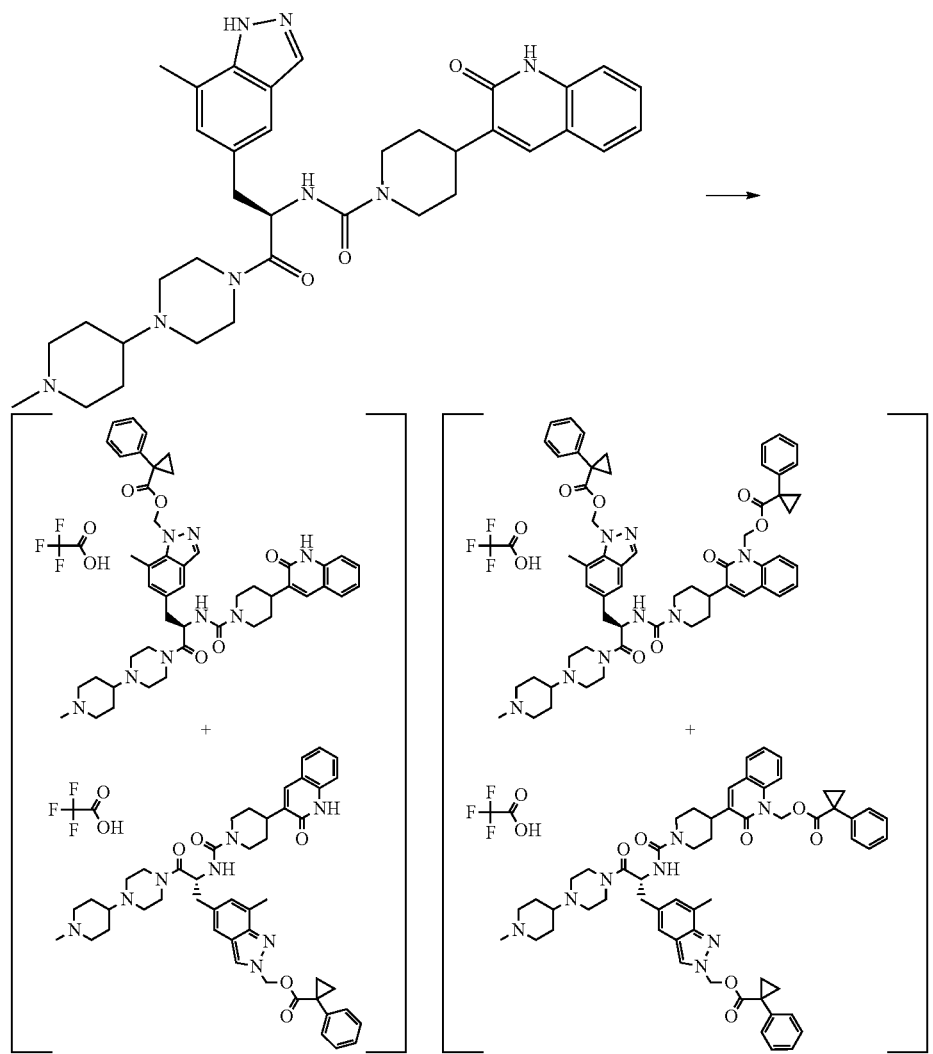

{7-methyl-5-[(2R)-3-[4-(1-methylpiperidin-4-yl)piperazin-1-yl]-3-oxo-2-{[4-(2-oxo-1,2-dihydroquinolin-3-yl)piperidine-1-carbonyl]amino}propyl]-1H-indazol-1-yl}methyl 1-phenylcyclopropane-1-carboxylate trifluoroacetate and {7-methyl-5-[(2R)-3-[4-(1-methylpiperidin-4-yl)piperazin-1-yl]-3-oxo-2-{[4-(2-oxo-1,2-dihydroquinolin-3-yl)piperidine-1-carbonyl]amino}propyl]-2H-indazol-2-yl}methyl 1-phenylcyclopropane-1-carboxylatetrifluoroacetate and {7-methyl-5-[(2R)-3-[4-(1-methylpiperidin-4-yl)piperazin-1-yl]-3-oxo-2-[(4-{2-oxo-1-[(1-phenylcyclopropanecarbonyloxy)methyl]-1,2-dihydroquinolin-3-yl}piperidine-1-carbonyl)amino]propyl]-1H-indazol-1-yl}methyl 1-phenylcyclopropane-1-carboxylatetrifluoroacetate and {7-methyl-5-[(2R)-3-[4-(1-methylpiperidin-4-yl)piperazin-1-yl]-3-oxo-2-[(4-{2-oxo-1-[(1-henylcyclopropanecarbonyloxy)methyl]-1,2-dihydroquinolin-3-yl}piperidine-1-carbonyl)amino]propyl]-2H-indazol-2-yl}methyl 1-phenylcyclopropane-1-carboxylatetrifluoroacetate. A solution of N-[(2R)-3-(7-methyl-1H-indazol-5-yl)-1-[4-(1-methylpiperidin-4-yl)piperazin-1-yl]-1-oxopropan-2-yl]-4-(2-oxo-1,2-dihydroquinolin-3-yl)piperidine-1-carboxamide (50 mg, 78.4 μmop in DMF (1.2 mL) under nitrogen was treated with lithium hexamethyldisilylamide (1.0 M in THF, 235 μL, 235 μmop and stirred for 20 minutes. Chloromethyl 1-phenylcyclopropane-1-carboxylate (49.5 mg, 235 μmol, 84 μl) in DMF (200 μL) was added via syringe and the mixture stirred overnight. The product mixture was quenched with saturated aqueous ammonium chloride (200 μL) and purified directly by RP-HPLC (method D). The product fractions were combined and lyophilized to provide the purified compounds as white solids consisting of mono-alkylated product as a 1:2 mixture of 1-alkylated indazole and 2-alkylated indazole regioisomers (19 mg, 26.1%) and bis-alkylated product as a 2:3 mixture of 1-alkylated indazole and 2-alkylated indazole regioisomers (22.4 mg, 25.9%).

1-Phenyl-cyclopropanecarboxylic acid 7-methyl-5-(3-[4-(1-methyl-piperidin-4-yl)-piperazin-1-yl]-3-oxo-2-{[4-(2-oxo-1,2-dihydro-quinolin-3-yl)-piperidine-1-carbonyl]-amino}-propyl)-indazol-1-ylmethyl ester; compound; trifluoro-acetic acid and 1-Phenyl-cyclopropanecarboxylic acid 7-methyl-5-(3-[4-(1-methyl-piperidin-4-yl)-piperazin-1-yl]-3-oxo-2-{[4-(2-oxo-1,2-dihydro-quinolin-3-yl)-piperidine-1-carbonyl]-amino}-propyl)-indazol-2-ylmethyl ester; compound; trifluoro-acetic acid (1:2) (41). $^1$H NMR (300 MHz, DMSO-d$_6$) δ=11.76 (s, 1H), 8.33 and 8.06 (S, 1H), 7.66-7.49 (m, 2H), 7.49-7.33 (m, 2H), 7.30-7.11 (m, 7H), 7.01 (s, 1H), 6.36 and 6.24 (s, 1H), 6.83 (br d, J=7.3 Hz, 1H), 6.36 and 6.24 (s, 1H), 4.76 (br d, J=7.3 Hz, 1H), 4.25-3.95 (m, 2H), 3.37-3.06 (m, 5H), 3.00-2.62 (m, 14H), 2.45-2.38 (m, 2H), 2.32-2.06 (m, 2H), 1.89 (s, 2H), 1.82-1.58 (m, 4H), 1.47-1.12 (m, 7H). LC/MS method A: R$_t$=3.58 mins., (M+H)$^+$=813, purity=84%.

{7-methyl-5-[(2R)-3-[4-(1-methylpiperidin-4-yl)piperazin-1-yl]-3-oxo-2-[(4-{2-oxo-1-[(1-phenylcyclopropanecarbonyloxy)methyl]-1,2-dihydroquinolin-3-yl}piperidine-1-carbonyl)amino]propyl]-1H-indazol-1-yl}methyl 1-phenylcyclopropane-1-carboxylatetrifluoroacetate and {7-methyl-5-[(2R)-3-[4-(1-methylpiperidin-4-yl)piperazin-1-yl]-3-oxo-2-[(4-{2-oxo-1-[(1-phenylcyclopropanecarbonyloxy)methyl]-1,2-dihydroquinolin-3-yl}piperidine-1-carbonyl)amino] propyl]-2H-indazol-2-yl}methyl 1-phenylcyclopropane-1-carboxylate trifluoroacetate (2:3) (42). $^1$H NMR (300 MHz, DMSO-d$_6$) δ=8.33 and 8.06 (s, 1H), 7.86-7.61 (m, 1H), 7.60-7.50 (m, 2H), 7.45-7.12 (m, 13H), 7.01 (s, 1H), 6.81 (m, 1H), 6.36 and 6.24 (m, 4H), 4.73 (m, 1H), 4.09 (br dd, J=8.7, 12.4 Hz, 2H), 3.41-3.24 (m, 2H), 3.14 (m, 2H), 3.01-2.82 (m, 8H), 2.82-2.63 (m, 6H), 2.45-2.36 (m, 6H), 2.25 (br t, J=1.6 Hz, 2H), 1.89, 1.80-1.56 (m, 4H), 1.51-1.30 (m, 4H), 1.30-0.98 (m, 6H). LC/MS method A: R$_t$=4.35 mins., (M+H)$^+$=987, purity=92%.

Examples 43-44

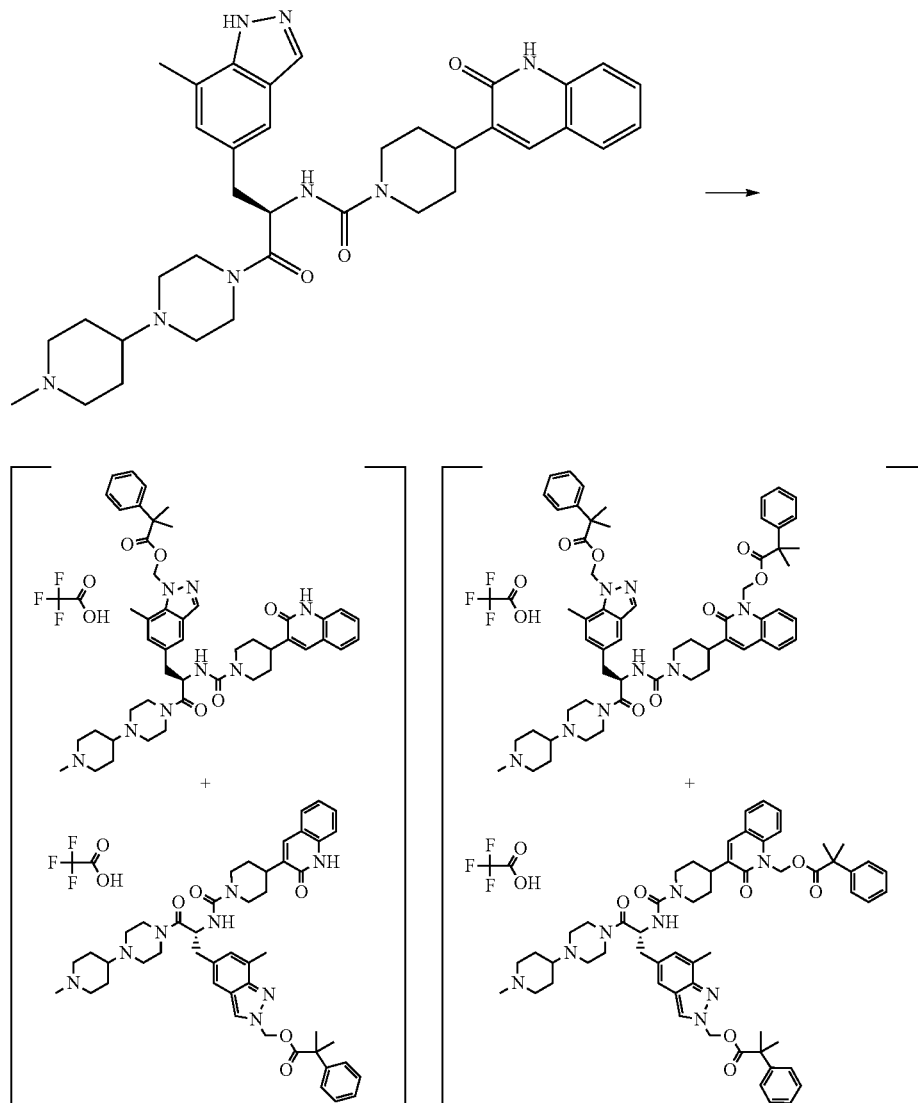

{7-methyl-5-[(2R)-3-[4-(1-methylpiperidin-4-yl)piperazin-1-yl]-3-oxo-2-{[4-(2-oxo-1,2-dihydroquinolin-3-yl)piperidine-1-carbonyl]amino}propyl]-1H-indazol-1-yl}methyl 2-methyl-2-phenylpropanoate trifluoroacetate and {7-methyl-5-[(2R)-3-[4-(1-methylpiperidin-4-yl)piperazin-1-yl]-3-oxo-2-{[4-(2-oxo-1,2-dihydroquinolin-3-yl)piperidine-1-carbonyl]amino}propyl]-2H-indazol-2-yl}methyl 2-methyl-2-phenylpropanoate trifluoroacetate and {7-methyl-5-[(2R)-2-{[4-(1-{[(2-methyl-2-phenylpropanoyl)oxy]methyl}-2-oxo-1,2-dihydroquinolin-3-yl)piperidine-1-carbonyl]amino}-3-[4-(1-methylpiperidin-4-yl)piperazin-1-yl]-3-oxopropyl]-1H-indazol-1-yl}methyl 2-methyl-2-phenylpropanoate trifluoroacetate and {7-methyl-5-[(2R)-2-{[4-(1-{[(2-methyl-2-phenylpropanoyl)oxy]methyl}-2-oxo-1,2-dihydroquinolin-3-yl)piperidine-1-carbonyl]amino}-3-[4-(1-methylpiperidin-4-yl)piperazin-1-yl]-3-oxopropyl]-2H-indazol-2-yl}methyl 2-methyl-2-phenylpropanoate trifluoroacetate. Prepared and purified following the method above utilizing chloromethyl 2-methyl-2-phenylpropanoate in place of chloromethyl 1-phenylcyclopropane-1-carboxylate providing mono-alkylated product as a 2:5 mixture of 1-alkylated indazole and 2-alkylated indazole regioisomers (20.4 mg, 28%) and bis-alkylated product as a 1:5 mixture of 1-alkylated indazole and 2-alkylated indazole regioisomers (23.9 mg, 27.6%).

{7-methyl-5-[(2R)-3-[4-(1-methylpiperidin-4-yl)piperazin-1-yl]-3-oxo-2-{[4-(2-oxo-1,2-dihydroquinolin-3-yl)piperidine-1-carbonyl]amino}propyl]-1H-indazol-1-yl}methyl 2-methyl-2-phenylpropanoatetrifluoroacetate and {7-methyl-5-[(2R)-3-[4-(1-methylpiperidin-4-yl)piperazin-1-yl]-3-oxo-2-{[4-(2-oxo-1,2-dihydroquinolin-3-yl)piperidine-1-carbonyl]amino}propyl]-2H-indazol-2-yl}methyl 2-methyl-2-phenylpropanoatetrifluoroacetate (2:5) (43). $^1$H NMR (300 MHz, DMSO-$d_6$) δ=11.75 (s, 1H), 8.34 and 8.07 (s, 1H), 7.64-7.51 (m, 2H), 7.47-7.32 (m, 2H), 7.27-7.08 (m, 6H), 7.01 (s, 1H), 6.82 (br d, J=7.7 Hz, 1H), 6.41-6.25 (m, 2H), 4.76 (br d, J=7.7 Hz, 1H), 4.10 (br t, J=9.5 Hz, 2H), 3.33 (br d, J=9.0 Hz, 2H), 3.22 (br s, 2H), 3.14 (s, 2H), 3.01-2.80 (m, 8H), 2.74 (br s, 2H), 2.80-2.61 (m, 5H), 2.45-2.35 (m, 4H), 2.33-2.16 (m, 1H), 2.06 (br s, 1H), 1.89 (s, 1H), 1.72 (br t, J=12.6 Hz, 4H), 1.39 (dd, J=3.2, 11.4 Hz, 6H), 1.25 (br dd, J=7.5, 17.4 Hz, 2H). LC/MS method A: $R_t$=3.63 mins., (M+H)$^+$=815, purity=96%.

{7-methyl-5-[(2R)-2-{[4-(1-{[(2-methyl-2-phenylpropanoyl)oxy]methyl}-2-oxo-1,2-dihydroquinolin-3-yl)piperidine-1-carbonyl]amino}-3-[4-(1-methylpiperidin-4-yl)piperazin-1-yl]-3-oxopropyl]-1H-indazol-1-yl}methyl 2-methyl-2-phenylpropanoatetrifluoroacetate and {7-methyl-5-[(2R)-2-{[4-(1-{[(2-methyl-2-phenylpropanoyl)oxy]methyl}-2-oxo-1,2-dihydroquinolin-3-yl)piperidine-1-carbonyl]amino}-3-[4-(1-methylpiperidin-4-yl)piperazin-1-yl]-3-oxopropyl]-2H-indazol-2-yl}methyl 2-methyl-2-phenylpropanoatetrifluoroacetate (1:5) (44). $^1$H NMR (300 MHz, DMSO-$d_6$) δ=8.34 and 8.07 (s, 1H), 7.64-7.51 (m, 2H), 7.46-7.42 (m, 1H), 7.27-7.11 (m, 13H), 7.01 (s, 1H), 6.81 (m, 1H), 6.32-6.26 (m, 4H), 4.73 (m, 1H), 4.09 (m, 2H), 3.38-3.26 (m, 3H), 3.14 (s, 3H), 2.97-2.81 (m, 8H), 2.75 (s, 8H), 2.55-2.50 (m, 2H), 2.41 (br d, J=10.5 Hz, 4H), 1.69 (br s, 3H), 1.46-1.35 (m, 13H). LC/MS method A: $R_t$=4.47 mins., (M+H)$^+$=991, purity=95%.

Examples 45-46

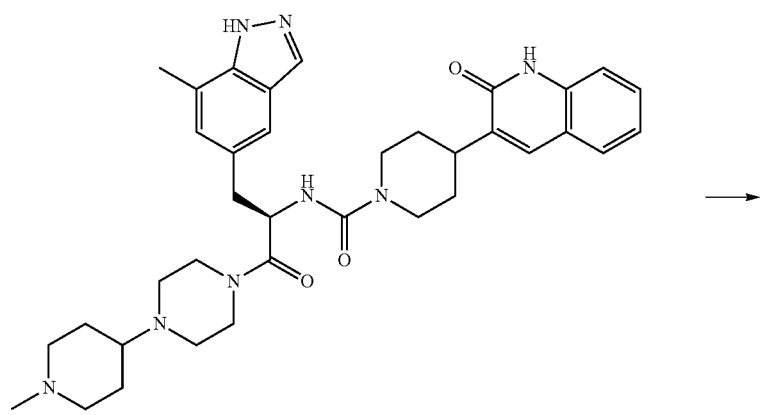

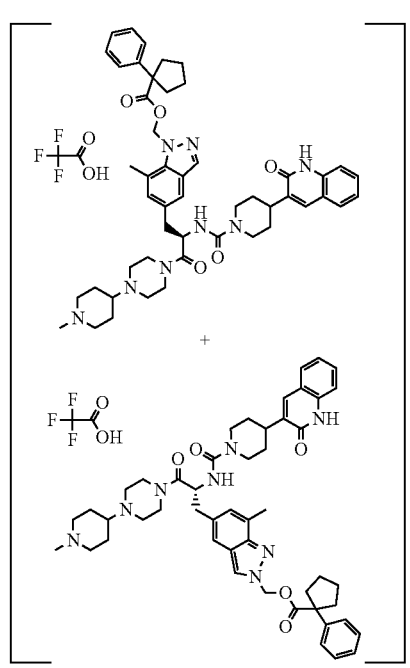
+
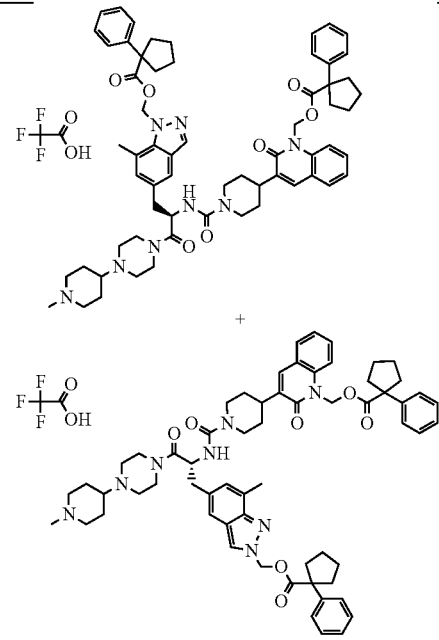

{7-methyl-5-[(2R)-3-[4-(1-methylpiperidin-4-yl)piperazin-1-yl]-3-oxo-2-{[4-(2-oxo-1,2-dihydroquinolin-3-yl)piperidine-1-carbonyl]amino}propyl]-1H-indazol-1-yl}methyl 1-phenylcyclopentane-1-carboxylate trifluoroacetate and {7-methyl-5-[(2R)-3-[4-(1-ethylpiperidin-4-yl)piperazin-1-yl]-3-oxo-2-{[4-(2-oxo-1,2-dihydroquinolin-3-yl)piperidine-1-carbonyl]amino}propyl]-2H-indazol-2-yl}methyl 1-phenylcyclopentane-1-carboxylate trifluoroacetate and {7-methyl-5-[(2R)-3-[4-(1-methylpiperidin-4-yl)piperazin-1-yl]-3-oxo-2-[(4-{2-oxo-1-[(1-phenylcyclopentanecarbonyloxy)methyl]-1,2-dihydroquinolin-3-yl}piperidine-1-carbonyl)amino]propyl]-1H-indazol-1-yl}methyl 1-phenylcyclopentane-1-carboxylate trifluoroacetate and {7-methyl-5-[(2R)-3-[4-(1-methylpiperidin-4-yl)piperazin-1-yl]-3-oxo-2-[(4-{2-oxo-1-[(1-phenylcyclopentanecarbonyloxy)methyl]-1,2-dihydroquinolin-3-yl}piperidine-1-carbonyl)amino]propyl]-2H-indazol-2-yl}methyl 1-phenylcyclopentane-1-carboxylate trifluoroacetate. Prepared and purified following the method above utilizing chloromethyl 1-phenylcyclopentane-1-carboxylate in place of chloromethyl 1-phenylcyclopropane-1-carboxylate providing mono-alkylated product as a 1:2 mixture of 1-alkylated indazole and 2-alkylated indazole regioisomers (32 mg, 42.7%) and bis-alkylated product as a 2:5 mixture of 1-alkylated indazole and 2-alkylated indazole regioisomers (28 mg, 30.9%).

{7-methyl-5-[(2R)-3-[4-(1-methylpiperidin-4-yl)piperazin-1-yl]-3-oxo-2-{[4-(2-oxo-1,2-dihydroquinolin-3-yl)piperidine-1-carbonyl]amino}propyl]-1H-indazol-1-yl}methyl 1-phenylcyclopentane-1-carboxylatetrifluoroacetate and {7-methyl-5-[(2R)-3-[4-(1-ethylpiperidin-4-yl)piperazin-1-yl]-3-oxo-2-{[4-(2-oxo-1,2-dihydroquinolin-3-yl)piperidine-1-carbonyl]amino}propyl]-2H-indazol-2-yl}methyl 1-phenylcyclopentane-1-carboxylatetrifluoroacetate (1:2) (45). $^1$H NMR (300 MHz, DMSO-$d_6$) δ=11.75 (s, 1H), 8.29 and 8.07 (s, 1H), 7.60-7.53 (m, 2H), 7.47-7.40 (m, 2H), 7.30-7.00 (m, 8H), 6.84 (m, 1H), 6.34-6.26 (m, 2H), 4.75 (m, 1H), 4.20-4.00 (m, 2H), 3.00-2.65 (m, 12H), 2.45-2.35 (m, 8H), 2.31-2.14 (m, 4H), 1.75-1.68 (m, 6H), 1.62-1.40 (m, 6H), 1.30-1.18 (m, 4H). LC/MS method A: $R_t$=3.80 mins., (M+H)$^+$=841, purity=93%.

{7-methyl-5-[(2R)-3-[4-(1-methylpiperidin-4-yl)piperazin-1-yl]-3-oxo-2-[(4-{2-oxo-1-[(1-phenylcyclopentanecarbonyloxy)methyl]-1,2-dihydroquinolin-3-yl}piperidine-1-carbonyl)amino]propyl]-1H-indazol-1-yl}methyl 1-phenylcyclopentane-1-carboxylatetrifluoroacetate and {7-methyl-5-[(2R)-3-[4-(1-methylpiperidin-4-yl)piperazin-1-yl]-3-oxo-2-[(4-{2-oxo-1-[(1-phenylcyclopentanecarbonyloxy)methyl]-1,2-dihydroquinolin-3-yl}piperidine-1-carbonyl)amino]propyl]-2H-indazol-2-yl}methyl 1-phenylcyclopentane-1-carboxylatetrifluoroacetate (2:5) (46). $^1$H NMR (300 MHz, DMSO-$d_6$) δ=8.28 and 8.06 (s, 1H), 7.64-7.51 (m, 2H), 7.46-7.42 (m, 1H), 7.27-7.11 (m, 13H), 7.01 (s, 1H), 6.84 (m, 1H), 6.25-6.22 (m, 4H), 4.75 (m, 1H), 4.09 (m, 2H), 3.38-3.00 (m, 4H), 2.97-2.81 (m, 10H), 2.80-2.60 (m, 8H), 2.50-2.40 (m, 2H), 1.69 (m, 20H), 1.40-1.15 (m, 4H). LC/MS method A: $R_t$=4.82 mins., (M+H)$^+$=1043, purity=93%.

Examples 47-48

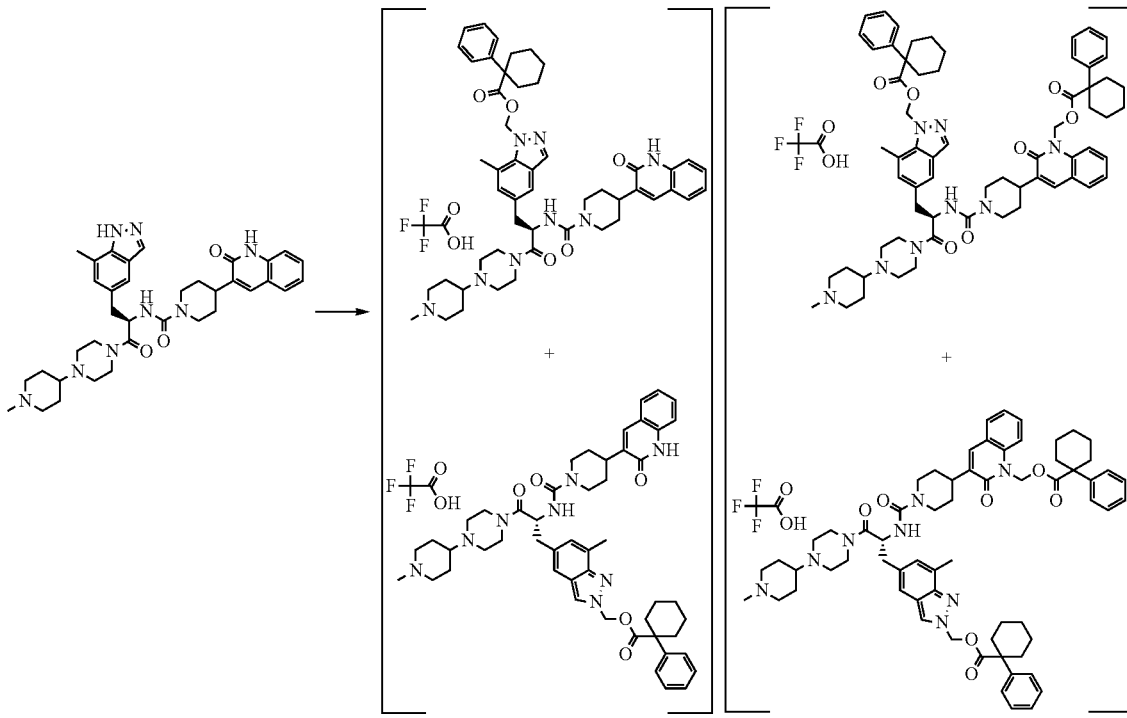

{7-methyl-5-[(2R)-3-[4-(1-methylpiperidin-4-yl)piperazin-1-yl]-3-oxo-2-{[4-(2-oxo-1,2-dihydroquinolin-3-yl)piperidine-1-carbonyl]amino}propyl]-1H-indazol-1-yl}methyl 1-phenylcyclohexane-1-carboxylate trifluoroacetate and {7-methyl-5-[(2R)-3-[4-(1-methylpiperidin-4-yl)piperazin-1-yl]-3-oxo-2-{[4-(2-oxo-1,2-dihydroquinolin-3-yl)piperidine-1-carbonyl]amino}propyl]-2H-indazol-2-yl}methyl 1-phenylcyclohexane-1-carboxylate trifluoroacetate and {7-methyl-5-[(2R)-3-[4-(1-methylpiperidin-4-yl)piperazin-1-yl]-3-oxo-2-[(4-{2-oxo-1-[(1-phenylcyclohexanecarbonyloxy)methyl]-1,2-dihydroquinolin-3-yl}piperidine-1-carbonyl)amino]propyl]-1H-indazol-1-yl}methyl 1-phenylcyclohexane-1-carboxylate trifluoroacetate and {7-methyl-5-[(2R)-3-[4-(1-methylpiperidin-4-yl)piperazin-1-yl]-3-oxo-2-[(4-{2-oxo-1-[(1-phenylcyclohexanecarbonyloxy)methyl]-1,2-dihydroquinolin-3-yl}piperidine-1-carbonyl)amino]propyl]-2H-indazol-2-yl}methyl 1-phenylcyclohexane-1-carboxylate trifluoroacetate. Prepared and purified following the method above utilizing chloromethyl 1-phenylcyclohexane-1-carboxylate in place of chloromethyl 1-phenylcyclopropane-1-carboxylate providing mono-alkylated product as a 2:5 mixture of 1-alkylated indazole and 2-alkylated indazole regioisomers (45 mg, 59.2%) and bis-alkylated product as a 1:9 mixture of 1-alkylated indazole and 2-alkylated indazole regioisomers (10 mg, 10.8%).

{7-methyl-5-[(2R)-3-[4-(1-methyl piperidin-4-yl)piperazin-1-yl]-3-oxo-2-{[4-(2-oxo-1,2-dihydroquinolin-3-yl)piperidine-1-carbonyl]amino}propyl]-1H-indazol-1-yl}methyl 1-phenylcyclohexane-1-carboxylate trifluoroacetate and {7-methyl-5-[(2R)-3-[4-(1-methylpiperidin-4-yl)piperazin-1-yl]-3-oxo-2-{[4-(2-oxo-1,2-dihydroquinolin-3-yl)piperidine-1-carbonyl]amino}propyl]-2H-indazol-2-yl}methyl 1-phenylcyclohexane-1-carboxylate trifluoroacetate (2:5) (47). $^1$H NMR (300 MHz, DMSO-$d_6$) δ=11.76 (s, 1H), 8.33 and 8.07 (s, 1H), 7.61-7.35 (m, 4H), 7.27-7.11 (m, 7H), 7.01 (s, 1H), 6.83 (m, 1H), 6.40-6.31 (m, 2H), 4.79-4.73 (m, 1H), 4.14-4.05 (m, 2H), 3.30-3.10 (m, 2H), 3.00-2.62 (m, 15H), 2.45-2.18 (m, 5H), 2.45-2.18 (m, 4H), 1.80-1.60 (m, 4H) 1.59-1.40 (m, 6H), 1.38-1.05 (m, 6H). LC/MS method A: $R_t$=3.88 mins., (M+H)$^+$=855, purity=97%.

{7-methyl-5-[(2R)-3-[4-(1-methyl piperidin-4-yl)piperazin-1-yl]-3-oxo-2-[(4-{2-oxo-1-[(1-phenylcyclohexanecarbonyloxy)methyl]-1,2-dihydroquinolin-3-yl}piperidine-1-carbonyl)amino]propyl]-1H-indazol-1-yl}methyl 1-phenylcyclohexane-1-carboxylatetrifluoroacetate and {7-methyl-5-[(2R)-3-[4-(1-methylpiperidin-4-yl)piperazin-1-yl]-3-oxo-2-[(4-{2-oxo-1-[(1-phenylcyclohexanecarbonyloxy)methyl]-1,2-dihydroquinolin-3-yl}piperidine-1-carbonyl)amino]propyl]-2H-indazol-2-yl}methyl 1-phenylcyclohexane-1-carboxylatetrifluoroacetate (1:9) (48). $^1$H NMR (300 MHz, DMSO-$d_6$) δ=8.32 and 8.07 (s, 1H), 7.72-7.69 (m, 1H), 7.57 (s, 1H), 7.45-7.42 (m, 1H), 7.35-7.17 (m, 13H), 7.01 (s, 1H), 6.82 (m, 1H), 6.37-6.27 (m, 4H), 4.75 (m, 1H), 4.09 (m, 2H), 3.60-3.00 (m, 6H), 2.99-2.80 (m, 6H), 2.79-2.40 (m, 8H), 2.50-2.40 (m, 6H), 2.25-2.15, (m, 6H), 1.80-1.40 (m, 12H), 1.39-1.05 (m, 8H). LC/MS method A: $R_t$=5.02 mins., (M+H)$^+$=1071, purity=96%.

Example 49
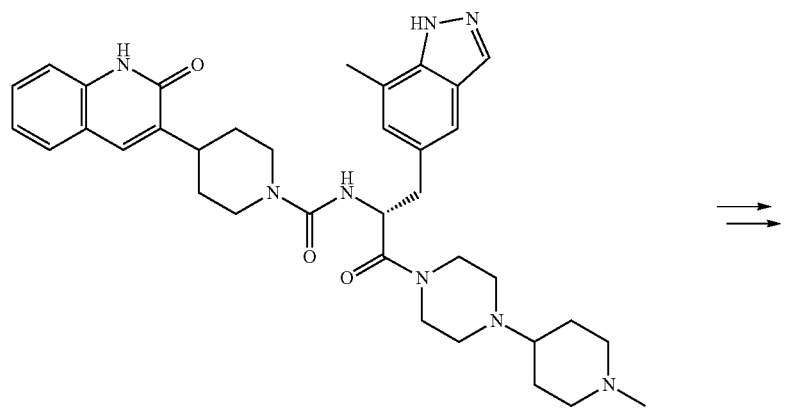
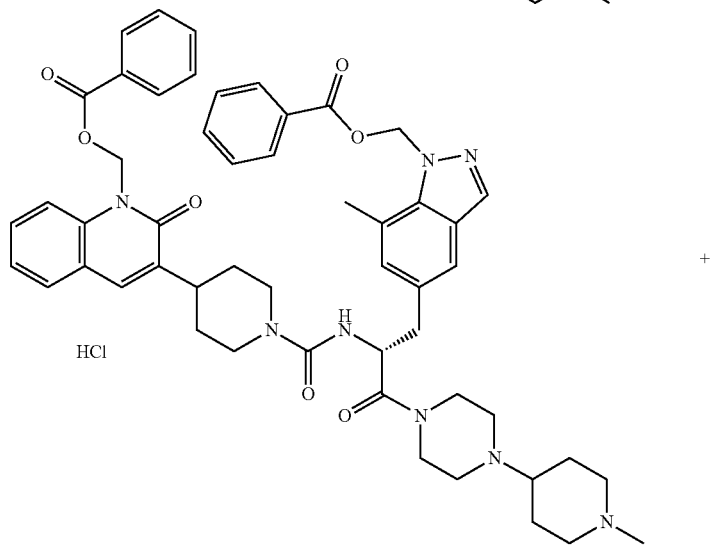
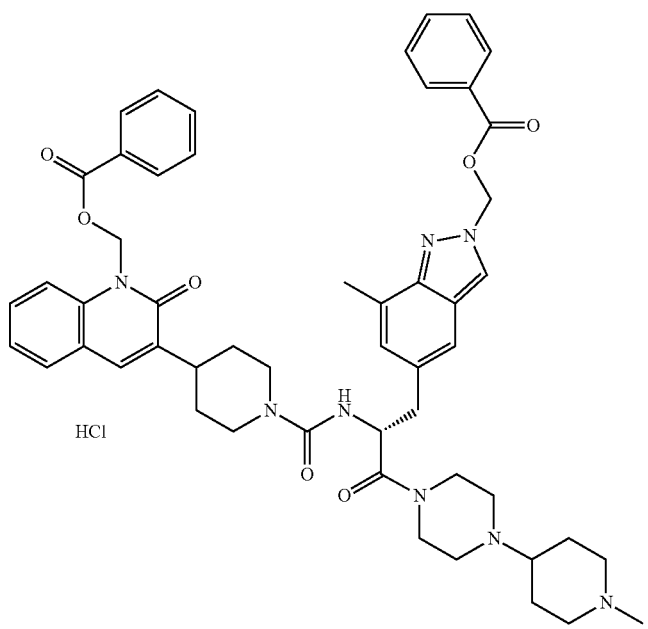

{5-[(2R)-2-[(4-{1-[(benzoyloxy)methyl]-2-oxo-1,2-dihydroquinolin-3-yl}piperidine-1-carbonyl)amino]-3-[4-(1-methylpiperidin-4-yl)piperazin-1-yl]-3-oxopropyl]-7-methyl-1H-indazol-1-yl}methyl benzoate hydrochloride and {5-[(2R)-2-[(4-{1-[(benzoyloxy)methyl]-2-oxo-1,2-dihydroquinolin-3-yl}piperidine-1-carbonyl)amino]-3-[4-(1-methylpiperidin-4-yl)piperazin-1-yl]-3-oxopropyl]-7-methyl-2H-indazol-2-yl}methyl benzoate hydrochloride (49). A solution of N-[(2R)-3-(7-methyl-1H-indazol-5-yl)-1-[4-(1-methylpiperidin-4-yl)piperazin-1-yl]-1-oxopropan-2-yl]-4-(2-oxo-1,2-dihydroquinolin-3-yl)piperidine-1-carboxamide (319 mg, 500 μmop in DMF (7.7 mL) under nitrogen was treated with lithium hexamethyldisilylamide (1.0 M in THF, 1.5 mL, 1.5 mmol) and stirred for 20 minutes. Chloromethyl benzoate (208 μL, 1.5 mmol) was added via syringe and the mixture was stirred 2 hours, at which time the reaction was quenched with the addition of saturated aqueous ammonium chloride solution. The crude product was taken up in ethyl acetate (100 mL), washed with water (2×100 mL) and brine (100 mL), and dried over MgSO₄. Normal-phase purification with a Silicycle column (40 g) in combination with an ISCO detection and collection system eluting with solvent A (methanol 20% and ammonia (1.4 N) in dichloromethane) versus solvent B (dichloromethane) (5% to 60% gradient over 24 minutes) provided the free base target (290 mg, 64%) from which (280 mg, 309 μmol) was taken up in THF (3.25 mL). Treatment with hydrochloric acid (4N in dioxane, 81 μL) followed by concentration and lyophilization provided the title compound as a white solid as a 1:2 mixture of 1-alkylated indazole and 2-alkylated indazole regioisomers (280 mg, 96.1%) with an overall yield of 61.5%. ¹H NMR (300 MHz, DMSO-d₆) δ=8.53 and 8.16 (s, 1H), 7.94-7.77 (m, 4H), 7.75-7.54 (m, 6H), 7.54-7.42 (m, 5H), 7.34 (br d, J=18.8 Hz, 2H), 6.70 (s, 2H), 6.60-6.48 (m, 3H), 4.78 (br d, J=8.1 Hz, 1H), 4.09 (s, 2H), 3.48-3.35 (m, 3H), 3.29-3.17 (m, 2H), 2.90 (br dd, J=13.0, 19.7 Hz, 5H), 2.78-2.53 (m, 9H), 2.46-2.23 (m, 4H), 2.16-2.05 (m, 1H), 1.75 (br d, J=12.9 Hz, 3H), 1.64 (s, 3H), 1.21 (s, 2H). LC/MS method A: R$_t$=4.01 mins., (M+H)⁺=907, purity=97.5%.

Example 50

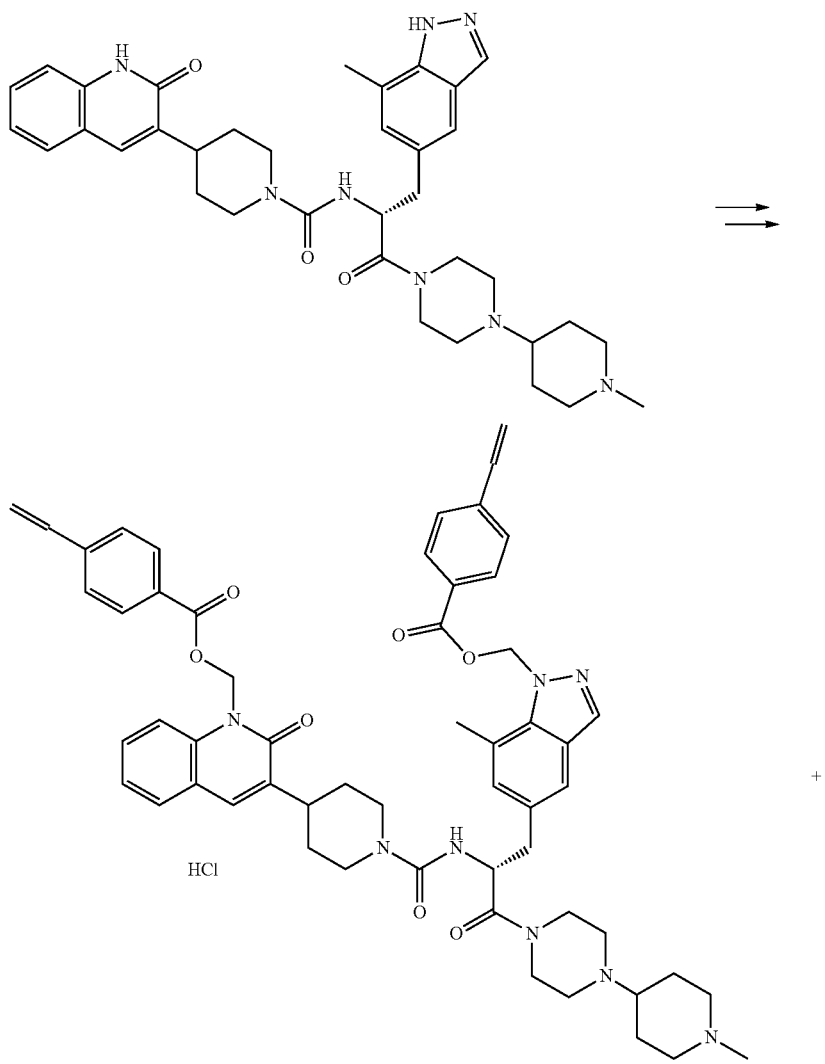

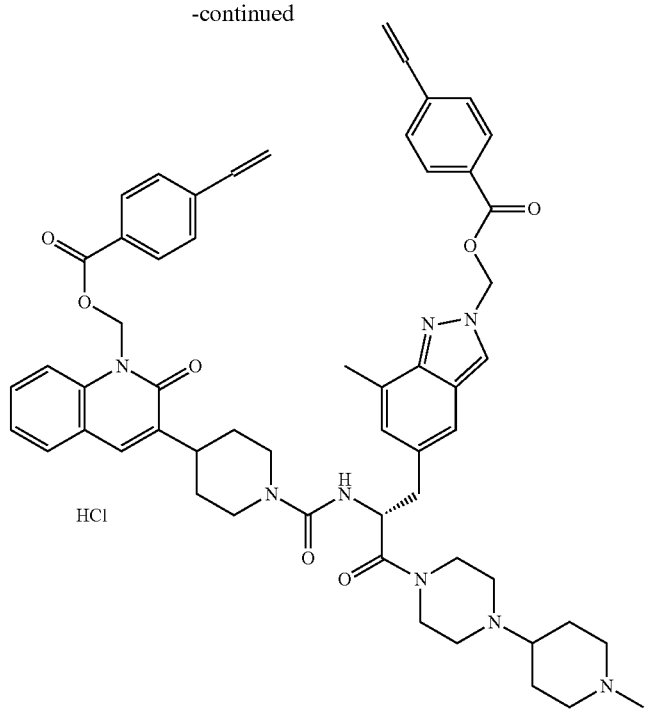

{5-[(2R)-2-[(4-{1-[(4-ethenylbenzoyloxy)methyl]-2-oxo-1,2-dihydroquinolin-3-yl}piperidine-1-carbonyl)amino]-3-[4-(1-methylpiperidin-4-yl)piperazin-1-yl]-3-oxopropyl]-7-methyl-1H-indazol-1-yl}methyl 4-ethenylbenzoate hydrochloride and {5-[(2R)-2-[(4-{1-[(4-ethenylbenzoyloxy)methyl]-2-oxo-1,2-dihydroquinolin-3-yl}piperidine-1-carbonyl)amino]-3-[4-(1-methylpiperidin-4-yl)piperazin-1-yl]-3-oxopropyl]-7-methyl-2H-indazol-2-yl}methyl 4-ethenylbenzoate hydrochloride (50). Prepared according to the procedure above, except that chloromethyl 4-ethenylbenzoate was used in place of chloromethyl benzoate to provide the title compound as a white solid as a 1:2 mixture of 1-alkylated indazole and 2-alkylated indazole regioisomers in an overall yield of 54.9%. $^1$H NMR (300 MHz, DMSO-d$_6$) δ=8.53 and 8.16 (s, 1H), 7.86-7.70 (m, 5H), 7.67-7.48 (m, 8H), 7.39-7.28 (m, 2H), 6.83-6.67 (m, 4H), 6.56-6.47 (m, 3H), 6.00-5.91 (m, 2H), 5.43-5.37 (m, 2H), 4.81 (m, 1H), 4.10 (br dd, J=5.3, 11.7 Hz, 2H), 3.53-3.38 (m, 7H), 3.27-3.23 (m, 1H), 2.99-2.82 (m, 6H), 2.81-2.62 (m, 10H), 2.62-2.50 (m, 2H), 1.72 (br dd, J=14.6, 19.9 Hz, 3H), 1.22 (br t, J=2.6 Hz, 3H). LC/MS method A: R$_t$=4.38 mins., (M+H)$^+$=959, purity >95%.

Example 51

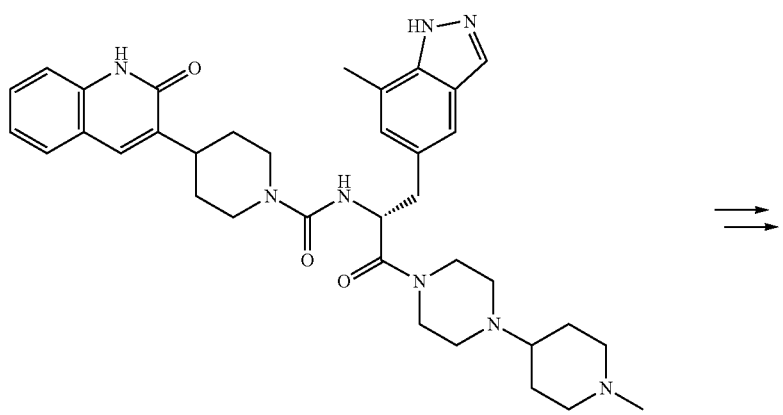

-continued

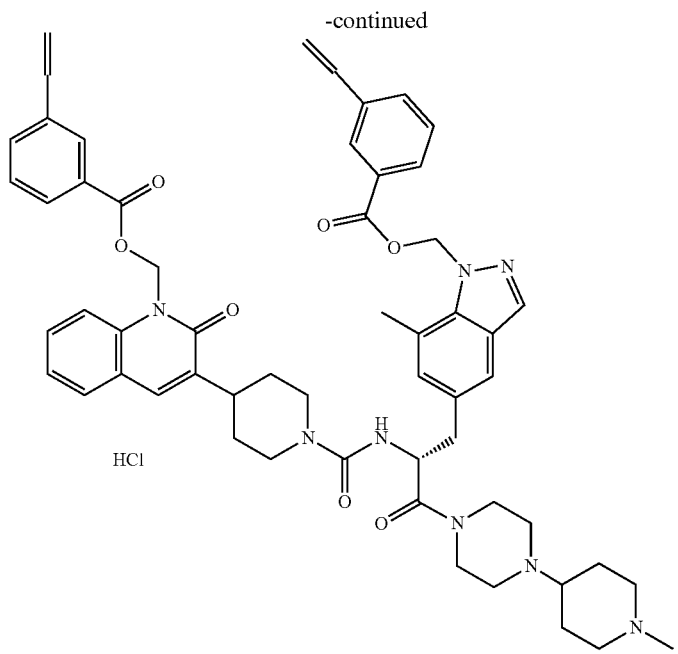

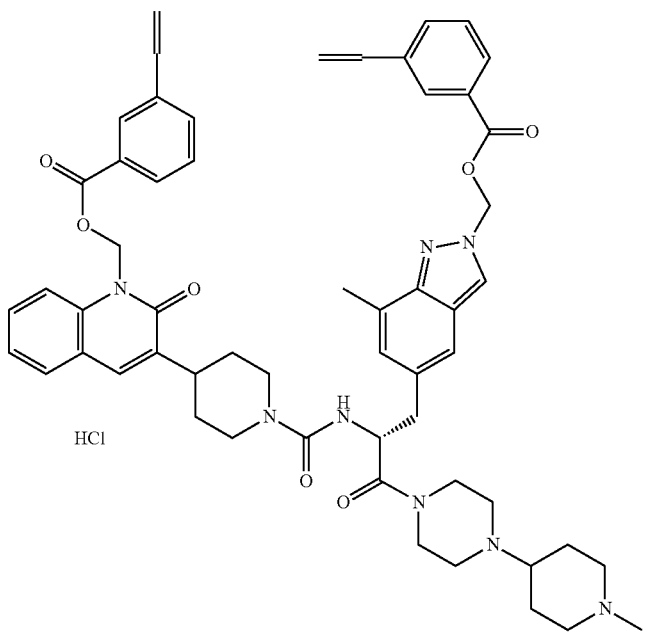

{5-[(2R)-2-[(4-{1-[(3-ethenylbenzoyloxy)methyl]-2-oxo-1,2-dihydroquinolin-3-yl}piperidine-1-carbonyl)amino]-3-[4-(1-methylpiperidin-4-yl)piperazin-1-yl]-3-oxopropyl]-7-methyl-1H-indazol-1-yl}methyl 3-ethenylbenzoate hydrochloride and {5-[(2R)-2-[(4-{1-[(3-ethenylbenzoyloxy)methyl]-2-oxo-1,2-dihydroquinolin-3-yl}piperidine-1-carbonyl)amino]-3-[4-(1-methylpiperidin-4-yl)piperazin-1-yl]-3-oxopropyl]-7-methyl-2H-indazol-2-yl}methyl 3-ethenylbenzoate hydrochloride (51). Prepared according to the procedure above, except that chloromethyl 3-ethenylbenzoate was used in place of chloromethyl benzoate to provide the title compound as a white solid as a 1:2 mixture of 1-alkylated indazole and 2-alkylated indazole regioisomers in an overall yield of 50.7%. $^1$H NMR (300 MHz, DMSO-$d_6$) δ=8.53 and 8.16 (s, 1H), 7.91 (s, 2H), 7.80-7.57 (m, 9H), 7.49-7.28 (m, 4H), 6.98 (s, 1H), 6.81-6.69 (m, 3H), 6.57-6.49 (m, 3H), 5.86 (d, J=17.7 Hz, 2H), 5.31 (d, J=11.0 Hz, 2H), 4.77 (m, 1H), 4.14-4.06 (m, 2H), 3.50-3.34 (m, 4H), 3.30-3.21 (m, 4H), 3.14 (d, J=5.2 Hz, 1H), 2.90 (br d, J=5.9 Hz, 4H), 2.79-2.59 (m, 4H), 2.71 (s, 3H), 2.59-2.51 (m, 3H), 2.46-2.45 (m, 1H), 2.25 (br s, 2H), 1.73 (br s, 1H), 1.64 (br s, 2H), 1.33-1.20 (m, 3H). LC/MS method A: $R_t$=4.14 mins., (M+H)$^+$=959, purity=93%.

141

Example 52

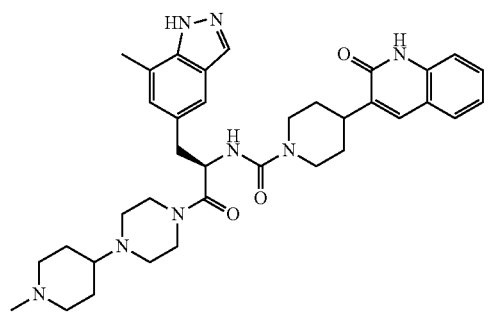

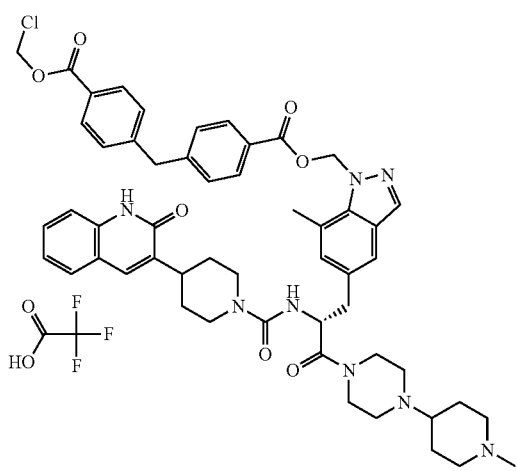

142

-continued

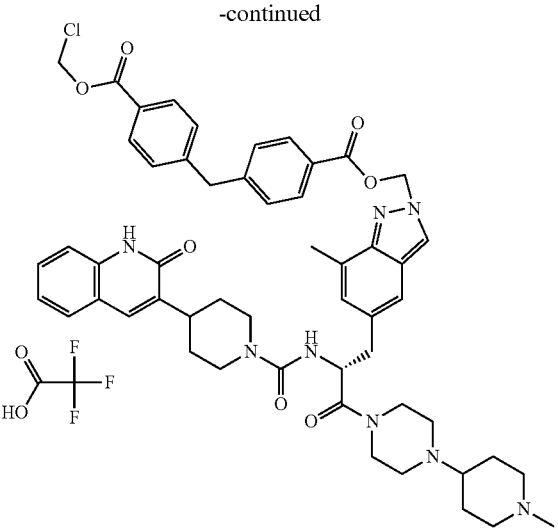

Chloromethyl 4-({4-[({7-methyl-5-[(2R)-3-[4-(1-methylpiperidin-4-yl)piperazin-1-yl]-3-oxo-2-{[4-(2-oxo-1,2-dihydroquinolin-3-yl)piperidine-1-carbonyl]amino}propyl]-1H-indazol-1-yl}methoxy)carbonyl]phenyl}methyl)benzoate trifluoroacetate and Chloromethyl 4-({4-[({7-methyl-5-[(2R)-3-[4-(1-methylpiperidin-4-yl)piperazin-1-yl]-3-oxo-2-{[4-(2-oxo-1,2-dihydroquinolin-3-yl)piperidine-1-carbonyl]amino}propyl]-2H-indazol-2-yl}methoxy)carbonyl]phenyl}methyl)benzoate trifluoroacetate. A solution of N-[(2R)-3-(7-methyl-1H-indazol-5-yl)-1-[4-(1-methylpiperidin-4-yl)piperazin-1-yl]-1-oxopropan-2-yl]-4-(2-oxo-1,2-dihydroquinolin-3-yl)piperidine-1-carboxamide (127 mg, 200 μmop in DMF (6.0 mL) under $N_2$ was treated with lithium hexamethyldisilylamide (1.0 M in THF, 220 μL, 220 μmop, and the reaction mixture was stirred for 20 minutes. Chloromethyl 4-({4-[(chloromethoxy)carbonyl]phenyl}methyl)benzoate (78 mg, 220 μmol) in DMF (2.0 mL) was added via syringe, and the mixture stirred for 2 hours. The mixture was purified directly by RP-HPLC (method D) and the product fractions were combined and lyophilized to provide the purified compounds as a white solids consisting of mono-alkylated product as a 1:2 mixture of 1-alkylated indazole and 2-alkylated indazole regioisomers (60 mg, 25%). $^1$H NMR (300 MHz, DMSO-$d_6$) δ=11.76, (s, 1H), 8.52 and 8.39 (s, 1H), 8.00-7.71 (m, 5H), 7.71-7.54 (m, 2H), 7.52-7.19 (m, 8H), 6.86 (br s, 1H), 6.52 (s, 2H), 6.06 (d, J=1.5 Hz, 2H), 4.76 (br d, J=7.0 Hz, 1H), 4.12-4.10 (m, 2H), 3.59-3.33 (m, 4H), 2.98-2.61 (m, 10H), 2.42 (s, 3H), 2.34-2.16 (m, 2H), 2.06 (s, 3H), 1.71 (br s, 6H), 1.21 (s, 4H). LC/MS method A: $R_t$=3.80 mins., (M+H)$^+$=955, 957, purity=88%.

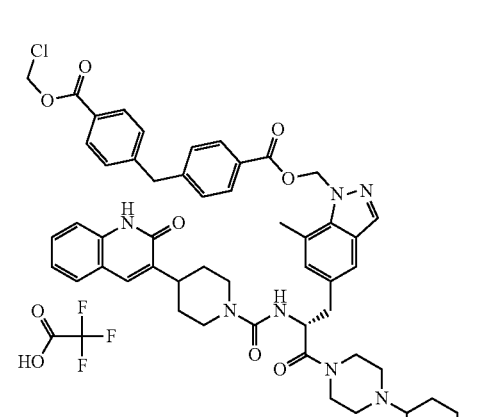

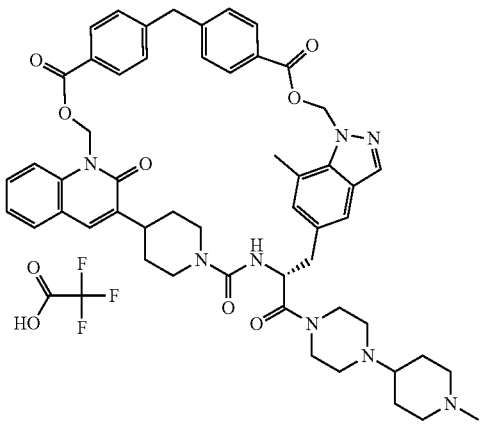

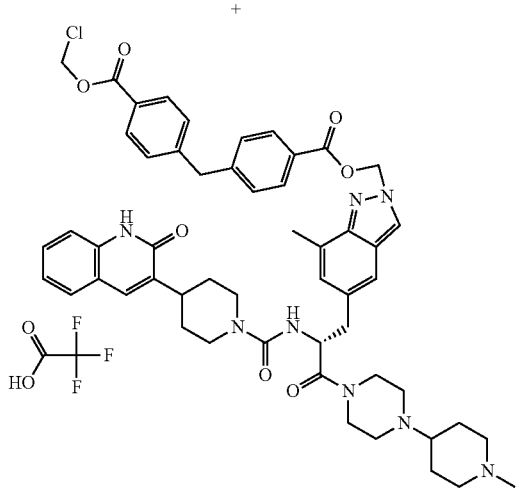

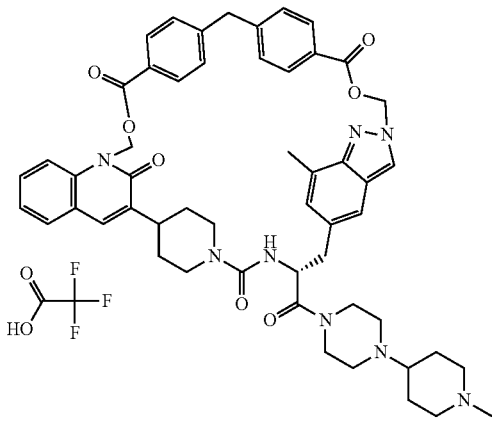

(35R)-31-methyl-35-[4-(1-methylpiperidin-4-yl)piperazine-1-carbonyl]-12,24-dioxa-10,26,27,36,38-pentaazaoctacyclo[36.2.2.2$^{14,17}$.2$^{19,22}$.1$^{2,10}$.1$^{29,33}$.0$^{4,9}$.0$^{26,30}$]octatetraconta-2,4(9),5,7,14,16,19,21,27,29(43),30,32,44,46-tetradecaene-13,23,37,48-tetrone; trifluoroacetic acid and (34R)-30-methyl-34-[4-(1-methylpiperidin-4-yl)piperazine-1-carbonyl]-12,24-dioxa-10,26,35,37,43-pentaazaoctacyclo[35.2.2.2$^{14,17}$.2$^{19,22}$.1$^{2,10}$.1$^{26,29}$.1$^{28,32}$.0$^{4,9}$]octatetraconta-2,4(9),5,7,14,16,19,21,27,29(43),30,32(42),44,46-tetradecaene-13,23,36,48-tetrone trifluoroacetate (52). A solution of chloromethyl 4-({4-[({7-methyl-5-[(2R)-3-[4-(1-methylpiperidin-4-yl)piperazin-1-yl]-3-oxo-2-{[4-(2-oxo-1,2-dihydroquinolin-3-yl)piperidine-1-carbonyl]amino}propyl]-1H-indazol-1-yl}methoxy)carbonyl]phenyl}methyl)benzoatetrifluoroacetate and chloromethyl 4-({4-[({7-methyl-5-[(2R)-3-[4-(1-methylpiperidin-4-yl)piperazin-1-yl]-3-oxo-2-{[4-(2-oxo-1,2-dihydroquinolin-3-yl)piperidine-1-carbonyl]amino}propyl]-2H-indazol-2-yl}methoxy)carbonyl]phenyl}methyl)benzoatetrifluoroacetate (80 mg, 74.8 μmop in THF (8.45 mL) under nitrogen was treated with lithium hexamethyldisilylamide (0.1 M in THF, 1.49 mL, 149 μmop, and the reaction mixture was stirred overnight. The solvent was removed via stream of nitrogen, the solid was taken up in a minimal volume of DMF and purified by RP-HPLC (method D) to provide the desired products as white solids, which were lyophilized as a 1:3 mixture of 1-alkylated indazole and 2-alkylated indazole regioisomers (6.3 mg, 7.8%). $^1$H NMR (300 MHz, DMSO-d$_6$) δ=8.39 and 8.06 (s, 1H), 7.93-7.75 (m, 3H), 7.74-7.65 (m, 4H), 7.64-7.61 (m, 1H), 7.46-7.16 (m, 7H), 7.00-6.95 (m, 1H), 6.65-6.25 (m, 6H), 4.85 (br s, 1H), 4.05 (s, 2H), 3.00-2.50 (m, 10H), 2.45-2.00 (m, 6H), 2.00-1.60 (m, 6H), 1.55-1.30 (m, 3H), 1.21 (br s, 5H), 1.90-1.80 (m, 2H). LC/MS method A: R$_t$=4.02 mins., (M+H)$^+$=919, purity=95%.

Example 53

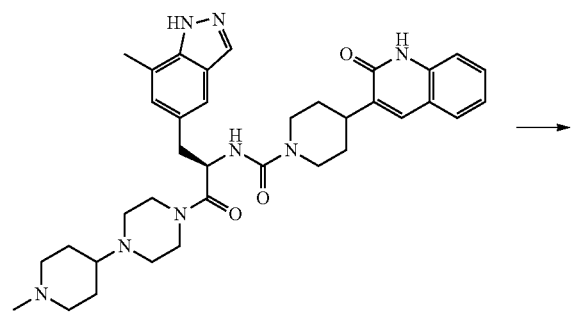

-continued

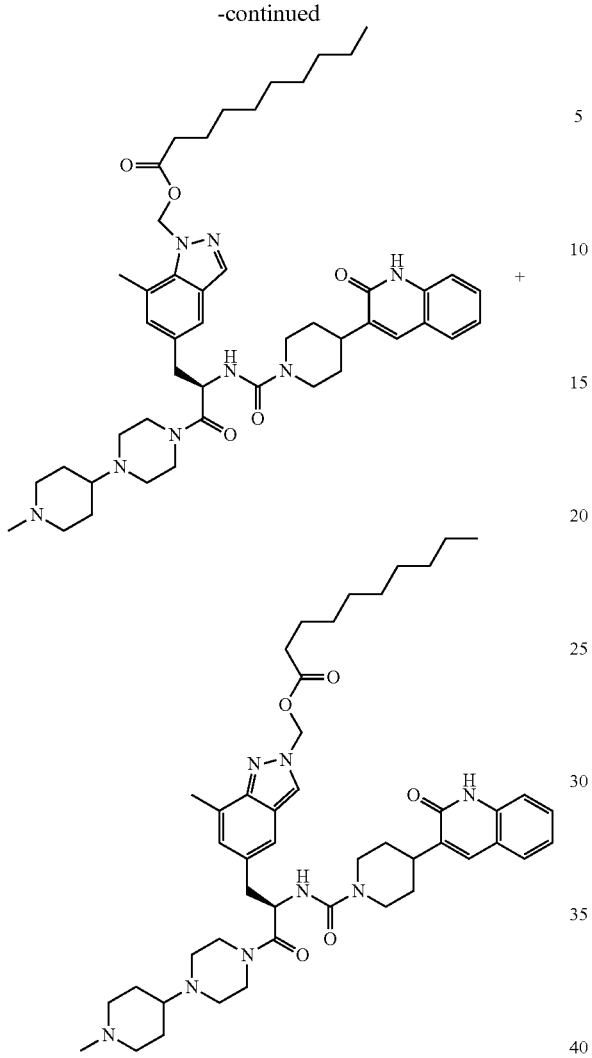

(R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-1H-indazol-1-yl)methyl decanoate and (R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl) methyl decanoate (53). A suspension of N-[(2R)-3-(7-methyl-1H-indazol-5-yl)-1-[4-(1-methylpiperidin-4-yl)piperazin-1-yl]-1-oxopropan-2-yl]-4-(2-oxo-1,2-dihydroquinolin-3-yl)piperidine-1-carboxamide (70 mg, 0.071 mmol) in THF (1 mL) was treated with lithium hexamethyldisilylamide (1.0 M in THF, 035 mL, 0.35 mmol), and the reaction mixture was stirred for 15 minutes. Then, chloromethyl decanoate (121 mg, 0.55 mmol) was added via syringe, and the mixture stirred 24 hours. The product mixture was purified directly by RP-HPLC (method B), and the product fractions were combined and lyophilized to yield the pure product as a solid consisting of a 1:1 mixture of 1-alkylated indazole and 2-alkylated indazole (13 mg). LC/MS method A: $R_t$=4.60 mins., $(M+H)^+$=823, purity >95%, isomers not separated. $^1$H-NMR (DMSO-$d_6$) δ 11.61-11.91 (m, 1H), 8.40 (s, 0.5H), 8.11 (s, 0.5H), 6.72-7.82 (m, 8H), 6.34-6.50 (m, 0.5H), 6.20-6.33 (m, 1H), 2.37-3.38 (m, 26H), 2.12-2.36 (m, 4H), 1.58-1.84 (m, 4H), 0.97-1.53 (m, 26H), 0.65-0.93 (m, 6H).

Example 54

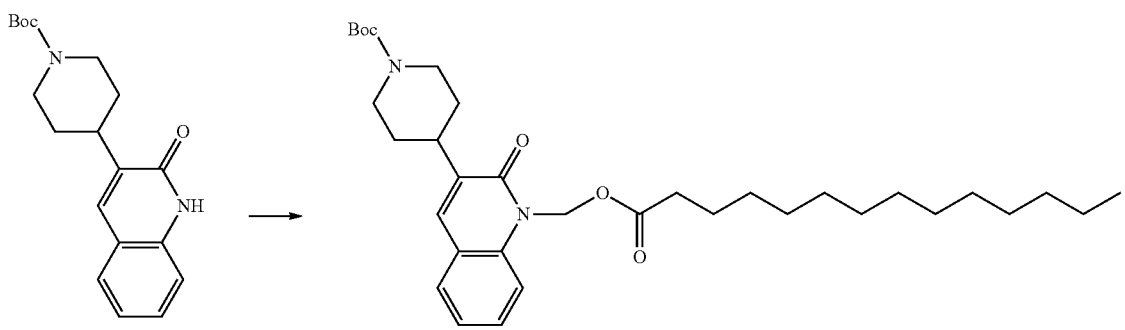 [SMILES: CC(C)(C)OC(=O)N1CCC(c2cc3ccccc3[nH]c2=O)CC1 ; CCCCCCCCCCCCCC(=O)OCn1c(=O)c(C2CCN(C(=O)OC(C)(C)C)CC2)cc2ccccc21]

tert-butyl 4-(2-oxo-1-(tetradecanoyloxymethyl)-1,2-dihydroquinolin-3-yl)piperidine-1-carboxylate. To suspension of 292 mg (0.89 mmol) of tert-butyl 4-(2-oxo-1,2-dihydroquinolin-3-yl)piperidine-1-carboxylate with THF (5 mL) was treated with lithium hexamethyldisilylamide (1.0 M in THF, 1.4 mL, 1.4 mmol), and the reaction mixture was stirred for 15 minutes. Then chloromethyl tetradecanoate (368 mg, 1.34 mmol) was added via syringe over five minutes as a solution in THF (5 mL), and the mixture was stirred for 4 h. The reaction was cooled in an ice/water bath and quenched by addition of 3 mL of saturated ammonium chloride solution. Then, 30 mL ethyl acetate and 15 mL water was added. The aqueous phase was back extracted with 20 mL ethyl acetate. The combined organic extracts were dried and concentrated under vacuum. The material was purified on a 40 gram silica column eluted with ethyl acetate/hexanes from 0 to 80%. Similar fractions were combined to yield 180 mg of the expected product of 95% purity. $^1$H NMR (CHLOROFORM-d) δ: 7.41-7.61 (m, 3H), 7.14-7.39 (m, 2H), 6.36 (s, 2H), 4.25 (s, 2H), 4.00-4.15 (m, 2H), 3.10 (s, 1H), 2.85 (br s, 3H), 2.33 (t, J=7.5 Hz, 2H), 1.93 (br d, J=12.6 Hz, 1H), 1.54-1.70 (m, 2H), 1.47 (s, 9H), 1.22 (br d, J=6.0 Hz, 2H), 0.77-1.01 (m, 3H).

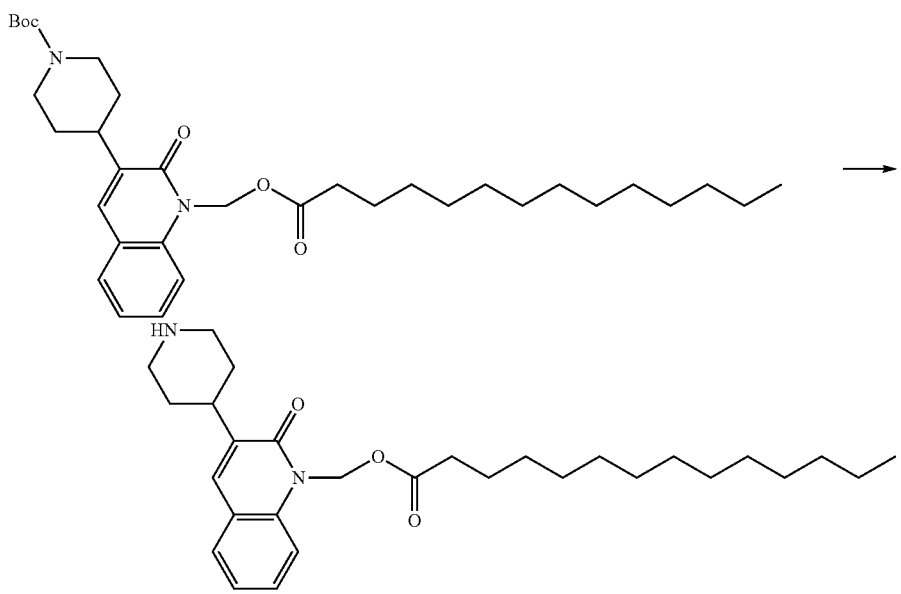

(2-oxo-3-(piperidin-4-yl)quinolin-1(2H)-yl)methyl tetradecanoate. To a solution (180 mg, 0.32 mmol) of tert-butyl 4-(2-oxo-1-(tetradecanoyloxymethyl)-1,2-dihydroquinolin-3-yl)piperidine-1-carboxylate in 2 mL dioxane was added 2 mL of 4.0 N HCl. After three hours of stirring, 20 mL of ether was added, and the reaction was allowed to stand for 18 h at room temperature. The solvents were removed by a pipette, and ether trituration was repeated once more. The resulting solid was stirred with 20 mL DCM, and saturated sodium bicarbonate added slowly until foaming stopped. The DCM layer was separated dried and concentrated under vacuum to yield 110 mg of the expected product. $^1$H NMR (DMSO-$d_6$) δ 7.70-7.88 (m, 3H), 7.23-7.60 (m, 2H), 6.28 (s, 2H), 3.01 (br d, J=3.1 Hz, 2H), 2.30 (t, J=7.3 Hz, 4H), 1.96 (s, 2H), 1.62-1.81 (m, 2H), 0.71-1.29 (m, 20H), 0.65-0.95 (m, 3H).

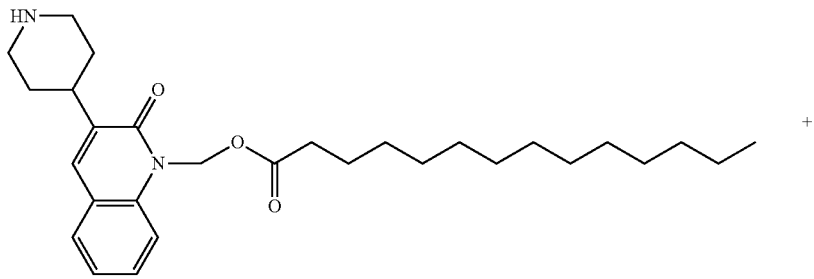

-continued

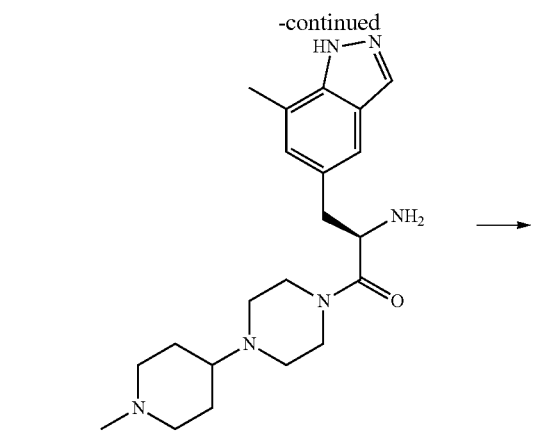

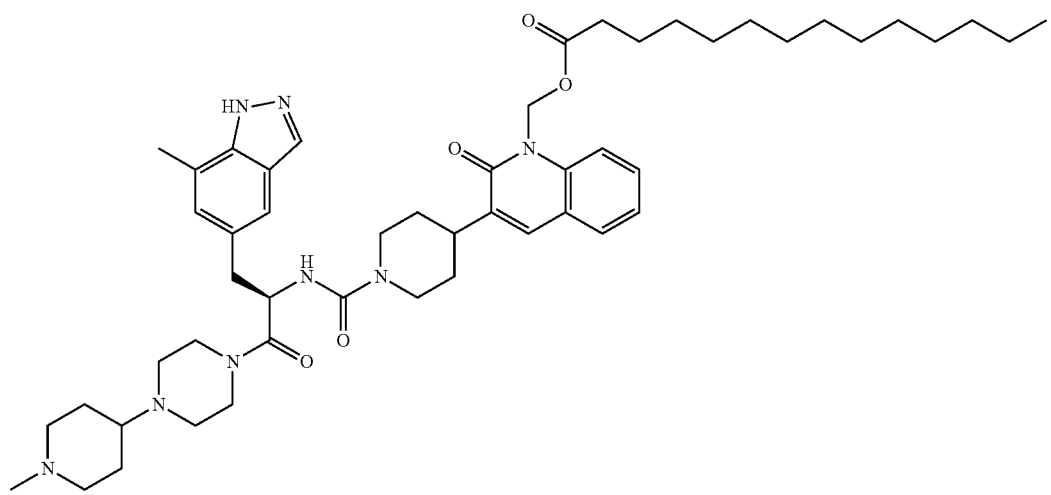

(R)-(3-(1-(3-(7-methyl-1H-indazol-5-yl)-1-(4-(1-methylpiperidin-4-yl)piperazin-1-yl)-1-oxopropan-2-ylcarbamoyl)piperidin-4-yl)-2-oxoquinolin-1(2H)-yl)methyl tetradecanoate (54). To a solution of (11 mg, 0.138 mmol) (2-oxo-3-(piperidin-4-yl)quinolin-1(2H)-yl)methyl tetradecanoate in 0.8 mL DCM was added (31 mg, 0.242 mmol) of DIEA, and the reaction was cooled in an ice/water bath. Then a solution of (11.3 mg, 0.038 mmol) of triphosgene was added in 0.5 mL DCM over 30 seconds. The cooling bath was removed after 30 seconds. Then, (42 mg, 0.109 mmol) of (R)-2-amino-3-(7-methyl-1H-indazol-5-yl)-1-(4-(1-methylpiperidin-4-yl)piperazin-1-yl)propan-1-one was added as a solid, and the reaction was allowed to stir for 18 h at room temperature. The DCM was removed under vacuum, and the concentrate was dissolved in 2.5 mL DMF. Then the reaction was purified directly by RP-HPLC (method B), and the product fractions were combined and lyophilized to yield the pure product as a white solid 52 mg. $^1$H NMR (DMSO-d$_6$) δ 7.98 (s, 1H), 7.61-7.75 (m, 1H), 7.54 (d, J=7.7 Hz, 2H), 7.23-7.46 (m, 2H), 7.04 (s, 1H), 6.27 (br s, 2H), 4.68-4.85 (m, 1H), 2.81-3.05 (m, 10H), 2.73 (s, 3H), 2.40-2.59 (m, 11H), 2.29 (t, J=7.2 Hz, 2H), 1.65-1.84 (m, 6H), 1.47 (br s, 2H), 1.18 (br d, J=10.3 Hz, 20H), 0.73-0.92 (m, 3H). LC/MS method A: R$_t$=5.85 mins., (M+H)$^+$=879, purity >95%.

Example 55

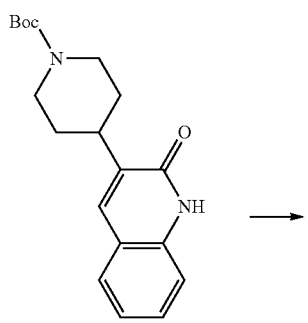

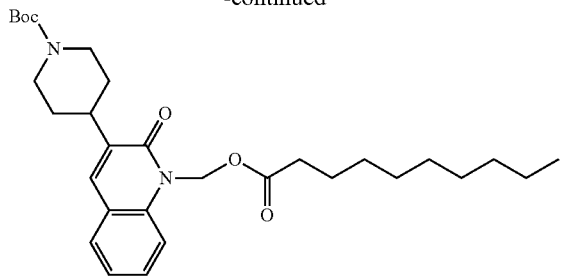

tert-Butyl 4-(1-(decanoyloxymethyl)-2-oxo-1,2-dihydroquinolin-3-yl)piperidine-1-carboxylate. A suspension of 220 mg (0.67 mmol) of tert-butyl 4-(2-oxo-1,2-dihydroquinolin-3-yl)piperidine-1-carboxylate in THF (4 mL) was treated with sodium hydride (40 mg of a 60% suspension in mineral oil, 1.01 mmol), and the reaction was stirred for 20 minutes. Then, chloromethyl decanoate (222 mg, 1.01 mmol) was added via syringe over one minute, and the reaction was stirred for 18 h. The reaction was quenched by dropwise addition of 0.5 mL of water. Once foaming ceased, 30 mL ethyl acetate and 15 mL of water was added. The aqueous phase was then back extracted with 20 mL ethyl acetate. The combined organic extracts were dried and concentrated under vacuum. The material was purified on a 20 gram silica column eluting with ethyl acetate/hexanes from 0 to 60%. Similar fractions were combined to yield 150 mg of the expected product. LC/MS method A: $R_t$=7.88 mins., $(M+H)^+$=535, purity >95%. $^1$H NMR (CDCl$_3$) δ 7.42-7.61 (m, 3H), 7.11-7.40 (m, 2H), 6.37 (s, 2H), 3.11 (s, 3H), 2.86 (br s, 3H), 2.34 (t, J=7.5 Hz, 3H), 1.93 (br d, J=12.6 Hz, 1H), 1.56-1.69 (m, 2H), 1.47 (s, 9H), 1.22 (s, 12H), 0.74-0.97 (m, 1H).

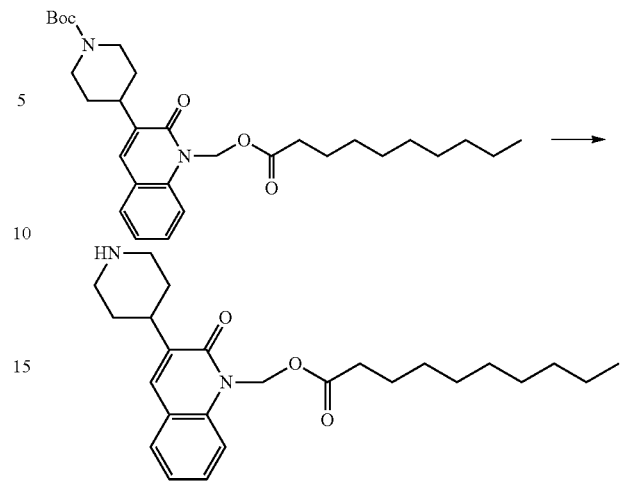

(2-oxo-3-(piperidin-4-yl)quinolin-1(2H)-yl)methyl decanoate. To a solution (150 mg, 0.29 mmol) of tert-butyl 4-(2-oxo-1-(decanoyloxymethyl)-1,2-dihydroquinolin-3-yl)piperidine-1-carboxylate in 2 mL of dioxane was added 2 mL of 4.0 N HCl. After three hours of stirring, 20 mL of ether was added, and the reaction was allowed to stand overnight at room temperature. The next day, the ether was removed by a pipette, and ether trituration was repeated once more. The resulting solid was stirred with 20 mL DCM, and saturated sodium bicarbonate was added slowly until foaming stopped. The DCM layer was separated, dried, and concentrated under vacuum to yield 110 mg of the expected product. LC/MS method A: $R_t$=4.02 mins., $(M+H)^+$=412, purity >95%. $^1$H NMR (DMSO-d$_6$) 7.64-7.95 (m, 3H), 7.40-7.62 (m, 2H), 7.22-7.39 (m, 2H), 6.28 (s, 2H), 3.31 (s, 3H), 2.89-3.12 (m, 2H), 2.30 (t, J=7.2 Hz, 4H), 1.65-2.12 (m, 2H), 1.47 (br t, J=7.0 Hz, 1H), 1.05-1.31 (m, 12H), 0.70-1.00 (m, 3H).

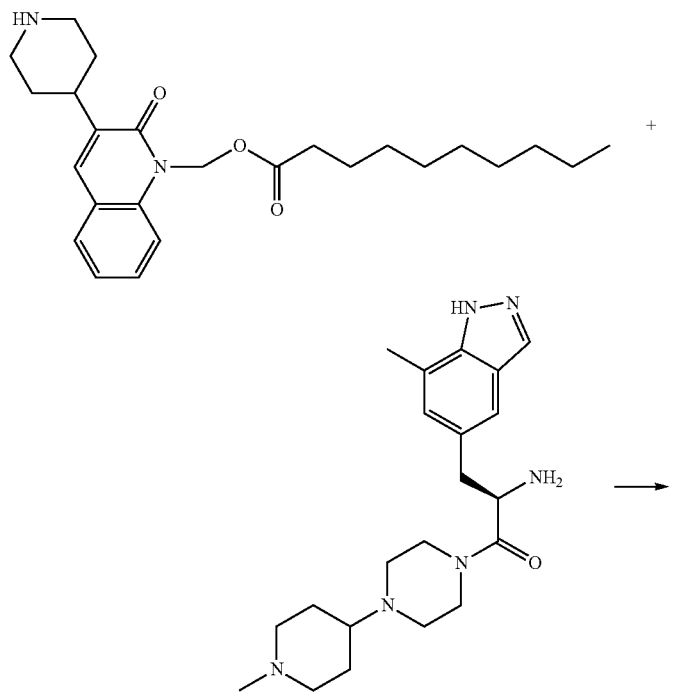

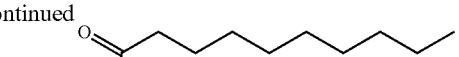
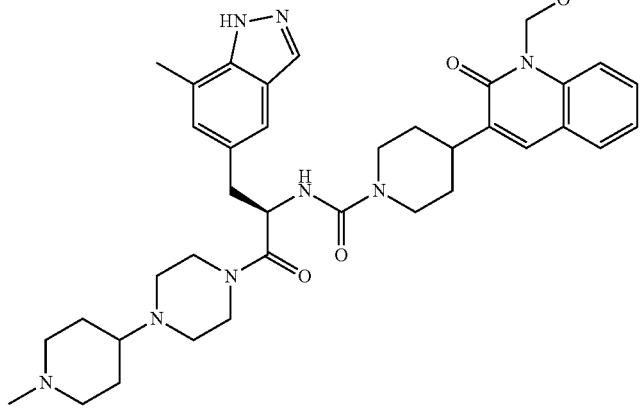

(R)-(3-(1-(3-(7-methyl-1H-indazol-5-yl)-1-(4-(1-methylpiperidin-4-yl)piperazin-1-yl)-1-oxopropan-2-ylcarbamoyl)piperidin-4-yl)-2-oxoquinolin-1(2H)-yl)methyl decanoate (55). To a solution of (43 mg, 0.037 mmol) (2-oxo-3-(piperidin-4-yl)quinolin-1(2H)-yl)methyl decanoate in 0.5 mL of DCM was added (29 mg, 0.222 mmol) of DIEA, and the reaction was cooled in an ice/water bath. Then, a solution of (11.3 mg, 0.037 mmol) of triphosgene was added in 0.5 mL DCM over 30 seconds. The cooling bath was removed after 30 seconds. Then, (43 mg, 0.111 mmol) of (R)-2-amino-3-(7-methyl-1H-indazol-5-yl)-1-(4-(1-methylpiperidin-4-yl)piperazin-1-yl)propan-1-one was added as a solid, and the reaction was allowed to stir for 2.5 hours at room temperature, and was then stored at 5° C. for 3 days. DCM was removed under vacuum, and the concentrate was dissolved with 2.5 mL of DMF. Then the reaction was purified directly by RP-HPLC (method B) and the product fractions were combined and lyophilized to yield the pure product as a solid (38 mg). LC/MS method A: $R_t$=4.68 mins., $(M+H)^+$=823, purity >95%. $^1$H NMR (DMSO-d$_6$) δ 7.98 (s, 1H), 7.62-7.78 (m, 2H), 7.37-7.60 (m, 2H), 7.24-7.33 (m, 1H), 7.04 (s, 1H), 6.27 (s, 2H), 4.11 (s, 2H), 2.79-3.00 (m, 5H), 2.73 (br s, 3H), 2.41-2.53 (m, 5H), 2.30 (t, J=7.2 Hz, 2H), 2.05 (s, 1H), 1.75 (br d, J=12.7 Hz, 3H), 1.41-1.60 (m, 2H), 1.18 (br d, J=7.4 Hz, 9H), 0.76-0.89 (m, 2H).

Example 56

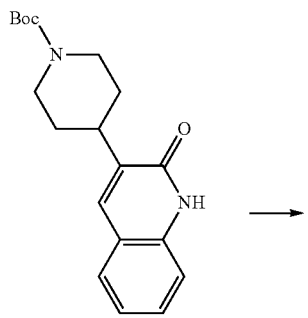

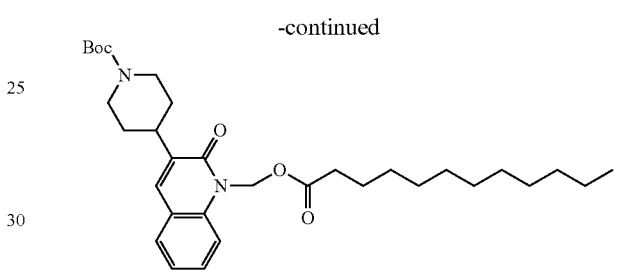

tert-butyl 4-(1-(dodecanoyloxymethyl)-2-oxo-1,2-dihydroquinolin-3-yl)piperidine-1-carboxylate. A suspension of 252 mg (0.77 mmol) of tert-butyl 4-(2-oxo-1,2-dihydroquinolin-3-yl)piperidine-1-carboxylate in THF (4 mL) was treated with sodium hydride (52 mg 60% with oil, 1.31 mmol), and the mixture was stirred 20 minutes. Then chloromethyl dodecanoate (255 mg, 1.15 mmol,) was added via syringe over one minute, and the reaction was stirred overnight. The reaction was diluted with 20 mL ethyl acetate, and the reaction was quenched by dropwise addition of 0.5 mL of water. Once foaming ceased, 30 mL ethyl acetate and 15 mL water added. The aqueous phase was then back extracted with 20 mL ethyl acetate. The combined organic extracts were dried and concentrated under vacuum. The material was purified on a 20 gram silica column eluted with ethyl acetate/hexanes from 0 to 60%. Similar fractions were combined to yield 340 mg of the expected product. $^1$H NMR (CDCl$_3$) δ: 7.42-7.61 (m, 3H), 7.11-7.40 (m, 2H), 6.37 (s, 2H), 3.11 (s, 3H), 2.86 (br s, 3H), 2.34 (t, J=7.5 Hz, 3H), 1.93 (br d, J=12.6 Hz, 1H), 1.56-1.69 (m, 2H), 1.47 (s, 9H), 1.22 (s, 16H), 0.74-0.97 (m, 3H).

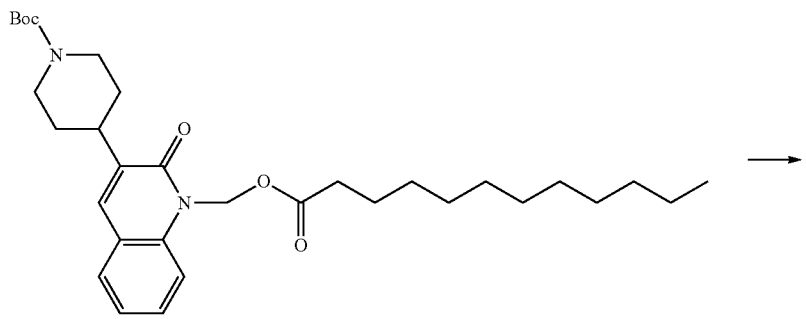

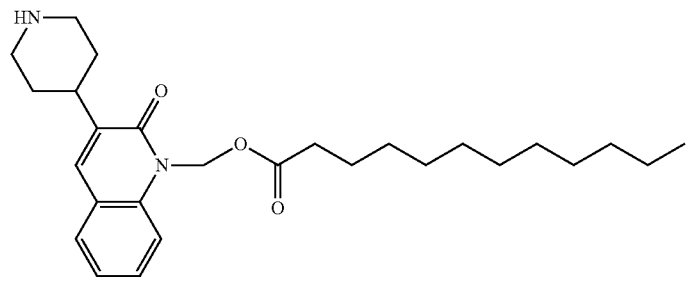

(2-oxo-3-(piperidin-4-yl)quinolin-1(2H)-yl)methyl dodecanoate. To a solution (340 mg, 0.57 mmol) of tert-butyl 4-(2-oxo-1-(dodecanoyloxymethyl)-1,2-dihydroquinolin-3-yl)piperidine-1-carboxylate in 4 mL of dioxane was added 4 mL of 4.0 N HCl in dioxane. After three hours of stirring, 30 mL of ether was added, and the reaction was allowed to stand overnight at room temperature. The ether was removed by a pipette, and ether trituration was repeated once more. The resulting solid was stirred with 20 mL DCM, and saturated sodium bicarbonate solution was added slowly until foaming stopped. The DCM layer was separated, dried (Na$_2$SO$_4$), and concentrated under vacuum to yield 240 mg of the expected product. LC/MS method A: R$_f$=5.53 mins., (M+H)$^+$=441, purity >90%. $^1$H NMR (DMSO-d$_6$) δ 7.70-7.88 (m, 3H), 7.23-7.60 (m, 32H), 6.28 (s, 2H), 3.01 (br d, J=3.1 Hz, 2H), 2.30 (t, J=7.3 Hz, 4H), 1.96 (s, 2H), 1.62-1.81 (m, 2H), 0.71-1.29 (m, 16H), 0.65-0.95 (m, 3H).

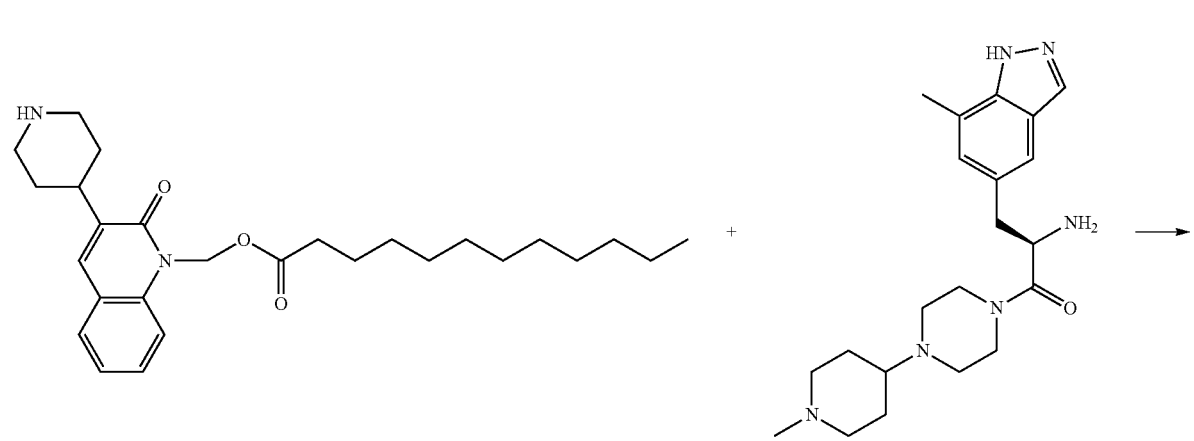

-continued

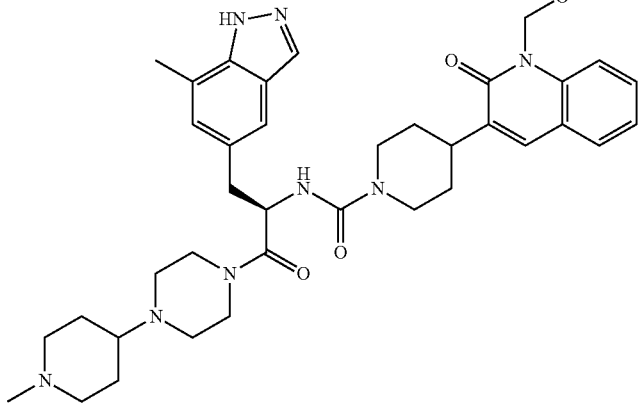

(R)-(3-(1-(3-(7-methyl-1H-indazol-5-yl)-1-(4-(1-methylpiperidin-4-yl)piperazin-1-yl)-1-oxopropan-2-ylcarbamoyl)piperidin-4-yl)-2-oxoquinolin-1(2H)-yl)methyl dodecanoate (56). To a solution of (52 mg, 0.107 mmol) (2-oxo-3-(piperidin-4-yl)quinolin-1(2H)-yl)methyl dodecanoate in 0.4 mL DCM was added (36 mg, 0.279 mmol) of DIEA, and the reaction was cooled in an ice/water bath. Then, a solution of (12 mg, 0.040 mmol) of triphosgene was added in 0.5 mL DCM over 30 seconds. The cooling bath was removed after 30 seconds. Two hours later (46 mg, 0.121 mmol) of (R)-2-amino-3-(7-methyl-1H-indazol-5-yl)-1-(4-(1-methylpiperidin-4-yl)piperazin-1-yl)propan-1-one was added as a solid, and the reaction was allowed to stir overnight at room temperature. The DCM was removed under vacuum, and the concentrate was dissolved with 3 mL of DMF. The reaction was purified directly by RP-HPLC (method C, 5 to 55%), and the product fractions were combined and lyophilized to yield the pure product as a solid 24 mg. LC/MS method A: $R_t$=5.22 mins., (M+H)$^+$=851, purity >95%. $^1$H NMR (DMSO-d$_6$) δ: 7.98 (s, 1H), 7.61-7.75 (m, 1H), 7.54 (d, J=7.7 Hz, 2H), 7.23-7.46 (m, 2H), 7.04 (s, 1H), 6.27 (br s, 2H), 4.68-4.85 (m, 1H), 2.81-3.05 (m, 10H), 2.73 (s, 3H), 2.40-2.59 (m, 11H), 2.29 (t, J=7.2 Hz, 2H), 1.65-1.84 (m, 6H), 1.47 (br s, 2H), 1.18 (br d, J=10.3 Hz, 16H), 0.73-0.92 (m, 3H).

Example 57

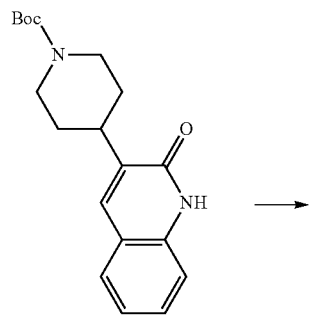

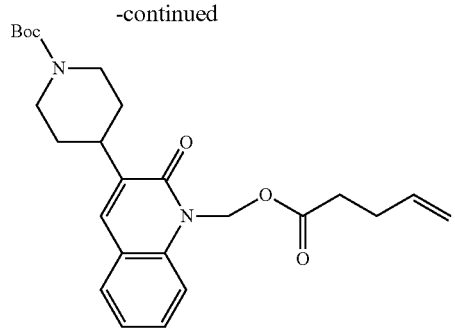

tert-Butyl 4-(1-((pent-5-enoyloxy) methyl)-2-oxo-1,2-dihydroquinolin-3-yl)piperidine-1-carboxylate. A suspension of 290 mg (0.88 mmol) of tert-butyl 4-(2-oxo-1,2-dihydroquinolin-3-yl)piperidine-1-carboxylate in THF (4 mL) was treated with sodium hydride (48 mg of a 60% suspension in mineral oil, 1.19 mmol), and the reaction was stirred for 30 minutes. The reaction was then cooled to −70° C., and chloromethyl pent-4-enoate (196 mg) was added via syringe. The reaction was allowed to warm to room temperature and stirred overnight. The reaction was quenched by addition of 2 mL saturated ammonium chloride, and diluted with 25 mL ethyl acetate and 10 mL of water. The aqueous phase was then back extracted with 20 mL of ethyl acetate. The combined organic extracts were dried (Na$_2$SO$_4$) and concentrated under vacuum. The material was purified on a 40 gram silica column eluted with ethyl acetate/hexanes from 0 to 70%. Similar fractions were combined to yield 210 mg of the expected product. $^1$H NMR (DMSO-d$_6$) 7.64-7.95 (m, 3H), 7.40-7.62 (m, 2H), 7.22-7.39 (m, 2H), 6.28 (s, 2H), 5.82 (m, 1H), 5.05 (m, 2H), 3.31 (s, 3H), 2.89-3.32 (m, 4H), 2.32 (t, J=7.2 Hz, 2H), 2.11-2.22 (M, 3H), 1.35-2.03 (m, 6H), 1.29 (s, 9H).

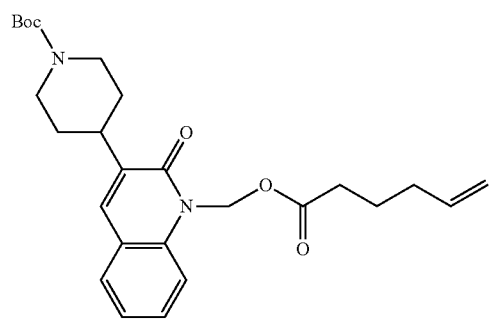

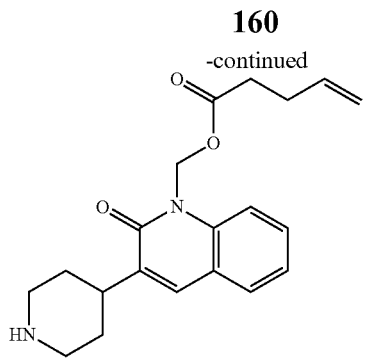

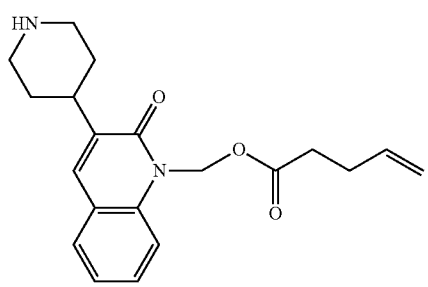

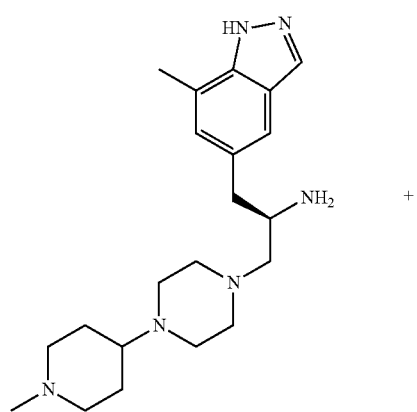

(2-oxo-3-(piperidin-4-yl)quinolin-1(2H)-yl)methyl pent-5-enoate. To a solution of tert-butyl 4-(1-((hex-5-enoyloxy)methyl)-2-oxo-1,2-dihydroquinolin-3-yl)piperidine-1-carboxylate in 2 mL of DCM was added 3 mL of trifluoroacetic acid. After two hours, the reaction was concentrated under vacuum and partitioned between 30 mL chloroform and 10 mL saturated sodium bicarbonate. Then, 1 gram of solid sodium bicarbonate was added slowly. The chloroform layer was separated, dried, and concentrated under vacuum to yield 210 mg of the expected product. LC/MS method A: $R_t$=4.02 mins., (M+H)$^+$=412, purity >95%. $^1$H NMR (DMSO-d$_6$) 7.64-7.95 (m, 3H), 7.40-7.62 (m, 2H), 7.22-7.39 (m, 2H), 6.28 (s, 2H), 5.82 (m, 1H), 5.05 (m, 2H)) 3.31 (s, 3H), 2.65-2.92 (m, 4H), 2.32 (t, J=7.2 Hz, 2H), 2.11-2.22 (M, 3H), 1.35-1.83 (m, 6H).

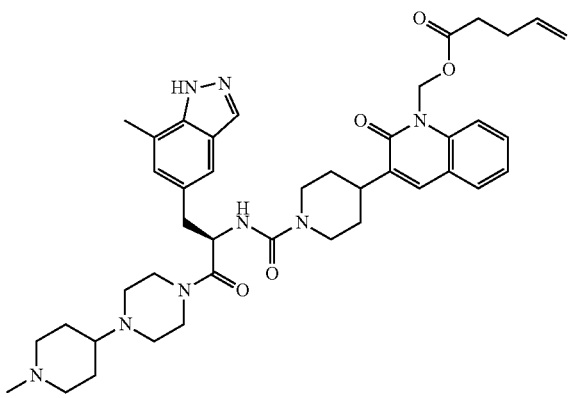

(R)-(3-(1-(3-(7-methyl-1H-indazol-5-yl)-1-(4-(1-methylpiperidin-4-yl)piperazin-1-yl)-1-oxopropan-2-ylcarbamoyl)piperidin-4-yl)-2-oxoquinolin-1(2H)-yl)methyl pent-4-enoate (57). To a solution of (237 mg 0.618 mmol) of (R)-1-(7-methyl-1H-indazol-5-yl)-3-(4-(1-methylpiperidin-4-yl)piperazin-1-yl)propan-2-amine in 1.5 mL DCM was added (340 ul 1.5 mmol) of DIEA and (158 mg 0.618 mmol) of DSC (N,N'-disuccinimidyl carbonate). The mixture was stirred for three hours at room temperature. A solution of (210 mg, 0.62 mmol) (2-oxo-3-(piperidin-4-yl)quinolin-1(2H)-yl)methyl pent-4-enoate in 1 mL of DCM was added dropwise over one minute. The reaction was allowed to stir 18 h at room temperature. The DCM was removed under vacuum, and the concentrate was dissolved in 5 mL of DMF. Then, the reaction was purified directly by RP-HPLC (method C, 5 to 55%), and the product fractions were combined and lyophilized to yield the pure product as a solid (120 mg). The product was free-based with 25 mL of chloroform and 10 mL of saturated sodium bicarbonate. Then, 1 g of solid sodium bicarbonate added slowly over 5 minutes. The reaction was stirred for 30 minutes, and the phases were separated. The chloroform phase was dried and concentrated under vacuum to yield 80 mg of the product. LC/MS method A: $R_t$=3.58 mins., (M+H)$^+$=751, purity >95%. $^1$H NMR (DMSO-d$_6$) δ 8.23 (s, 1H), 6.94-7.82 (m, 7H), 5.56-5.76 (m, 3H), 4.56-4.98 (m, 3H), 3.07-3.83 (m 10H), 1.85-2.92 (m, 14H), 1.92 (s, 3H), 1.27-1.72 (m, 8H). LC/MS method A: $R_t$=3.58 mins., (M+H)$^+$=751, purity >95%.

Example 58

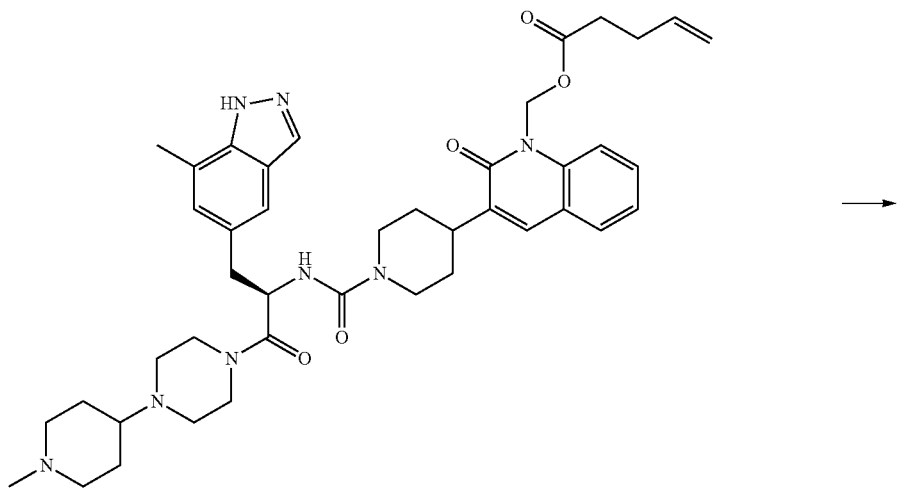

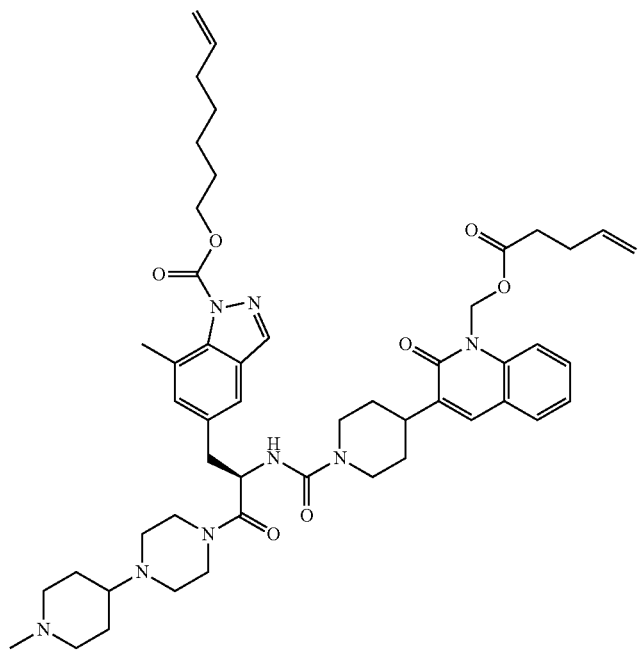

(R)-hept-6-enyl 7-methyl-5-(3-(4-(1-methylpiperidin-4-yl)piperazin-1-yl)-3-oxo-2-(4-(2-oxo-1-((pent-4-enoyloxy)methyl)-1,2-dihydroquinolin-3-yl)piperidine-1-carboxamido)propyl)-1H-indazole-1-carboxylate (58). A solution (80 mg, 0.107 mmol) of (R)-3-(1-(3-(7-methyl-1H-indazol-5-yl)-1-(4-(1-methylpiperidin-4-yl)piperazin-1-yl)-1-oxopropan-2-ylcarbamoyl)piperidin-4-yl)-2-oxoquinolin-1(2H)-yl)methyl pent-4-enoate in 2 mL DCM was added dropwise over 30 seconds to a solution of (48 mg, 0.25 mmol) of hept-6-enylchloroformate, and the reaction was allowed to stir overnight at room temperature. DCM was removed under vacuum, and the concentrate was dissolved with 3 mL of DMF. The reaction was purified directly by RP-HPLC (method B 17 to 95%), and the product fractions were combined and lyophilized to yield the pure product as a solid (17 mg). LC/MS method A: $R_t$=4.62 mins., $(M+H)^+$=906, purity >95%, inseparable isomers. $^1$H NMR (DMSO-$d_6$) δ 8.33 (s, 0.5H), 8.12 (s, 0.5H), 6.90-7.82 (m, 8H), 5.60-5.82 (m, 6H), 5.03-5.25 (m, 4H), 3.03-3.67 (m, 9H), 1.98-2.67 (m, 16H), 1.82 (s, 3H), 1.23-1.67 (m, 20H).

Example 59

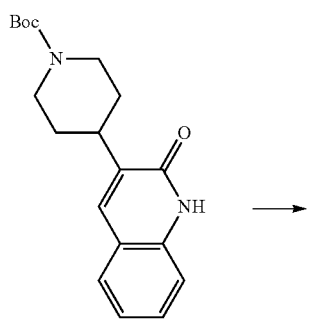

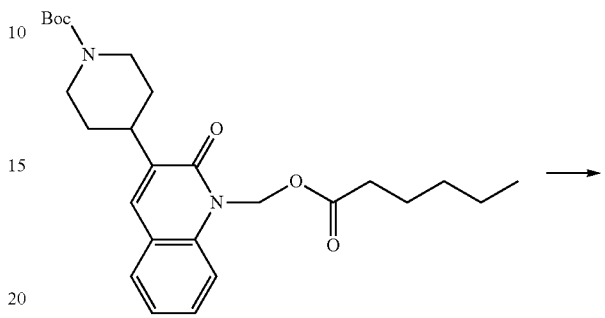

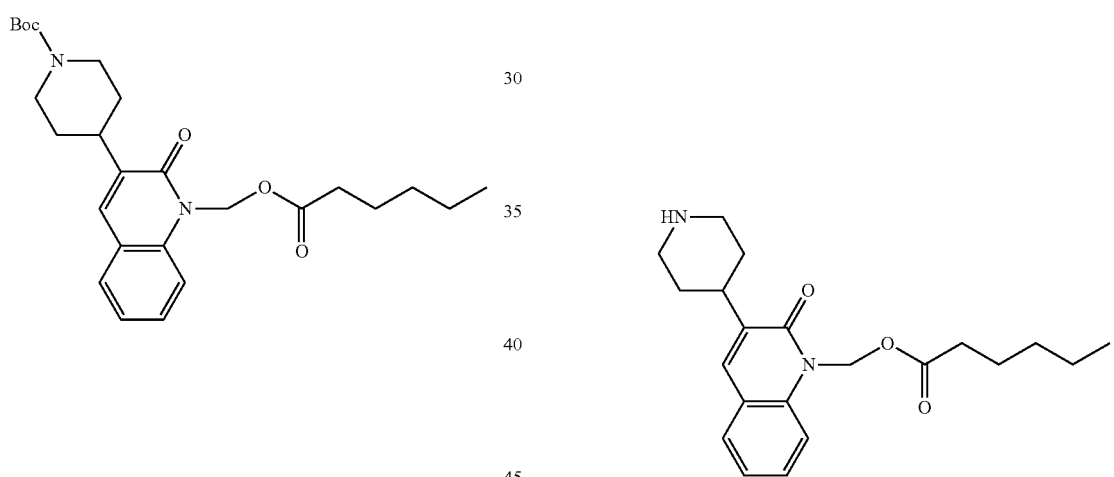

tert-Butyl 4-(1-(hexanoyloxymethyl)-2-oxo-1,2-dihydroquinolin-3-yl)piperidine-1-carboxylate. To a slurry (270 mg 0.82 mmol) of tert-butyl 4-(2-oxo-1,2-dihydroquinolin-3-yl)piperidine-1-carboxylate in THF (4 mL) was added sodium hydride (41 mg of a 60% suspension in mineral oil, 107 mmol), and the mixture was stirred for 20 minutes and cooled to −70° C. Then, chloromethyl hexanoate (203 mg, 1.23 mmol) in 1 mL of THF was added via syringe over one minute, and the reaction was allowed to slowly warm to room temperature while stirring overnight. The reaction was diluted with 20 mL ethyl acetate and quenched by dropwise addition of 2 mL of saturated ammonium chloride. Once foaming ceased, then 15 mL of water was added. The aqueous phase was then back extracted with 20 mL of ethyl acetate. The combined organic extracts were dried and concentrated under vacuum. The residue was purified on a 40 gram silica column eluted with ethyl acetate/hexanes from 0 to 100%. Similar fractions were combined to yield 180 mg of the expected product. LC/MS method A: $R_t$=4.68 mins., $(M+H)^+$=457, purity >95%. $^1$H NMR (CDCl$_3$) δ: 7.42-7.61 (m, 3H), 7.11-7.40 (m, 2H), 6.37 (s, 2H), 3.11 (s, 3H), 2.86 (m, 3H), 2.34 (t, J=7.5 Hz, 3H), 1.93 (br d, J=12.6 Hz, 1H), 1.56-1.69 (m, 2H), 1.47 (s, 9H), 1.22 (m, 6H), 0.74-0.97 (m, 3H).

2-oxo-3-(piperidin-4-yl)quinolin-1(2H)-yl)methyl hexanoate. To a solution (180 mg, 395 mmol) of tert-butyl 4-(1-(hexanoyloxymethyl)-2-oxo-1,2-dihydroquinolin-3-yl)piperidine-1-carboxylate in 3 mL of dichloromethane was added 3 mL of trifluoroacetic acid. After two hours, the reaction was concentrated under vacuum and partitioned between 30 mL of chloroform and 10 mL of saturated sodium bicarbonate. Then, 1 gram of solid sodium bicarbonate was added slowly. The chloroform layer was separated, dried, and concentrated under vacuum to yield 150 mg of the expected product. LC/MS method A: $R_t$=3.22 mins., $(M+H)^+$=3.57, purity >95%. $^1$H NMR (DMSO-d$_6$) δ: 7.70-7.88 (m, 3H), 7.23-7.60 (m, 32H), 6.28 (s, 2H), 3.01 (br d, J=3.1 Hz, 2H), 2.30 (t, J=7.3 Hz, 4H), 1.96 (s, 2H), 1.62-1.81 (m, 2H), 0.71-1.29 (m, 6H), 0.65-0.95 (m, 3H).

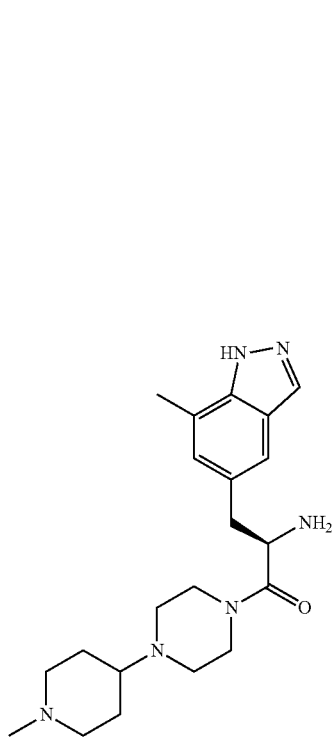
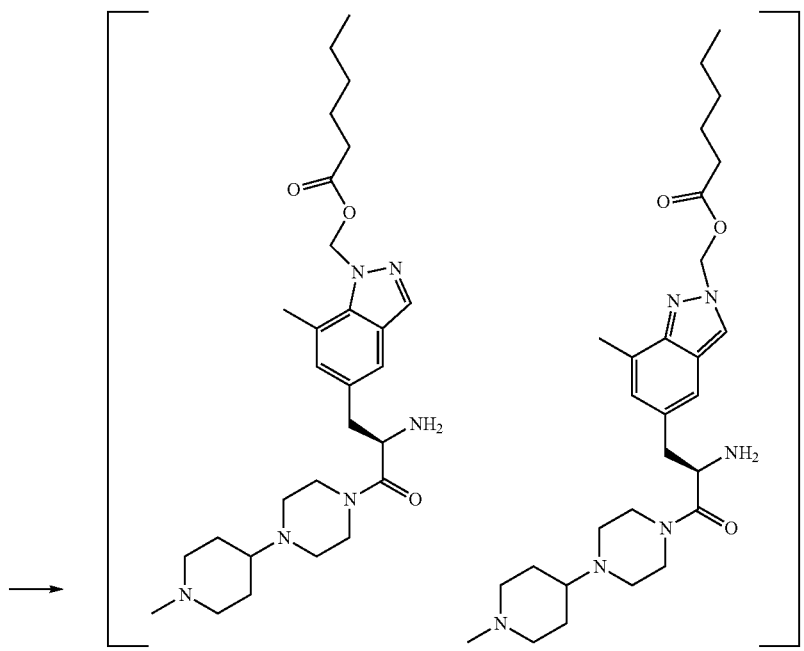

(R)-(5-(2-amino-3-(4-(1-methylpiperidin-4-yl)piperazin-1-yl)propyl)-7-methyl-1H-indazol-1-yl)methyl hexanoate compound with (R)-(5-(2-amino-3-(4-(1-methyl piperidin-4-yl)piperazin-1-yl)propyl)-7-methyl-2H-indazol-2-yl) methyl hexanoate (1:1). To a suspension (234 mg 0.672 mmol) of (R)-1-(7-methyl-1H-indazol-5-yl)-3-(4-(1-methylpiperidin-4-yl)piperazin-1-yl)propan-2-amine in 3 mL THF was added (39 mg, 0.974 mmol) of sodium hydride. After 30 minutes, the reaction was cooled to −70° C. Then, chloromethyl hexanoate (203 mg, 1.23 mmol) in 1 mL of THF was added via syringe over ten minutes, and the reaction mixture was stirred. The reaction mixture was allowed to slowly warm to room temperature, and was stirred for three hours at room temperature. The reaction was concentrated under vacuum and dissolved with 5 mL of DMF. Then, the reaction was purified directly by RP-HPLC (method B 10 to 85%), and the product fractions were combined and lyophilized to yield the pure product as a solid (72 mg). The solid was free based with 60 mL chloroform and 15 mL saturated sodium bicarbonate. The organic phase was dried and concentrated under vacuum. Yield was 48 mg. $^1$H NMR (CD$_3$OD) δ: 8.16 (s, 0.5H), 8.02 (s, 0.5H), 7.42-7.56 (m, 1H), 6.92-7.07 (m, 1H), 6.15-6.25 (m, 2H), 3.13-3.27 (m, 1H), 2.58-2.80 (m, 1H), 2.06-2.34 (m, 12H), 1.96 (s, 3H), 1.32-1.83 (m, 8H), 0.90 (t, J=6.8 Hz, 3H).

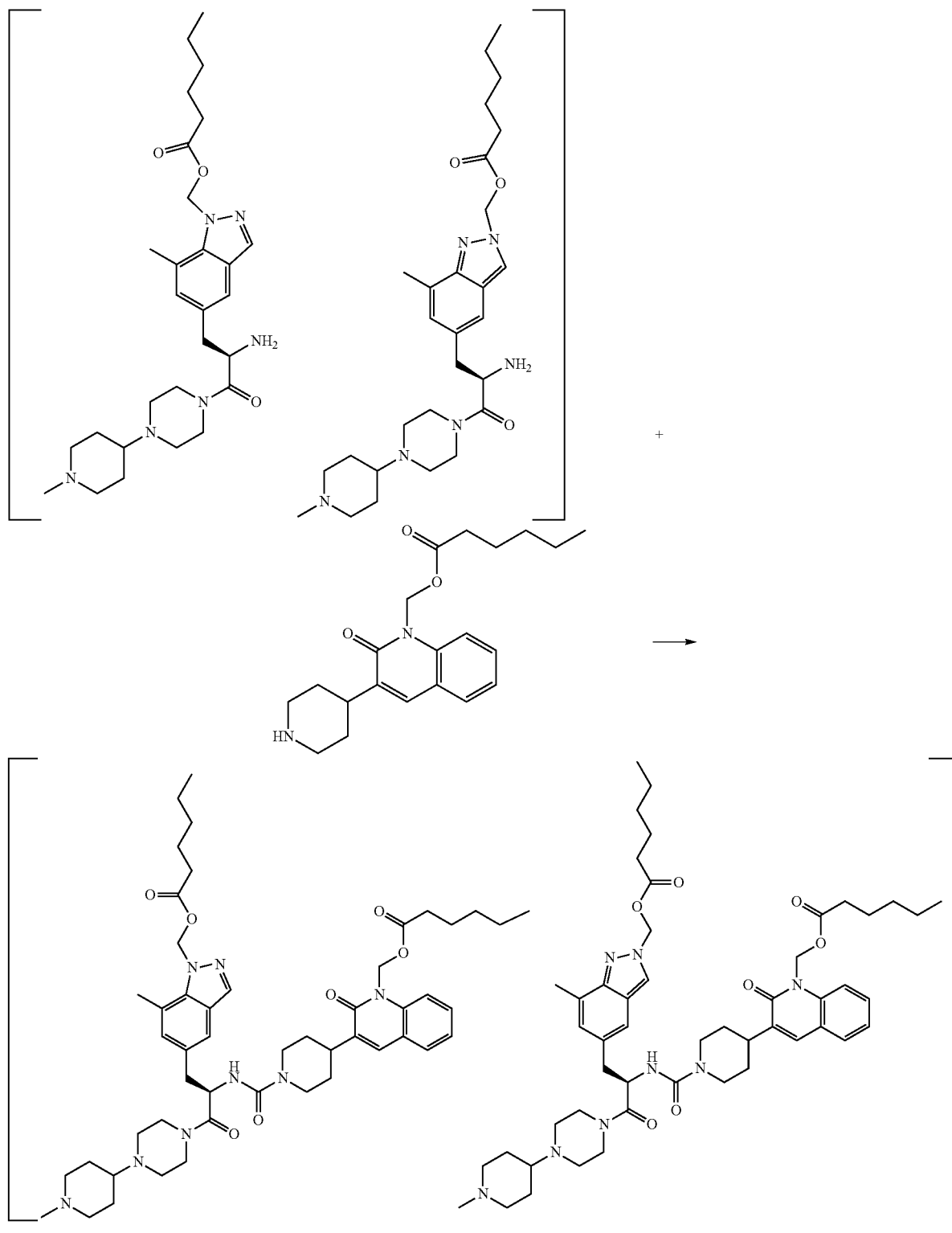

((R)-(5-(2-(4-(1-(hexanoyloxymethyl)-2-oxo-1,2-dihydroquinolin-3-yl)piperidine-1-carboxamido)-3-(4-(1-methylpiperidin-4-yl)piperazin-1-yl)-3-oxopropyl)-7-methyl-2H-indazol-2-yl)methyl hexanoate compound with (R)-pentyl 5-(2-(4-(1-(hexanoyloxymethyl)-2-oxo-1,2-dihydroquinolin-3-yl)piperidine-1-carboxamido)-3-(4-(1-methylpiperidin-4-yl)piperazin-1-yl)-3-oxopropyl)-7-methyl-1H-indazole-1-carboxylate (1:1) (58). To a solution of (R)-(5-(2-amino-3-(4-(1-methylpiperidin-4-yl)piperazin-1-yl)propyl)-7-methyl-1H-indazol-1-yl)methyl hexanoate compound with (R)-(5-(2-amino-3-(4-(1-methylpiperidin-4-yl)piperazin-1-yl)propyl)-7-methyl-2H-indazol-2-yl)methyl hexanoate (1:1) was added (50 ul, 35 mg 0.27 mmol) of DIEA. Ten minutes later, (23 mg, 0.090 mmol) of DSC (N,N'-disuccinimidyl carbonate) was added as a solid, and the reaction was allowed to stir for two hours at room temperature. Then, a solution (32 mg, 0.090 mmol) of (2-oxo-3-(piperidin-4-yl)quinolin-1(2H)-yl)methyl hexanoate in 2 mL of DCM was added over two minutes. The reaction was allowed to stir at room temperature overnight. The reaction was concentrated under vacuum, dissolved in 4 mL of DMF, purified directly by RP-HPLC (method B 10 to 95%), and the product fractions were combined and lyophilized to yield the pure product as a solid 56 mg. $^1$H-NMR (DMSO-d$_6$), 8.23-8.59 (m, 0.5H), 8.13 (s, 0.5H), 6.71-7.93 (m, 8H), 6.07-6.45 (m, 2H), 4.79 (br d, J=8.2 Hz, 1H), 3.92-4.40 (m, 1H), 2.44-3.16 (m, 24H), 2.16-2.42 (m, 13H), 1.59-1.95 (m, 2H), 1.40-1.53 (m, 4H), 1.00-1.36 (m, 12H), 0.69-0.94 (m, 6H). LC/MS method A: R$_t$=5.50 mins., (M+H)$^+$=896, purity >95%.

Example 59

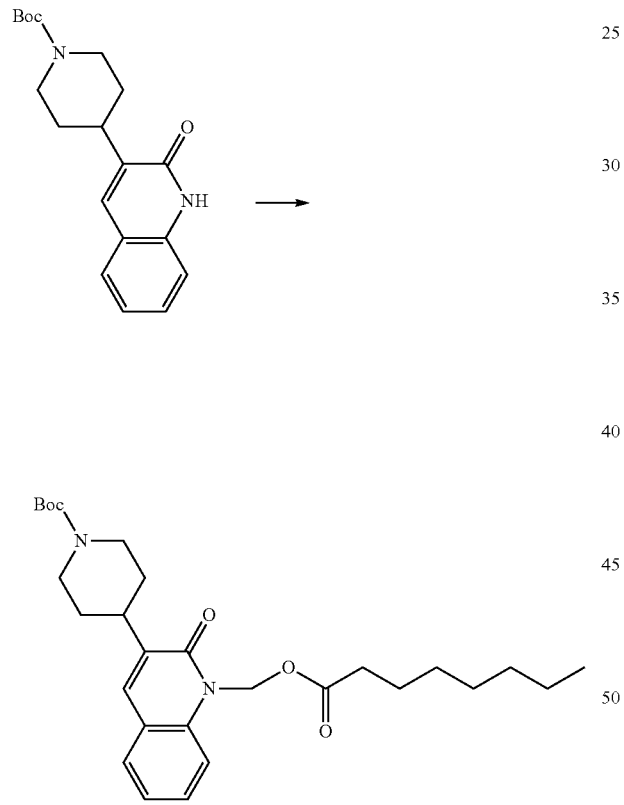

tert-Butyl 4-(1-(octanoyloxymethyl)-2-oxo-1,2-dihydroquinolin-3-yl)piperidine-1-carboxylate. To a slurry (270 mg 0.82 mmol) of tert-butyl 4-(2-oxo-1,2-dihydroquinolin-3-yl)piperidine-1-carboxylate in THF (4 mL) was added sodium hydride (41 mg of a 60% suspension in mineral oil, 107 mmol), and the reaction mixture was stirred for 20 min and cooled to −70° C. Then, chloromethyl octanoate (203 mg, 1.23 mmol) in 1 mL of THF was added via syringe over one minute, and the reaction was allowed to slowly warm to room temperature while stirring overnight. The reaction was diluted with 20 mL of ethyl acetate and quenched by dropwise addition of 2 mL of saturated ammonium chloride. Once foaming ceased, 15 mL of water was added. The aqueous phase was then back extracted with 20 mL ethyl acetate. The combined organic extracts were dried and concentrated under vacuum. The material was purified on a 40 gram silica column eluted with ethyl acetate/hexanes from 0 to 100%. Similar fractions were combined to yield 130 mg of the expected product. LC/MS method A: R$_t$=6.98 mins., (M+H)$^+$=485, purity >95%. $^1$H NMR (CDCl$_3$) δ: 7.42-7.61 (m, 3H), 7.11-7.40 (m, 2H), 6.37 (s, 2H), 3.11 (s, 3H), 2.86 (m, 3H), 2.34 (t, J=7.5 Hz, 3H), 1.93 (br d, J=12.6 Hz, 1H), 1.56-1.69 (m, 2H), 1.47 (s, 9H), 1.22 (m, 8H), 0.74-0.97 (m, 3H).

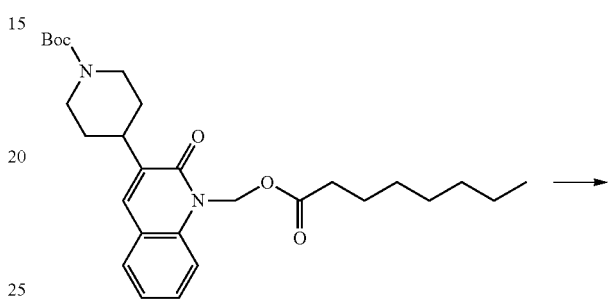

(2-oxo-3-(piperidin-4-yl)quinolin-1(2H)-yl)methyl octanoate. To a solution (130 mg 269 mmol) of tert-butyl 4-(1-(hexanoyloxymethyl)-2-oxo-1,2-dihydroquinolin-3-yl)piperidine-1-carboxylate in 3 mL of DCM was added 3 mL of trifluoroacetic acid. After two hours, the reaction was concentrated under vacuum and partitioned between 30 mL of chloroform and 10 mL of saturated sodium bicarbonate. Then, 1 gram of solid sodium bicarbonate was added slowly. The chloroform layer was separated, dried (Na$_2$SO$_4$), and concentrated under vacuum to yield 100 mg of the expected product. LC/MS method A: R$_t$=4.41 mins., (M+H)$^+$=385, purity >95%. $^1$H NMR (DMSO-d$_6$) δ: 7.70-7.88 (m, 3H), 7.23-7.60 (m, 32H), 6.28 (s, 2H), 3.01 (br d, J=3.1 Hz, 2H), 2.30 (t, J=7.3 Hz, 4H), 1.96 (s, 2H), 1.62-1.81 (m, 2H), 0.71-1.29 (m, 8H), 0.65-0.95 (m, 3H).

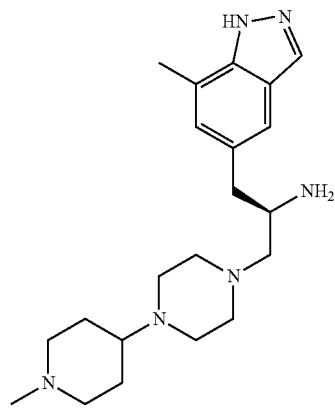
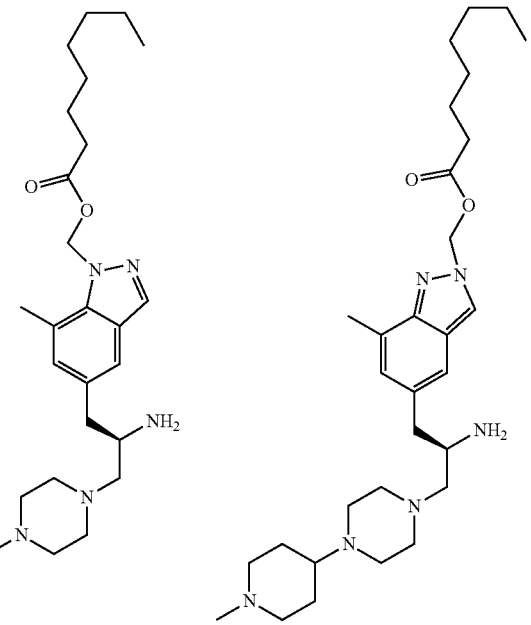

(R)-(5-(2-amino-3-(4-(1-methylpiperidin-4-yl)piperazin-1-yl)propyl)-7-methyl-1H-indazol-1-yl)methyl octanoate compound with (R)-(5-(2-amino-3-(4-(1-methyl piperidin-4-yl)piperazin-1-yl)propyl)-7-methyl-2H-indazol-2-yl) methyl octanoate (1:1). To a suspension (259 mg 0.67 mmol) of (R)-1-(7-methyl-1H-indazol-5-yl)-3-(4-(1-methylpiperidin-4-yl)piperazin-1-yl)propan-2-amine in 3 mL of THF was added (41 mg, 01.01 mmol) of sodium hydride. After 30 min, the reaction was cooled to −70° C. Then, chloromethyl octanoate (237 mg, 123 mmol) in 1 mL of THF was added via syringe over ten minutes, and the mixture was stirred. The reaction was allowed to slowly warm to room temperature and was stirred for three hours at room temperature. The reaction was concentrated under vacuum and dissolved in 5 mL of DMF. Then, the reaction was purified directly by RP-HPLC (method B 10 to 95%), and the product fractions were combined and lyophilized to yield 222 mg of pure product as a solid. The solid was free-based with 30 mL of chloroform and 13 mL of saturated sodium bicarbonate. The organic phase was dried and concentrated under vacuum. Yield was 180 mg. $R_t$=3.90 mins. LC/MS method A: $(M+H)^+$=541, purity >95%. $^1$H NMR (CD$_3$OD) δ: 8.16 (s, 0.5H), 8.02 (s, 0.5H), 7.42-7.56 (m, 1H), 6.92-7.07 (m, 1H), 6.15-6.25 (m, 2H), 3.13-3.27 (m, 1H), 2.58-2.80 (m, 1H), 2.06-2.349 (m, 12H), 1.96 (s, 3H), 1.32-1.83 (m, 12H), 0.90 (t, J=6.8 Hz, 3H).

173 174
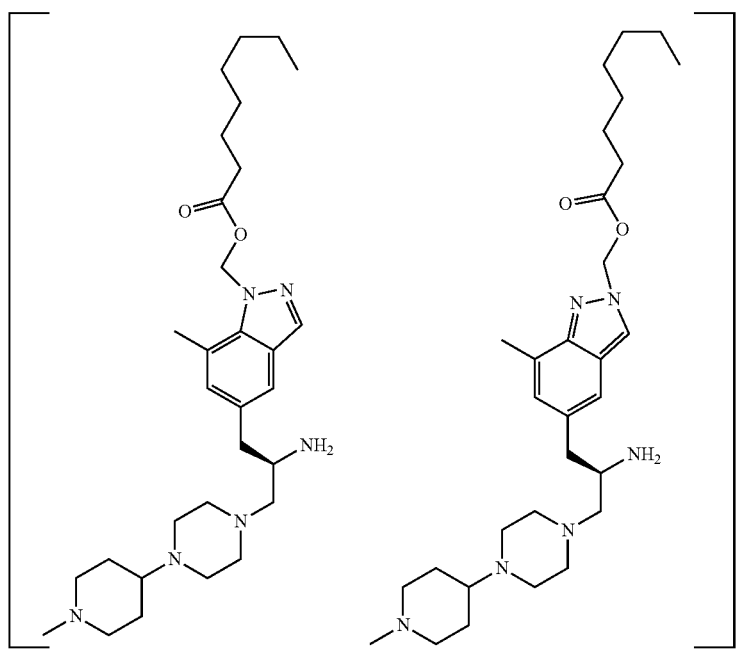
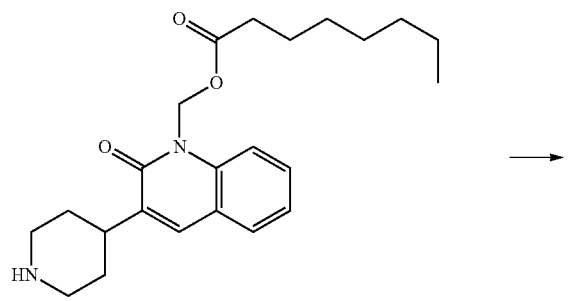
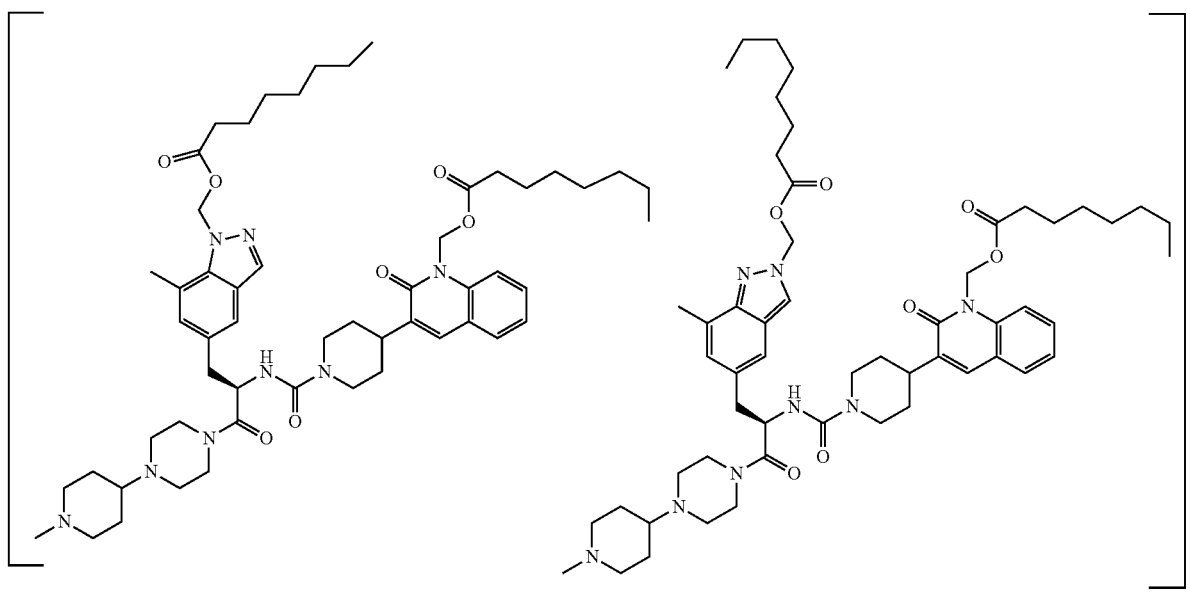

(R)-(3-(1-(3-(7-methyl-2-(octanoyloxymethyl)-2H-indazol-5-yl)-1-(4-(1-methylpiperidin-4-yl)piperazin-1-yl)-1-oxopropan-2-ylcarbamoyl)piperidin-4-yl)-2-oxoquinolin-1(2H)-yl)methyl octanoate compound with (R)-heptyl 7-methyl-5-(3-(4-(1-methylpiperidin-4-yl)piperazin-1-yl)-2-(4-(1-(octanoyloxymethyl)-2-oxo-1,2-dihydroquinolin-3-yl)piperidine-1-carboxamido)-3-oxopropyl)-1H-indazole-1-carboxylate (1:1) (59). To a solution of (80 mg 0.156 mmol) (R)-(5-(2-amino-3-(4-(1-methylpiperidin-4-yl)piperazin-1-yl)propyl)-7-methyl-1H-indazol-1-yl)methyl octanoate compound with (R)-(5-(2-amino-3-(4-(1-methylpiperidin-4-yl)piperazin-1-yl)propyl)-7-methyl-2H-indazol-2-yl)methyl octanoate (1:1) in DMF was added (50 ul, 61 mg 0.47 mmol) of DIEA. Ten minutes later, DSC (N,N'-disuccinimidyl carbonate) (23 mg 0.090 mmol) was added as a solid, and the reaction was allowed to stir for two hours at room temperature. Then, a solution (60 mg, 0.156 mmol) of ((2-oxo-3-(piperidin-4-yl)quinolin-1(2H)-yl)methyl octanoate in 1 mL of DCM was added over ten minutes. The reaction was allowed to stir at room temperature overnight. The reaction was concentrated under vacuum and dissolved in 4 mL of DMF. Then, the reaction was purified directly by RP-HPLC (method B 10 to 93%), and the product fractions were combined and lyophilized to yield the pure product as a solid 96 mg. LC/MS method A: $R_f$=6.401 mins., $(M+H)^+$=952, purity >95% (isomers not separated). $^1$H NMR (DMSO-$d_6$), 8.23-8.59 (m, 0.5H), 8.13 (s, 0.5H), 6.71-7.93 (m, 8H), 6.07-6.45 (m, 2H), 4.79 (br d, J=8.2 Hz, 1H), 3.92-4.40 (m, 1H), 2.44-3.16 (m, 24H), 2.16-2.42 (m, 13H), 1.59-1.95 (m, 2H), 1.40-1.53 (m, 4H), 1.00-1.36 (m, 20H), 0.69-0.94 (m, 6H).

Example 60

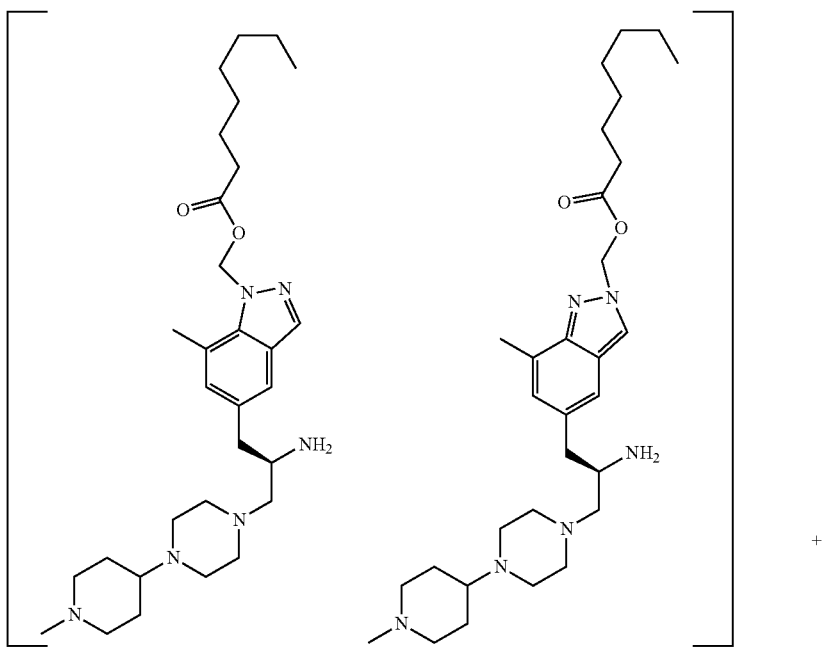

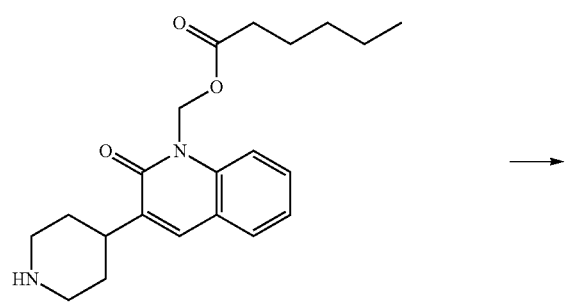

-continued

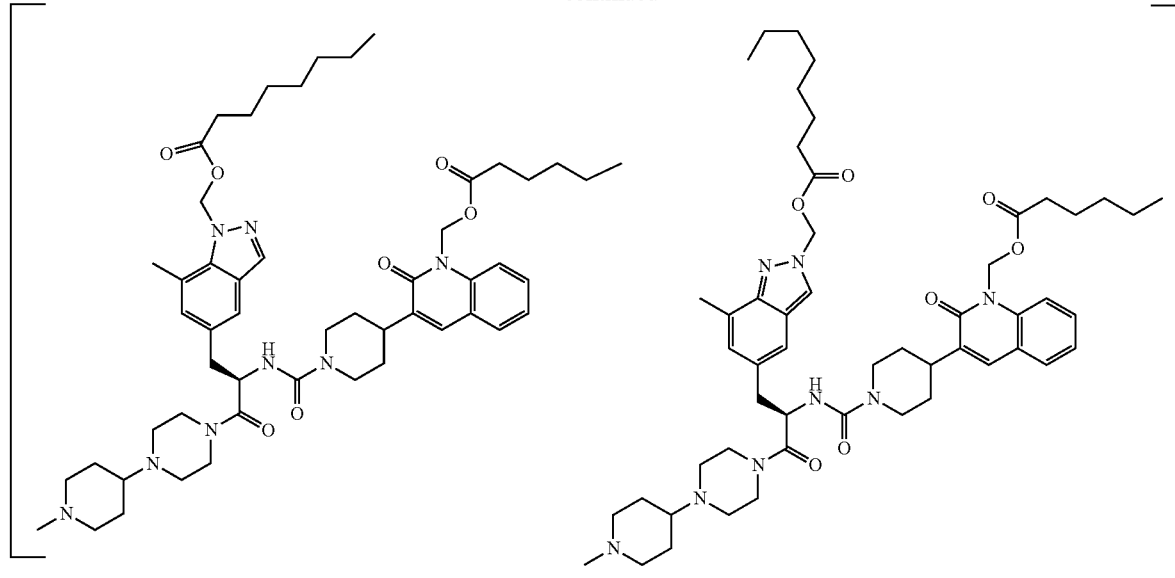

(R)-(5-(2-(4-(1-(hexanoyloxymethyl)-2-oxo-1,2-dihydroquinolin-3-yl)piperidine-1-carboxamido)-3-(4-(1-methylpiperidin-4-yl)piperazin-1-yl)-3-oxopropyl)-7-methyl-2H-indazol-2-yl)methyl octanoate compound with (R)-heptyl 5-(2-(4-(1-(hexanoyloxymethyl)-2-oxo-1,2-dihydroquinolin-3-yl)piperidine-1-carboxamido)-3-(4-(1-methylpiperidin-4-yl)piperazin-1-yl)-3-oxopropyl)-7-methyl-1H-indazole-1-carboxylate (1:1) (60). To a solution of (80 mg, 0.156 mmol) of (R)-(5-(2-amino-3-(4-(1-methylpiperidin-4-yl)piperazin-1-yl)propyl)-7-methyl-1H-indazol-1-yl)methyl octanoate compound with (R)-(5-(2-amino-3-(4-(1-methylpiperidin-4-yl)piperazin-1-yl)propyl)-7-methyl-2H-indazol-2-yl)methyl octanoate (1:1) was added (90 ul, 63 mg 0.47 mmol) of DIEA. Ten minutes later, (42 mg, 0.156 mmol) of DSC (N,N'-disuccinimidyl carbonate) was added as a solid, and the reaction was allowed to stir for two hours at room temperature. Then, a solution (71 mg, 0.156 mmol) of (2-oxo-3-(piperidin-4-yl)quinolin-1(2H)-yl)methyl hexanoate in 2 mL DCM was added over two minutes. The reaction was allowed to stir at room temperature overnight. The reaction was concentrated under vacuum and dissolved with 4 mL of DMF. Then, the reaction was purified directly by RP-HPLC (method B 10 to 88%), and the product fractions were combined and lyophilized to yield the pure product as a solid 66 mg. $^1$H NMR (DMSO-$d_6$) δ: 8.41 (s, 0.5H), 8.13 (s, 0.5H), 6.71-7.80 (m, 8H), 6.17-6.53 (m, 2H), 4.66-4.95 (m, 2H), 4.01-4.29 (m, 1H), 2.09-3.06 (m, 37H), 1.61-1.83 (m, 12H), 1.35-1.60 (m, 4H), 1.02-1.31 (m, 22H), 0.67-0.96 (m, 6H). LC/MS method A: $R_t$=5.91 mins., (M+H)$^+$=924, purity >95%.

Example 61

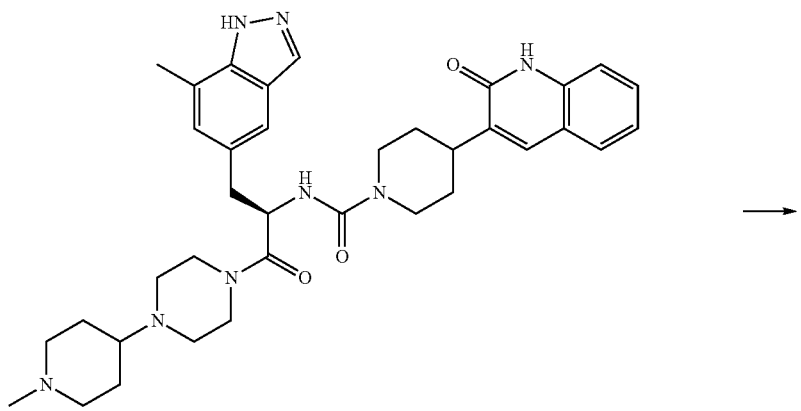

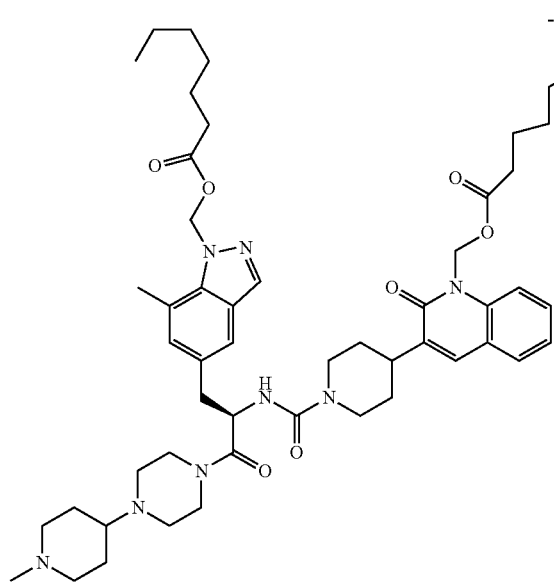

-continued

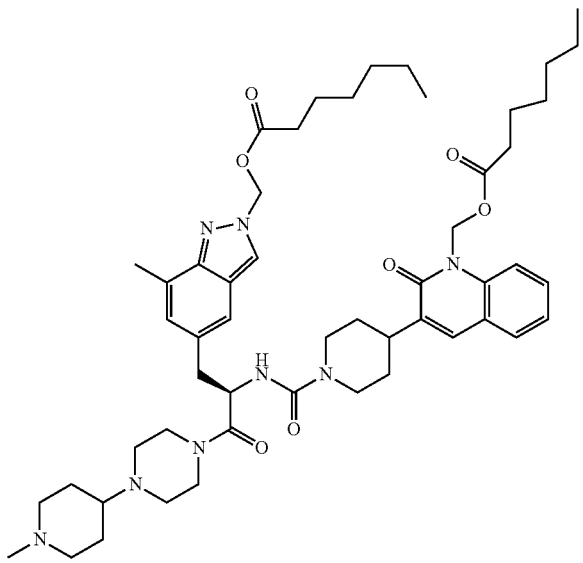

(R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-1H-indazol-1-yl)methyl heptanoate compound with (R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl)methyl heptanoate (1:1) (61). To a solution (42 mg, 0.066 mmol) of (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide in 1.5 mL of DMF was added (130 ul, 0.130 mmol) of lithium bis(trimethylsilyl)amide (1.0 M in THF) over 30 seconds, and the reaction was stirred for 30 minutes. Chloromethyl heptanoate (32 mg 0.164 mmol) was added over 30 seconds. The reaction was allowed to stir for 40 hours at room temperature. The reaction was then quenched by addition of 1 mL of saturated ammonium chloride. The reaction was purified directly by RP-HPLC (method B 15 to 95%), and the product fractions were combined and lyophilized to yield the pure product as a white solid (33 mg) of indazole isomers in roughly a 1:1 ratio. LC/MS method A: $R_f$=5.83 mins., $(M+H)^+$=923, purity >95% (inseparable isomers). $^1$H NMR (DMSO-$d_6$) δ: 8.40 (s, 0.5H), 8.11 (s, 0.5H), 6.72-7.82 (m, 8H), 6.34-6.50 (m, 0.5H), 6.20-6.33 (m, 1H), 2.37-3.38 (m, 26H), 2.12-2.36 (m, 4H), 1.58-1.84 (m, 4H), 0.97-1.53 (m, 16H), 0.65-0.93 (m, 6H).

Examples 62-63

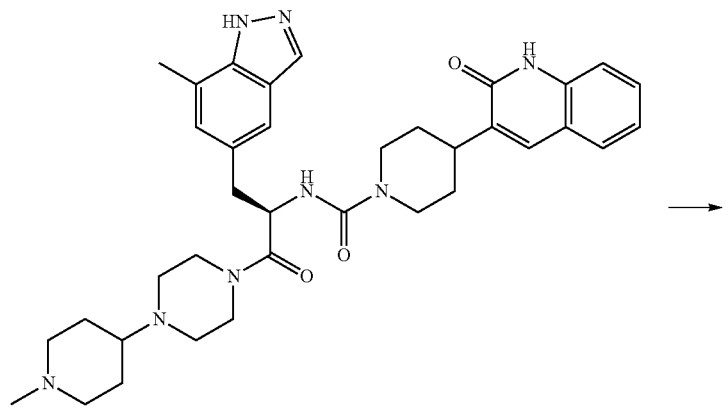

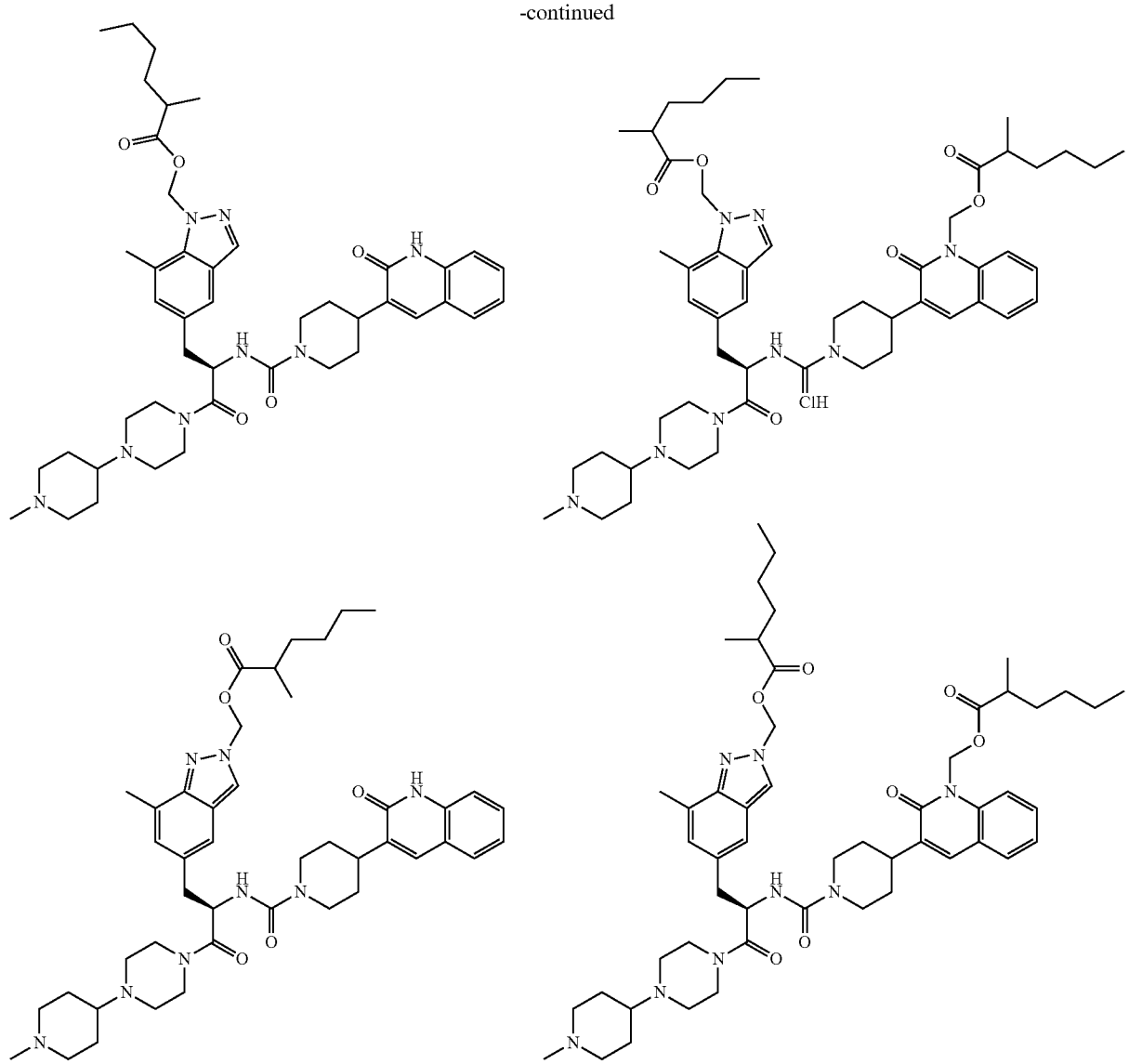

((3-(1-((2R)-3-(7-methyl-1-(2-methylhexanoyl)-1H-indazol-5-yl)-1-(4-(1-methylpiperidin-4-yl)piperazin-1-yl)-1-oxopropan-2-ylcarbamoyl)piperidin-4-yl)-2-oxoquinolin-1(2H)-yl)methyl 2-methyl hexanoate compound with (3-(1-((2R)-3-(7-methyl-2-((2-methylhexanoyloxy)methyl)-2H-indazol-5-yl)-1-(4-(1-methylpiperidin-4-yl)piperazin-1-yl)-1-oxopropan-2-ylcarbamoyl)piperidin-4-yl)-2-oxoquinolin-1(2H)-yl)methyl 2-methylhexanoate (1:1) and (7-methyl-5-((R)-3-(4-(1-methylpiperidin-4-yl)piperazin-1-yl)-3-oxo-2-(4-(2-oxo-1,2-dihydroquinolin-3-yl)piperidine-1-carboxamido)propyl)-1H-indazol-1-yl)methyl 2-methylhexanoate compound with (7-methyl-5-((R)-3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl)methyl 2-methylhexanoate (1:1). To a solution (47 mg, 0.074 mmol) of (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide in 1.5 mL of DMF was added (160 ul, 0.160 mmol) of lithium bis(trimethylsilyl)amide (1.0 M in THF) over 30 seconds, and the reaction was stirred for 30 minutes. Then, the (34 mg 0.192 mmol) of chloromethyl 2-methylhexanoate was added over 1 minute. The reaction was allowed to stir overnight at room temperature. The reaction was then quenched by addition of 1 mL of saturated ammonium chloride. After ten minutes, 3 mL of DMF added. Then, the reaction was purified directly by RP-HPLC (method D 20 to 85%), and the product fractions were combined and lyophilized to yield the pure product as a solid (16 mg) of dialkylated product as a mix of indazole isomers (1:1). An additional 39 mg of monoalkylated indazole isomers, in a roughly 1/1 ratio, was also isolated.

((3-(1-((2R)-3-(7-methyl-1-(2-methylhexanoyl)-1H-indazol-5-yl)-1-(4-(1-methylpiperidin-4-yl)piperazin-1-yl)-1-oxopropan-2-ylcarbamoyl)piperidin-4-yl)-2-oxoquinolin-1(2H)-yl)methyl 2-methyl hexanoate compound with (3-(1-((2R)-3-(7-methyl-2-((2-methylhexanoyloxy)methyl)-2H-indazol-5-yl)-1-(4-(1-methylpiperidin-4-yl)piperazin-1-yl)-1-oxopropan-2-ylcarbamoyl)piperidin-4-yl)-2-oxoquinolin-1(2H)-yl)methyl 2-methylhexanoate (1:1) (62). Yield was 16 mg. LC/MS method A: $R_t$=4.44 mins., $(M+H)^+$=781, purity >95%, inseparable isomers. $^1$H NMR (DMSO-$d_6$) δ:

11.61-11.91 (m, 1H), 8.27-8.53 (m, 0.5H), 7.98-8.21 (m, 0.5H), 6.56-7.74 (m, 7H), 6.14-6.48 (m, 2H), 4.55-4.91 (m, 1H), 3.92-4.26 (m, 2H), 2.08-3.34 (m, 24H), 1.36-1.98 (m, 4H), 0.48-1.24 (m, 12H).

(7-methyl-5-((R)-3-(4-(1-methylpiperidin-4-yl)piperazin-1-yl)-3-oxo-2-(4-(2-oxo-1,2-dihydroquinolin-3-yl)piperidine-1-carboxamido)propyl)-1H-indazol-1-yl)methyl 2-methylhexanoate compound with (7-methyl-5-((R)-3-(4-(1-methylpiperidin-4-yl)piperazin-1-yl)-3-oxo-2-(4-(2-oxo-1,2-dihydroquinolin-3-yl)piperidine-1-carboxamido)pro-pyl)-2H-indazol-2-yl)methyl 2-methylhexanoate (1:1) (63). Yield 39 mg. LC/MS method A: $R_t$=5.78 mins., $(M+H)^+$=924, purity >95%, inseparable isomers. $^1$H NMR (DMSO-d$_6$) δ: 8.39 (s, 0.5H), 8.11 (s, 0.5H), 6.73-7.85 (m, 8H), 6.29 (s, 2H), 4.62-4.93 (m, 1H), 3.97-4.31 (m, 2H), 2.19-3.04 (m, 30H), 1.53-1.82 (m, 2H), 0.87-1.52 (m, 16H), 0.60-0.87 (m, 14H).

Examples 64-67

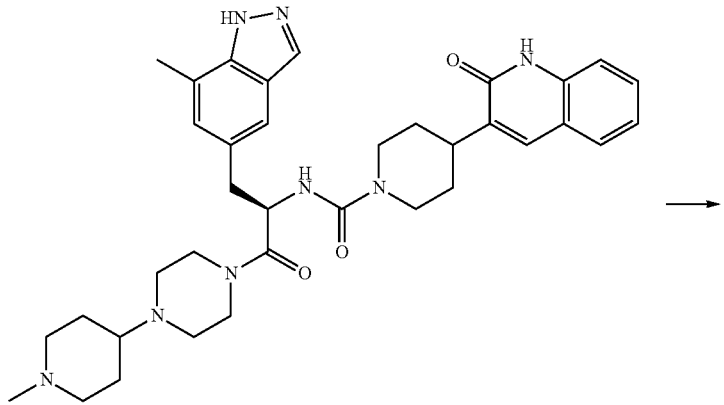

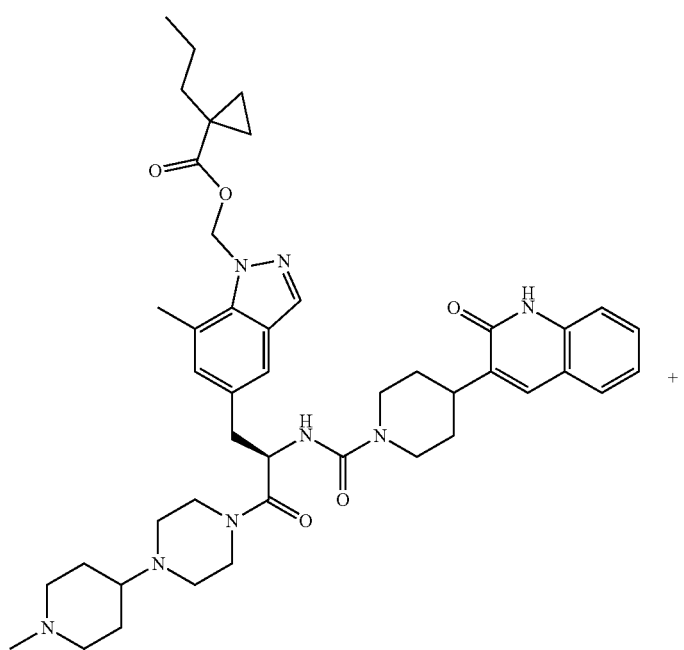

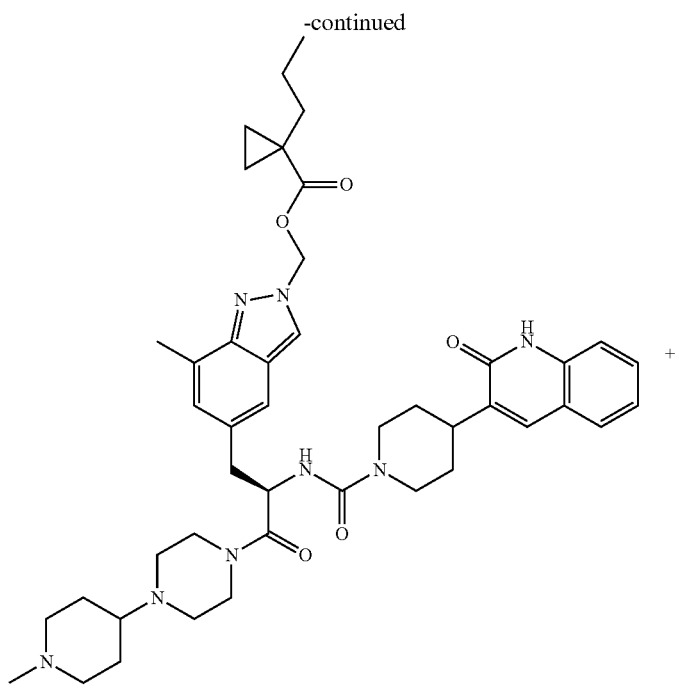
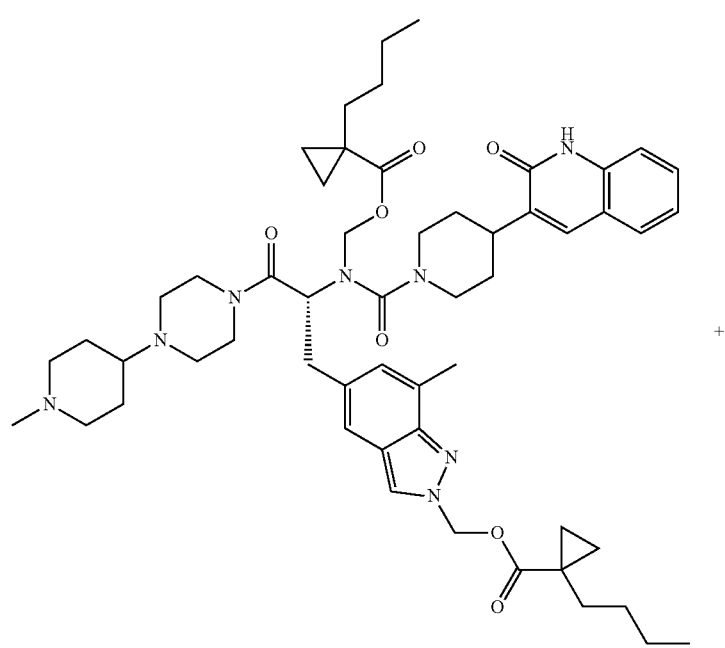

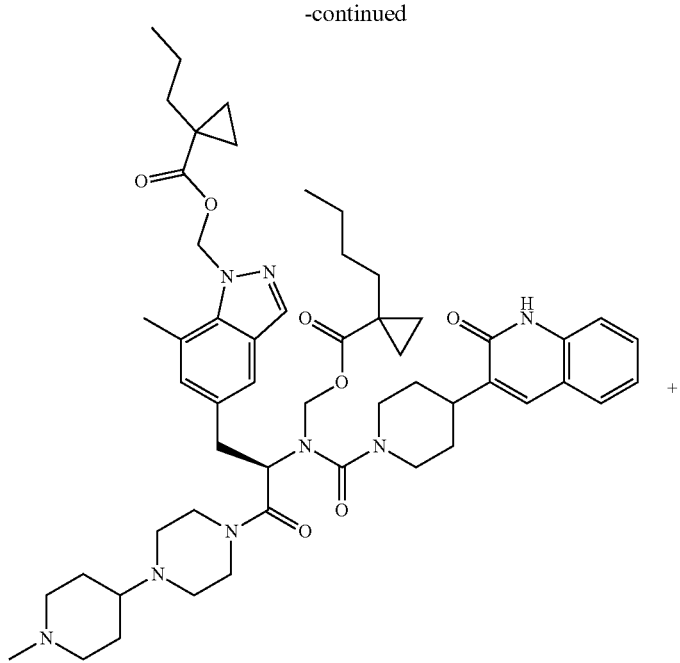
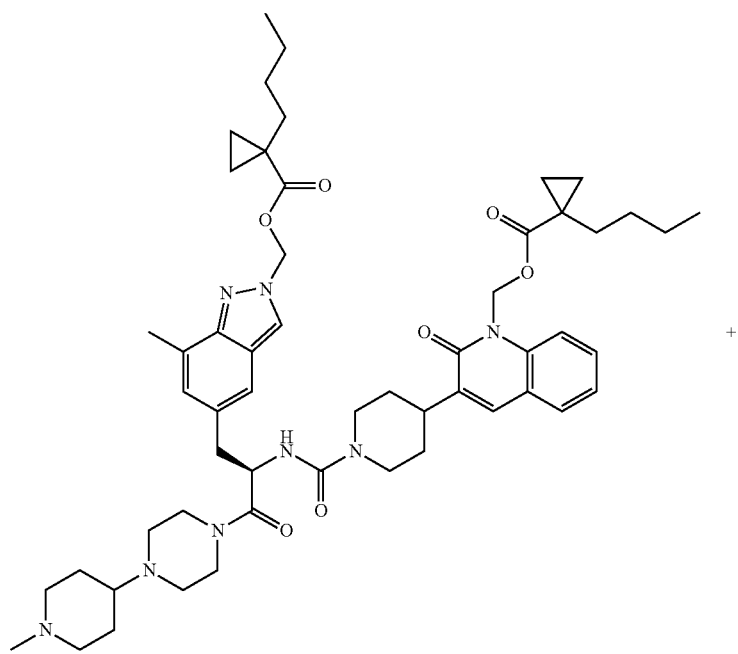

-continued
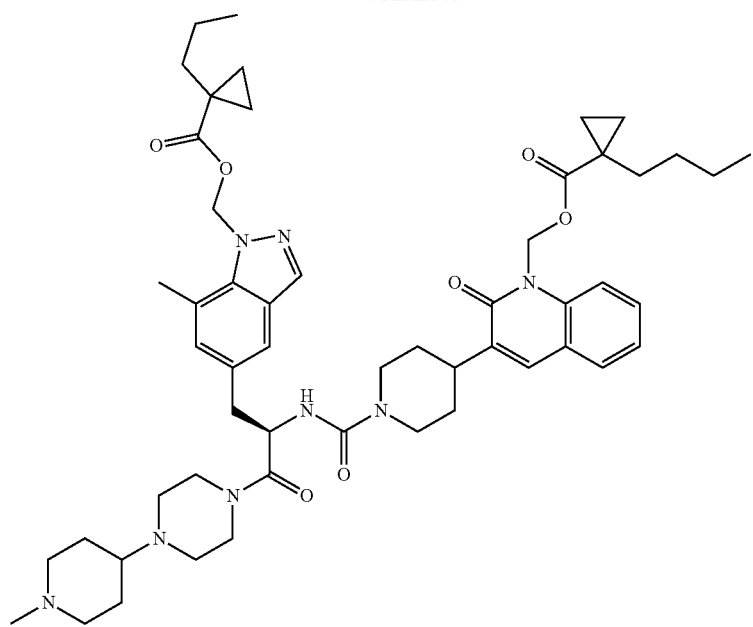
+
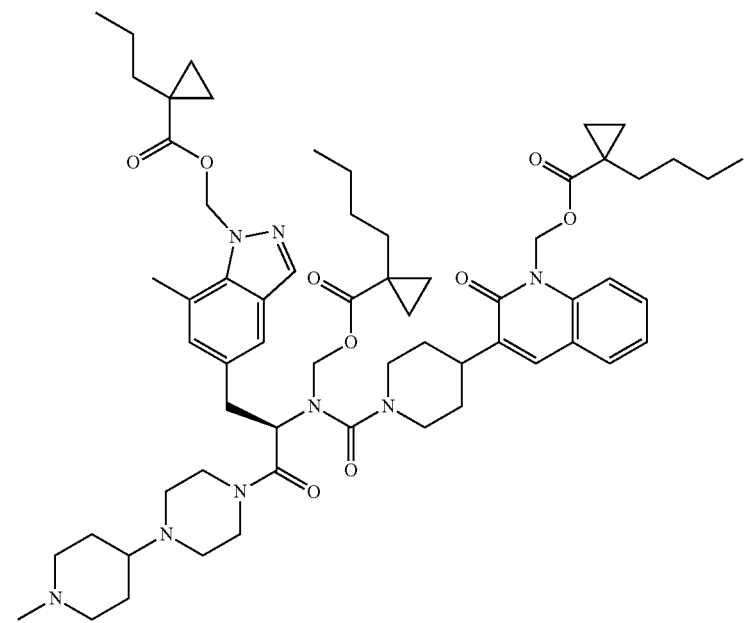
+

-continued

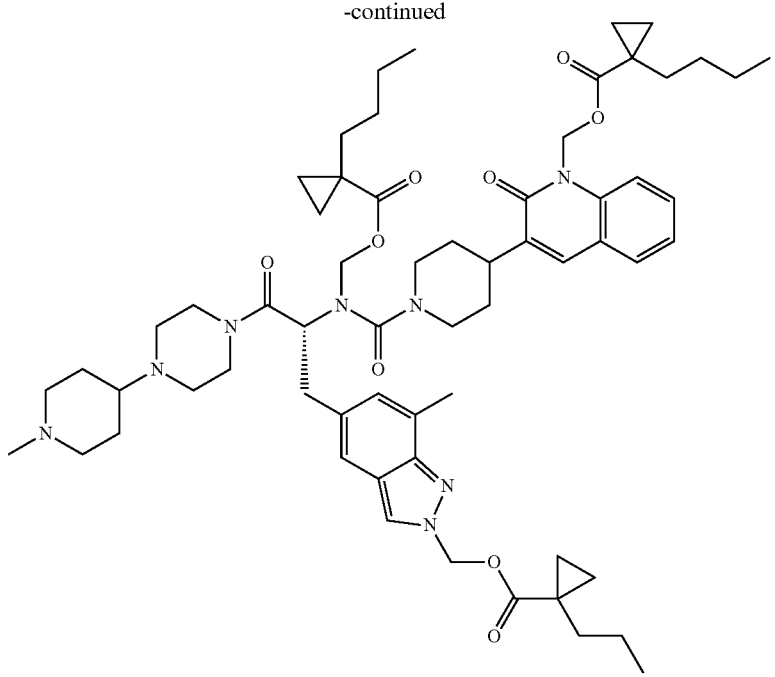

(R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl)methyl 1-butylcyclopropanecarboxylate compound with (R)—N-(3-(1-(1-butylcyclopropanecarbonyl)-7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide (1:1) (64).

(R)-(5-(2-(N-((1-butylcyclopropanecarbonyloxy)methyl)-4-(2-oxo-1,2-dihydroquinolin-3-yl)piperidine-1-carboxamido)-3-(4-(1-methylpiperidin-4-yl)piperazin-1-yl)-3-oxopropyl)-7-methyl-2H-indazol-2-yl)methyl 1-butylcyclopropanecarboxylate compound with (R)—(N-(3-(1-(1-butylcyclopropanecarbonyl)-7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamido)methyl 1-butylcyclopropanecarboxylate (1:1) (65).

(R)-(3-(1-(3-(1-(1-butylcyclopropanecarbonyl)-7-methyl-1H-indazol-5-yl)-1-(4-(1-methylpiperidin-4-yl)piperazin-1-yl)-1-oxopropan-2-ylcarbamoyl)piperidin-4-yl)-2-oxoquinolin-1(2H)-yl)methyl 1-butylcyclopropanecarboxylate compound with (R)-(5-(2-(4-(1-(((1-butylcyclopropanecarbonyloxy)methyl)-2-oxo-1,2-dihydroquinolin-3-yl)piperidine-1-carboxamido)-3-(4-(1-methylpiperidin-4-yl)piperazin-1-yl)-3-oxopropyl)-7-methyl-2H-indazol-2-yl)methyl 1-butylcyclopropanecarboxylate (1:1) (66).

[3-(1-{[(2R)-3-[1-(1-butylcyclopropanecarbonyl)-7-methyl-1H-indazol-5-yl]-1-[4-(1-methylpiperidin-4-yl)piperazin-1-yl]-1-oxopropan-2-yl][(1-butylcyclopropanecarbonyloxy)methyl]carbamoyl}piperidin-4-yl)-2-oxo-1,2-dihydroquinolin-1-yl]methyl 1-butylcyclopropane-1-carboxylate and [3-(1-{[((1-butylcyclopropanecarbonyloxy)methyl][(2R)-3-{7-methyl-2-[(1-propylcyclopropanecarbonyloxy)methyl]-2H-indazol-5-yl}-1-[4-(1-methylpiperidin-4-yl)piperazin-1-yl]-1-oxopropan-2-yl]carbamoyl}piperidin-4-yl)-2-oxo-1,2-dihydroquinolin-1-yl]methyl 1-butylcyclopropane-1-carboxylate (67).

To a solution (52 mg, 0.81 mmol) of (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide in 2 mL of DMF was added (195 ul, 0.195 mmol) of lithium bis(trimethylsilyl)amide (1.0 M in THF) over 30 seconds, and the reaction was stirred for 30 minutes. The chloromethyl 1-(propyl)cyclopropanecarboxylate (84 mg 0.436 mmol) was added over 1 minute. The reaction was allowed to stir overnight at room temperature. The reaction was then quenched by addition of 1 mL of saturated ammonium chloride. After ten minutes, 3 mL of DMF added. Then the reaction was purified directly by RP-HPLC (method D 0 to 78%), and the product fractions were combined and lyophilized to yield the pure products as solids.

(R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl)methyl 1-butylcyclopropanecarboxylate compound with (R)—N-(3-(1-(1-butylcyclopropanecarbonyl)-7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide (1:1) (64) (16 mg). LC/MS method A: $R_t$=4.31 mins., (M+H)$^+$=794, purity >95%, inseparable isomers. $^1$H NMR (DMSO-d$_6$) δ: 11.57-11.86 (m, 1H), 8.25-8.59 (m, 0.5H), 8.00-8.25 (m, 0.5 H), 6.69-7.70 (m, 6H), 6.14-6.56 (m, 2H), 4.57-4.95 (m, 1H), 3.90-4.28 (m, 2H), 2.48-3.32 (m, 26H), 1.49-2.19 (m, 4H), 0.45-1.45 (m, 8H).

(R)-(5-(2-(N-((1-butylcyclopropanecarbonyloxy)methyl)-4-(2-oxo-1,2-dihydroquinolin-3-yl)piperidine-1-carboxamido)-3-(4-(1-methylpiperidin-4-yl)piperazin-1-yl)-3-oxopropyl)-7-methyl-2H-indazol-2-yl)methyl 1-butylcyclopropanecarboxylate compound with (R)—N-(3-(1-(1-butylcyclopropanecarbonyl)-7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamido)methyl 1-butylcyclopropanecarboxylate (1:1) (65). Yield was 13 mg. LC/MS method A: $R_t$=4.85 mins., (M+H)$^+$=948, purity >95%, inseparable isomers. $^1$H NMR (DMSO-d$_6$) δ: 11.53-11.97 (m, 1H), 8.25-8.52 (m, 0.5H), 8.00-8.17 (m, 0.5H), 6.79-7.74 (m, 7H), 6.16-6.79 (m, 1H), 5.06-5.59 (m, 1H), 4.60-4.85 (m, 1H), 3.83-4.34 (m, 1H), 2.48-3.42 (m, 26H), 2.05 (s, 2H), 0.54-1.91 (m, 16H).

(R)-(3-(1-(3-(1-(1-butylcyclopropanecarbonyl)-7-methyl-1H-indazol-5-yl)-1-(4-(1-methylpiperidin-4-yl)piperazin-1-yl)-1-oxopropan-2-ylcarbamoyl)piperidin-4-yl)-2-oxoquinolin-1(2H)-yl)methyl 1-butylcyclopropanecarboxylate compound with (R)-(5-(2-(4-(1-(((1-butylcyclopropanecarbonyloxy)methyl)-2-oxo-1,2-dihydroquinolin-3-yl)piperidine-1-carboxamido)-3-(4-(1-methylpiperidin-4-yl)piperazin-1-yl)-3-oxopropyl)-7-methyl-2H-indazol-2-yl)methyl 1-butylcyclopropanecarboxylate (1:1) (66). Yield was 22 mg. LC/MS method A: LC/MS method A: $R_t$=5.44 mins., (M+H)$^+$=948, purity >95%, inseparable isomers. $^1$H NMR (DMSO-d$_6$) δ: 8.36 (s, 0.5H), 8.09 (s, 0.5H), 7.38-7.86 (m, 2H), 6.84-7.38 (m, 6H), 6.70-6.82 (m, 1H), 6.15-6.52 (m, 2H), 4.58-4.95 (m, 1H), 4.01-4.23 (m, 2H), 2.32-3.02 (m, 28H), 1.60-1.92 (m, 6H), 0.39-1.52 (m, 18H).

[3-(1-{[(2R)-3-[1-(1-butylcyclopropanecarbonyl)-7-methyl-1H-indazol-5-yl]-1-[4-(1-methylpiperidin-4-yl)piperazin-1-yl]-1-oxopropan-2-yl][(1-butylcyclopropanecarbonyloxy)methyl]carbamoyl}piperidin-4-yl)-2-oxo-1,2-dihydroquinolin-1-yl]methyl 1-butylcyclopropane-1-carboxylate and [3-(1-{[(1-butylcyclopropanecarbonyloxy)methyl][(2R)-3-{7-methyl-2-[(1-propylcyclopropanecarbonyloxy)methyl]-2H-indazol-5-yl}-1-[4-(1-methylpiperidin-4-yl)piperazin-1-yl]-1-oxopropan-2-yl]carbamoyl}piperidin-4-yl)-2-oxo-1,2-dihydroquinolin-1-yl]methyl 1-butylcyclopropane-1-carboxylate (67). Yield was 13 mg. LC/MS method A: $R_t$=6.10 mins., (M+H)$^+$=1102, purity >95%, inseparable isomers. $^1$H NMR (DMSO-d$_6$) δ: 8.36 (s, 0.5H), 7.99-8.18 (m, 0.5H), 7.47 (s, 1H), 6.86-7.35 (m, 7H), 6.71-6.84 (m, 1H), 6.16-6.44 (m, 2H), 4.62-4.92 (m, 1H), 4.00-4.28 (m, 2H), 2.54-3.20 (m, 8H), 2.22-2.50 (m, 22H), 1.65-1.98 (m, 6H), 1.45-1.62 (m, 6H), 0.40-1.45 (m, 28H).

Example 68

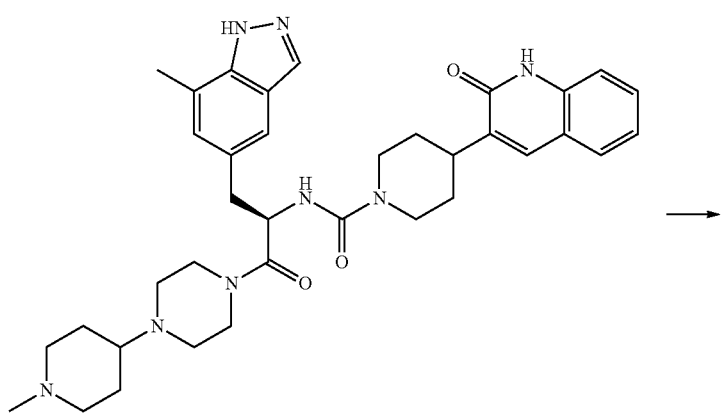

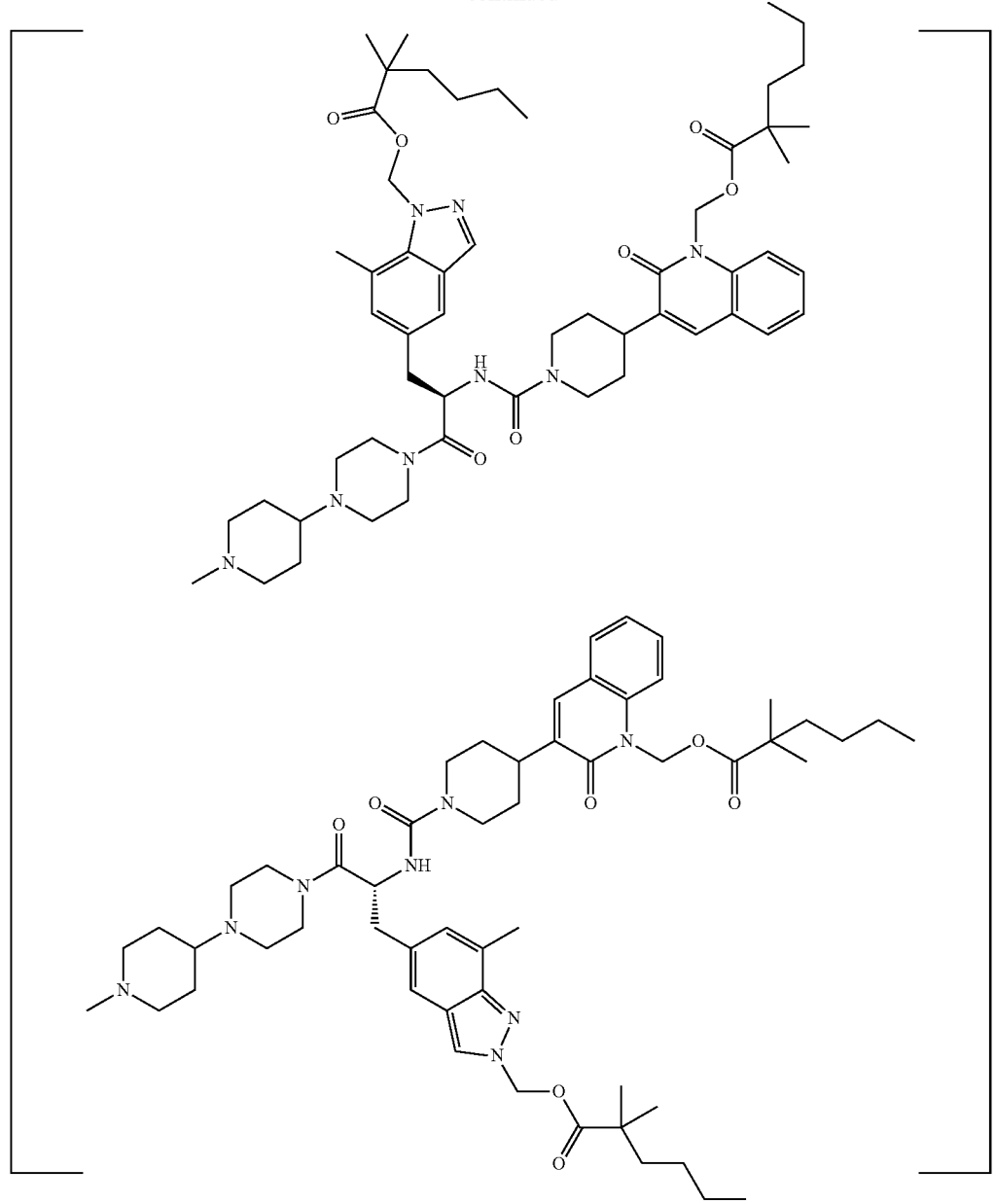

((R)-(3-(1-(3-(1-(2,2-dimethylhexanoyl)-7-methyl-1H-indazol-5-yl)-1-(4-(1-methylpiperidin-4-yl)piperazin-1-yl)-1-oxopropan-2-ylcarbamoyl)piperidin-4-yl)-2-oxoquinolin-1(2H)-yl)methyl 2,2-dimethylhexanoate compound with (R)-(5-(2-(4-(1-((2,2-dimethylhexanoyloxy)methyl)-2-oxo-1,2-dihydroquinolin-3-yl)piperidine-1-carboxamido)-3-(4-(1-methylpiperidin-4-yl)piperazin-1-yl)-3-oxopropyl)-7-methyl-2H-indazol-2-yl)methyl 2,2-dimethylhexanoate (1:1) (68). To a solution (57 mg, 0.89 mmol) of (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide in 1.5 mL of DMF was added (180 ul, 0.180 mmol) of lithium bis(trimethylsilyl)amide (1.0 M in THF) over 30 seconds, and the reaction was stirred for 30 minutes. Chloromethyl 2,2-dimethylhexanoate (43 mg 0.223 mmol) was added over 1 minute.

The reaction was allowed to stir overnight at room temperature. The reaction was then quenched by addition of 1 mL of saturated ammonium chloride. After ten minutes, THF removed under vacuum, and 3 mL of DMF was added. Then, the reaction was purified directly by RP-HPLC (method D 10 to 55%), and the product fractions were combined and lyophilized to yield the pure products as a solid 10 mg with roughly a 1/1 ratio of indazole isomers. LC/MS method A: $R_t$=4.86 mins., $(M+H)^+$=952, purity >95%, inseparable isomers. $^1$H NMR (CD$_3$OD) δ: 8.23-8.39 (m, 0.5H), 7.97-8.10 (m, 0.5H), 7.25-7.76 (m, 6H), 7.16-7.25 (m, 1H), 6.97-7.12 (m, 1H), 6.16-6.56 (m, 4H), 4.06-4.30 (m, 1H), 3.46-3.80 (m, 2H), 2.86 (s, 3H), 2.71-2.77 (m, 1H), 2.56 (s, 3H), 1.82-2.14 (m, 4H), 1.22-1.63 (m, 4H), 0.95-1.15 (m, 12H), 0.44-0.94 (m, 18H).

Example 69-70

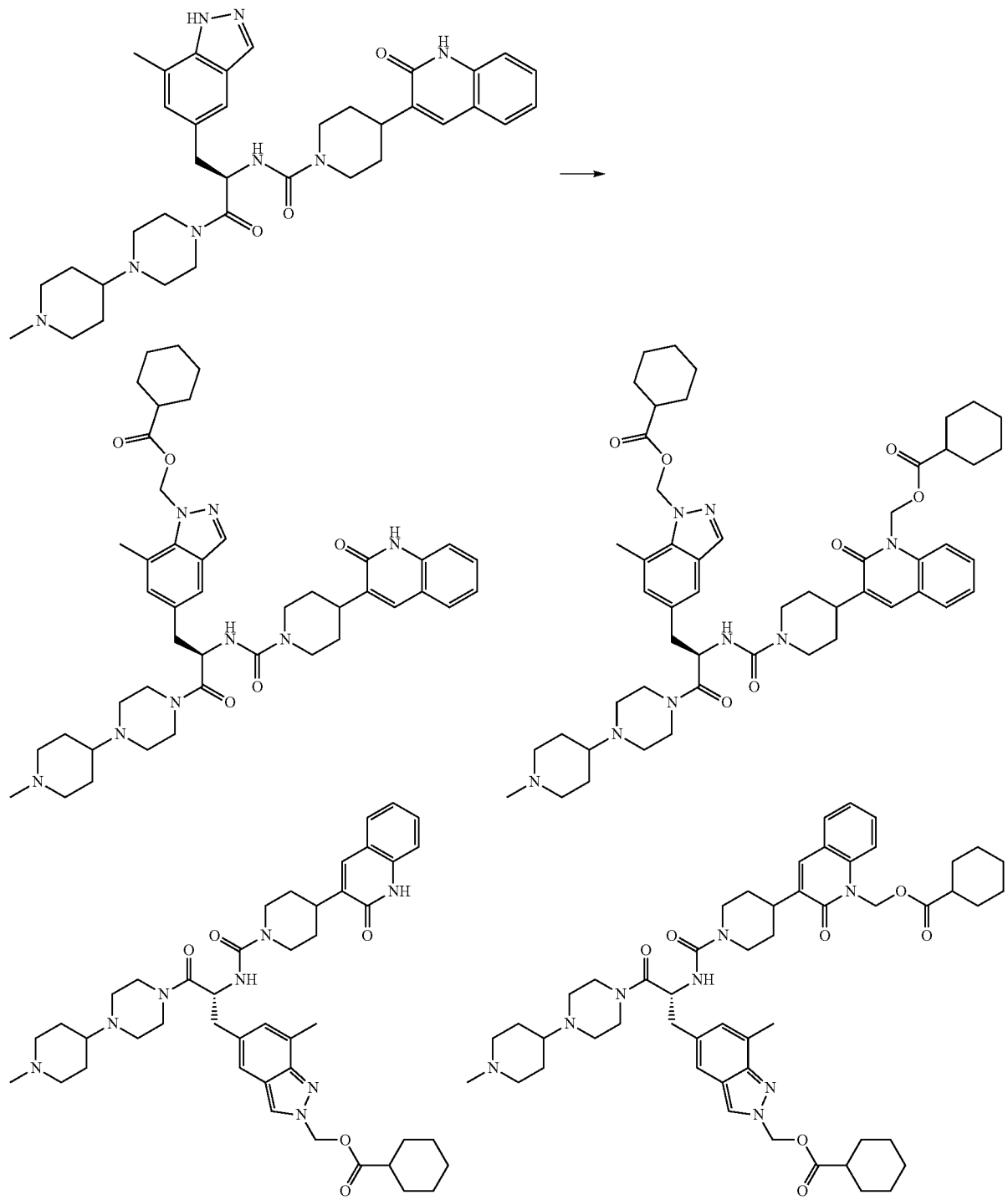

(R)-(5-(2-(4-(1-(cyclohexanecarbonyloxymethyl)-2-oxo-1,2-dihydroquinolin-3-yl)piperidine-1-carboxamido)-3-(4-(1-methylpiperidin-4-yl)piperazin-1-yl)-3-oxopropyl)-7-methyl-1H-indazol-1-yl)methyl cyclohexanecarboxylate compound with (R)-(5-(2-(4-(1-(cyclohexanecarbonyloxymethyl)-2-oxo-1,2-dihydroquinolin-3-yl)piperidine-1-carboxamido)-3-(4-(1-methylpiperidin-4-yl)piperazin-1-yl)-3-oxopropyl)-7-methyl-2H-indazol-2-yl)methyl cyclohexanecarboxylate (1:1) and ((R)-(3-(1-(3-(7-methyl-1-(nonanoyloxymethyl)-1H-indazol-5-yl)-1-(4-(1-methylpiperidin-4-yl)piperazin-1-yl)-1-oxopropan-2-ylcarbamoyl)piperidin-4-yl)-2-oxoquinolin-1(2H)-yl)methyl nonanoate compound with (R)-(3-(1-(3-(7-methyl-2-(nonanoyloxymethyl)-2H-indazol-5-yl)-1-(4-(1-methylpiperidin-4-yl)piperazin-1-yl)-1-oxopropan-2-ylcarbamoyl)piperidin-4-yl)-2-oxoquinolin-1(2H)-yl)methyl nonanoate (1:1). To a solution (76 mg, 0.119 mmol) of (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide in 1.5 mL of DMF was added (240 ul, 0.240 mmol) of lithium bis(trimethylsilyl)amide (1.0 M in THF) over 30 seconds, and the reaction was stirred for 30 minutes. Chloromethyl cyclohexanecarboxylate (55 mg 0.309 mmol) was added over 1 minute. The reaction was allowed to stir overnight at room temperature. The reaction was then quenched by addition of 1 mL of saturated ammonium chloride. After ten minutes, 3 mL DMF was added. Then, the reaction was purified directly by RP-HPLC (method D 10 to 55%), and the product fractions were combined and lyophilized to yield the pure products as a solid 31 mg of monoalkylated with a 1/1 mixture of indazole isomers and 33 mg of dialkylated product with a roughly 1/1 ratio of indazole isomers.

(R)-(5-(2-(4-(1-(cyclohexanecarbonyloxymethyl)-2-oxo-1,2-dihydroquinolin-3-yl)piperidine-1-carboxamido)-3-(4-(1-methylpiperidin-4-yl)piperazin-1-yl)-3-oxopropyl)-7-methyl-1H-indazol-1-yl)methyl cyclohexanecarboxylate compound with (R)-(5-(2-(4-(1-(cyclohexanecarbonyloxymethyl)-2-oxo-1,2-dihydroquinolin-3-yl)piperidine-1-carboxamido)-3-(4-(1-methylpiperidin-4-yl)piperazin-1-yl)-3-oxopropyl)-7-methyl-2H-indazol-2-yl)methyl cyclohexanecarboxylate (1:1) (69). Yield 31 mg. LC/MS method A: $R_t$=3.58 mins., $(M+H)^+$=780, purity >95%, inseparable isomers. $^1$H NMR (DMSO-$d_6$) δ: 11.65-11.95 (m, 1H), 8.25-8.52 (m, 0.5H), 7.98-8.25 (m, 0.5H), 6.67-7.83 (m, 8H), 6.09-6.52 (m, 2H), 4.59-5.06 (m, 2H), 3.84-4.24 (m, 4H), 2.32-3.05 (m, 16H), 1.34-2.21 (m, 5H), 0.94-1.30 (m, 10H).

((R)-(3-(1-(3-(7-methyl-1-(nonanoyloxymethyl)-1H-indazol-5-yl)-1-(4-(1-methylpiperidin-4-yl)piperazin-1-yl)-1-oxopropan-2-ylcarbamoyl)piperidin-4-yl)-2-oxoquinolin-1(2H)-yl)methyl nonanoate compound with (R)-(3-(1-(3-(7-methyl-2-(nonanoyloxymethyl)-2H-indazol-5-yl)-1-(4-(1-methylpiperidin-4-yl)piperazin-1-yl)-1-oxopropan-2-ylcarbamoyl)piperidin-4-yl)-2-oxoquinolin-1(2H)-yl) methyl nonanoate (1:1) (70). Yield 33 mg. LC/MS method A: $R_t$=4.45 mins, $(M+H)^+$=920, purity >95%, inseparable isomers. $^1$H NMR (DMSO-$d_6$) δ: 8.25-8.52 (m, 0.5H), 7.98-8.25 (m, 0.5H), 6.67-7.83 (m, 8H), 6.09-6.52 (m, 2H), 4.59-5.06 (m, 2H), 3.84-4.24 (m, 4H), 2.32-3.05 (m, 16H), 1.34-2.21 (m, 6H), 0.94-1.30 (m, 20H).

Examples 71-72

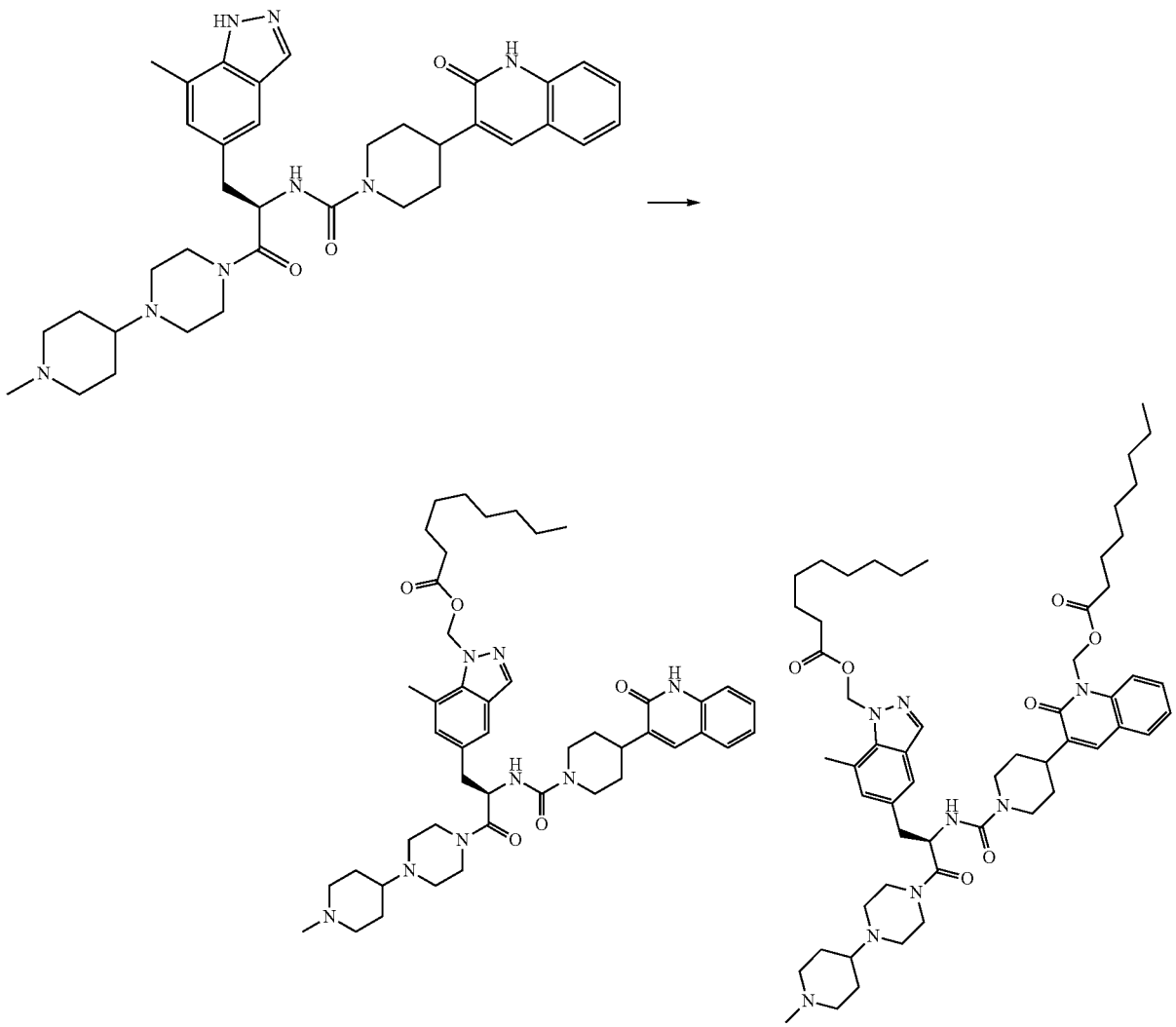

201

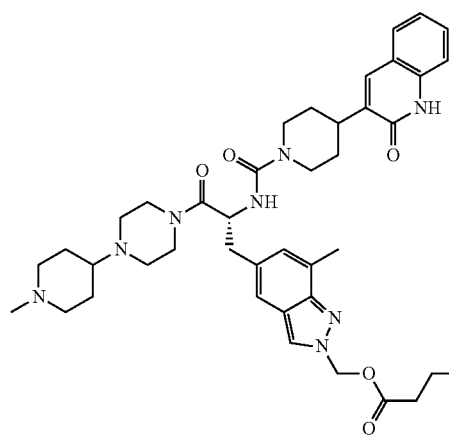

202

-continued

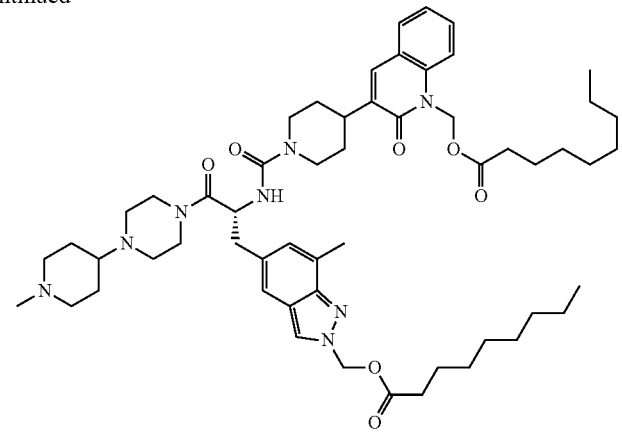

(R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-1H-indazol-1-yl)methyl nonanoate compound with (R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl)methyl nonanoate (1:1) and (R)-(3-(1-(3-(7-methyl-1-(nonanoyloxymethyl)-1H-indazol-5-yl)-1-(4-(1-methylpiperidin-4-yl)piperazin-1-yl)-1-oxopropan-2-ylcarbamoyl)piperidin-4-yl)-2-oxoquinolin-1(2H)-yl) methyl nonanoate compound with (R)-(3-(1-(3-(7-methyl-2-(nonanoyloxymethyl)-2H-indazol-5-yl)-1-(4-(1-methylpiperidin-4-yl)piperazin-1-yl)-1-oxopropan-2-ylcarbamoyl)piperidin-4-yl)-2-oxoquinolin-1(2H)-yl) methyl nonanoate (1:1). To a solution (62 mg, 0.97 mmol) of (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide in 1.5 mL of DMF was added (200 ul, 0.200 mmol) of lithium bis(trimethylsilyl)amide (1.0 M in THF) over 30 seconds, and the reaction was stirred for 30 minutes. Chloromethyl nonanoate (48 mg, 0.233 mmol) was added over 1 minute. The reaction was allowed to stir overnight at room temperature. The reaction was then quenched by addition of 1 mL of saturated ammonium chloride. After ten minutes, 3 mL of DMF was added. Then, the reaction was purified directly by RP-HPLC (method D 17 to 90%), and the product fractions were combined and lyophilized to yield the pure products as solids.

(R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-1H-indazol-1-yl)methyl nonanoate compound with (R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl)methyl nonanoate (1:1) (71). Yield 34 mg. LC/MS method A: $R_f$=4.18 mins., (M+H)$^+$=824, purity >95%, inseparable isomers. $^1$H NMR (DMSO-$d_6$) δ: 11.65-11.95 (m, 1H), 8.25-8.52 (m, 0.5H), 7.98-8.25 (m, 0.5H), 6.67-7.83 (m, 8H), 6.09-6.52 (m, 2H), 4.59-5.06 (m, 2H), 3.84-4.24 (m, 1H), 2.34-3.46 (m, 20H), 1.34-2.21 (m, 14H), 0.94-1.30 (m, 3H).

(R)-(3-(1-(3-(7-methyl-1-(nonanoyloxymethyl)-1H-indazol-5-yl)-1-(4-(1-methylpiperidin-4-yl)piperazin-1-yl)-1-oxopropan-2-ylcarbamoyl)piperidin-4-yl)-2-oxoquinolin-1(2H)-yl)methyl nonanoate compound with (R)-(3-(1-(3-(7-methyl-2-(nonanoyloxymethyl)-2H-indazol-5-yl)-1-(4-(1-methylpiperidin-4-yl)piperazin-1-yl)-1-oxopropan-2-ylcarbamoyl)piperidin-4-yl)-2-oxoquinolin-1(2H)-yl) methyl nonanoate (1:1) (72). Yield 21 mg. LC/MS method A: $R_f$=5.55 mins., (M+H)$^+$=980, purity >95%, isomers not separated. $^1$H NMR (DMSO-$d_6$) δ: 8.34-8.45 (m, 0.5H), 8.03-8.21 (m, 0.5H), 6.86-7.84 (m, 7H), 6.68-6.82 (m, 1H), 6.35-6.47 (m, 2H), 6.20-6.34 (m, 2H), 4.64-4.95 (m, 1H), 3.98-4.22 (m, 2H), 2.80-3.01 (m, 2H), 2.52-2.80 (m, 4H), 2.05-2.52 (m, 20H), 1.63-1.86 (m, 2H), 1.22-1.56 (m, 24).

Examples 73-74

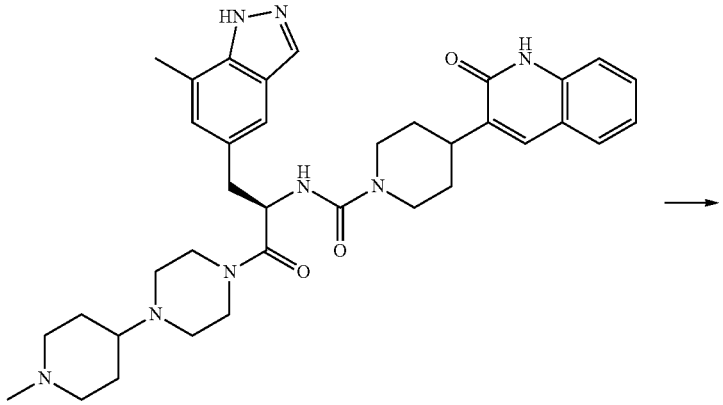

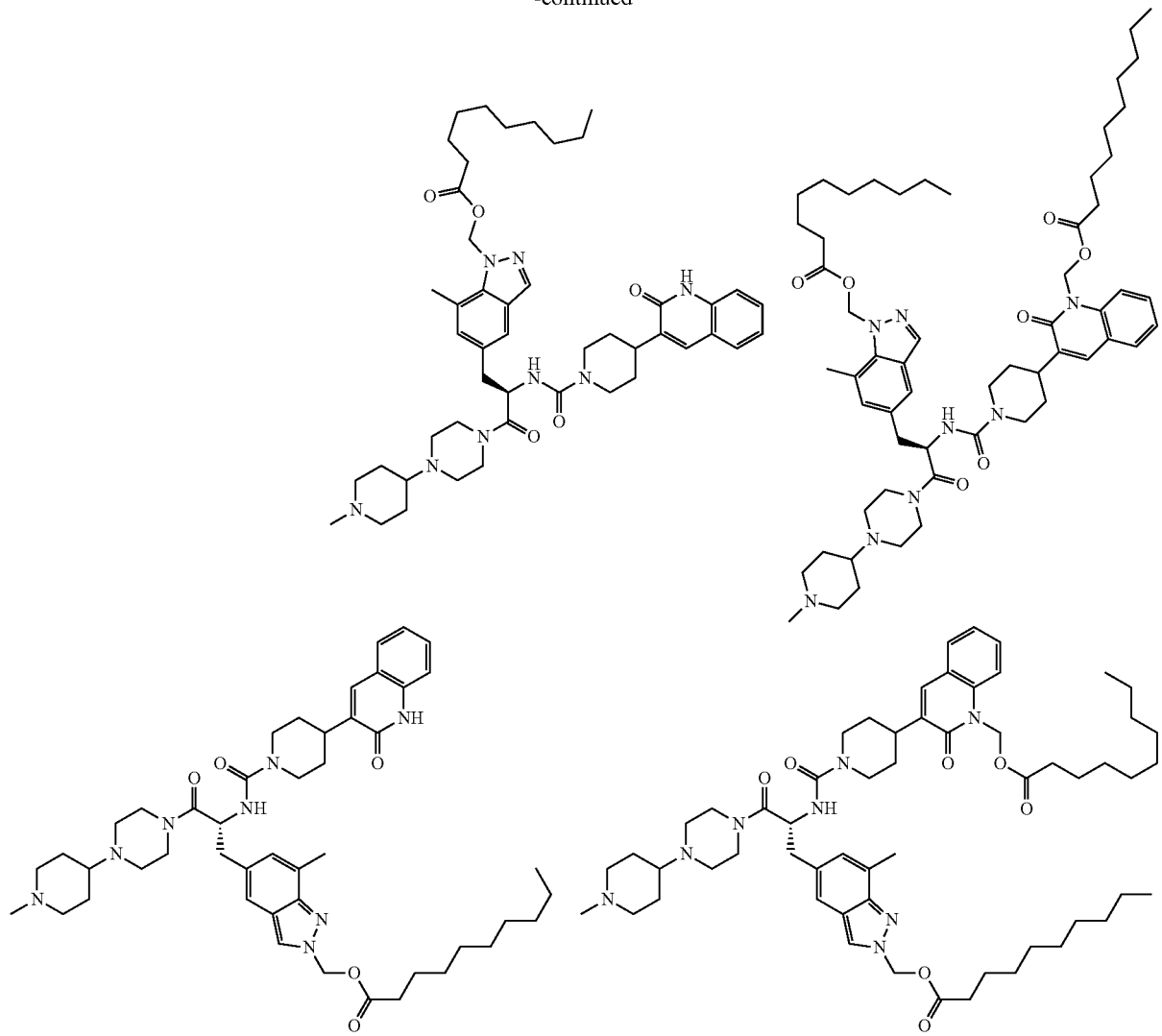

(R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-1H-indazol-1-yl)methyl decanoate compound with (R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl)methyl decanoate (1:1) and (R)-(3-(1-(3-(7-methyl-1-(nonanoyloxymethyl)-1H-indazol-5-yl)-1-(4-(1-methylpiperidin-4-yl)piperazin-1-yl)-1-oxopropan-2-ylcarbamoyl)piperidin-4-yl)-2-oxoquinolin-1(2H)-yl) methyl decanoate compound with (R)-(5-(2-(4-(1-(decanoyloxymethyl)-2-oxo-1,2-dihydroquinolin-3-yl)piperidine-1-carboxamido)-3-(4-(1-methylpiperidin-4-yl)piperazin-1-yl)-3-oxopropyl)-7-methyl-2H-indazol-2-yl) methyl decanoate (1:1)carboxamido)-3-(4-(1-methylpiperidin-4-yl)piperazin-1-yl)-3-oxopropyl)-7-methyl-2H-indazol-2-yl)methyl decanoate (1:1). To a solution (50 mg, 0.078 mmol) of (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide in 1.5 mL of DMF was added (170 ul, 0.170 mmol) of lithium bis(trimethylsilyl)amide (1.0 M in THF) over 30 seconds, and the reaction was stirred for 30 minutes. Chloromethyl decanoate (46 mg 0.203 mmol) was added over 1 minute. The reaction was allowed to stir overnight at room temperature. The reaction was then quenched by addition of 1 mL of saturated ammonium chloride. After ten minutes, THF removed under vacuum and 5 mL DMF was added. Then, the reaction was purified directly by RP-HPLC (method D 31 to 93%), and the product fractions were combined and lyophilized to yield the pure products as solids.

(R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-1H-indazol-1-yl)methyl decanoate compound with (R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl)methyl decanoate (1:1) (73). Yield 76 mg. LC/MS method A: $R_t$=4.18 mins., $(M+H)^+$=824, purity >95%, inseparable isomers. $^1$H NMR (DMSO-$d_6$) δ: 11.53-11.95 (m, 1H) 8.34-8.45 (m, 0.5H), 8.03-8.21 (m, 0.5H), 6.86-7.84 (m, 7H), 6.68-6.82 (m, 1H), 6.20-6.34 (m, 2H), 4.64-4.95 (m, 1H), 3.98-4.22 (m, 2H), 2.80-3.01 (m, 4H), 2.52-2.80 (m, 4H), 2.05-2.52 (m, 16H), 1.63-1.86 (m, 2H), 1.33-1.56 (m, 2H), 1.01-1.22 (m, 16H), 0.71-0.89 (m, 3H).

(R)-(3-(1-(3-(7-methyl-1-(nonanoyloxymethyl)-1H-indazol-5-yl)-1-(4-(1-methylpiperidin-4-yl)piperazin-1-yl)-1-oxopropan-2-ylcarbamoyl)piperidin-4-yl)-2-oxoquinolin-1(2H)-yl)methyl decanoate compound with (R)-(5-(2-(4-(1-(decanoyloxymethyl)-2-oxo-1,2-dihydroquinolin-3-yl)piperidine-1-carboxamido)-3-(4-(1-methylpiperidin-4-yl)piperazin-1-yl)-3-oxopropyl)-7-methyl-2H-indazol-2-yl)methyl decanoate (1:1)carboxamido)-3-(4-(1-methylpiperidin-4-yl)piperazin-1-yl)-3-oxopropyl)-7-methyl-2H-indazol-2-yl)methyl decanoate (1:1) (74). Yield 30 mg. LC/MS method A: $R_t$=6.03 mins., $(M+H)^+$=1008, purity >95%, isomers not separated. $^1$H NMR (METHANOL-$d_4$) δ: 8.33 (s, 0.5H), 7.97-8.13 (m, 0.5H), 7.12-7.82 (m, 7H), 7.00-7.11 (m, 1H), 6.34-6.58 (m, 4H), 3.97-4.40 (m, 2H), 3.33-3.74 (m, 4H), 2.66-3.14 (m, 16H), 2.56 (s, 3H), 2.19-2.43 (m, 4H), 1.42-2.04 (m, 4H), 1.02-1.38 (m, 24H), 0.78-0.98 (m, 6H).

Examples 75-76

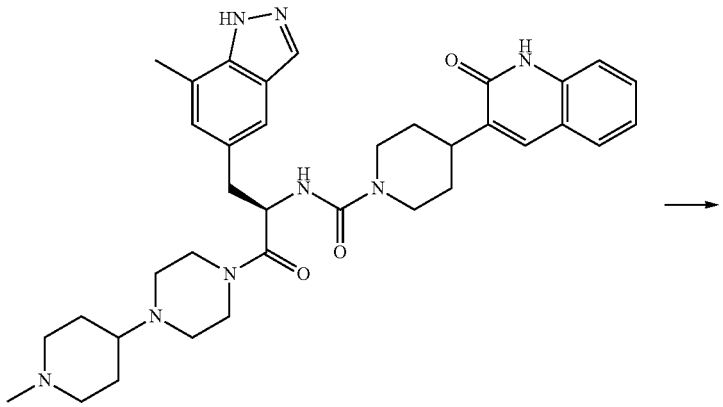

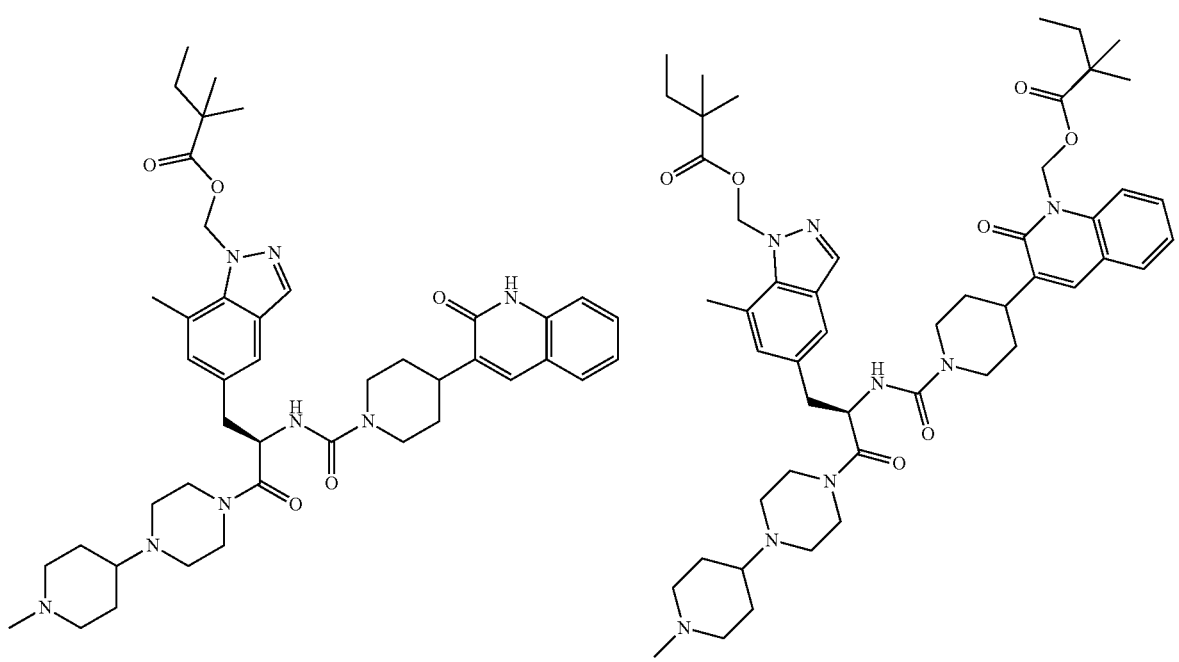

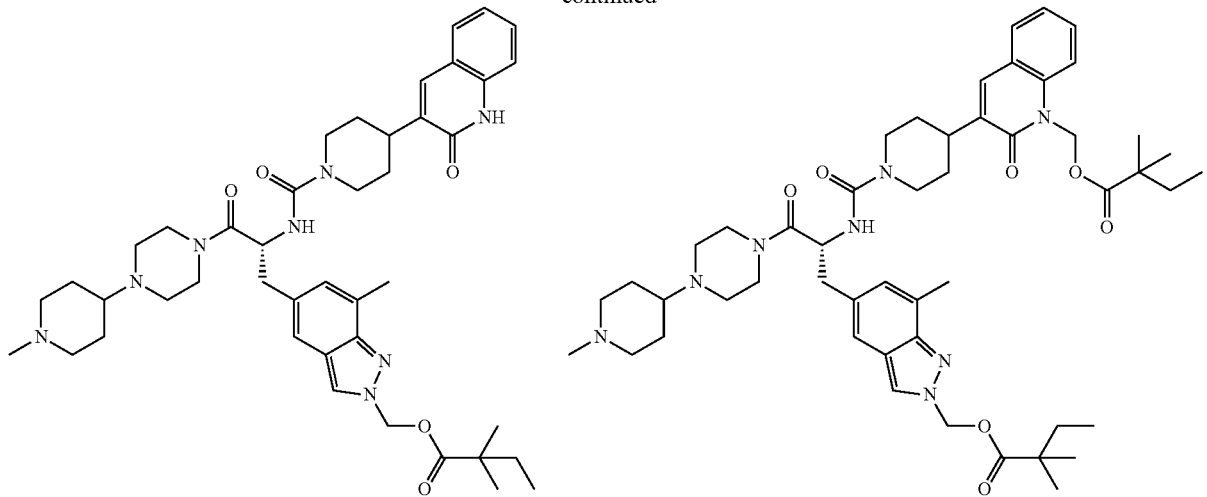

-continued (R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-1H-indazol-1-yl)methyl 2,2-dimethylbutanoate compound with (R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl)methyl 2,2-dimethylbutanoate (1:1) and (R)-(5-(2-(4-(1-(((2,2-dimethylbutanoyloxy)methyl)-2-oxo-1,2-dihydroquinolin-3-yl)piperidine-1-carboxamido)-3-(4-(1-methylpiperidin-4-yl)piperazin-1-yl)-3-oxopropyl)-7-methyl-1H-indazol-1-yl)methyl 2,2-dimethylbutanoate compound with (R)-(5-(2-(4-(1-(((2,2-dimethyl butanoyloxy)methyl)-2-oxo-1,2-dihydroquinolin-3-yl)piperidine-1-carboxamido)-3-(4-(1-methylpiperidin-4-yl)piperazin-1-yl)-3-oxopropyl)-7-methyl-2H-indazol-2-yl) methyl 2,2-dimethylbutanoate (1:1). To a solution (101 mg, 0.158 mmol) of (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide in 1.4 mL of DMF was added (380 ul, 0.38 mmol) of lithium bis(trimethylsilyl)amide (1.0 M in THF) over 30 seconds, and the reaction was stirred for 45 minutes. Then, the (70 mg 0.410 mmol) of chloromethyl 2,2-dimethylbutanoate was added over 1 minute. The reaction was allowed to stir overnight at room temperature. The reaction was then quenched by addition of 1 mL of saturated ammonium chloride. After ten minutes THF was removed under vacuum and 5 mL of DMF was added. Then, the reaction was purified directly by RP-HPLC (method D 15 to 70%), and the product fractions were combined and lyophilized to yield the pure products as a solid 21 mg of monoalkylated with a 1/1 mixture of indazole isomers and 21 mg of dialkylated product with a roughly 1/1 ratio of indazole isomers.

(R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-1H-indazol-1-yl)methyl 2,2-dimethylbutanoate compound with (R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl)methyl 2,2-dimethylbutanoate (1:1) (75). Yield 21 mg. LC/MS method A: $R_f$=4.21 mins., $(M+H)^+$=896, purity >95%, inseparable isomers. $^1$H NMR (DMSO-$d_6$) δ: 8.29-8.49 (m, 0.5H), 8.02-8.17 (m, 0.5H), 6.75-7.80 (m, 8H), 6.19-6.47 (m, 4H), 4.69-4.83 (m, 1H), 4.02-4.25 (m, 2H), 2.32-3.28 (m, 24H), 1.51-1.82 (m, 4H), 0.34-1.04 (m, 22H).

(R)-(5-(2-(4-(1-(((2,2-dimethylbutanoyloxy)methyl)-2-oxo-1,2-dihydroquinolin-3-yl)piperidine-1-carboxamido)-3-(4-(1-methylpiperidin-4-yl)piperazin-1-yl)-3-oxopropyl)-7-methyl-1H-indazol-1-yl)methyl 2,2-dimethylbutanoate compound with (R)-(5-(2-(4-(1-(((2,2-dimethylbutanoyloxy)methyl)-2-oxo-1,2-dihydroquinolin-3-yl)piperidine-1-carboxamido)-3-(4-(1-methylpiperidin-4-yl)piperazin-1-yl)-3-oxopropyl)-7-methyl-2H-indazol-2-yl)methyl 2,2-dimethylbutanoate (1:1) (76). Yield 21 mg. LC/MS method A: $R_f$=3.48 mins., $(M+H)^+$=767, purity >95%, inseparable isomers. $^1$H NMR (DMSO-$d_6$) δ: 11.53-11.95 (m, 1H), 8.37 (s, 0.5H), 7.93-8.23 (m, 0.5H), 7.12-7.96 (m, 8H), 6.20-6.56 (m, 2H), 4.52-4.92 (m, 1H), 3.97-4.27 (m, 2H), 2.37-3.32 (m, 24H), 1.90-2.13 (m, 2H), 1.56-1.87 (m, 2H), 0.34-1.04 (m, 11H).

209 210
Examples 77-78
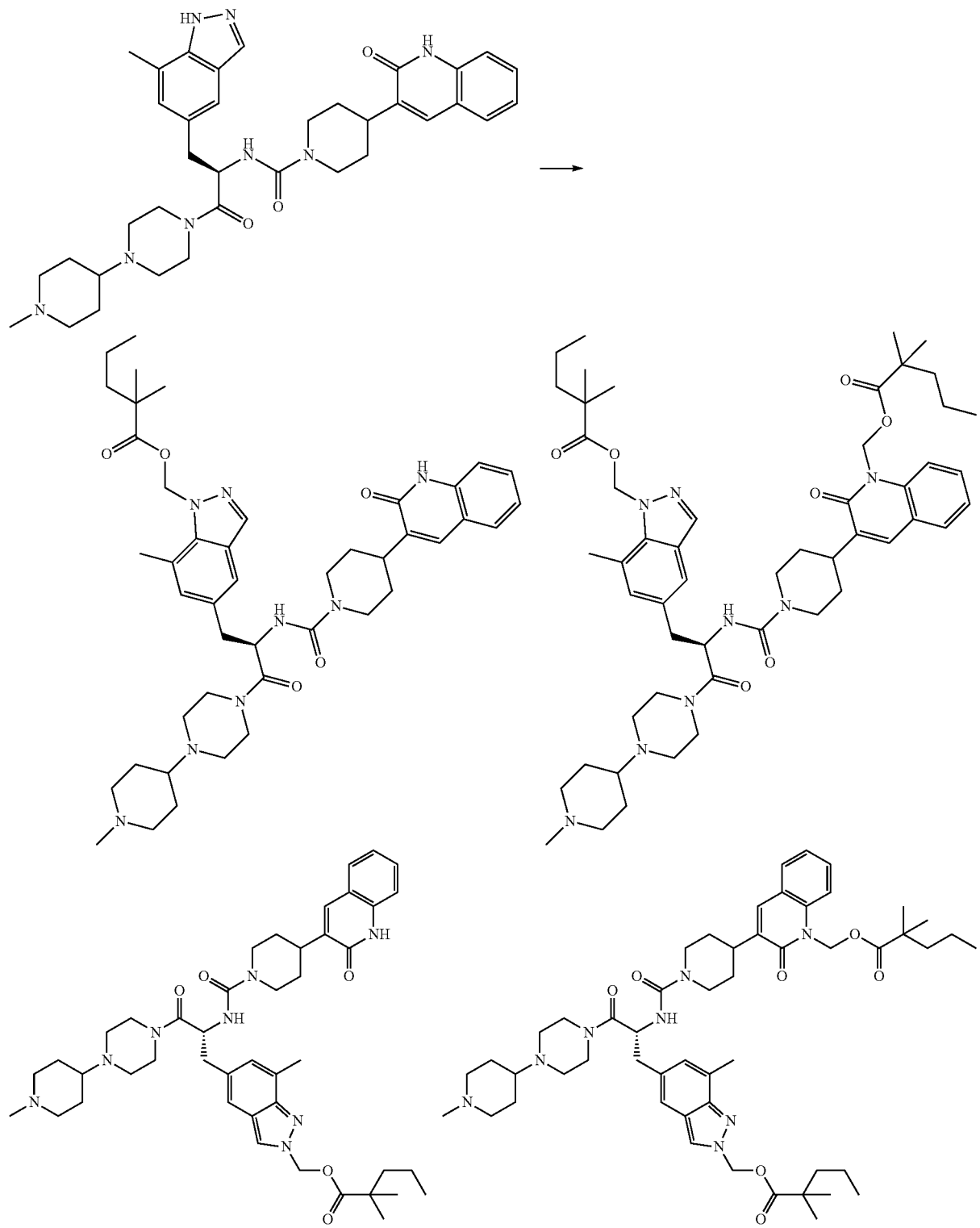
(R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-1H-indazol-1-yl)methyl 2,2-dimethylpentanoate compound with (R)-(7-methyl-5-(3-(4- (1-methylpiperidin-4-yl)piperazin-1-yl)-3-oxo-2-(4-(2-oxo-1,2-dihydroquinolin-3-yl)piperidine-1-carboxamido) propyl)-2H-indazol-2-yl)methyl 2,2-dimethylpentanoate (1:1) and (R)-(7-methyl-5-(3-(4-(1-methylpiperidin-4-yl)

piperazin-1-yl)-3-oxo-2-(4-(2-oxo-1,2-dihydroquinolin-3-yl)piperidine-1-carboxamido)propyl)-1H-indazol-1-yl) methyl 2,2-dimethylbutanoate compound with (R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl)methyl 2,2-dimethylbutanoate (1:1). To a solution (85 mg, 0.133 mmol) of (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide in 1.5 mL of DMF was added (360 ul, 0.360 mmol) of lithium bis(trimethylsilyl)amide (1.0 M in THF) over 30 seconds, and the reaction was stirred for 30 minutes. Chloromethyl decanoate (64 mg, 0.360 mmol) was added over 1 minute. The reaction was allowed to stir overnight at room temperature. The reaction was then quenched by addition of 1 mL of saturated ammonium chloride. After ten minutes, THF was removed under vacuum and 5 mL of DMF was added. The reaction was purified directly by RP-HPLC (method D 15 to 70%), and the product fractions were combined and lyophilized to yield the pure products as solids.

(R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-1H-indazol-1-yl)methyl 2,2-dimethylbutanoate compound with (R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl)methyl 2,2-dimethylbutanoate (1:1) (77). Yield 30 mg. LC/MS method A: $R_t$=3.48 mins., $(M+H)^+$=767, purity >95%, inseparable isomers. $^1$H NMR (DMSO-$d_6$) δ: 11.53-11.95 (m, 1H), 8.37 (s, 0.5H), 7.93-8.23 (m, 0.5H), 7.12-7.96 (m, 8H), 6.20-6.56 (m, 2H), 4.52-4.92 (m, 1H), 3.97-4.27 (m, 2H), 2.37-3.32 (m 24H), 1.90-2.13 (m, 2H), 1.56-1.87 (m, 2H), 0.34-1.04 (m, 13H).

(R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-1H-indazol-1-yl)methyl 2,2-dimethylpentanoate compound with (R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl)methyl 2,2-dimethylpentanoate (1:1) (78). Yield 76 mg. LC/MS method A: $R_t$=4.78 mins., $(M+H)^+$=924, purity >95%, inseparable isomers. $^1$H NMR (DMSO-$d_6$) δ: 8.29-8.49 (m, 0.5H), 8.02-8.17 (m, 0.5H), 6.75-7.80 (m, 8H), 6.19-6.47 (m, 4H), 4.69-4.83 (m, 1H), 4.02-4.25 (m, 2H), 2.32-3.28 (m, 24H), 1.51-1.82 (m, 4H), 0.30-1.04 (m, 26H).

Examples 79-81

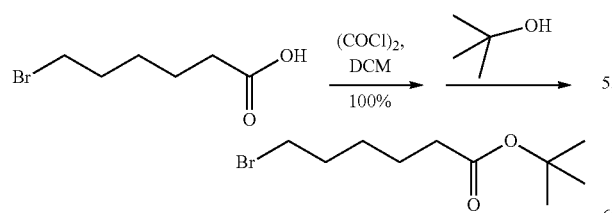

tert-Butyl 6-bromohexanoate. To a solution of 6-bromohexanoic acid (1.08 g, 5.52 mmol) in dichloromethane (10 mL) cooled at 0° C. was added oxalyl chloride (1.05 g, 8.29 mmol) and 5 drops of DMF. The mixture was stirred at room temperature for 20 h and concentrated. Tert-butanol (10 mL) was added, and the reaction mixture was stirred for 30 minutes. The solution was then concentrated and dried over vacuum to give the crude product as a colorless oil (1.1 g, 79%).

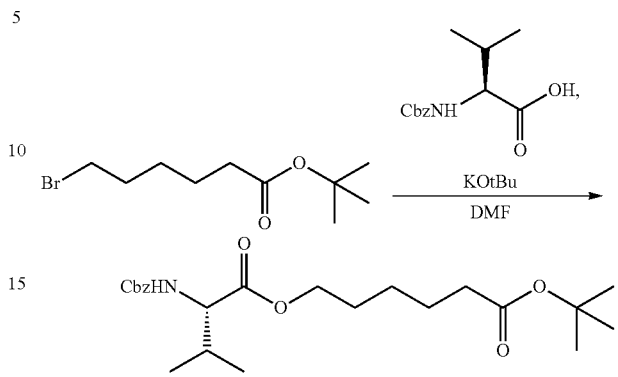

(S)-tert-butyl 6-((2-(((benzyloxy)carbonyl)amino)-3-methylbutanoyl)oxy)hexanoate. To a solution of (S)-2-(((benzyloxy)carbonyl)amino)-3-methylbutanoic acid (1 g, 4 mmol) in DMF (15 mL) was added potassium tert-butoxide (0.54 g, 4.8 mmol), and the mixture was stirred at room temperature for 10 minutes. Tert-butyl 6-bromohexanoate (1 g, 4.8 mmol) was added, and the reaction mixture was heated at 65° C. for 3 hours. After cooling to room temperature, the mixture was poured into saturated sodium bicarbonate aqueous solution and extracted by ethyl acetate (20 mL×3). The combined extracts were dried (Na$_2$SO$_4$), filtered, and purified by silica chromatography eluted with 20% EtOAc/hexanes to get the product as a white solid (1 g, 59%).

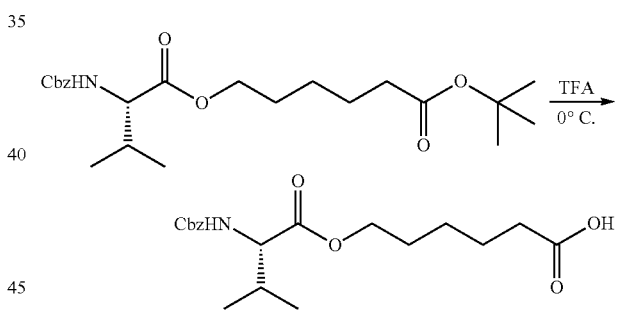

(S)-6-((2-(((benzyloxy)carbonyl)amino)-3-methyl butanoyl)oxy)hexanoic acid. (S)-tert-butyl 6-((2-(((benzyloxy)carbonyl)amino)-3-methylbutanoyl)oxy)hexanoate (1 g, 2.37 mmol) was added trifluoroacetic acid (5 mL) at 0° C. The solution was kept stirring at 0° C. for 2 hour and concentrated to give 0.9 g of the crude product as thick oil.

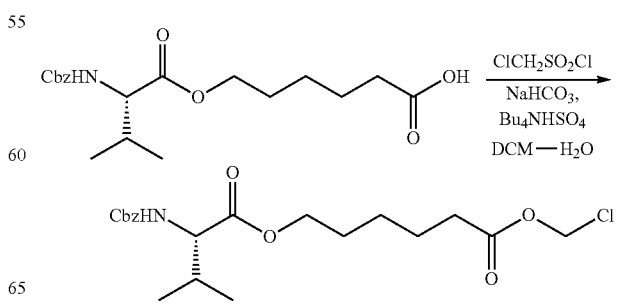

(S)-chloromethyl 6-((2-(((benzyloxy)carbonyl)amino)-3-methylbutanoyl)oxy)hexanoate. To a solution of (S)-6-((2-(((benzyloxy)carbonyl)amino)-3-methylbutanoyl)oxy) hexanoic acid (1.2 g, 3.27 mmol) in dichloromethane (10 mL) and water (10 mL) was added sodium bicarbonate (1.1 g, 13.1 mmol) and $Bu_4HSO_4$ (111 mg, 0.327 mmol) followed by dropwise addition of chloromethyl chlorosulfonate (650 mg, 3.93 mmol). The mixture was stirred for 20 h, diluted with water (30 mL) and extracted with dichloromethane (50 mL). The organic layer was separated and washed with water (25 mL), dried ($MgSO_4$), and evaporated. The product mixture was purified by silica chromatography eluted with 20% EtOAc/hexanes to get the product as a white solid (800 mg, 59%).

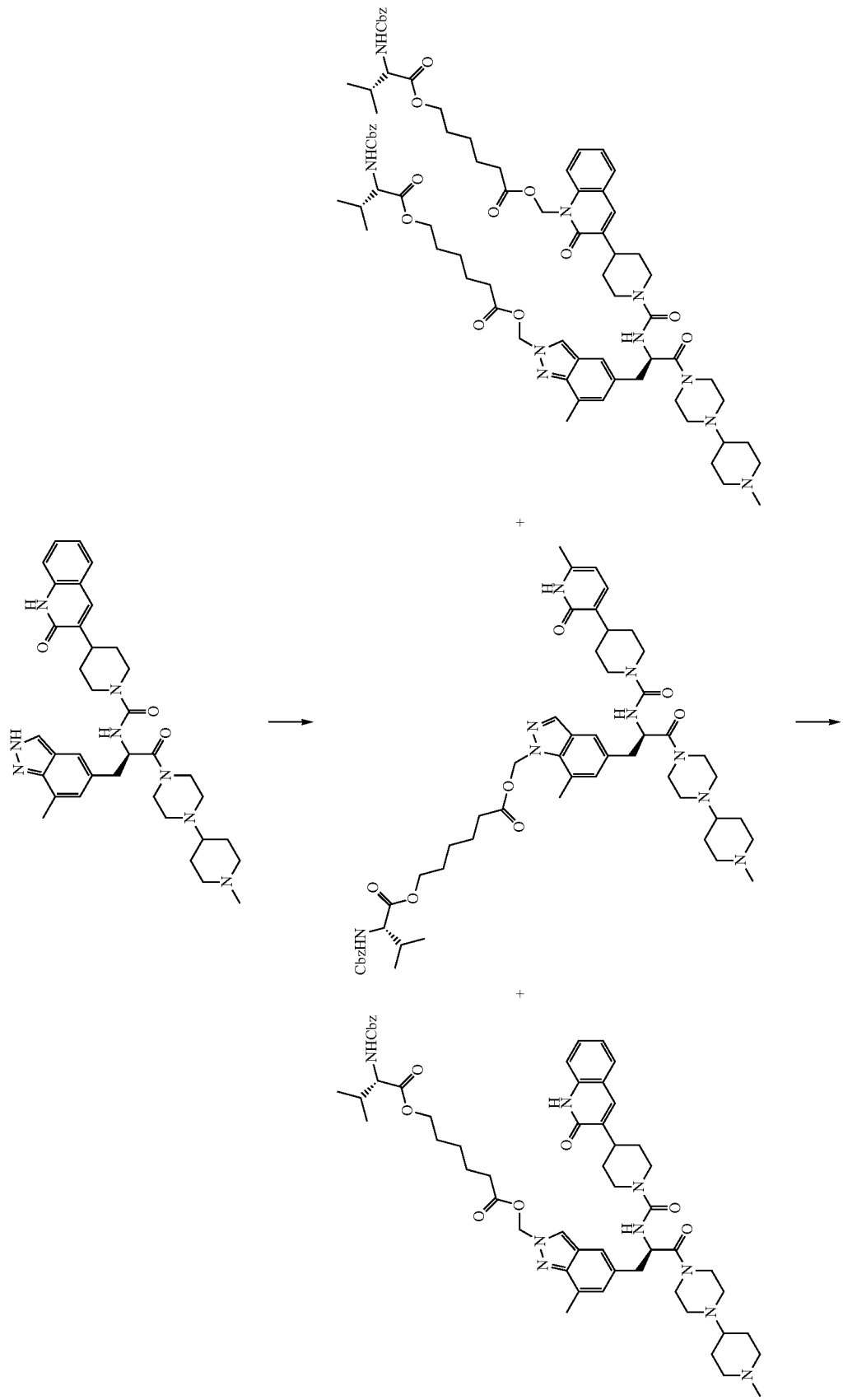

-continued
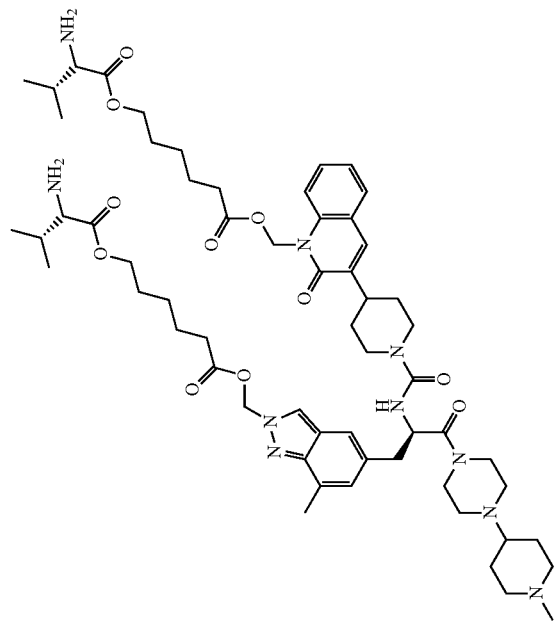
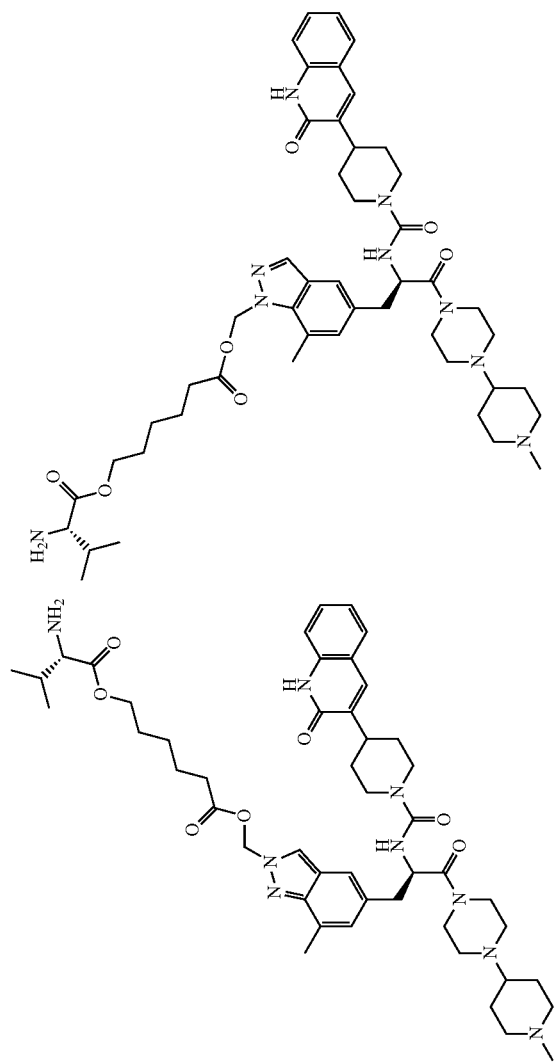

(7-methyl-5-((R)-3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl)methyl 6-(((S)-2-(((benzyloxy)carbonyl)amino)-3-methylbutanoyl)oxy)hexanoate was prepared from (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide, by the same procedure as in Example 1 above on a 100 mg scale purified by Method B as a white solid (25 mg, 15% yield). $^1$H NMR (DMSO-$d_6$) δ: 11.75 (s, 1H), 8.40 (s, 1H), 7.61-7.71 (m, 2H), 7.51 (s, 1H), 7.22-7.46 (m, 8H), 7.11-7.19 (m, 1H), 7.01 (s, 1H), 6.84 (br d, J=7.6 Hz, 1H), 6.27 (s, 2H), 5.01 (s, 2H), 4.71-4.81 (m, 1H), 3.73-4.13 (m, 12H), 3.40-3.62 (m, 2H), 3.28 (br m, 2H), 2.79-3.06 (m, 4H), 2.53-2.79 (m, 4H), 2.37-2.51 (m, 5H), 2.13-2.37 (m, 2H), 1.99 (br m, 1H), 1.61-1.81 (m, 4H), 1.35-1.58 (m, 4H), 1.14-1.35 (m, 4H), 0.81-0.90 (m, 6H). LC/MS method A: $R_t$=4.01 mins., (M+H)$^+$=1016, purity >95%.

(7-methyl-5-((R)-2-(4-(6-methyl-2-oxo-1,2-dihydropyridin-3-yl)piperidine-1-carboxamido)-3-(4-(1-methylpiperidin-4-yl)piperazin-1-yl)-3-oxopropyl)-1H-indazol-1-yl)methyl 6-(((S)-2-(((benzyloxy)carbonyl)amino)-3-methylbutanoyl)oxy)hexanoate (79). The target compound was purified from the above reaction mixture by RP-HPLC (Method B) as a white solid (25 mg, 15% yield). $^1$H NMR (DMSO-$d_6$) δ: 11.75 (s, 1H), 8.40 (s, 1H), 8.11 (s, 1H), 7.58-7.67 (m, 3H), 7.48-7.55 (m, 2H), 7.11-7.45 (m, 12H), 6.84 (br s, 1H), 6.40 (s, 2H), 5.00 (s, 2H), 4.71-4.81 (m, 1H), 3.73-4.13 (m, 12H), 3.40-3.62 (m, 2H), 3.28 (br m, 2H), 2.79-3.06 (m, 4H), 2.53-2.79 (m, 4H), 2.37-2.51 (m, 5H), 2.13-2.37 (m, 2H), 1.99 (br m, 1H), 1.61-1.81 (m, 4H), 1.35-1.58 (m, 4H), 1.14-1.35 (m, 4H), 0.81-0.90 (m, 6H). LC/MS method A: $R_t$=4.03 mins., (M+H)$^+$=1016, purity >95%.

(7-methyl-5-((R)-3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl)methyl 6-(((S)-2-amino-3-methylbutanoyl)oxy)hexanoate (80). To a solution of (7-methyl-5-((R)-3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl)methyl 6-(((S)-2-(((benzyloxy)carbonyl)amino)-3-methylbutanoyl)oxy)hexanoate, (18 mg, 0.018 mmol) in EtOAc (0.5 mL) and MeOH (0.5 mL) protected under N$_2$ was added 10% Pd—C (5 mg). Replacing the nitrogen by hydrogen balloon, the reaction mixture was degassed for 10 minutes and kept stirring under H$_2$ and was monitored by LC-MS. The reaction was complete in 3 hours and filtered through celite. The filtrate was concentrated, and the residue was purified by RP-HPLC (Method B) as a white solid (5 mg, 33%). $^1$H NMR (DMSO-$d_6$) δ: 11.75 (s, 1H), 8.40 (s, 2H), 8.26-8.34 (m, 3H), 7.64 (d, J=7.6, 1.8 Hz, 1H), 7.52 (s, 1H), 7.36-7.45 (m, 2H), 7.21-7.27 (m, 1H), 7.05-7.10 (s, 1H), 7.01 (s, 2H), 6.84 (br d, J=7.6 Hz, 1H), 6.27 (s, 2H), 4.77 (br m, 1H), 4.04-4.15 (m, 4H), 3.40-3.62 (m, 2H), 3.28 (br m, 2H), 2.79-3.06 (m, 4H), 2.53-2.79 (m, 4H), 2.37-2.51 (m, 5H), 2.13-2.37 (m, 2H), 1.99 (br m, 1H), 1.61-1.81 (m, 4H), 1.35-1.58 (m, 8H), 1.14-1.35 (m, 4H), 0.81-0.90 (m, 6H). LC/MS method A: $R_t$=3.07 mins., (M+H)$^+$=882, purity >95%.

(7-methyl-5-((R)-3-(4-(1-methylpiperidin-4-yl)piperazin-1-yl)-3-oxo-2-(4-(2-oxo-1,2-dihydroquinolin-3-yl)piperidine-1-carboxamido)propyl)-1H-indazol-1-yl)methyl 6-(((S)-2-amino-3-methylbutanoyl)oxy)hexanoate (81). The target compound was prepared in a similar manner to Example 80 above on 20 mg scale and purified by Method B as a white solid (5 mg, 29% yield). $^1$H NMR (DMSO-$d_6$) δ: 11.76 (s, 1H), 8.23-8.31 (m, 2H), 8.11 (s, 1H), 7.40-7.61 (m, 2H), 7.26 (d, J=7.6 Hz, 1H), 7.06-7.21 (m, 2H), 6.81 (br m, 1H), 6.40 (s, 2H), 4.76 (br m, 1H), 4.04-4.15 (m, 4H), 3.40-3.62 (m, 2H), 3.28 (br m, 2H), 2.79-3.06 (m, 4H), 2.53-2.79 (m, 4H), 2.37-2.51 (m, 5H), 2.13-2.37 (m, 2H), 1.99 (br m, 1H), 1.61-1.81 (m, 4H), 1.35-1.58 (m, 8H), 1.14-1.35 (m, 4H), 0.81-0.90 (m, 6H). LC/MS method A: $R_t$=3.07 mins., (M+H)$^+$=882, purity >95%.

Example 82

(5-((R)-2-(4-(1-(((6-(((R)-2-amino-3-methyl butanoyl)oxy)hexanoyl)oxy)methyl)-2-oxo-1,2-dihydroquinolin-3-yl)piperidine-1-carboxamido)-3-(4-(1-methylpiperidin-4-yl)piperazin-1-yl)-3-oxopropyl)-7-methyl-2H-indazol-2-yl)methyl 6-(((R)-2-amino-3-methylbutanoyl)oxy)hexanoate (82). The target compound was prepared in a manner similar to Example 80 above on 20 mg scale purified by Method B as a white solid (5 mg, 29% yield). $^1$H NMR (DMSO-$d_6$) δ: 8.40 (s, 1H), 8.16-8.35 (m, 4H), 7.65-7.81 (m, 1H), 7.53-7.60 (m, 1H), 7.40-7.51 (m, 1H), 7.36 (d, 1H), 7.30 (m, 1H), 7.07-7.20 (m, 1H), 6.93-7.07 (m, 1H), 6.70-6.93 (m, 1H), 6.10-6.37 (m, 4H), 4.65-4.94 (m, 1H), 4.07-4.18 (m, 6H), 3.83-4.02 (m, 2H), 3.51-3.58 (m, 5H), 3.12-3.30 (m, 8H), 2.81-2.97 (m, 7H), 2.67-2.79 (m, 9H), 2.54-2.58 (m, 3H), 2.40-2.51 (m, 8H), 2.24-2.36 (m, 5H), 1.64-1.84 (m, 2H), 1.47-1.62 (m, 7H), 1.24-1.35 (m, 4H), 0.87-1.01 (m, 20H). LC/MS method A: $R_t$=3.22 mins., (M+Na)$^+$=1148, purity >95%.

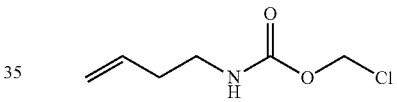

But-3-enyl-carbamic acid chloromethyl ester. To a solution of but-3-enylamine HCl salt (1.9 g, 17.5 mmol) in dichloromethane (20 mL) at 0° C. was added Et$_3$N (6 mL, 43 mmol) followed by dropwise addition of chloromethyl chloroformate (1.6 mL, 17.5 mmol). The mixture was stirred at room temperature for 20 h and quenched with water (50 mL). The organic layer was separated, dried (MgSO$_4$), and concentrated. The product mixture was purified by silica chromatography eluted with 10% EtOAc in hexanes to get the product as a colorless oil (1.5 g, 52%). $^1$H NMR (CDCl$_3$) δ: 5.68-5.84 (m, 1H), 5.74 (s, 2H), 5.05-5.17 (m, 2H), 4.91 (br s, 1H), 3.22-3.35 (m, 2H), 2.29 (qt, J=6.7, 1.4 Hz, 2H).

Examples 83-85

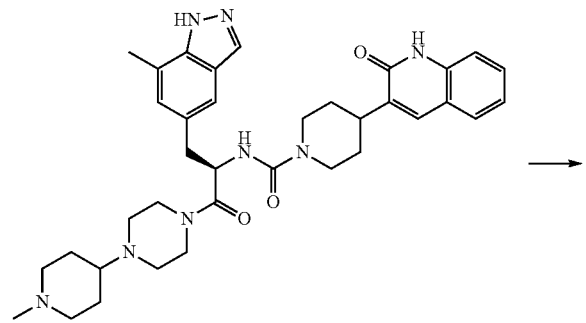

-continued

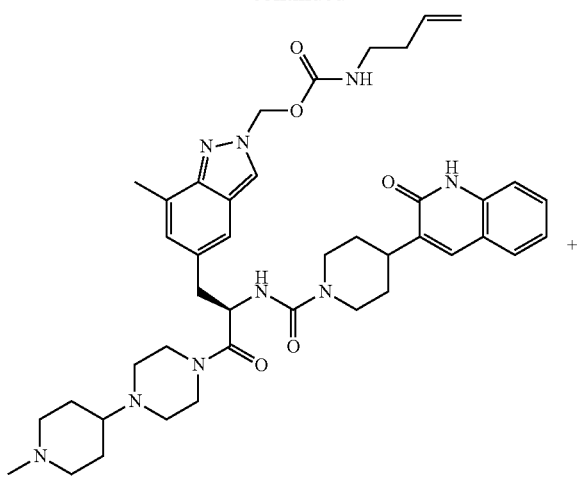

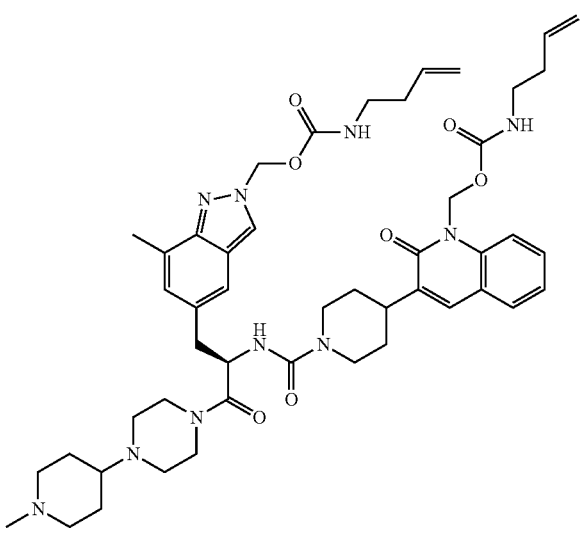 [SMILES: C=CCCNC(=O)OCn1cc2cc(C[C@@H](NC(=O)N3CCC(c4cc5ccccc5n(COC(=O)NCCC=C)c4=O)CC3)C(=O)N3CCN(C4CCN(C)CC4)CC3)cc(C)c2n1]

But-3-enyl-carbamic acid 7-methyl-5-(3-[4-(1-methyl-piperidin-4-yl)-piperazin-1-yl]-3-oxo-2-{[4-(2-oxo-1,2-dihydro-quinolin-3-yl)-piperidine-1-carbonyl]-amino}-propyl)-indazol-2-ylmethyl ester (83) was prepared from (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide and but-3-enyl-carbamic acid chloromethyl ester using the above procedure for Example 1 on 200 mg scale and purified by Method B to yield a white solid (10 mg, 4% yield). $^1$H NMR (DMSO-$d_6$) δ: 11.75 (s, 1H), 8.35 (s, 1H), 7.48-7.75 (m, 3H), 7.35-7.46 (m, 2H), 7.26 (d, J=7.6 Hz, 1H), 7.06-7.21 (m, 1H), 6.98 (s, 1H), 6.80-6.86 (m, 1H), 6.20 (s, 2H), 5.64-5.92 (m, 1H), 4.87-5.08 (m, 2H), 4.66-4.91 (m, 1H), 4.03-4.24 (m, 2H), 3.25-3.61 (m, 13H), 2.63-3.11 (m, 14H), 2.51 (s, 3H), 2.00-2.17 (m, 2H), 1.55-1.85 (m, 2H), 1.20-1.38 (m, 2H). (M+H)$^+$=766, purity >95%.

But-3-enyl-carbamic acid 7-methyl-5-(3-[4-(1-methyl-piperidin-4-yl)-piperazin-1-yl]-3-oxo-2-{[4-(2-oxo-1,2-dihydro-quinolin-3-yl)-piperidine-1-carbonyl]-amino}-propyl)-indazol-1-ylmethyl ester (84). The target compound was purified twice from the above reaction mixture by RP-HPLC (Method B) to yield a white solid (16 mg, 6% yield). $^1$H NMR (DMSO-$d_6$) δ: 13.15 (s, 1H), 7.98 (s, 1H), 7.62-7.75 (m, 2H), 7.45-7.62 (m, 2H), 7.33-7.45 (m, 2H), 7.18-7.31 (m, 1H), 7.05 (s, 1H), 6.74-6.93 (m, 1H), 6.22 (s, 2H), 5.74 (td, J=10.3, 6.4 Hz, 1H), 4.91-5.11 (m, 2H), 4.65-4.80 (m, 1H), 4.05-4.18 (m, 2H), 3.25-3.52 (m, 13H), 2.80-3.12 (m, 8H), 2.61-2.80 (m, 6H), 2.42 (s, 3H), 2.10-2.21 (m, 2H), 1.70-1.80 (m, 2H), 2.10-2.21 (m, 2H). (M+H)$^+$=766, purity >95%.

But-3-enyl-carbamic acid 5-{2-{[4-(1-but-3-enylcarbamoyloxymethyl-2-oxo-1,2-dihydro-quinolin-3-yl)-piperidine-1-carbonyl]-amino}-3-[4-(1-methyl-piperidin-4-yl)-piperazin-1-yl]-3-oxo-propyl}-7-methyl-indazol-2-ylmethyl ester (85). The target compound was purified twice from the above reaction mixture for Example 83 by RP-HPLC (Method B) to yield a white solid (56 mg, 20% yield). $^1$H NMR (DMSO-$d_6$) δ: 8.39 (s, 1H), 7.62-7.80 (m, 2H), 7.45-7.62 (m, 3H), 7.33-7.45 (m, 2H), 7.22-7.33 (m, 1H), 7.00 (s, 1H), 6.80-6.93 (m, 1H), 6.12-6.27 (m, 4H), 5.74 (td, J=10.3, 6.4 Hz, 1H), 4.91-5.11 (m, 4H), 4.65-4.87 (m, 1H), 4.02-4.25 (m, 2H), 3.12-3.55 (m, 12), 2.80-3.12 (m, 12H), 2.61-2.80 (m, 6H), 2.53 (s, 3H), 2.05-2.20 (m, 4H), 1.61-1.78 (m, 2H), 1.21-1.39 (m, 2H). (M+H)$^+$=894, purity >95%.

Examples 86-88

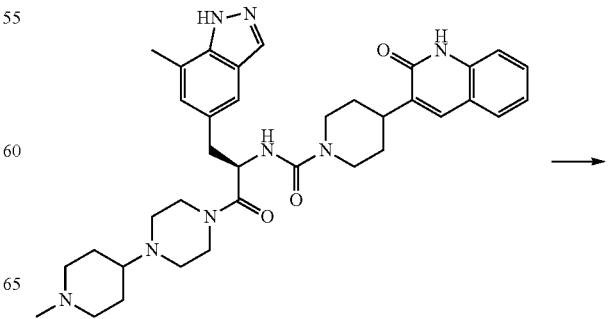

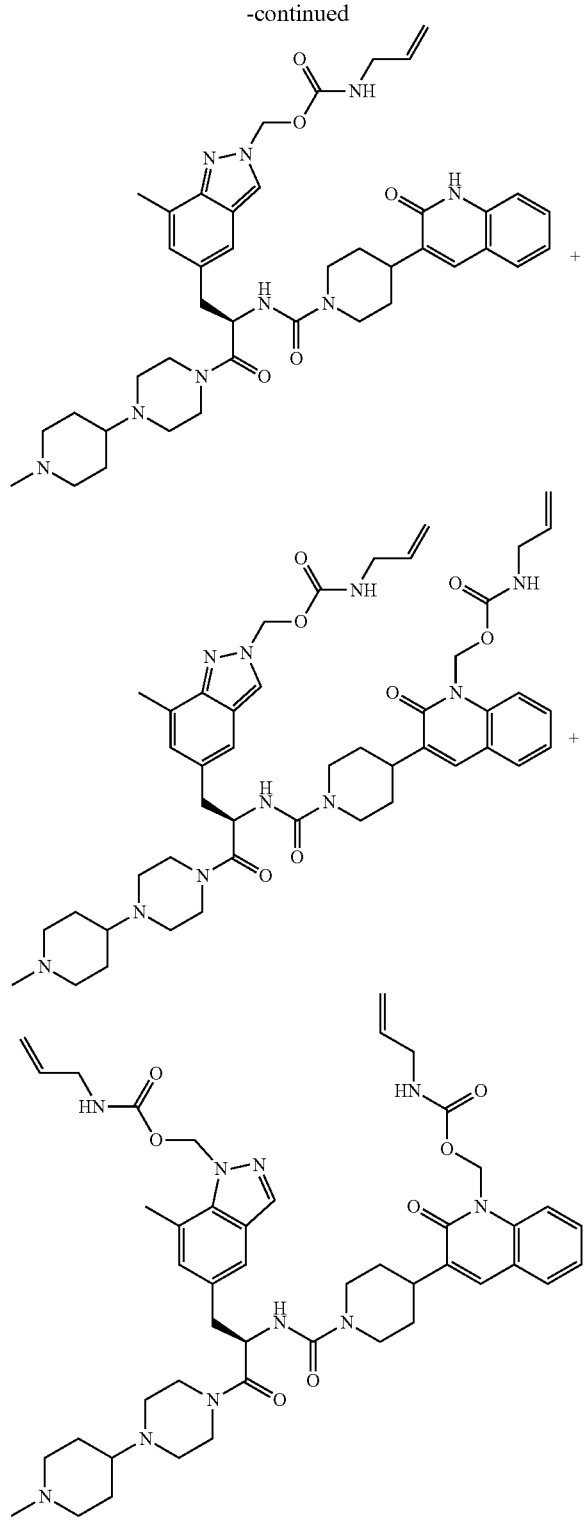

Allyl-carbamic acid 7-methyl-5-(3-[4-(1-methyl-piperidin-4-yl)-piperazin-1-yl]-3-oxo-2-{[4-(2-oxo-1,2-dihydroquinolin-3-yl)-piperidine-1-carbonyl]-amino}-propyl)-indazol-2-ylmethyl ester (86) was prepared from (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide, by the same procedure as above on 200 mg scale and purified by Method B to yield a white solid (22 mg, 9% yield). $^1$H NMR (DMSO-d$_6$) δ: 11.76 (br s, 1H), 8.36 (s, 1H), 7.55-7.78 (m, 3H), 7.35-7.46 (m, 2H), 7.23-7.28 (m, 1H), 7.11-7.18 (m, 1H), 7.00 (s, 1H), 6.81-6.88 (m, 1H), 6.21 (s, 2H), 5.67-5.80 (m, 1H), 4.97-5.11 (m, 2H), 4.71-4.81 (m, 1H), 3.97-4.35 (m, 2H), 3.33-3.85 (m, 17H), 2.63-3.02 (m, 8H), 2.50 (s, 3H), 1.57-1.86 (m, 4H), 1.21-1.37 (m, 2H). (M+H)$^+$=752, purity >95%.

Allyl-carbamic acid 5-{2-{[4-(1-allylcarbamoyloxymethyl-2-oxo-1,2-dihydro-quinolin-3-yl)-piperidine-1-carbonyl]-amino}-3-[4-(1-methyl-piperidin-4-yl)-piperazin-1-yl]-3-oxo-propyl}-7-methyl-indazol-2-ylmethyl ester (87). The target compound was purified twice from the above reaction mixture for example 86 by RP-HPLC (Method B) to yield a white solid (57 mg, 21% yield). $^1$H NMR (DMSO-d$_6$) δ: 8.35 (s, 1H), 7.64-7.81 (m, 3H), 7.45-7.64 (m, 3H), 7.36 (s, 1H), 7.20-7.33 (m, 1H), 7.00 (s, 1H), 6.86 (br d, J=7.0 Hz, 1H), 6.07-6.39 (m, 4H), 5.66-5.93 (m, 2H), 4.91-5.18 (m, 4H), 4.72-4.65 (m, 1H), 3.95-4.23 (m, 2H), 3.31-3.62 (m, 18H), 2.58-2.81 (m, 9H), 2.48 (s, 3H), 1.56-1.89 (m, 4H), 1.11-1.51 (m, 2H). (M+H)$^+$=865, purity >95%.

Allyl-carbamic acid 5-{2-{[4-(1-allylcarbamoyloxymethyl-2-oxo-1,2-dihydro-quinolin-3-yl)-piperidine-1-carbonyl]-amino}-3-[4-(1-methyl-piperidin-4-yl)-piperazin-1-yl]-3-oxo-propyl}-7-methyl-indazol-2-ylmethyl ester (88). The target compound was purified twice from the above reaction mixture for Example 86 and purified by RP-HPLC (Method B) to yield a white solid (3 mg, 1% yield). $^1$H NMR (DMSO-d$_6$) δ: 8.08 (s, 1H), 7.64-7.78 (m, 2H), 7.40-7.64 (m, 4H), 7.23-7.40 (m, 2H), 7.16 (s, 1H), 6.73-6.95 (m, 1H), 6.34 (s, 2H), 6.23 (s, 2H), 5.58-5.89 (m, 2H), 4.91-5.17 (m, 4H), 4.76 (br dd, J=6.4, 1.2 Hz, 1H), 3.97-4.25 (m, 2H), 3.52-3.71 (m, 5H), 3.30-3.52 (m, 11H), 3.15 (s, 3H), 2.81-3.04 (m, 4H), 2.58-2.81 (m, 6H), 2.48 (s, 3H), 1.68-1.88 (m, 2H), 1.21-1.34 (m, 2H). (M+H)$^+$=865, purity >95%.

Example 89

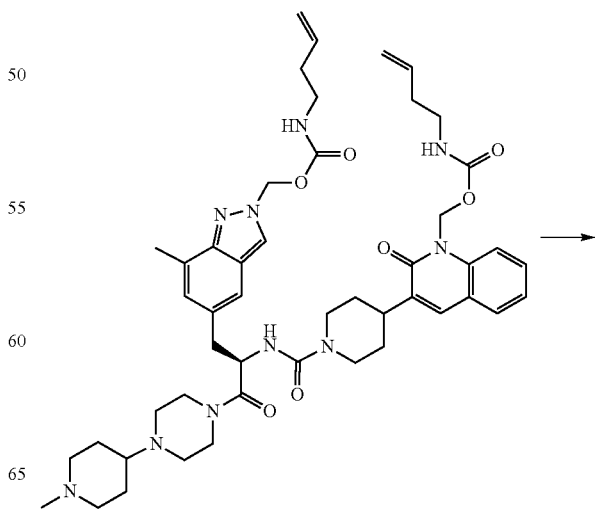

225
-continued

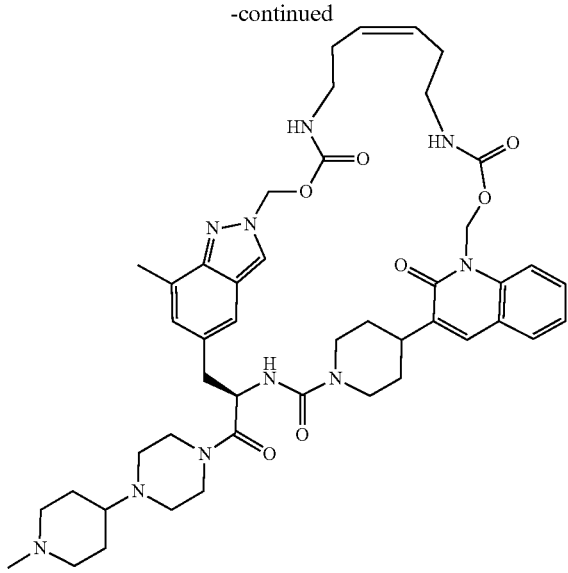

(17Z,33R)-29-methyl-33-[4-(1-methylpiperidin-4-yl)piperazine-1-carbonyl]-12,23-dioxa-10,14,21,25,34,36,42-heptaazahexacyclo[34.2.2.1$^{2,10}$.1$^{25,28}$.1$^{27,31}$.0$^{4,9}$]tritetraconta-2,4(9),5,7,17,26,28(42),29,31(41)-nonaene-13,22,35,43-tetrone (89). To a solution of but-3-enyl-carbamic acid 5-{2-{[4-(1-but-3-enylcarbamoyloxymethyl-2-oxo-1,2-dihydro-quinolin-3-yl)-piperidine-1-carbonyl]-amino}-3-[4-(1-methyl-piperidin-4-yl)-piperazin-1-yl]-3-oxo-propyl}-7-methyl-indazol-2-ylmethyl ester, (40 mg, 0.045 mmol) in dichloromethane (35 mL) was added Grubbs 2$^{nd}$ generation catalyst (5 mg). The mixture was degassed with N$_2$ for 15 minutes and stirred under N$_2$ for 20 h monitored by LC-MS. More Grubbs 2$^{nd}$ generation catalyst (10 mg) was added, and the reaction was stirred under N$_2$ for additional 20 h to completion. The reaction mixture was concentrated and purified by RP-HPLC (Method B) to yield a white solid (6 mg, 15% yield). $^1$H NMR (DMSO-d$_6$) δ: 8.22 (s, 1H), 7.45-7.62 (m, 3H), 7.33-7.45 (m, 2H), 7.22-7.33 (m, 2H), 7.00-7.08 (m, 1H), 6.97 (s, 1H), 6.61-6.75 (m, 1H), 6.05-6.32 (m, 4H), 5.74 (td, J=10.3, 6.4 Hz, 1H), 5.10-5.40 (m, 1H), 4.79-4.85 (m, 1H), 3.75-4.07 (m, 2H), 3.14 (s, 3H), 3.22-3.65 (m, 12), 2.62-3.10 (m, 12H), 2.53 (s, 3H), 2.20-2.30 (m, 2H), 2.02-2.30 (m, 2H), 1.75-2.01 (m, 4H), 1.51-1.65 (m, 2H). (M+H)$^+$=865, purity >95%.

Examples 90-91

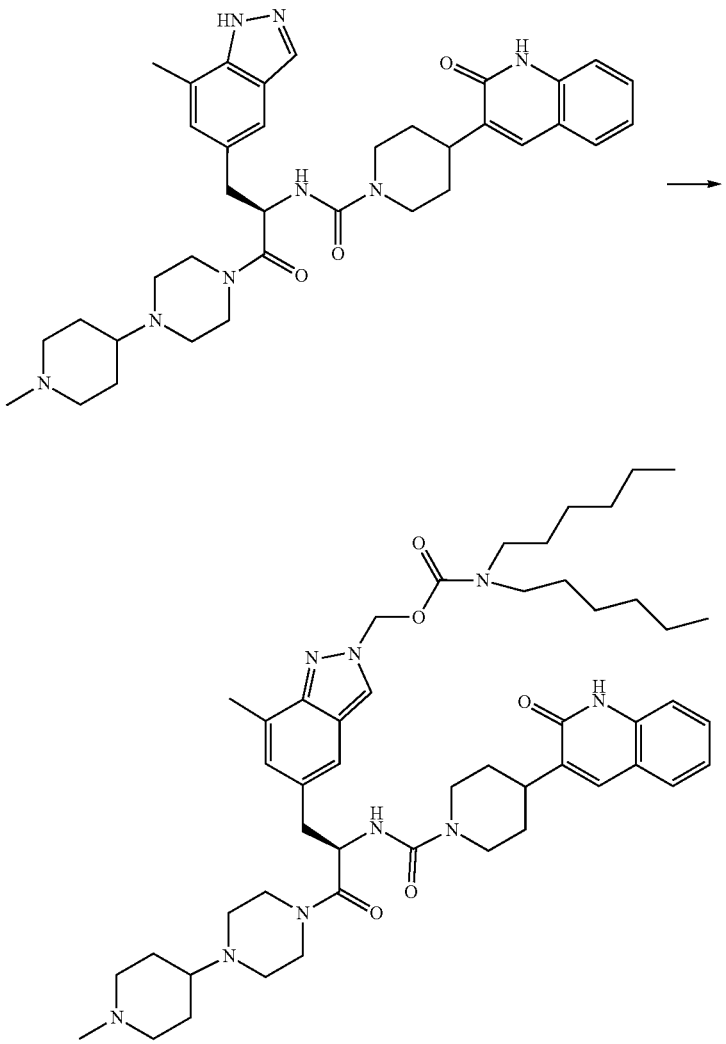

-continued

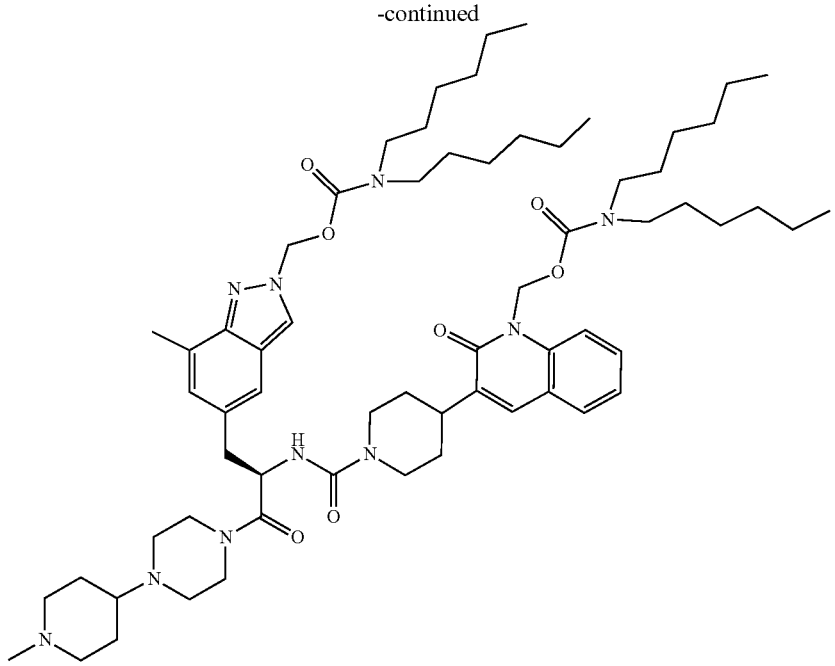

(R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl)methyl dihexylcarbamate (90) was prepared from (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide using a procedure similar to Examples 86-88 above on 150 mg scale. Purification by Method B followed by lyophilization of the product left a white solid (7 mg, 3% yield). $^1$H NMR (DMSO-d$_6$) δ: 11.75 (s, 1H), 8.34 (s, 1H), 8.04 (s, 1H), 7.55-7.77 (m, 2H), 7.33-7.53 (m, 4H), 7.25 (d, 1H), 7.06-7.21 (m, 1H), 7.00 (s, 1H), 6.74-6.95 (m, 1H), 6.38 (s, 2H), 6.13-6.33 (m, 2H), 4.70-4.82 (m, 1H), 3.93-4.19 (m, 2H), 3.32-3.63 (m, 8H), 3.20-3.32 (m, 7H), 3.20-3.32 (m, 5H), 2.81-3.20 (m, 5H), 2.41-2.57 (m, 10H), 1.58-1.84 (m, 4H), 1.11-1.44 (m, 9H), 0.93-1.11 (m, 4H), 0.76-0.93 (m, 4H), 0.55-0.76 (m, 2H). LC/MS method A: R$_t$=4.96 mins., (M+H)$^+$=881, purity >95%.

{5-[(2R)-2-{[4-(1-{[(dihexylcarbamoyl)oxy]methyl}-2-oxo-1,2-dihydroquinolin-3-yl)piperidine-1-carbonyl]amino}-3-[4-(1-methylpiperidin-4-yl)piperazin-1-yl]-3-oxopropyl]-7-methyl-2H-indazol-2-yl}methyl N,N-dihexylcarbamate (91). The target compound was purified from Example 90 reaction mixture by RP-HPLC (Method B). Product fractions were lyophilized to yield a white solid (25 mg, 9% yield). $^1$H NMR (DMSO-d$_6$) δ: 8.33 (s, 1H), 7.65-7.86 (m, 1H), 7.46-7.65 (m, 2H), 7.21-7.46 (m, 1H), 7.01 (s, 1H), 6.84 (br d, 1H), 6.10-6.33 (m, 4H), 4.76 (br m, 1H), 3.93-4.29 (m, 2H), 3.32-3.63 (m, 12H), 3.20-3.32 (m, 7H), 3.20-3.32 (m, 9H), 2.81-3.20 (m, 5H), 2.41-2.57 (m, 10H), 1.58-1.84 (m, 4H), 1.11-1.44 (m, 18H), 0.93-1.11 (m, 7H), 0.76-0.93 (m, 8H), 0.55-0.76 (m, 4H). (M+H)$^+$=1122, purity >95%.

229
Examples 92-95
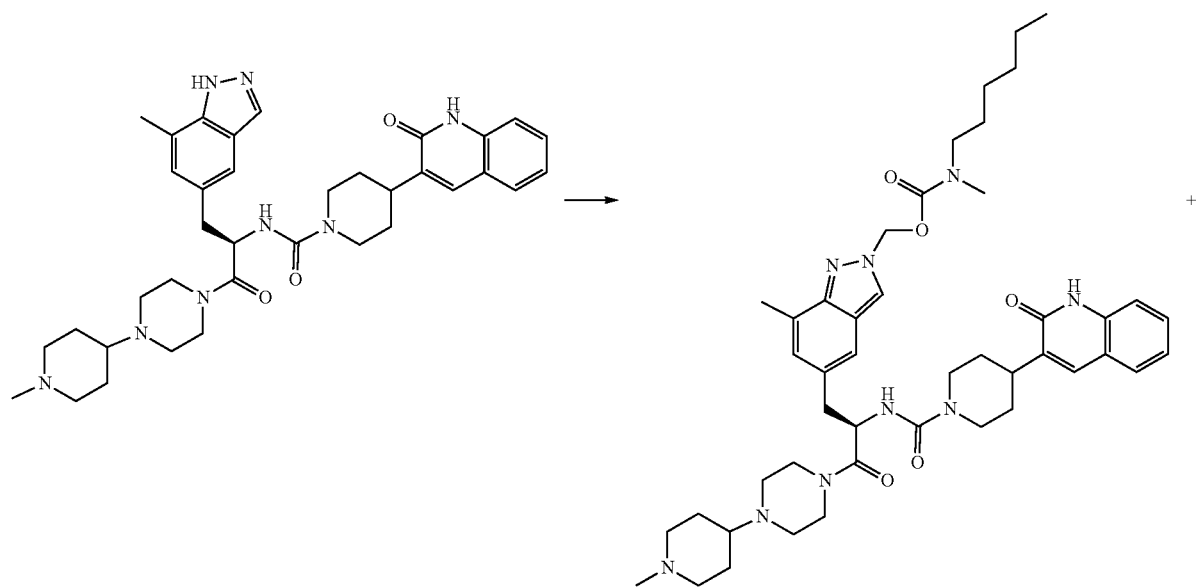
230
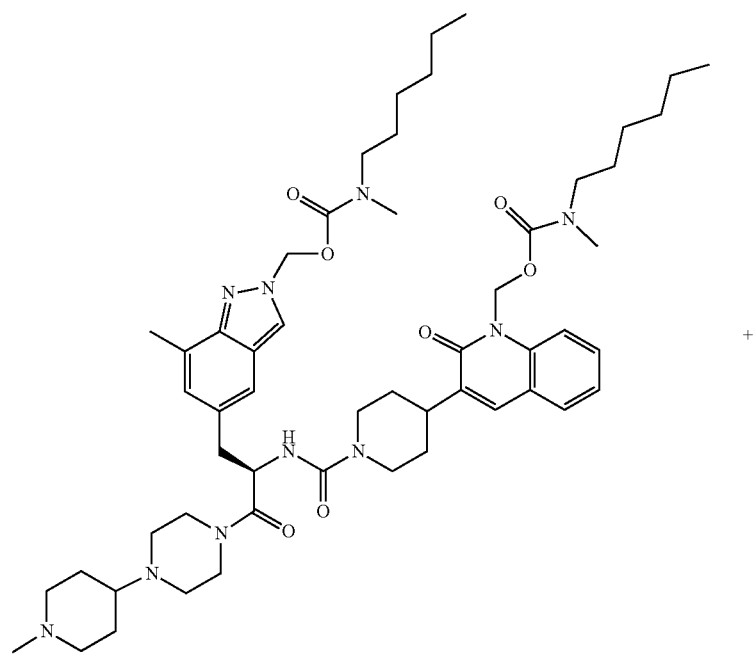

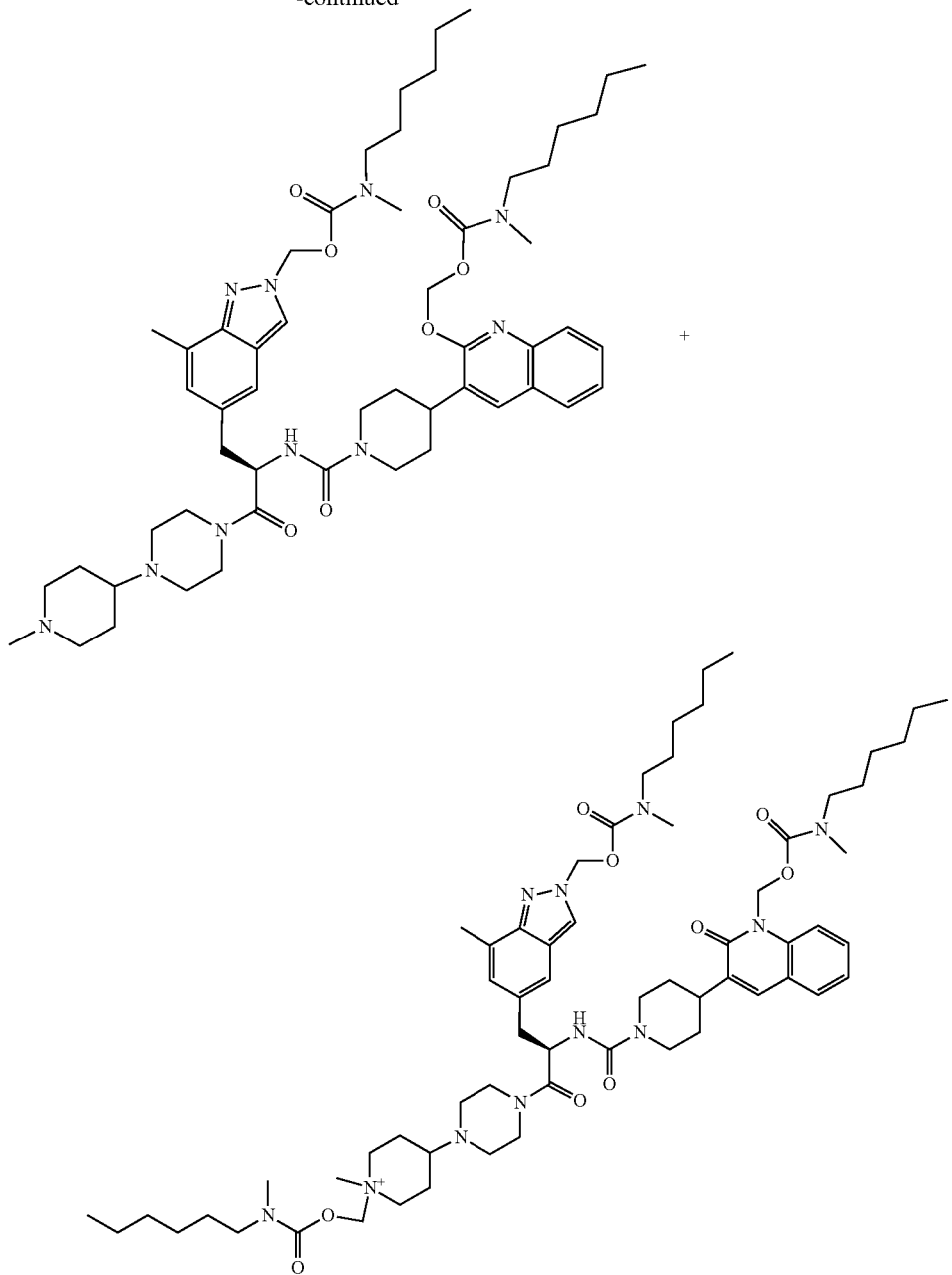

(R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl)methyl hexyl (methyl)carbamate (92). Prepared from (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide, by the same procedure as in Examples 86-88 above on 150 mg scale purified by Method B as a white solid (21 mg, 11% yield). $^1$H NMR (DMSO-d$_6$) δ: 11.75 (s, 2H), 8.34 (d, J=7.6, 1.8 Hz, 1H), 8.06 (s, 1H), 7.55-7.66 (m, 3H), 7.38-7.45 (m, 2H), 7.32 (s, 1H), 7.25 (m, 2H), 7.10-7.17 (m, 2H), 6.95 (s, 1H), 6.70 (br m, 1H), 6.41 (s, 2H), 6.24 (br s, 2H), 4.77 (br d, 1H), 4.05-4.16 (m, 2H), 3.35-3.54 (m, 6H), 3.04-3.26 (m, 4H), 2.81-3.01 (m, 2H), 2.44-2.79 (m, 8H), 2.10-2.36 (m, 4H), 1.54-1.82 (m, 4H), 1.12-1.51 (m, 4H), 0.70-1.08 (m, 6H). LC/MS method A: R$_t$=3.67 mins., (M+H)$^+$=810, purity >95%.

{5-[(2R)-2-({4-[1-({[hexyl(methyl)carbamoyl]oxy}methyl)-2-oxo-1,2-dihydroquinolin-3-yl]piperidine-1-carbonyl}amino)-3-[4-(1-methylpiperidin-4-yl)piperazin-1-yl]-3-oxopropyl]-7-methyl-2H-indazol-2-yl}methyl N-hexyl-N-methylcarbamate (93). 2:1 mixture of isomers. The target compound was purified from Example 92 reaction mixture by RP-HPLC (Method B) as a white solid (41 mg, 18% yield). $^1$H NMR (DMSO-d$_6$) δ: 8.34 (d, 1H), 8.06 (s, 1H), 7.64-7.77 (m, 2H), 7.48-7.58 (m, 2H), 7.42 (s, 1H), 7.25-7.34 (m, 1H), 7.13 (s, 1H), 6.95 (s, 1H), 6.58-6.85 (m, 1H), 6.23-6.48 (m, 4H), 4.77 (br m, 1H), 4.06-4.16 (m, 2H), 3.35-3.54 (m, 8H), 3.04-3.26 (m, 4H), 2.81-3.01 (m, 2H), 2.44-2.79 (m, 12H), 2.10-2.36 (m, 4H), 1.54-1.82 (m, 4H), 1.12-1.51 (m, 15H), 0.70-1.08 (m, 8H). LC/MS method A: $R_t$=4.58 mins., (M+H)$^+$=981, purity >95%.

{5-[(2R)-2-({4-[2-({[hexyl(methyl)carbamoyl]oxy}methoxy)quinolin-3-yl]piperidine-1-carbonyl}amino)-3-[4-(1-methylpiperidin-4-yl)piperazin-1-yl]-3-oxopropyl]-7-methyl-2H-indazol-2-yl}methyl N-hexyl-N-methylcarbamate (94). Mixture of 2-:1-=2:1. The target compound was purified from Example 92 reaction mixture by RP-HPLC (Method B) as a white solid (15 mg, 7% yield). $^1$H NMR (DMSO-d$_6$) δ: 8.34 (d, J=6.3 Hz, 1H), 7.95-8.13 (m, 2H), 7.80-7.95 (m, 1H), 7.69-7.80 (m, 1H), 7.62 (m, 1H), 7.41-7.47 (m, 2H), 7.32 (s, 1H), 6.95 (s, 1H), 6.65-6.87 (m, 1H), 6.35 (br s, 1H), 6.22 (br s, 1H), 6.13-6.22 (m, 2H), 4.71-4.82 (m, 1H), 4.06-4.18 (m, 6H), 3.35-3.54 (m, 8H), 3.04-3.26 (m, 8H), 2.81-3.01 (m, 2H), 2.44-2.79 (m, 8H), 2.10-2.36 (m, 4H), 1.54-1.82 (m, 4H), 1.12-1.51 (m, 10H), 0.70-1.08 (m, 6H). LC/MS method A: $R_t$=4.96 mins., (M+H)$^+$=981, purity >95%.

1-({[Hexyl(methyl)carbamoyl]oxy}methyl)-4-{4-[(2R)-2-({4-[1-({[hexyl(methyl)carbamoyl]oxy}methyl)-2-oxo-1,2-dihydroquinolin-3-yl]piperidine-1-carbonyl}amino)-3-[2-({[hexyl(methyl)carbamoyl]oxy}methyl)-7-methyl-2H-indazol-5-yl]propanoyl]piperazin-1-yl}-1-methylpiperidin-1-ium (95). The target compound was purified from Example 92 reaction mixture by RP-HPLC (Method B) as a white solid (19 mg, 7% yield). $^1$H NMR (DMSO-d$_6$) δ: 8.34 (d, J=6.3 Hz, 1H), 7.69-7.81 (m, 1H), 7.61-7.69 (m, 1H), 7.48-7.58 (m, 1H), 7.24-7.35 (m, 2H), 7.10-7.18 (m, 1H), 6.98 (br s, 1H), 6.62-6.83 (m, 1H), 6.23 (br s, 4H), 5.31 (br s, 1H), 5.23 (br s, 1H), 4.71-4.82 (m, 1H), 4.06-4.18 (m, 6H), 3.35-3.54 (m, 8H), 3.04-3.26 (m, 12H), 2.81-3.01 (m, 4H), 2.44-2.79 (m, 8H), 2.10-2.36 (m, 8H), 1.54-1.82 (m, 4H), 1.12-1.51 (m, 16H), 0.70-1.08 (m, 6H). LC/MS method A: $R_t$=5.16 mins., (M+H)$^+$=1152, purity >95%.

Examples 96-98

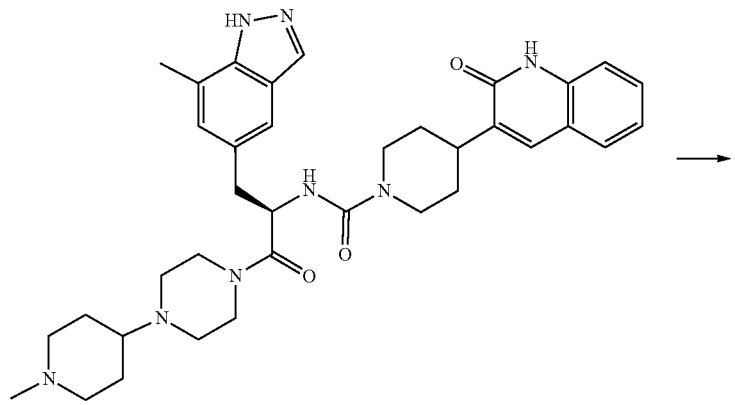

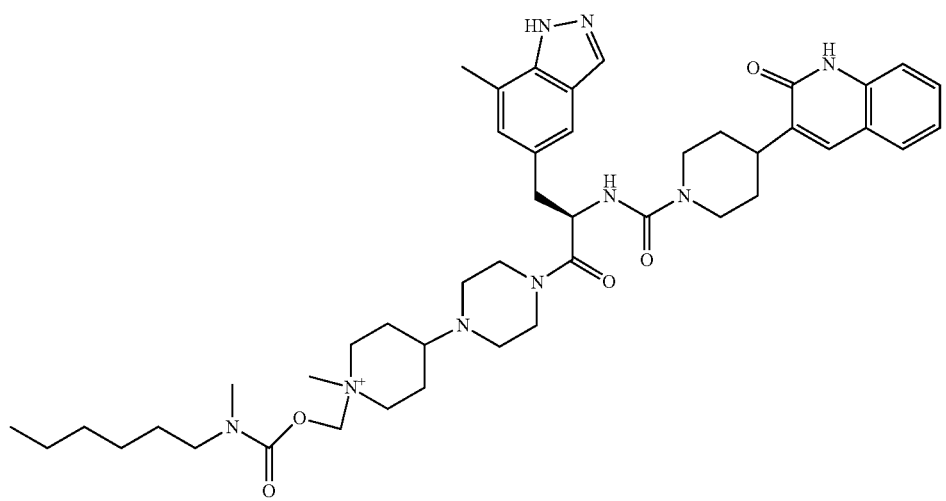

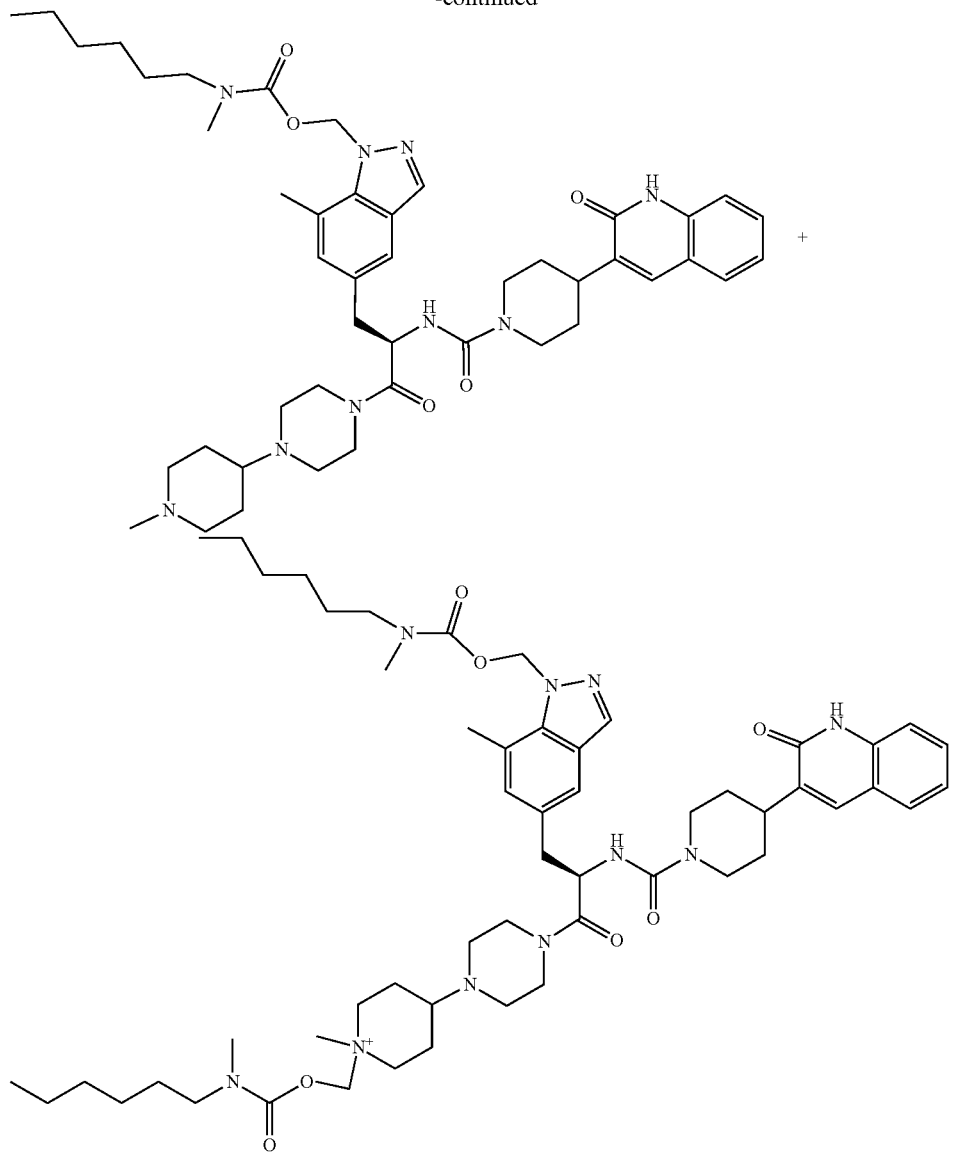

(R)-1-(((hexyl(methyl)carbamoyl)oxy)methyl)-1-methyl-4-(4-(3-(7-methyl-1H-indazol-5-yl)-2-(4-(2-oxo-1,2-dihydroquinolin-3-yl)piperidine-1-carboxamido)propanoyl)piperazin-1-yl)piperidin-1-ium (96). The target compound was prepared from (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide, by the same procedure as in Examples 86-88 above, with 1.1 equivalent of LiHMDS on 140 mg scale purified by Method B as a white solid (15 mg, 8% yield). $^1$H NMR (DMSO-d$_6$) δ: 13.05 (s, 1H), 11.76 (s, 1H), 7.98 (s, 1H), 7.61 (d, J=7.6 Hz, 1H), 7.54 (s, 1H), 7.39-7.45 (m, 2H), 7.23-7.29 (m, 1H), 7.10-7.17 (m, 1H), 7.05 (s, 1H), 6.84 (br s, 1H), 5.35 (br s, 2H), 4.70-4.81 (m, 1H), 4.03-4.17 (m, 2H), 3.09-3.41 (m, 8H), 2.81-3.09 (m, 15H), 2.65-2.79 (m, 3H), 2.05 (br s, 2H), 1.83-2.02 (m, 3H), 1.67-1.83 (m, 3H), 1.39-1.55 (m, 2H), 1.20-1.38 (m, 9H), 0.80-0.89 (m, 3H). LC/MS method A: R$_t$=3.27 mins., (M+H)$^+$=810, purity >95%.

(R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-1H-indazol-1-yl)methyl hexyl (methyl)carbamate (97). The target compound was purified from Example 96 reaction mixture by RP-HPLC (Method B) as a white solid (32 mg, 18% yield). $^1$H NMR (DMSO-d$_6$) δ: 9.90 (br s, 1H), 7.98 (s, 1H), 7.60-7.76 (m, 2H), 7.48-7.60 (m, 2H), 7.41 (s, 1H), 7.25-7.32 (m, 1H), 7.06 (s, 1H), 6.87 (br d, J=7.6 Hz, 1H), 6.24 (br s, 2H), 4.71-4.80 (m, 1H), 3.85-4.25 (m, 10H), 3.44-3.66 (m, 4H), 3.14-3.25 (m, 2H), 2.84-3.06 (m, 9H), 2.66-2.82 (m, 10H), 1.54-1.83 (m, 4H), 1.13-1.52 (m, 6H), 0.84-1.02 (m, 5H). LC/MS method A: R$_t$=3.72 mins., (M+H)$^+$=810, purity >95%.

(R)-1-(((hexyl(methyl)carbamoyl)oxy)methyl)-4-(4-(3-(1-(((hexyl(methyl)carbamoyl)oxy)methyl)-7-methyl-1H-indazol-5-yl)-2-(4-(2-oxo-1,2-dihydroquinolin-3-yl)piperidine-1-carboxamido)propanoyl)piperazin-1-yl)-1-methylpiperidin-1-ium (98). The target compound was purified from Example 96 reaction mixture by RP-HPLC (Method B) as a white solid (20 mg, 9% yield). $^1$H NMR (DMSO-d$_6$) δ: 7.99 (s, 1H), 7.60-7.86 (m, 2H), 7.48-7.60 (m, 2H), 7.42 (s, 1H), 7.22-7.26 (m, 1H), 7.06 (s, 1H), 6.85

(br d, J=7.6 Hz, 2H), 6.24 (br s, 2H), 5.23-5.44 (m, 2H), 4.72-4.80 (m, 1H), 3.89-4.28 (m, 17H), 3.49-3.71 (m, 3H), 3.14-3.42 (m, 6H), 2.86-3.12 (m, 11H), 2.63-2.83 (m, 5H), 1.87-2.27 (m, 3H), 1.73 (br s, 2H), 1.39-1.56 (m, 2H), 1.24-1.32 (br d, 11H), 0.79-0.95 (m, 6H). LC/MS method A: $R_t$=3.72 mins., (M+H)$^+$=981, purity >95%.

Examples 99-101

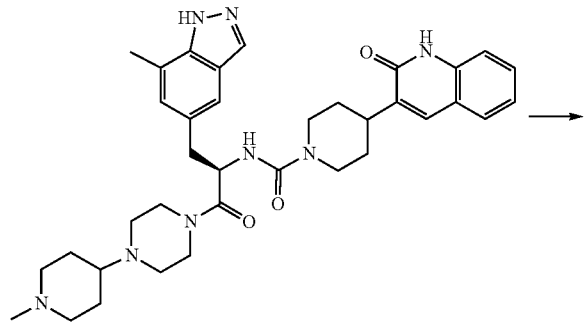

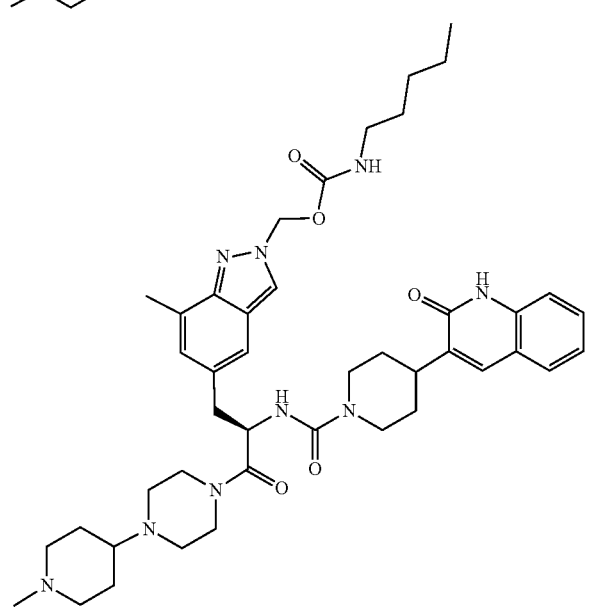

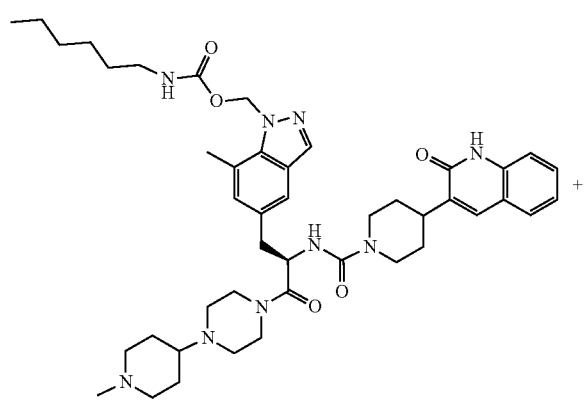

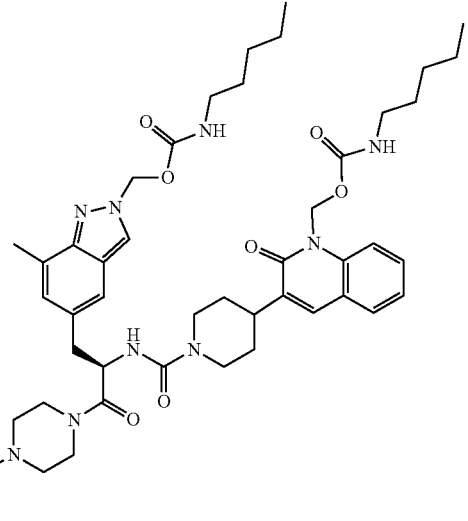

(R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl)methyl pentylcarbamate (99) was prepared from (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl) piperidine-1-carboxamide, by the same procedure as in Examples 86-88 above on 150 mg scale purified by Method B as a white solid (30 mg, 16% yield). $^1$H NMR (DMSO-d$_6$) δ: 11.76 (br s, 1H), 8.34 (br s, 1H), 7.52-7.70 (m, 2H), 7.33-7.52 (m, 3H), 7.20-7.29 (m, 1H), 7.08-7.14 (m, 2H), 7.00 (br s, 1H), 6.80-6.89 (m, 1H), 6.20 (br s, 2H), 4.69-4.81 (m, 1H), 3.74-4.23 (m, 14H), 3.44-3.60 (m, 2H), 3.07-3.28 (m, 2H), 2.62-3.02 (m, 9H), 1.52-1.89 (m, 5H), 1.04-1.40 (m, 10H), 0.75-0.89 (m, 3H). LC/MS method A: $R_t$=3.24 mins., (M+H)$^+$=782, purity >95%.

(R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-1H-indazol-1-yl)methyl pentylcarbamate (100). The target compound was purified from Example 99 reaction mixture by RP-HPLC (Method B) as a white solid (25 mg, 14% yield). $^1$H NMR (DMSO-d$_6$) δ: 11.78 (s, 1H), 7.98 (s, 1H), 7.39-7.74 (m, 3H), 7.24-7.37 (m, 4H), 7.04 (s, 1H), 6.86 (br d, d, J=7.6 Hz, 1H), 6.21 (s, 2H), 4.71-4.80 (m, 1H), 4.01-4.25 (m, 2H), 3.43-3.75 (m, 5H), 3.27-3.43 (m, 5H), 3.22 (br s, 3H), 2.79-3.11 (m, 8H), 2.60-2.79 (m, 4H), 2.15-2.52 (m, 4H), 1.48-1.83 (m, 4H), 1.12-1.44 (m, 5H), 0.77-0.88 (m, 5H). LC/MS method A: $R_t$=3.55 mins, (M+H)$^+$=782, purity >95%.

{7-methyl-5-[(2R)-3-[4-(1-methylpiperidin-4-yl)piperazin-1-yl]-3-oxo-2-{[4-(2-oxo-1-{[(pentylcarbamoyl)oxy]methyl}-1,2-dihydroquinolin-3-yl)piperidine-1-carbonyl]amino}propyl]-2H-indazol-2-yl}methyl N-pentylcarbamate (101). The target compound was purified from Example 99 reaction mixture by RP-HPLC (Method B) as a white solid (30 mg, 14% yield). $^1$H NMR (DMSO-d$_6$) δ: 8.35 (s, 1H), 7.64-7.73 (m, 2H), 7.41-7.60 (m, 3H), 7.24-7.37 (m, 3H), 6.99 (s, 1H), 6.84 (br d, d, J=7.6 Hz, 1H), 6.14-6.25 (m, 4H), 4.71-4.81 (m, 1H), 4.06-4.20 (m, 2H), 3.15-3.35 (m, 15H), 2.80-3.05 (m, 10H), 2.61-2.80 (m, 4H), 2.40-2.55 (m, 4H), 1.56-1.81 (m, 2H), 1.12-1.42 (m, 13H), 0.77-0.88 (m, 6H). LC/MS method A: $R_t$=3.99 mins., (M+H)$^+$=925, purity >95%.

Example 102

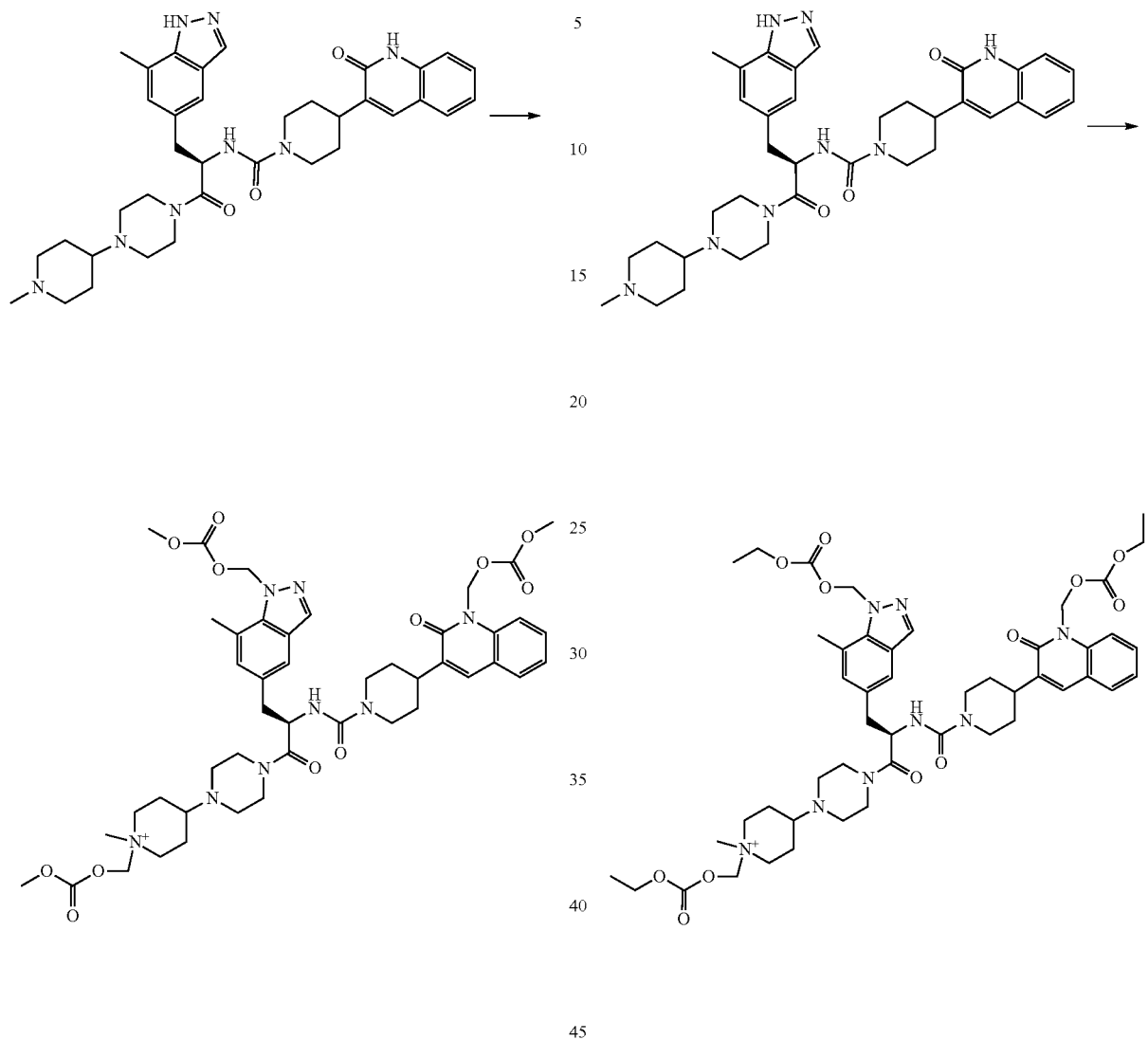

(R)-1-(((methoxycarbonyl)oxy)methyl)-4-(4-(2-(4-(1-(((methoxycarbonyl)oxy)methyl)-2-oxo-1,2-dihydroquinolin-3-yl)piperidine-1-carboxamido)-3-(1-(((methoxycarbonyl)oxy)methyl)-7-methyl-1H-indazol-5-yl)propanoyl)piperazin-1-yl)-1-methylpiperidin-1-ium (102) was prepared from (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide, by the same procedure as in Examples 86-88 above replacing the base with NaH (2.5 eq), on 60 mg scale purified by Method B as a white solid (9 mg, 10% yield). $^1$H NMR (DMSO-d$_6$) δ: 8.44 (s, 1H), 7.66-7.75 (m, 2H), 7.53-7.60 (m, 2H), 7.37 (s, 1H), 7.30 (m, 1H), 7.01 (s, 1H), 6.84 (br s, 1H), 6.31 (s, 4H), 5.18-5.46 (m, 2H), 4.59-4.91 (m, 1H), 4.07-4.16 (m, 2H), 3.84 (s, 3H), 3.38-3.74 (m, 16H), 2.83-3.12 (m, 4H), 2.67-2.80 (m, 4H), 2.32-2.48 (m, 12H), 1.67-1.80 (m, 2H). LC/MS method A: R$_t$=3.31 mins., (M+H)$^+$=903, purity >95%.

Example 103

(R)-1-(((ethoxycarbonyl)oxy)methyl)-4-(4-(2-(4-(1-(((ethoxycarbonyl)oxy)methyl)-2-oxo-1,2-dihydroquinolin-3-yl)piperidine-1-carboxamido)-3-(1-(((ethoxycarbonyl)oxy)methyl)-7-methyl-1H-indazol-5-yl)propanoyl)piperazin-1-yl)-1-methylpiperidin-1-ium (103) was prepared from (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide, by the same procedure as in Examples 86-88 above replacing the base with NaH (2.5 eq), on 60 mg scale purified by Method B as a white solid (4 mg, 5% yield). $^1$H NMR (DMSO-d$_6$) δ: 8.43 (s, 1H), 7.62-7.79 (m, 3H), 7.47-7.62 (m, 3H), 7.24-7.44 (m, 1H), 6.90-7.06 (m, 1H), 6.30 (s, 4H), 5.12-5.47 (m, 2H), 4.78 (br m, 1H), 4.20-4.34 (m, 2H), 4.08-4.17 (m, 6H), 3.17-3.55 (m, 11H), 3.05 (s, 3H), 2.85-2.95 (m, 6H), 2.67-2.75 (m, 4H), 2.45-2.56 (m, 6H), 1.56-1.88 (m, 2H), 1.16-1.29 (m, 9H). LC/MS method A: R$_t$=3.63 mins., (M+H)$^+$=945, purity >95%.

Example 104

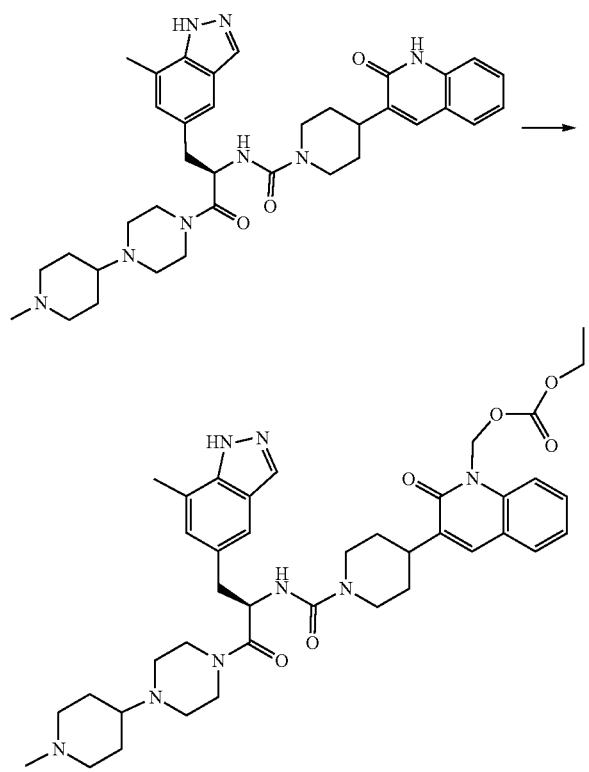

(R)-ethyl ((3-(1-((3-(7-methyl-1H-indazol-5-yl)-1-(4-(1-methylpiperidin-4-yl)piperazin-1-yl)-1-oxopropan-2-yl)carbamoyl)piperidin-4-yl)-2-oxoquinolin-1(2H)-yl)methyl) carbonate (104) was prepared from (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide, by the same procedure as in Examples 86-88 above on 40 mg scale purified by Method B as a white solid (7 mg, 15% yield). $^1$H NMR (DMSO-$d_6$) δ: 13.06 (br s, 1H), 7.91-8.05 (m, 1H), 7.63-7.81 (m, 2H), 7.50-7.63 (m, 2H), 7.35-7.50 (m, 1H), 7.19-7.35 (m, 1H), 6.96-7.19 (m, 1H), 6.67-6.96 (m, 1H), 6.25 (s, 2H), 4.64-4.86 (m, 1H), 4.09-4.17 (m, 6H), 3.19-3.53 (m, 14H), 2.83-2.97 (m, 6H), 2.51-2.80 (m, 4H), 1.63-1.84 (m, 4H), 1.05-1.24 (m, 5H). LC/MS method A: $R_t$=3.31 mins., (M+H)$^+$=843, purity >95%.

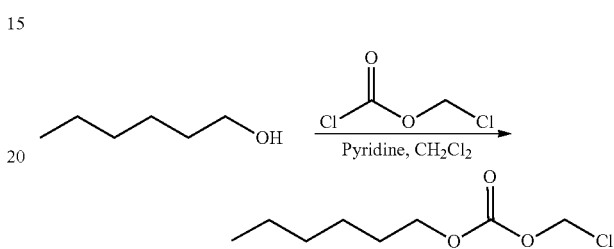

Chloromethyl hexyl carbonate. To a solution of chloromethyl chloroformate (0.96 mL, 10.8 mmol) in dichloromethane (10 mL) at 0° C. was added pyridine (0.87 mL, 10.8 mmol) and hexanol (1 g, 9.8 mmol) in dichloromethane (2 mL). The mixture was stirred at room temperature for 20 h, diluted with 20 mL of dichloromethane, washed with 1N HCl (10 mL), sodium bicarbonate saturated solution (10 mL) and water (20 mL). The organic layer was separated, dried (MgSO$_4$), and concentrated. The crude mixture was purified by silica chromatography eluted with 10% EtOAc in hexanes to get the product as a colorless oil (1.2 g, 63%).

Example 105

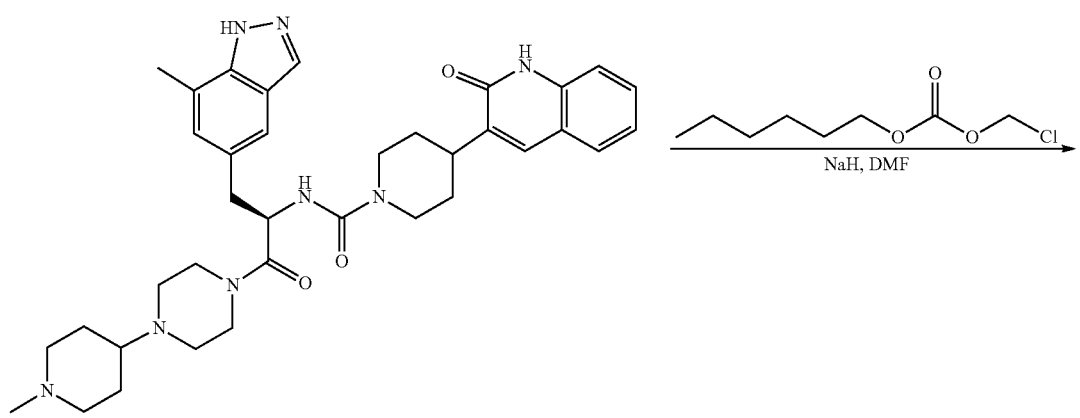

-continued

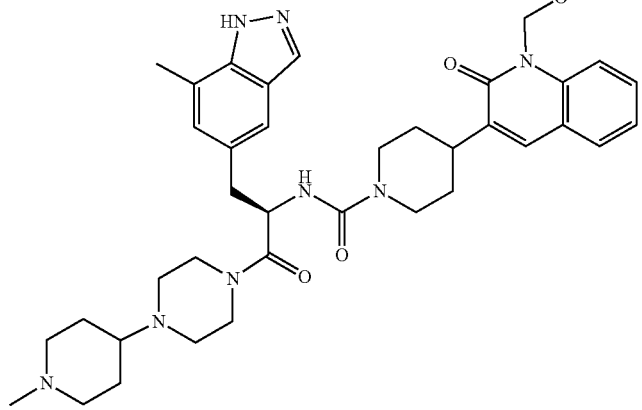

(R)-hexyl ((3-(1-((3-(7-methyl-1H-indazol-5-yl)-1-(4-(1-methylpiperidin-4-yl)piperazin-1-yl)-1-oxopropan-2-yl)carbamoyl)piperidin-4-yl)-2-oxoquinolin-1(2H)-yl)methyl) carbonate (105) was prepared from (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl) piperidine-1-carboxamide, by the same procedure as in Examples 86-88 above replacing the base with NaH (2 eq), on 40 mg scale purified by Method B as a white solid (5 mg, 10% yield). $^1$H NMR (DMSO-d$_6$) δ: 13.16 (s, 1H), 7.98 (s, 1H), 7.67-7.74 (m, 2H), 7.46-7.63 (m, 2H), 7.40 (s, 1H), 7.25-735 (m, 1H), 7.05 (br s, 1H), 6.78-6.97 (m, 1H), 6.30 (br s, 2H), 4.64-4.86 (m, 1H), 4.08-4.17 (m, 6H), 3.24-3.60 (m, 10H), 2.67-2.99 (m, 6H), 2.45-2.51 (m, 6H), 1.71-1.80 (m, 2H), 1.51-1.60 (m, 4H), 1.19-1.34 (m, 10H), 0.79-0.85 (m, 3H). LC/MS method A: R$_t$=4.05 mins., (M+H)$^+$=797, purity >95%.

Examples 106-107

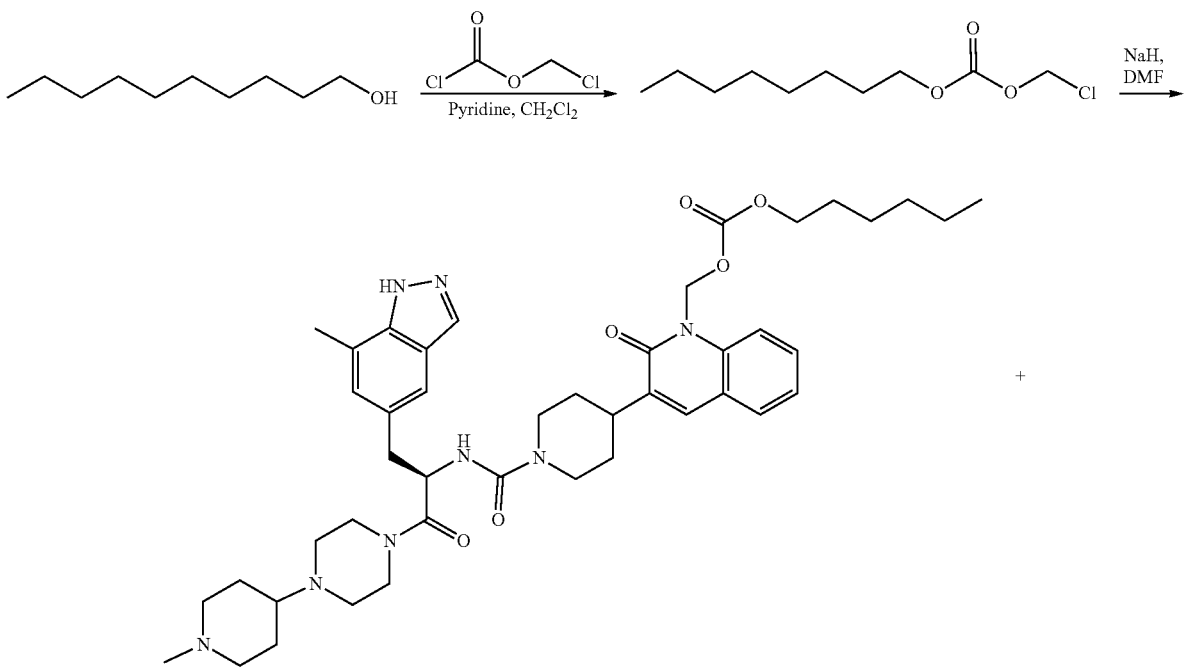

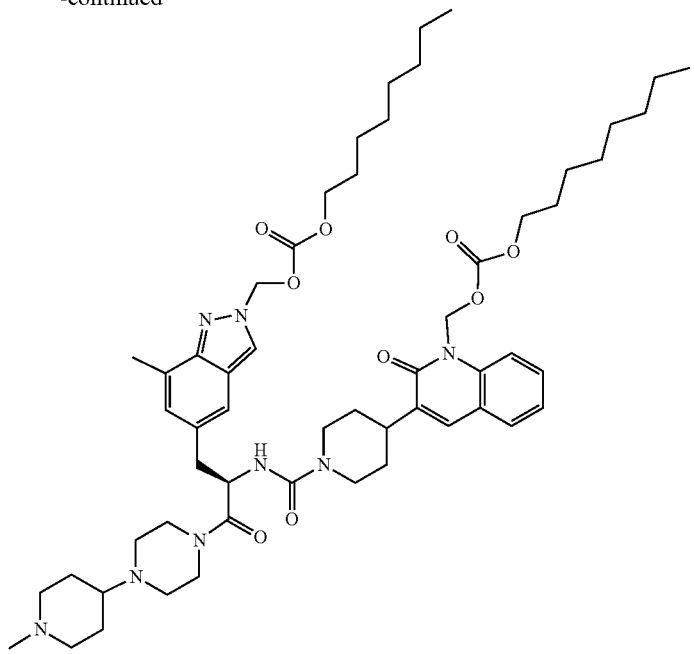

(R)-hexyl ((3-(1-((3-(7-methyl-1H-indazol-5-yl)-1-(4-(1-methylpiperidin-4-yl)piperazin-1-yl)-1-oxopropan-2-yl)carbamoyl)piperidin-4-yl)-2-oxoquinolin-1(2H)-yl)methyl) carbonate (106) was prepared from (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide, by the same procedure as in Example 105 above on 40 mg scale purified by Method B as a white solid (6 mg, 12% yield). $^1$H NMR (DMSO-$d_6$) δ: 13.05 (s, 1H), 7.98 (s, 1H), 7.66-7.74 (m, 2H), 7.52-7.60 (m, 2H), 7.41 (s, 1H), 7.30 (m, 1H), 7.06 (s, 1H), 6.88 (br d, J=7.2 Hz, 1H), 6.30 (br s, 2H), 4.70-4.80 (m, 1H), 4.06-4.20 (br m, 4H), 3.40-3.71 (m, 8H), 2.63-3.03 (m, 10H), 2.33-2.49 (m, 4H), 1.66-1.83 (m, 4H), 1.50-1.66 (m, 4H), 1.16-1.37 (m, 14H), 0.79-0.86 (m, 3H). LC/MS method A: R$_t$=4.42 mins., (M+H)$^+$=825, purity >95%.

{7-methyl-5-[(2R)-3-[4-(1-methylpiperidin-4-yl)piperazin-1-yl]-2-({4-[1-({[(octyloxy)carbonyl]oxy}methyl)-2-oxo-1,2-dihydroquinolin-3-yl]piperidine-1-carbonyl}amino)-3-oxopropyl]-2H-indazol-2-yl}methyl octyl carbonate (107). The target compound was purified from Example 106 reaction mixture by RP-HPLC (Method B) as a white solid (5 mg, 8% yield). $^1$H NMR (DMSO-$d_6$) δ: 8.44 (s, 1H), 7.60-7.73 (m, 2H), 7.43-7.60 (m, 2H), 7.38 (s, 1H), 7.25-7.35 (m, 1H), 7.02 (s, 1H), 6.86 (br d, J=7.6 Hz, 1H), 6.30 (s, 4H), 4.7-4.80 (m, 1H), 3.97-4.16 (m, 7H), 3.35-3.72 (m, 8H), 2.61-3.00 (m, 10H), 2.33-2.51 (m, 4H), 1.46-1.80 (m, 6H), 1.12-1.35 (m, 26H), 0.78-0.86 (m, 6H). LC/MS method A: R$_t$=5.38 mins., (M+H)$^+$=1012, purity >95%.

Examples 108-109

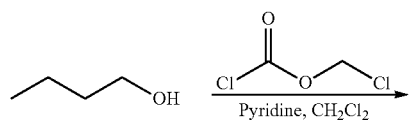

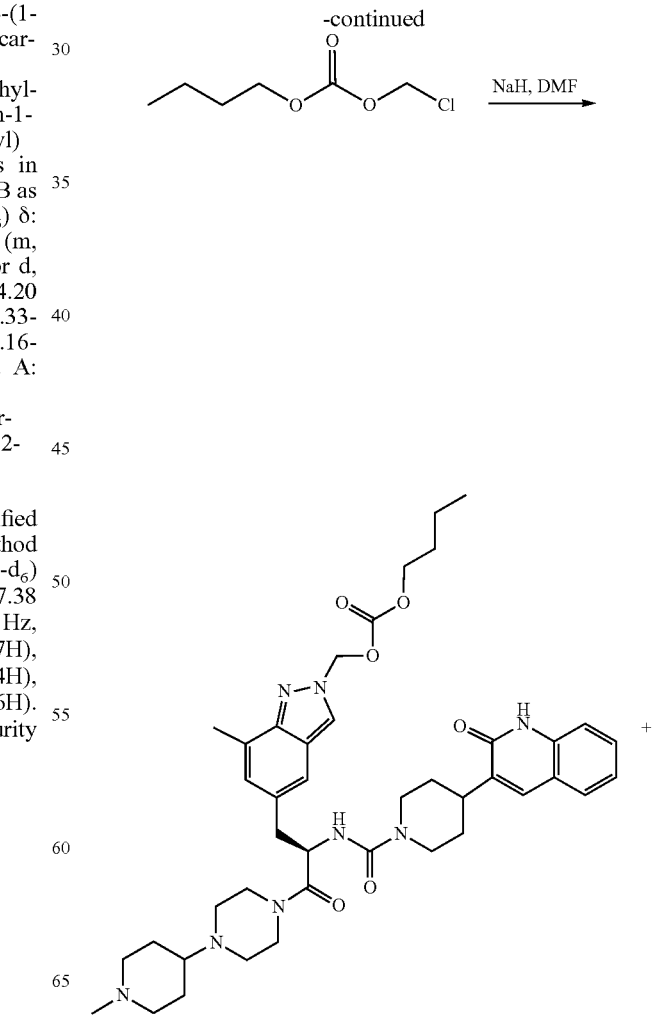

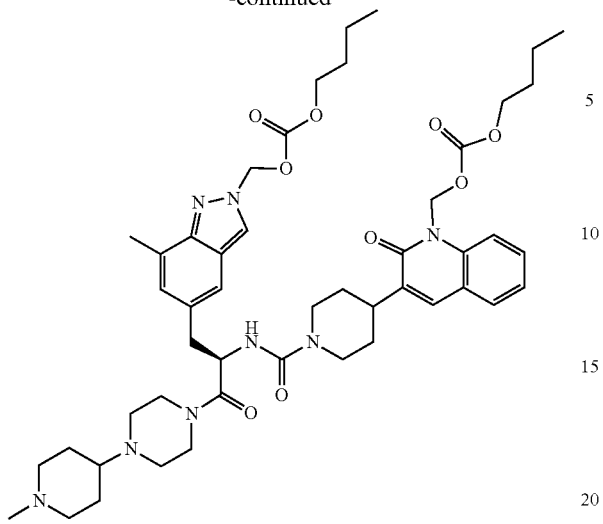
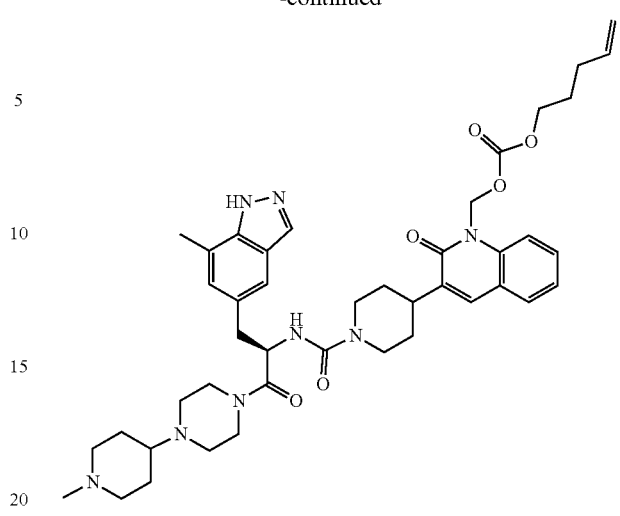

(R)-butyl ((7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl)methyl) carbonate (108) was prepared from (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide, by the same procedure as in Example 105 above on 40 mg scale purified by Method B as a white solid (5 mg, 10% yield). $^1$H NMR (DMSO-d$_6$) δ: 11.76 (s, 1H), 8.37 (s, 1H), 7.62 (br d, 1H), 7.55 (s, 1H), 7.37-7.45 (m, 2H), 7.21-7.33 (m, 1H), 7.08-7.21 (m, 1H), 7.01 (s, 1H), 6.83 (br d, J=7.6 Hz, 1H), 6.30 (s, 2H), 4.64-4.88 (m, 1H), 4.05-4.19 (m, 4H), 3.40-3.71 (m, 13H), 2.63-3.03 (m, 4H), 2.33-2.49 (m, 8H), 1.66-1.83 (m, 4H), 1.50-1.66 (m, 4H), 1.16-1.37 (m, 3H), 0.79-0.86 (m, 3H). LC/MS method A: R$_t$=3.31 mins., (M+H)$^+$=769, purity >95%.

{5-[(2R)-2-{[4-(1-{[(butoxycarbonyl)oxy]methyl}-2-oxo-1,2-dihydroquinolin-3-yl)piperidine-1-carbonyl]amino}-3-[4-(1-methylpiperidin-4-yl)piperazin-1-yl]-3-oxopropyl]-7-methyl-2H-indazol-2-yl}methyl butyl carbonate (109). The target compound was purified from Example 108 reaction mixture by RP-HPLC (Method B) as a white solid (5 mg, 11% yield). $^1$H NMR (DMSO-d$_6$) δ: 8.42 (s, 1H), 7.76-7.71 (m, 2H), 7.59-7.50 (m, 2H), 7.39 (s, 1H), 7.28-7.35 (m, 1H), 7.06 (s, 1H), 6.85 (br d, J=7.2 Hz, 1H), 6.30 (br s, 4H), 4.70-4.80 (m, 1H), 4.06-4.20 (m, 6H), 3.40-3.71 (m, 14H), 2.63-3.03 (m, 4H), 2.41-2.50 (m, 6H), 1.46-1.81 (m, 10H), 1.16-1.37 (m, 6H), 0.79-0.86 (m, 6H). LC/MS method A: R$_t$=4.03 mins, (M+H)$^+$=899, purity >95%.

Example 110

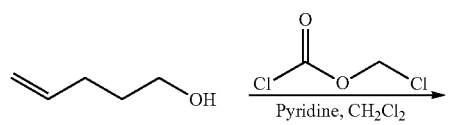

(R)-(3-(1-((3-(7-methyl-1H-indazol-5-yl)-1-(4-(1-methylpiperidin-4-yl)piperazin-1-yl)-1-oxopropan-2-yl)carbamoyl)piperidin-4-yl)-2-oxoquinolin-1(2H)-yl)methyl pent-4-en-1-yl carbonate (110) was prepared from (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide, by the same procedure as in Example 105 above on 40 mg scale purified by Method B as a white solid (3 mg, 5% yield). $^1$H NMR (DMSO-d$_6$) δ: 13.07 (m, 1H), 7.98 (s, 1H), 7.63-7.82 (m, 2H), 7.49-7.63 (m, 2H), 7.36-7.49 (m, 1H), 7.30 (m, 1H), 7.07 (br s, 1H), 6.72-6.95 (m, 1H), 6.30 (m, 2H), 5.61-5.94 (m, 1H), 4.84-5.09 (m, 2H), 4.62-4.80 (m, 1H), 4.02-4.16 (m, 5H), 3.10-3.55 (m, 12H), 2.67-3.04 (m, 12H), 2.44-2.51 (m, 4H), 2.00-2.08 (m, 2H), 1.61-1.80 (m, 6H). LC/MS method A: R$_t$=3.65 mins, (M+H)$^+$=781, purity >95%.

Example 111

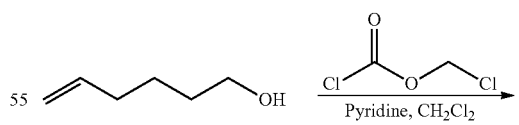

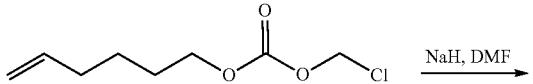

-continued

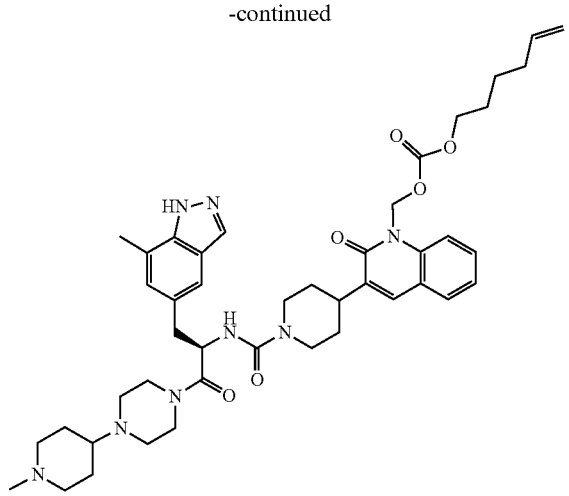

(R)-hex-5-en-1-yl ((3-(1-((3-(7-methyl-1H-indazol-5-yl)-1-(4-(1-methylpiperidin-4-yl)piperazin-1-yl)-1-oxopropan- 2-yl)carbamoyl)piperidin-4-yl)-2-oxoquinolin-1(2H)-yl)methyl) carbonate (111) was prepared from (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide, by the same procedure as in Example 105 above on 40 mg scale purified by Method B as a white solid (5 mg, 10% yield). $^{1}$H NMR (DMSO-d$_6$) δ: 13.06 (br d, 3H), 7.98 (s, 1H), 7.66-7.74 (m, 2H), 7.52-7.58 (m, 2H), 7.40 (s, 1H), 7.25-7.32 (m, 1H), 7.05 (s, 1H), 6.85 (br d, J=7.6 Hz, 1H), 6.28 (br s, 2H), 5.66-5.80 (m, 1H), 4.88-5.02 (m, 2H), 4.65-4.80 (m, 1H), 4.08-4.16 (m, 5H), 3.06-3.60 (m, 8H), 2.66-3.05 (m, 12H), 2.45-2.57 (m, 8H), 1.96-2.04 (m, 2H), 1.71-1.80 (m, 2H), 1.53-1.63 (m, 2H), 1.27-1.41 (m, 4H). LC/MS method A: R$_t$=3.78 mins, (M+H)$^{+}$=795, purity >95%.

Example 112-115

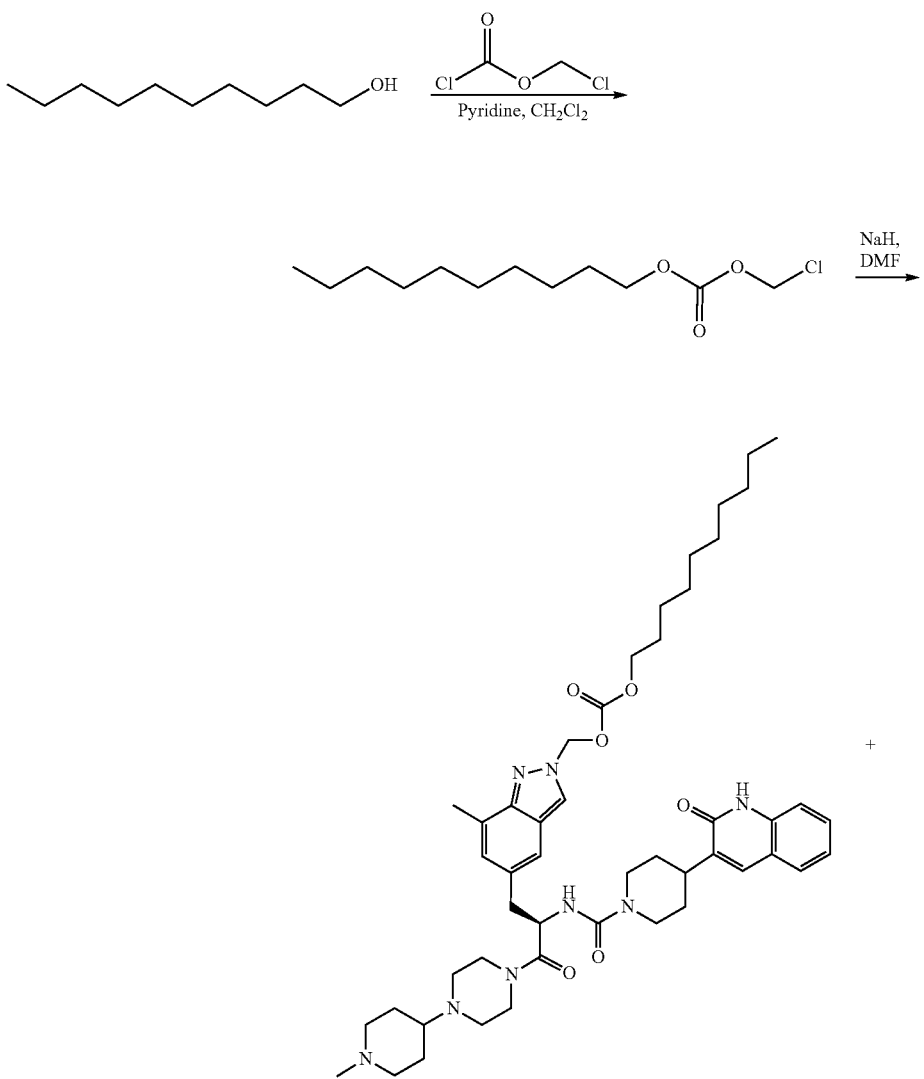

-continued
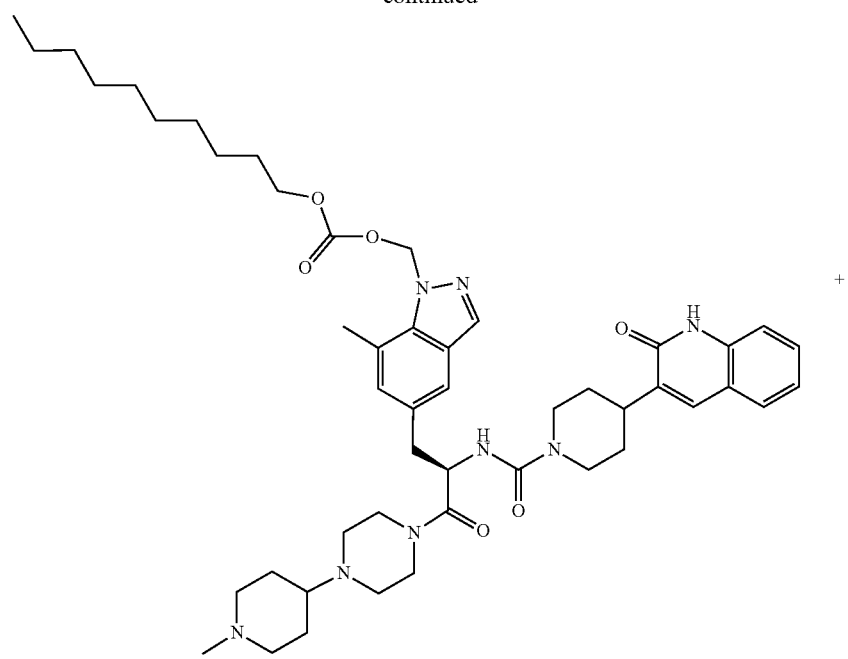
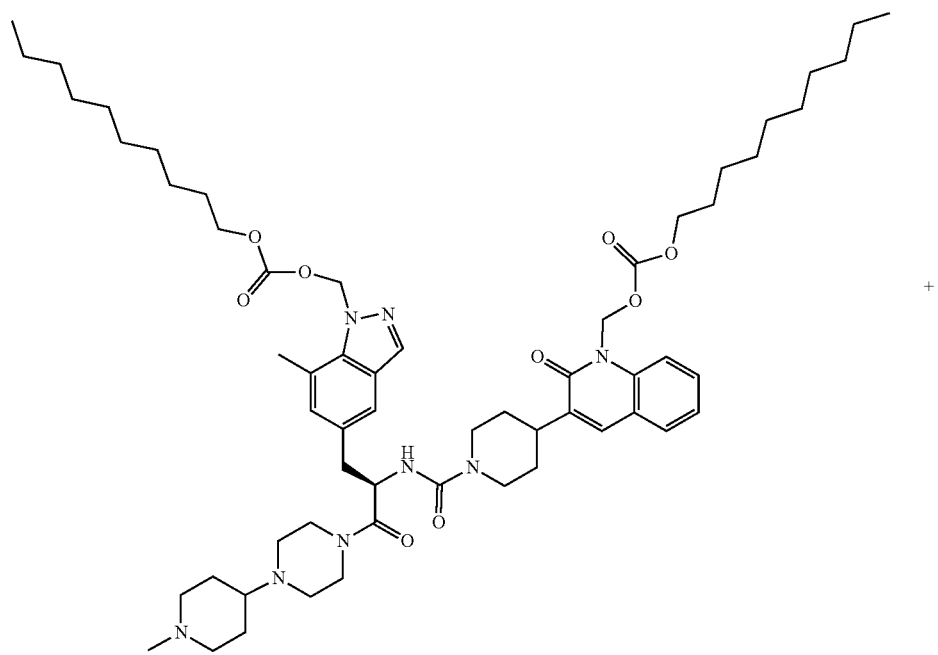

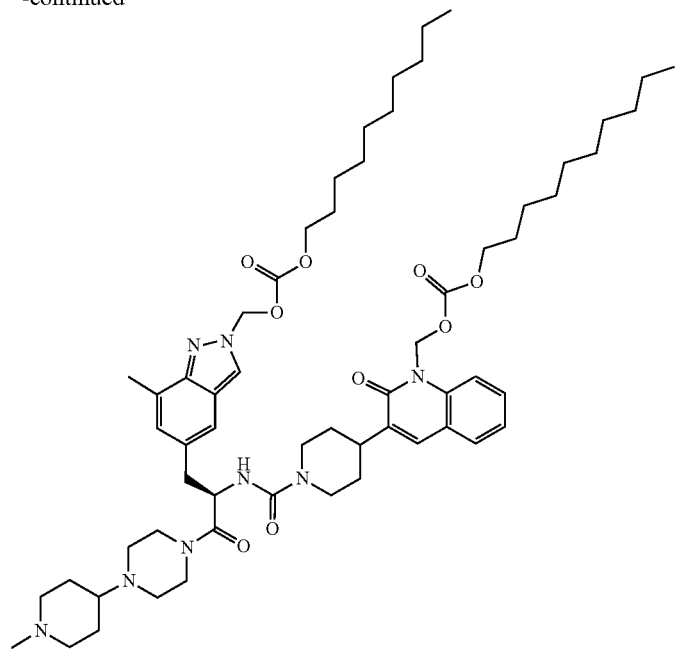

(R)-decyl ((7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl)methyl) carbonate (112) was prepared from (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide, by the same procedure as in Example 105 above on 40 mg scale purified by Method B as a white solid (32 mg, 60% yield). $^1$H NMR (DMSO-d$_6$) δ: 11.75 (s, 1H), 8.44 (s, 1H), 7.62 (d, J=7.6 Hz, 1H), 7.54 (s, 1H), 7.37-7.45 (m, 2H), 7.25 (d, J=7.6 Hz, 1H), 7.10-7.18 (m, 1H), 7.02 (s, 1H), 6.84 (br d, J=7.2 Hz, 1H), 6.30 (s, 2H), 4.70-4.82 (m, 1H), 3.99-4.16 (m, 4H), 3.45-3.75 (m, 14H), 2.65-3.02 (m, 8H), 2.32-2.46 (m, 8H), 1.61-1.81 (m, 4H), 1.49-1.58 (m, 2H), 1.18-1.30 (m, 16H), 0.79-0.85 (m, 3H). LC/MS method A: R$_t$=4.32 mins, (M+H)$^+$=853, purity >95%.

(R)-decyl ((7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-1H-indazol-1-yl)methyl) carbonate (113). The target compound was purified from Example 112 reaction mixture by RP-HPLC (Method B) as a white solid (10 mg, 19% yield). $^1$H NMR (DMSO-d$_6$) δ: 11.76 (s, 1H), 8.14 (s, 1H), 7.49-7.67 (m, 3H), 7.37-7.46 (m, 1H), 7.11-7.28 (m, 2H), 6.86 (br s, 1H), 6.44 (s, 1H), 4.70-4.82 (m, 1H), 4.34 (s, 3H), 3.99-4.16 (m, 4H), 3.45-3.75 (m, 11H), 2.65-3.02 (m, 8H), 2.32-2.46 (m, 8H), 1.61-1.81 (m, 4H), 1.49-1.58 (m, 2H), 1.18-1.30 (m, 16H), 0.79-0.85 (m, 3H). LC/MS method A: R$_t$=4.39 mins, (M+H)$^+$=853, purity >95%.

Decyl {5-[(2R)-2-({4-[1-({[(decyloxy)carbonyl]oxy}methyl)-2-oxo-1,2-dihydroquinolin-3-yl]piperidine-1-carbonyl}amino)-3-[4-(1-methylpiperidin-4-yl)piperazin-1-yl]-3-oxopropyl]-7-methyl-2H-indazol-2-yl}methyl carbonate (114). The target compound was purified from Example 112 reaction mixture by RP-HPLC (Method B) as a white solid (5 mg, 7% yield). $^1$H NMR (DMSO-d$_6$) δ: 8.43 (s, 1H), 7.74 (d, J=8.2 Hz, 1H), 7.65 (s, 1H), 7.51-7.60 (m, 2H), 7.38 (s, 1H), 7.30 (m, 1H), 7.02 (s, 1H), 6.85 (br d, J=7.3 Hz, 1H), 6.30 (s, 4H), 4.73-4.81 (m, 1H), 3.99-4.16 (m, 4H), 3.21-3.59 (m, 2H), 2.81-3.00 (m, 6H), 2.60-2.81 (m, 6H), 2.40-2.46 (m, 8H), 1.62-1.79 (m, 8H), 1.09-1.31 (m, 44H), 0.71-0.89 (m, 6H). LC/MS method A: R$_t$=6.18 mins, (M+H)$^+$=1067, purity >95%.

Decyl {5-[(2R)-2-({4-[1-({[(decyloxy)carbonyl]oxy}methyl)-2-oxo-1,2-dihydroquinolin-3-yl]piperidine-1-carbonyl}amino)-3-[4-(1-methylpiperidin-4-yl)piperazin-1-yl]-3-oxopropyl]-7-methyl-1H-indazol-1-yl}methyl carbonate (115). The target compound was purified from Example 112 reaction mixture by RP-HPLC (Method B) as a white solid (2 mg, 3% yield). $^1$H NMR (DMSO-d$_6$) δ: 8.14 (s, 1H), 7.65-7.75 (m, 2H), 7.54-7.62 (m, 4H), 6.43 (s, 1H), 6.30 (br s, 1H), 7.30 (m, 1H), 7.20 (s, 1H), 6.85 (br m, 1H), 6.45 (br s, 2H), 6.30 (br s, 2H), 4.73-4.81 (m, 1H), 3.99-4.16 (m, 8H), 3.41-3.85 (m, 2H), 2.81-3.00 (m, 6H), 2.60-2.81 (m, 6H), 2.40-2.46 (m, 4H), 1.62-1.79 (m, 4H), 1.42-1.79 (m, 6H), 1.09-1.31 (m, 42H), 0.71-0.89 (m, 6H). LC/MS method A: R$_t$=6.28 mins, (M+H)$^+$=1067, purity >95%.

Examples 116-117

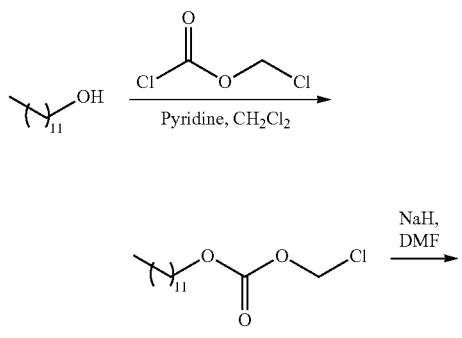

Example 118-119

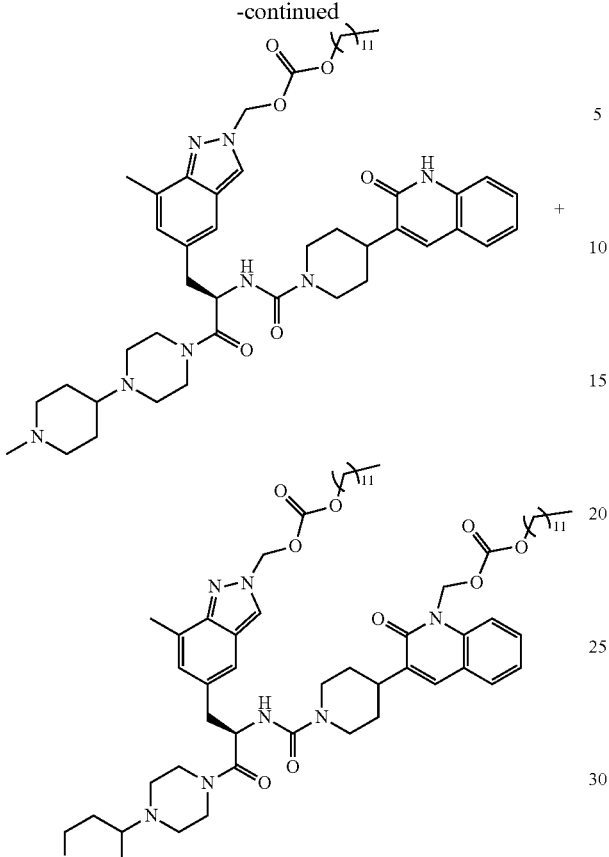
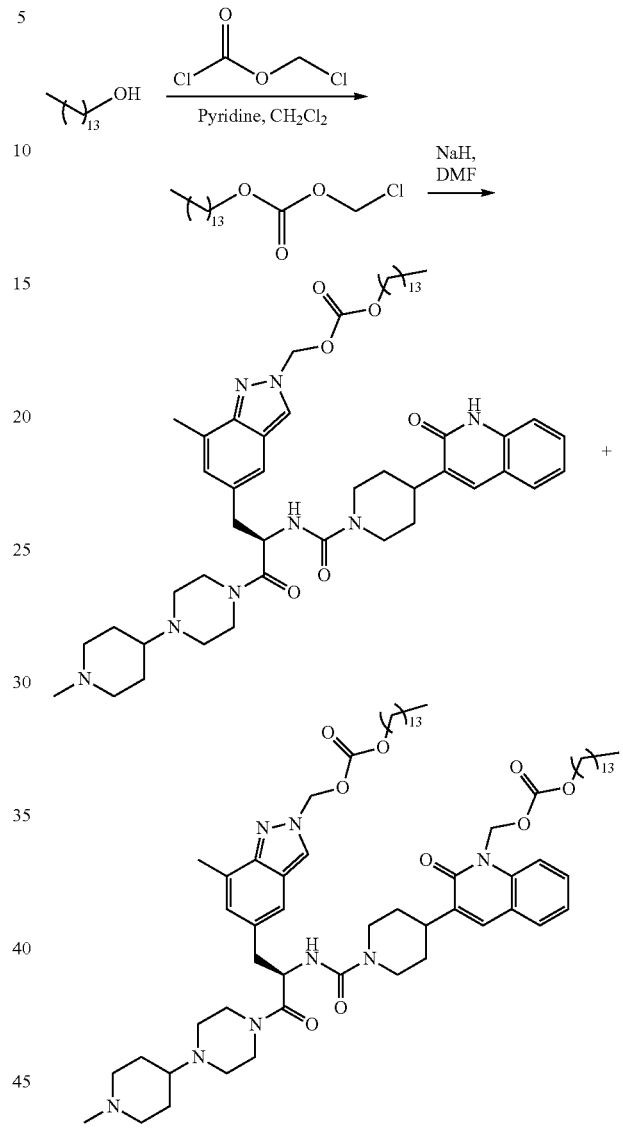

(R)-dodecyl ((7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl)methyl) carbonate (116) was prepared from (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide, by the same procedure as in Example 105 above, on a 40 mg scale purified by Method B as a white solid (15 mg, 27% yield). $^1$H NMR (DMSO-d$_6$) δ: 11.76 (br s, 1H), 8.44 (br s, 1H), 7.51-7.65 (m, 2H), 7.35-7.45 (m, 2H), 7.25 (br m, 1H), 7.10-7.18 (m, 1H), 7.02 (s, 1H), 6.80-6.88 (m, 1H), 6.30 (br s, 4H), 4.72-4.80 (m, 1H), 3.77-4.15 (m, 4H), 3.21-3.61 (m, 2H), 2.60-3.00 (m, 8H), 2.10-2.45 (m, 19H), 1.59-1.80 (m, 2H), 1.45-1.59 (m, 2H), 1.05-1.18 (m, 20H), 0.82 (br m, 2H). LC/MS method A: R$_t$=3.01 mins, (M+H)$^+$=881, purity >95%.

Dodecyl {5-[(2R)-2-({4-[1-({[(dodecyloxy)carbonyl]oxy}methyl)-2-oxo-1,2-dihydroquinolin-3-yl]piperidine-1-carbonyl}amino)-3-[4-(1-methylpiperidin-4-yl)piperazin-1-yl]-3-oxopropyl]-7-methyl-2H-indazol-2-yl}methyl carbonate (117). The target compound was purified from Example 116 reaction mixture by RP-HPLC (Method B) as a white solid (9 mg, 13% yield). $^1$H NMR (DMSO-d$_6$) δ: 8.42 (s, 1H), 7.67-7.76 (m, 2H), 7.52-7.58 (m, 2H), 7.27-7.36 (m, 2H), 6.88-7.05 (m, 1H), 6.60-6.88 (m, 1H), 6.27-6.34 (m, 4H), 4.61-4.87 (m, 1H), 4.02-4.15 (m, 6H), 3.25-3.50 (m, 18H), 2.57-2.96 (m, 11H), 2.22-2.37 (m, 3H), 1.14-1.78 (m, 40H), 0.77-0.86 (m, 6H). LC/MS method A: R$_t$=6.42 mins, (M+H)$^+$=1124, purity >95%.

(R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl)methyl tetradecyl carbonate (118) was prepared from (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide, by the same procedure as in Example 105 above on a 40 mg scale purified by Method B as a white solid (11 mg, 19% yield). $^1$H NMR (DMSO-d$_6$) δ: 11.75 (s, 1H), 8.44 (s, 1H), 7.62 (d, J=7.6, 1H), 7.54 (s, 1H), 7.36-7.45 (m, 2H), 7.25 (d, J=7.5 Hz, 1H), 7.14 (m, 1H), 7.01 (s, 1H), 6.84 (br d, J=7.2 Hz, 1H), 6.30 (s, 2H), 4.77 (br m, 1H), 4.07 (br m, 4H), 3.41-3.87 (m, 14H), 2.61-3.00 (m, 8H), 2.33-2.48 (m, 6H), 1.46-1.82 (m, 4H), 0.96-1.33 (m, 24H), 0.82 (m, 3H). LC/MS method A: R$_t$=5.18 mins, (M+H)$^+$=909, purity >95%.

{7-methyl-5-[(2R)-3-[4-(1-methylpiperidin-4-yl)piperazin-1-yl]-3-oxo-2-({4-[2-oxo-1-({[(tetradecyloxy)carbonyl]oxy}methyl)-1,2-dihydroquinolin-3-yl]piperidine-1-carbonyl}amino)propyl]-2H-indazol-2-yl}methyl tetradecyl carbonate (119). The target compound was purified from Example 118 reaction mixture by RP-HPLC (Method B) as a white solid (17 mg, 23% yield). $^1$H NMR (300 MHz, DMSO-$d_6$) δ=8.43 (s, 1H), 7.68-7.77 (m, 1H), 7.51-7.68 (m, 3H), 7.38 (s, 1H), 7.27-7.33 (m, 1H), 7.02 (s, 1H), 6.83 (br d, J=7.0 Hz, 1H), 6.29 (s, 4H), 4.77 (br d, J=7.0 Hz, 1H), 3.97-4.15 (m, 8H), 3.65-3.95 (m, 6H), 3.23-3.60 (m, 5H), 2.79-3.04 (m, 7H), 2.59-2.79 (m, 3H), 2.74 (br s, 3H), 2.31-2.46 (m, 3H), 1.70 (td, J=7.3, 14.7 Hz, 3H), 1.53 (ddd, J=6.9, 7.0, 13.6 Hz, 5H), 0.96-1.35 (m, 43H), 0.75-0.89 (m, 6H). LC/MS method A: $R_t$=6.4 mins, (M+H)$^+$=1179, purity >95%.

Examples 120-121

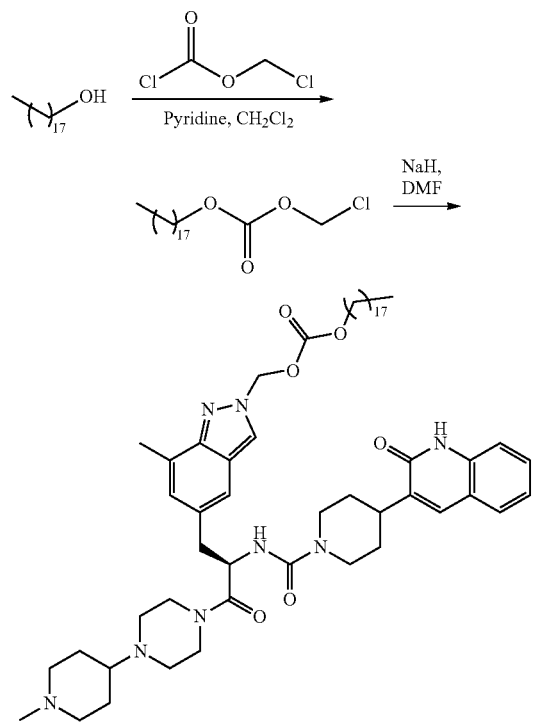

+

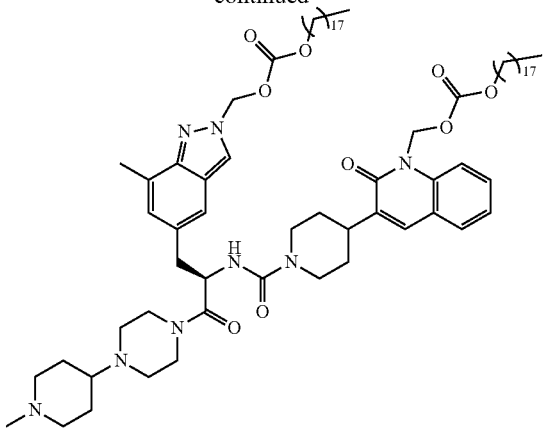

(R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl)methyl octadecyl carbonate (120) was prepared from (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide, by the same procedure as in Example 105 on 40 mg scale purified by Method B as a white solid (12 mg, 20% yield). $^1$H NMR (DMSO-$d_6$) δ: 11.75 (s, 1H), 8.44 (s, 1H), 7.60-7.64 (m, 1H), 7.54 (s, 1H), 7.36-7.45 (m, 2H), 7.25 (d, (d, J=7.6, 1H), 7.14 (m, 1H), 7.01 (s, 1H), 6.84 (br m, 1H), 6.30 (s, 2H), 4.77 (br m, 1H), 4.07 (br m, 4H), 3.12-3.34 (m, 12H), 2.78-3.12 (m, 4H), 2.61-2.78 (m, 4H), 2.33-2.48 (m, 6H), 1.62-1.98 (m, 2H), 1.46-1.62 (m, 2H), 0.96-1.32 (m, 34H), 0.77-0.86 (m, 3H). LC/MS method A: $R_t$=6.18 mins, (M+H)$^+$=965, purity >95%.

[3-(1-{[(2R)-3-(7-methyl-1H-indazol-5-yl)-1-[4-(1-methylpiperidin-4-yl)piperazin-1-yl]-1-oxopropan-2-yl]carbamoyl}piperidin-4-yl)-2-oxo-1,2-dihydroquinolin-1-yl] methyl octadecyl carbonate (121). The target compound was purified from Example 120 reaction mixture by RP-HPLC (Method B) as a white solid (4 mg, 7% yield). $^1$H NMR (DMSO-$d_6$) δ: 13.05 (s, 1H), 8.02 (s, 1H), 7.65-7.79 (m, 1H), 7.51-7.60 (m, 2H), 7.26-7.42 (m, 2H), 7.11-7.17 (m, 1H), 6.92-7.07 (m, 2H), 6.26 (s, 2H), 4.71-4.85 (m, 1H), 4.03-4.20 (m, 4H), 3.12-3.42 (m, 12H), 2.61-2.98 (m, 8H), 2.33-2.48 (m, 4H), 2.25 (br m, 2H), 1.62-1.98 (m, 2H), 1.46-1.62 (m, 4H), 0.96-1.32 (m, 32H), 0.77-0.86 (m, 3H). LC/MS method A: $R_t$=6.18 mins, (M+H)$^+$=966, purity >95%.

Examples 122-124

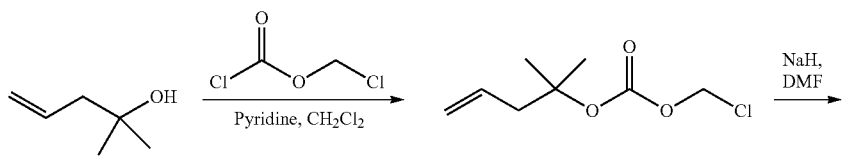

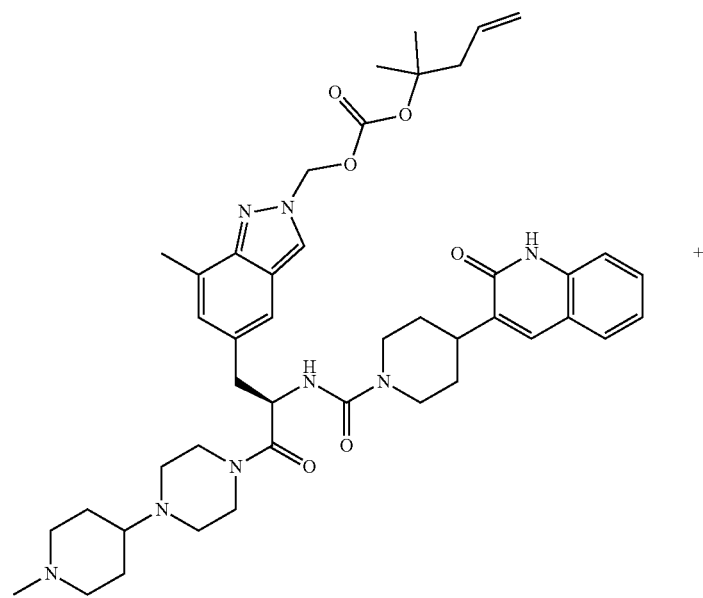
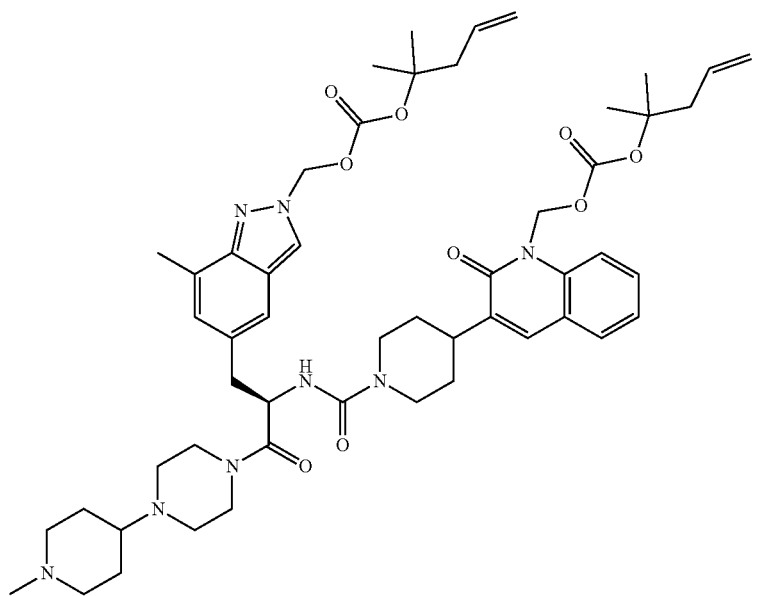

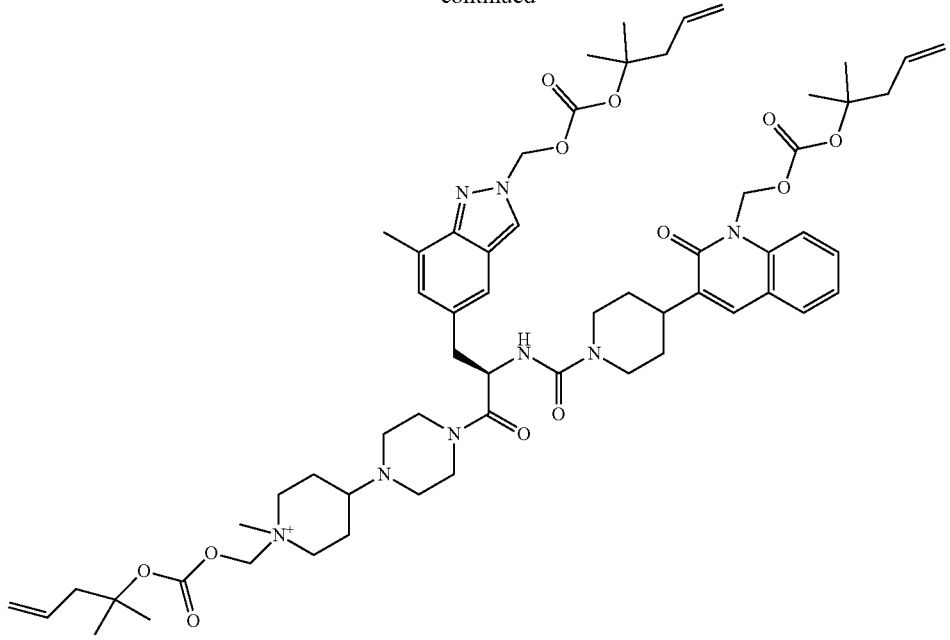

(R)-(7-methyl-5-(3-(4-(1-methylpiperidin-4-yl)piperazin-1-yl)-3-oxo-2-(4-(2-oxo-1,2-dihydroquinolin-3-yl)piperidine-1-carboxamido)propyl)-2H-indazol-2-yl)methyl (2-methylpent-4-en-2-yl) carbonate (122) was prepared from (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide, by the same procedure as in Example 105 on a 40 mg scale purified by Method B as a white solid (6 mg, 12% yield). $^1$H NMR (DMSO-d$_6$) δ: 11.79 (s, 1H), 8.42 (br s, 1H), 7.62-7.81 (m, 1H), 7.45-7.62 (m, 1H), 7.38-7.45 (m, 2H), 7.10-7.34 (m, 2H), 7.01 (br s, 1H), 6.81-6.90 (m, 1H), 6.24 (br s, 2H), 5.60-5.81 (m, 1H), 4.88-5.15 (m, 2H), 4.71-4.81 (m, 1H), 4.06-4.17 (m, 2H), 3.26-3.65 (m, 18H), 2.62-3.01 (m, 8H), 2.36-2.49 (m, 4H), 1.58-1.82 (m, 2H), 1.17-1.43 (m, 8H). LC/MS method A: R$_t$=3.58 mins, (M+H)$^+$=796, purity >95%.

{7-methyl-5-[(2R)-2-[(4-{1-[({[(2-methylpent-4-en-2-yl)oxy]carbonyl}oxy)methyl]-2-oxo-1,2-dihydroquinolin-3-yl}piperidine-1-carbonyl)amino]-3-[4-(1-methylpiperidin-4-yl)piperazin-1-yl]-3-oxopropyl]-2H-indazol-2-yl}methyl 2-methylpent-4-en-2-yl carbonate (123). The target compound was purified from Example 122 reaction mixture by RP-HPLC (Method B) as a white solid (9 mg, 15% yield). $^1$H NMR (DMSO-d$_6$) δ: 8.42 (1H), 7.62-7.78 (m, 2H), 7.45-7.62 (m, 2H), 7.39 (s, 1H), 7.24-7.34 (m, 1H), 7.01 (br s, 1H), 6.81-6.85 (m, 1H), 6.24 (br s, 4H), 5.60-5.81 (m, 2H), 4.88-5.15 (m, 4H), 4.71-4.81 (m, 1H), 4.06-4.47 (m, 20H), 3.46-3.65 (m, 2H), 2.62-3.01 (m, 8H), 2.36-2.49 (m, 4H), 1.58-1.82 (m, 2H), 1.17-1.43 (m, 14H). LC/MS method A: R$_t$=4.40 mins, (M+H)$^+$=951, purity >95%.

1-methyl-4-{4-[(2R)-3-{7-methyl-2-[({[(2-methylpent-4-en-2-yl)oxy]carbonyl}oxy)methyl]-2H-indazol-5-yl}-2-{[4-(2-oxo-1,2-dihydroquinolin-3-yl)piperidine-1-carbonyl]amino}propanoyl]piperazin-1-yl}-1-[({[(2-methyl pent-4-en-2-yl)oxy]carbonyl}oxy)methyl]piperidin-1-ium trifluoroacetate (124). The target compound was purified from Example 122 reaction mixture by RP-HPLC (Method B) as a white solid (7 mg, 10% yield). LC/MS method A:

R$_t$=4.65 mins, (M+H)$^+$=1109, purity >95%. $^1$H NMR (300 MHz, DMSO-d$_6$) δ=8.41 (s, 1H), 8.00 (s, 1H), 7.90 (dd, J=1.2, 8.2 Hz, 1H), 7.74 (d, J=8.2 Hz, 1H), 7.62-7.68 (m, 1H), 7.44-7.51 (m, 1H), 7.39 (s, 1H), 7.02 (s, 1H), 6.81 (br d, J=7.8 Hz, 2H), 6.13-6.29 (m, 4H), 5.70 (tdd, J=8.6, 10.8, 17.1 Hz, 2H), 4.87-5.15 (m, 6H), 4.77 (br m, 1H), 4.23-4.48 (m, 4H), 4.08-4.19 (m, 4H), 3.53 (br d, J=10.5 Hz, 3H), 2.65-3.01 (m, 15H), 2.51-2.57 (m, 2H), 2.38-2.46 (m, 4H), 1.74 (br m, 4H), 1.30-1.48 (m, 12H). LC/MS method A: R$_t$=4.65 mins, (M+H)$^+$=951, purity >95%.

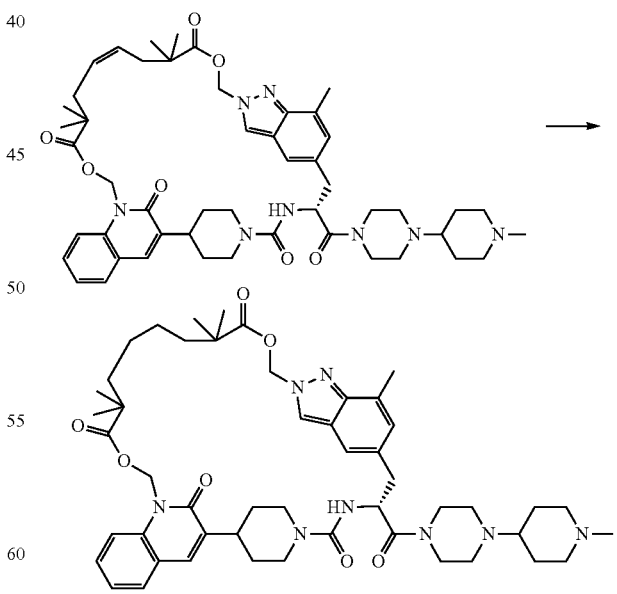

Example 125

(31R)-14,14,19,19,27-pentamethyl-31-[4-(1-methylpiperidin-4-yl)piperazine-1-carbonyl]-12,21-dioxa-10,23,32, 34,40-pentaazahexacyclo[32.2.2.1$^{2,10}$.1$^{23,26}$.1$^{25,29}$.0$^{4,9}$]hentetraconta-2,4,6,8,24,26(40),27,29(39)-octaene-13,20,33,41-tetrone (125). To a solution of (16Z,31R)-14,14,19,19,27-pentamethyl-31-[4-(1-methylpiperidin-4-yl)piperazine-1-carbonyl]-12,21-dioxa-10,23,32,34,40-pentaazahexacyclo[32.2.2.1$^{2,10}$.1$^{23,26}$.1$^{25,29}$.0$^{4,9}$]hentetraconta-2,4(9),5,7,16,24,26(40),27,29(39)-nonaene-13,20,33,41-tetrone, (40 mg, 0.044 mmol) in MeOH (10 mL) protected under N$_2$ was added 10% Pd—C (40 mg). The reaction mixture was hydrogenated with par shaker under 65 psi H2 pressure and was monitored by LC-MS. The reaction was complete in 48 hours, filtered through celite and the filtrate was concentrated and the residue was purified by RP-HPLC (Method B) as a white solid (9 mg, 23%). $^1$H NMR (DMSO-d$_6$) δ: 8.40 (s, 1H), 7.96 (br d, 1H), 7.45-7.84 (m, 1H), 7.20-7.36 (m, 1H), 7.07 (s, 1H), 6.75 (br d, 1H), 6.13-6.52 (m, 1H), 4.73 (br d, 1H), 3.83-4.05 (m, 1H), 2.54-3.49 (m, 1H), 2.38-2.46 (m, 1H), 2.03-2.38 (m, 1H), 1.71-1.94 (m, 1H), 1.53-1.71 (m, 1H), 1.14-1.35 (m, 1H), 1.07 (br d, 1H), 0.88-1.14 (m, 1H), 0.67-0.88 (m, 1H), 0.54-0.67 (m, 1H), 0.63 (br s, 1H), 0.35-0.54 (m, 1H). LC/MS method A: R$_t$=4.02 mins, (M+H)$^+$=894, purity >95%.

Example 126

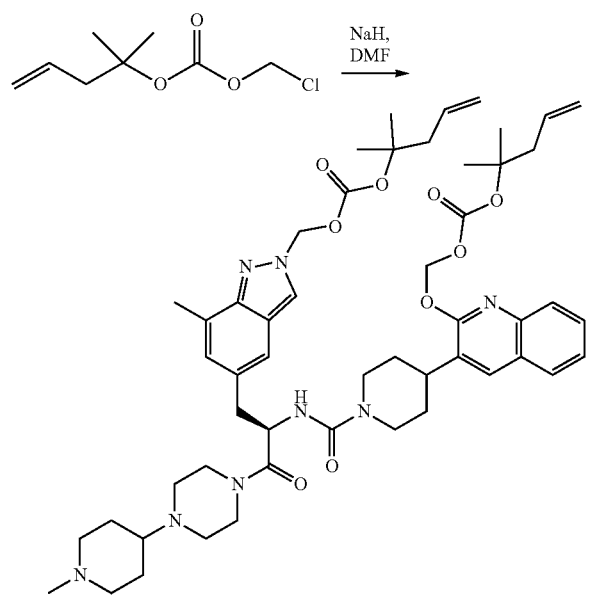

{5-[(2R)-2-{[4-(2-{[(2,2-dimethylpent-4-enoyl)oxy]methoxy}quinolin-3-yl)piperidine-1-carbonyl]amino}-3-[4-(1-methylpiperidin-4-yl)piperazin-1-yl]-3-oxopropyl]-7-methyl-2H-indazol-2-yl}methyl 2,2-dimethylpent-4-enoate (126) was prepared from (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide, by the same procedure as in Example 105 above on a 500 mg scale purified by Method B as a white solid (29 mg, 4% yield). $^1$H NMR (DMSO-d$_6$) δ: 8.37 (s, 1H), 7.97 (s, 1H), 7.91 (d, J=7.6 Hz, 1H), 7.62-7.75 (m, 2H), 7.45 (m, 1H), 7.38 (s, 1H), 7.02 (s, 1H), 6.84 (br d, J=7.4 Hz, 1H), 6.29 (s, 2H), 6.21 (s, 2H), 5.45-568 (m, 2H), 4.73-5.05 (m, 4H), 4.05-4.18 (m, 2H), 3.36-3.70 (m, 12H), 3.18 (s, 3H), 2.67-2.98 (m, 8H), 2.41-2.51 (m, 4H), 2.07-2.24 (m, 4H), 1.67-1.81 (m, 2H), 1.20-1.43 (m, 2H), 1.01-1.12 (d, 14H). LC/MS method A: R$_t$=4.70 mins, (M+H)$^+$=920, purity >95%.

Example 127

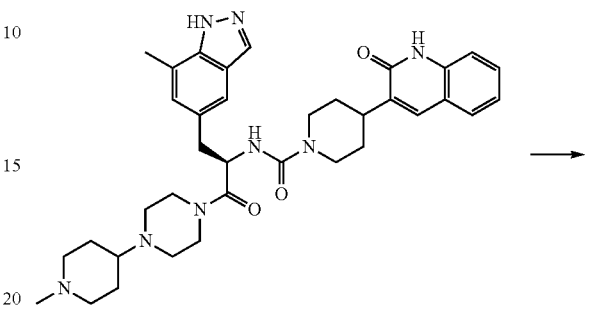

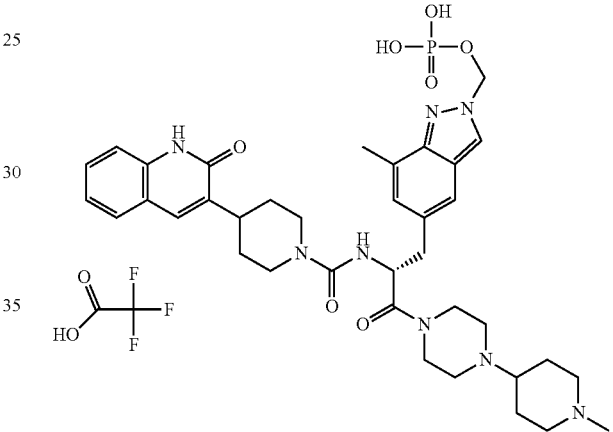

({7-methyl-5-[(2R)-3-[4-(1-methylpiperidin-4-yl)piperazin-1-yl]-3-oxo-2-{[4-(2-oxo-1,2-dihydroquinolin-3-yl)piperidine-1-carbonyl]amino}propyl]-2H-indazol-2-yl}methoxy)phosphonic acid trifluoroacetate (127). A solution of N-[(2R)-3-(7-methyl-1H-indazol-5-yl)-1-[4-(1-methylpiperidin-4-yl)piperazin-1-yl]-1-oxopropan-2-yl]-4-(2-oxo-1,2-dihydroquinolin-3-yl)piperidine-1-carboxamide (200 mg, 313.5 µmop in DMF (4.8 mL) under nitrogen was treated with lithium hexamethyldisilylamide (1.0 M in THF, 936 µL, 936 µmop and stirred for 20 mins. Di-tert-butyl chloromethyl phosphate (405 mg, 1.57 mmol) was added via syringe, and the mixture was stirred overnight. The mixture was purified directly by RP-HPLC (method D) followed by two subsequent purifications (method B) with combined product fractions lyophilized to provide the purified title compound as a white solid (5 mg, 1.8%). $^1$H NMR (300 MHz, DMSO-d$_6$) δ=11.77 (s, 1H), 8.42 (s, 1H), 7.83-7.60 (m, 2H), 7.53-7.22 (m, 3H), 7.15 (t, J=7.3 Hz, 1H), 6.95 (s, 1H), 6.89 (br s, 1H), 5.97 (br d, J=12.3 Hz, 2H), 4.87-4.67 (m, 1H), 4.35-4.01 (m, 2H), 3.79-3.49 (m, 4H), 3.25-2.86 (m, 9H), 2.82-2.61 (m, 5H), 2.44-2.39 (m, 1H), 2.35 (br s, 1H), 2.31-2.12 (m, 1H), 1.98 (br d, J=8.2 Hz, 1H), 1.89-1.68 (m, 2H), 1.54 (br dd, J=3.5, 9.4 Hz, 1H), 1.48-1.14 (m, 6H), 1.00-0.75 (m, 1H). LC/MS method A: R$_t$=2.92 mins., (M+H)$^+$=749, purity=97%.

Example 128

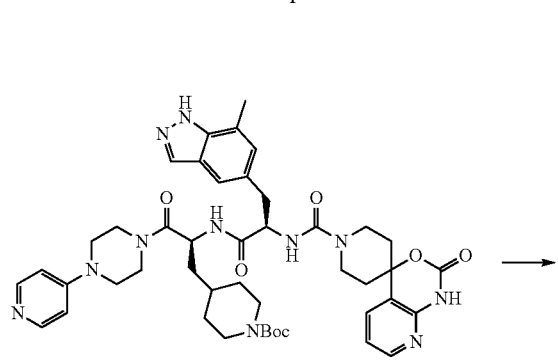

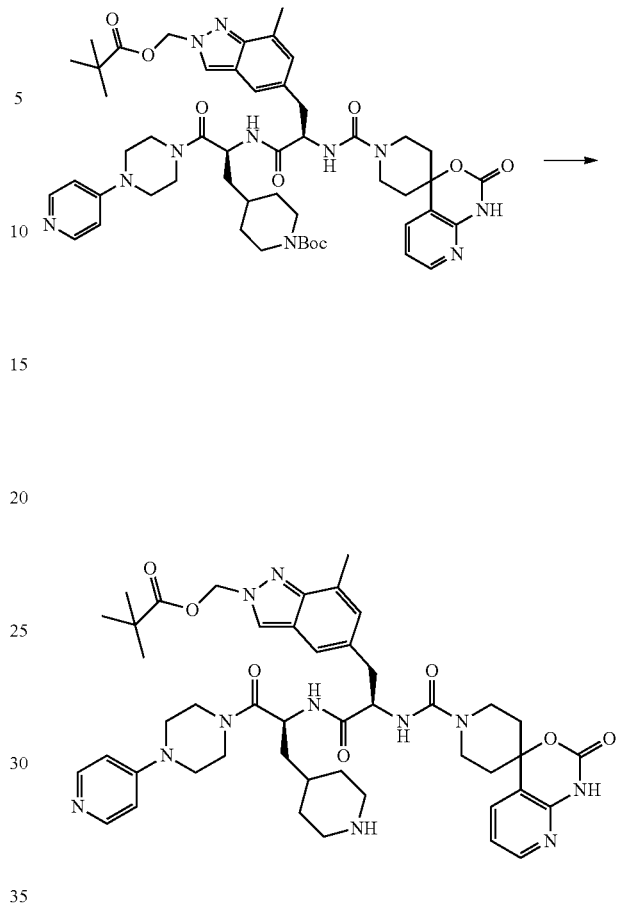

tert-butyl 4-[(2S)-2-[(2R)-3-(2-{[(2,2-dimethylpropanoyl)oxy]methyl}-7-methyl-2H-indazol-5-yl)-2-[({2'-oxo-1',2'-dihydrospiro[piperidine-4,4'-pyrido[2,3-d][1,3]oxazin]-1-yl}carbonyl)amino]propanamido]-3-oxo-3-[4-(pyridin-4-yl)piperazin-1-yl]propyl]piperidine-1-carboxylate. A solution of tert-butyl 4-[(2S)-2-[(2R)-3-(7-methyl-1H-indazol-5-yl)-2-[({2'-oxo-1',2'-dihydrospiro[piperidine-4,4'-pyrido[2,3-d][1,3]oxazin]-1-yl}carbonyl)amino]propanamido]-3-oxo-3-[4-(pyridin-4-yl)piperazin-1-yl]propyl]piperidine-1-carboxylate (WO 2018/178938 A1, 50 mg, 58 μmol) in THF (1 mL) under $N_2$ was treated with a solution of lithium hexamethyldisilylamide (1.0 M in THF, 87 μl, 87 μmol), and the reaction mixture was stirred for 30 minutes. To the solution was added chloromethyl pivalate (17 mg, 0.12 mmol, 17 μl), and the mixture stirred for 18 h. Pure product was isolated following purification with RP-HPLC (method B) and lyophilization of the product fractions to yield 44 mg of white powder (mono trifluoroacetate salt).

{7-methyl-5-[(2R)-2-[({2'-oxo-1',2'-dihydrospiro[piperidine-4,4'-pyrido[2,3-d][1,3]oxazin]-1-yl}carbonyl)amino]-2-{[(2S)-1-oxo-3-(piperidin-4-yl)-1-[4-(pyridin-4-yl)piperazin-1-yl]propan-2-yl]carbamoyl}ethyl]-2H-indazol-2-yl}methyl 2,2-dimethylpropanoate (128). A suspension of tert-butyl 4-[(2S)-2-[(2R)-3-(2-{[(2,2-dimethylpropanoyl)oxy]methyl}-7-methyl-2H-indazol-5-yl)-2-[({2'-oxo-1',2'-dihydrospiro[piperidine-4,4'-pyrido[2,3-d][1,3]oxazin]-1-yl}carbonyl)amino]propanamido]-3-oxo-3-[4-(pyridin-4-yl)piperazin-1-yl]propyl]piperidine-1-carboxylate mono trifluoroacetate salt (39 mg, 36 μmol) was rapidly stirred in 4N HCl/dioxane (1 mL) for 4 h. The mixture was centrifuged for 5 minutes, and the supernatant liquid was decanted. The product was suspended in dioxane (2 mL), centrifuged, and decanted again. The process was repeated one more time with ether. The white powder was dried under high vacuum to yield 19 mg of the product. LCMS (method A): $R_t$=4.58, purity >95%, $(M+H)^+$=879. $^1$H-NMR (DMSO-$d_6$) δ=13.48 (bs, 1H), 10.80 (s, 1H), 8.52-8.42 (m, 2H), 8.40 (s, 1H), 8.26 (d, 2H, J=6.9 Hz), 8.17 (dd, 1H, J=4.8 Hz, J=1.6 Hz), 7.41 (s, 1H), 7.27 (d, 1H, J=6.4 Hz), 7.14 (d, 2H, J=6.5 Hz), 7.11 (s, 1H), 7.02 (dd, 1H, J=7.4 Hz, J=4.7 Hz), 6.75 (d, 1H, J=8.0 Hz), 6.28 (ABq, 2H, J=10.6 Hz), 4.81 (dd, 1H, J=7.4 Hz, J=6.9 Hz), 4.39 (dd, 1H, J=9.5 Hz, J=8.5 Hz), 3.70-3.95 (m, 5H), 3.40-3.62 (m, 4H), 3.20 (m, 1H), 2.80-3.10 (m, 3H), 2.60-2.72 (m, 2H), 2.41 (s, 3H), 1.18-1.88 (m, 12H), 1.05 (s, 9H).

Examples 129-131

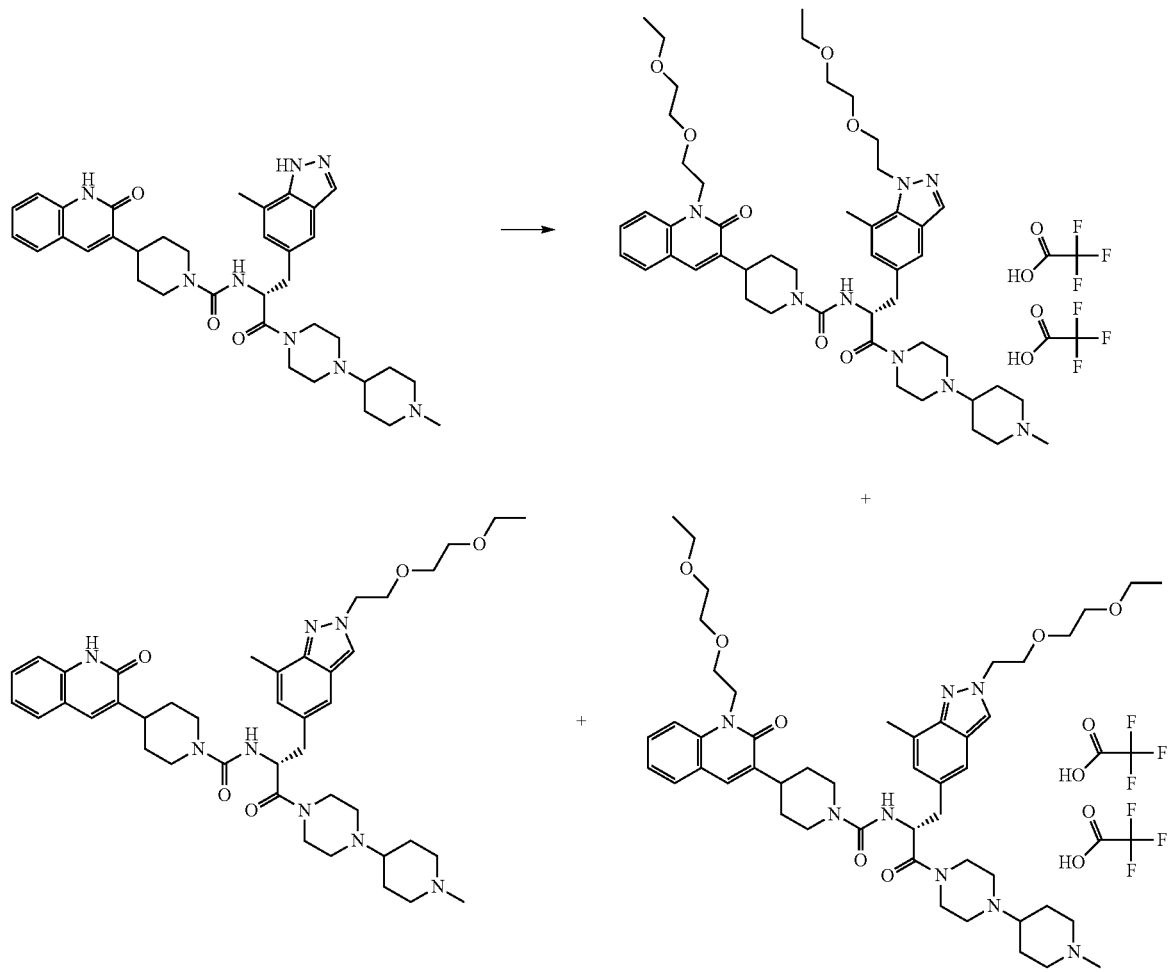

N-[(2R)-3-{2-[2-(2-ethoxyethoxy)ethyl]-7-methyl-2H-indazol-5-yl}-1-[4-(1-methylpiperidin-4-yl)piperazin-1-yl]-1-oxopropan-2-yl]-4-(2-oxo-1,2-dihydroquinolin-3-yl)piperidine-1-carboxamide and 4-{1-[2-(2-ethoxyethoxy)ethyl]-2-oxo-1,2-dihydroquinolin-3-yl}-N-[(2R)-3-{2-[2-(2-ethoxyethoxy)ethyl]-7-methyl-2H-indazol-5-yl}-1-[4-(1-methylpiperidin-4-yl)piperazin-1-yl]-1-oxopropan-2-yl]piperidine-1-carboxamide; bis(trifluoroacetic acid) and 4-{1-[2-(2-ethoxyethoxy)ethyl]-2-oxo-1,2-dihydroquinolin-3-yl}-N-[(2R)-3-{1-[2-(2-ethoxyethoxy)ethyl]-7-methyl-1H-indazol-5-yl}-1-[4-(1-methylpiperidin-4-yl)piperazin-1-yl]-1-oxopropan-2-yl]piperidine-1-carboxamide; bis(trifluoroacetic acid). A solution of N-[(2R)-3-(7-methyl-1H-indazol-5-yl)-1-[4-(1-methylpiperidin-4-yl)piperazin-1-yl]-1-oxopropan-2-yl]-4-(2-oxo-1,2-dihydroquinolin-3-yl)piperidine-1-carboxamide (400 mg, 627 μmop in DMF (10 mL) under nitrogen was treated with lithium hexamethyldisilylamide (1.0 M in THF, 1.38 mL, 1.38 mmol), and the reaction mixture was stirred for 20 minutes. 1-Bromo-2-(2-ethoxyethoxy)ethane (231.5 μL, 1.57 mmol) was added via syringe, and the mixture stirred overnight. The mixture was purified directly by RP-HPLC (method D), re-purified, and lyophilized to provide the single compounds as TFA salts (64 mg, 9.3%), (39 mg, 5.7%), which were converted to the free-base by extraction with dichloromethane from aqueous sodium bicarbonate (24 mg, 5.1%).

4-{1-[2-(2-ethoxyethoxy)ethyl]-2-oxo-1,2-dihydroquinolin-3-yl}-N-[(2R)-3-{2-[2-(2-ethoxyethoxy)ethyl]-7-methyl-2H-indazol-5-yl}-1-[4-(1-methylpiperidin-4-yl)piperazin-1-yl]-1-oxopropan-2-yl]piperidine-1-carboxamide; bis(trifluoroacetic acid) (129). $^1$H NMR (300 MHz, DMSO-$d_6$) δ=8.23 (s, 1H), 7.69 (dd, J=1.5, 7.9 Hz, 1H), 7.58-7.53 (m, 3H), 7.34 (m, 1H), 7.25-7.20 (m, 1H), 6.94 (s, 1H), 6.84 (br s, 1H), 4.80-4.75 (m, 1H), 4.55-4.26 (m, 4H), 4.10-4.05 (m, 2H), 3.84-3.79 (m, 2H), 3.65 (br t, J=6.1 Hz, 7H), 3.59-3.25 (m, 22H), 3.14 (s, 3H), 2.90 (br d, J=8.5 Hz, 4H), 2.82-2.63 (m, 3H), 2.46-2.40 (m, 5H), 1.74 (br s, 1H), 1.05-0.99 (m, 7H). LC/MS method A: $R_t$=3.21 mins., (M+H)$^+$=871, purity >98%.

4-{1-[2-(2-ethoxyethoxy)ethyl]-2-oxo-1,2-dihydroquinolin-3-yl}-N-[(2R)-3-{1-[2-(2-ethoxyethoxy)ethyl]-7-methyl-1H-indazol-5-yl}-1-[4-(1-methylpiperidin-4-yl)piperazin-1-yl]-1-oxopropan-2-yl]piperidine-1-carboxamide; bis(trifluoroacetic acid) (130). $^1$H NMR (300 MHz, DMSO-$d_6$) δ=7.97 (s, 1H), 7.70-7.50 (m, 4H), 7.40 (s, 1H), 7.25-7.20 (m, 1H), 7.06 (s, 1H), 6.84 (m, 1H), 4.75-4.73 (m, 1H), 4.63 (br t, J=5.6 Hz, 2H), 4.43 (br t, J=6.4 Hz, 2H), 3.84 (br d, J=6.3 Hz, 1H), 3.80-3.60 (m, 4H), 3.58-3.21 (m, 23H), 3.14 (s, 2H), 3.05-2.83 (m, 6H), 2.81-2.62 (m, 7H), 2.41 (br s, 1H), 1.81-1.60 (m, 2H), 1.08-0.95 (m, 10H). LC/MS method A: $R_f$=3.25 mins., (M+H)$^+$=871, purity=85%.

N-[(2R)-3-{2-[2-(2-ethoxyethoxy)ethyl]-7-methyl-2H-indazol-5-yl}-1-[4-(1-methylpiperidin-4-yl)piperazin-1-yl]-1-oxopropan-2-yl]-4-(2-oxo-1,2-dihydroquinolin-3-yl)piperidine-1-carboxamide (131). $^1$H NMR (300 MHz, DMSO-d$_6$) δ=11.76 (s, 1H), 8.21 (s, 1H), 7.69-7.53 (m, 2H), 7.48-7.33 (m, 1H), 7.32-7.19 (m, 2H), 7.19-7.10 (m, 1H), 6.88 (t, J=1.6 Hz, 1H), 6.69-6.66 (m, 1H), 4.80-4.76 (m, 1H), 4.62-4.44 (m, 2H), 4.20-3.98 (m, 3H), 3.95-3.77 (m, 2H), 3.56-3.34 (m, 7H), 3.30-3.25 (m, 2H), 3.14 (d, J=5.3 Hz, 1H), 2.86 (br d, J=8.8 Hz, 1H), 2.76-2.61 (m, 4H), 2.56-2.51 (m, 2H), 2.45-2.40 (m, 3H), 2.35-2.20 (m, 2H), 2.07-1.89 (m, 3H), 1.67 (br dd, J=5.3, 7.1 Hz, 3H), 1.47-1.26 (m, 4H), 1.26-1.12 (m, 6H), 1.03 (t, J=7.0 Hz, 2H). LC/MS method A: $R_f$=2.82 mins., (M+H)$^+$=755, purity=97%.

Example 132

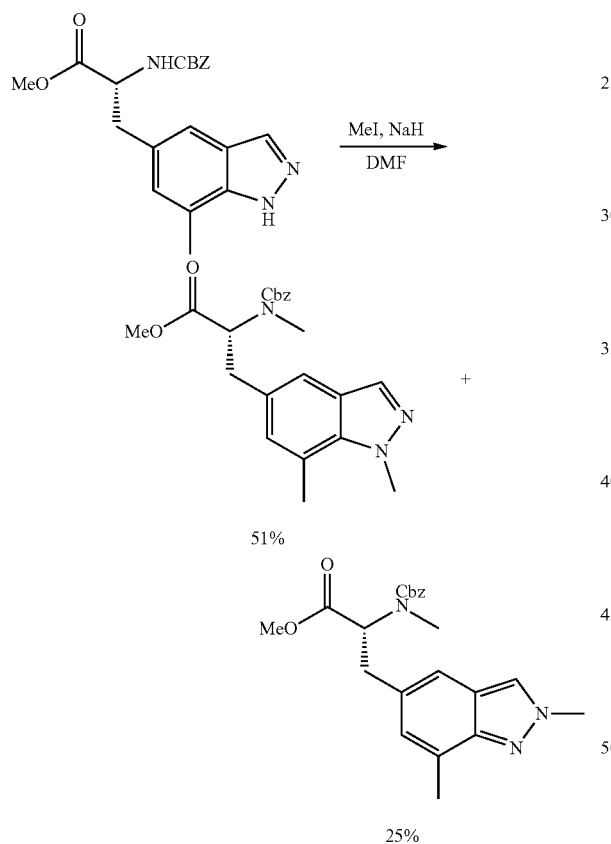

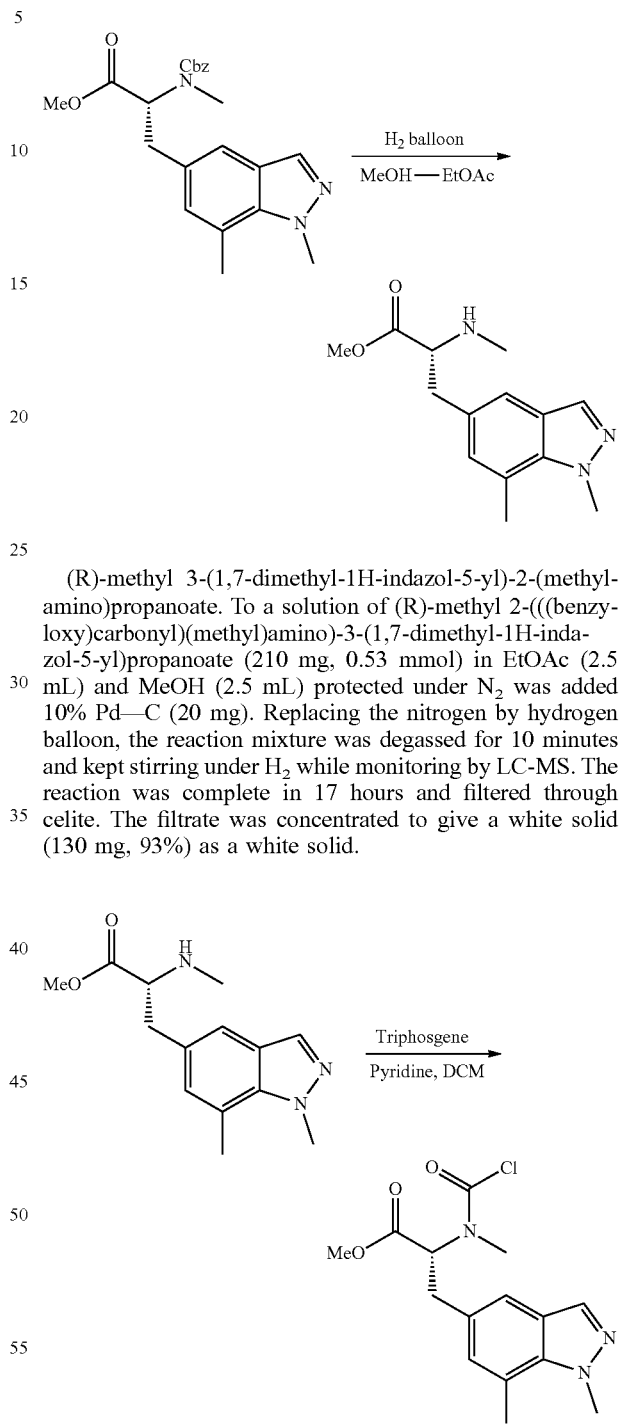

product as a white solid (200 mg, 51%), and 100 mg (25%) of another isomer (R)-methyl 2-no)-3-(2,7-dimethyl-2H-indazol-5-yl)propanoate.

(R)-methyl 3-(1,7-dimethyl-1H-indazol-5-yl)-2-(methylamino)propanoate. To a solution of (R)-methyl 2-(((benzyloxy)carbonyl)(methyl)amino)-3-(1,7-dimethyl-1H-indazol-5-yl)propanoate (210 mg, 0.53 mmol) in EtOAc (2.5 mL) and MeOH (2.5 mL) protected under N$_2$ was added 10% Pd—C (20 mg). Replacing the nitrogen by hydrogen balloon, the reaction mixture was degassed for 10 minutes and kept stirring under H$_2$ while monitoring by LC-MS. The reaction was complete in 17 hours and filtered through celite. The filtrate was concentrated to give a white solid (130 mg, 93%) as a white solid.

(R)-methyl 2-((chlorocarbonyl)(methyl)amino)-3-(1,7-dimethyl-1H-indazol-5-yl)propanoate. To a solution of triphosgene (113 mg, 0.38 mmol) in dichloromethane (1 mL) at 0° C. was added (R)-methyl 3-(1,7-dimethyl-1H-indazol-5-yl)-2-(methylamino)propanoate (90 mg, 0.345 mmol) and triethyl amine (0.144 mL, 1.035 mmol) in dichloromethane (0.5 mL). The mixture was stirred at room temperature for 1 hour, concentrated and partitioned with dichloromethane (R)-methyl 2-(((benzyloxy)carbonyl)(methyl)amino)-3-(1,7-dimethyl-1H-indazol-5-yl)propanoate. To a solution of (R)-methyl 2-(((benzyloxy)carbonyl)amino)-3-(7-methyl-1H-indazol-5-yl)propanoate (367 mg, 1 mmol) in DMF (3 mL) was added sodium hydride (60%, 100 mg, 2.5 mmol), and the mixture was stirred at room temperature for 30 minutes. Methyl iodide (0.155 mL, 2.5 mmol) was added, and the reaction mixture was stirred at room temperature for 18 hours. The mixture was poured into water (20 mL) and extracted by dichloromethane (20 mL×3). The combined extracts were dried (Na$_2$SO$_4$), filtered, and purified by silica chromatography eluted with 10% EtOAc/CH$_2$Cl$_2$ to get the (5 mL) and water (5 mL). The organic layer was separated, dried (Na$_2$SO$_4$), and concentrated. The crude mixture was purified by silica chromatography eluted with 8% MeOH in dichloromethane to get the product as a white solid (90 mg, 81%).

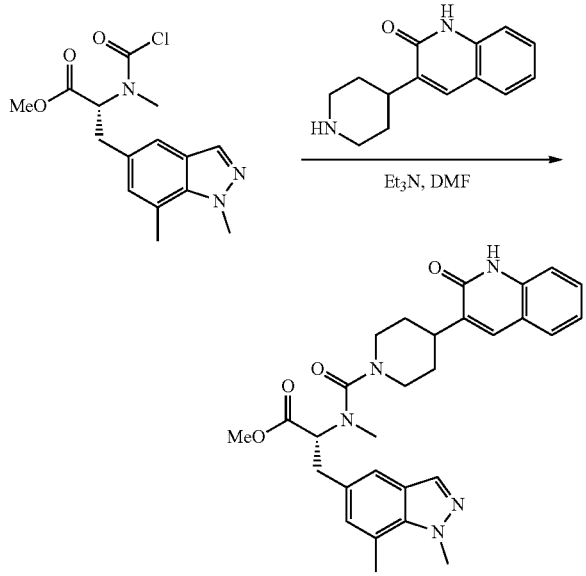

(R)-methyl 3-(1,7-dimethyl-1H-indazol-5-yl)-2-(N-methyl-4-(2-oxo-1,2-dihydroquinolin-3-yl)piperidine-1-carboxamido)propanoate. To a solution of (R)-methyl 2-((chlorocarbonyl)(methyl)amino)-3-(1,7-dimethyl-1H-indazol-5-yl)propanoate (90 mg, 0.28 mmol) and 3-(piperidin-4-yl)quinolin-2(1H)-one (70 mg, 0.31 mmol) in DMF (3 mL) was added triethyl amine (0.078 mL, 0.56 mmol). The reaction mixture was stirred at room temperature for 18 hours. The mixture was poured into water (10 mL), filtered, and dried to get the product as a white solid (100 mg, 69%).

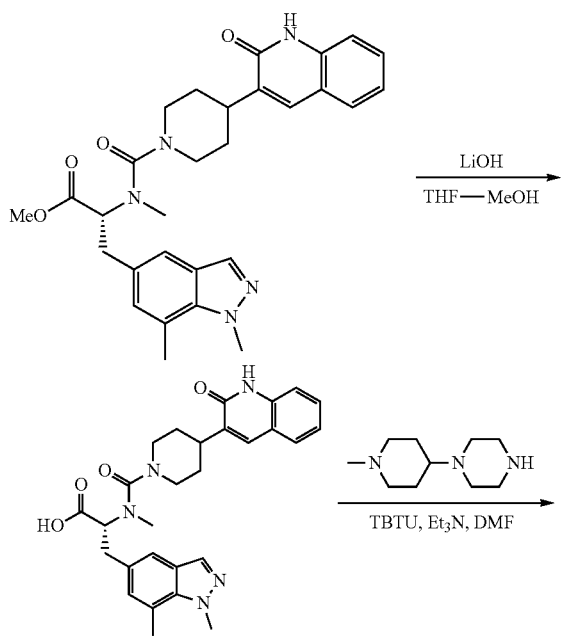

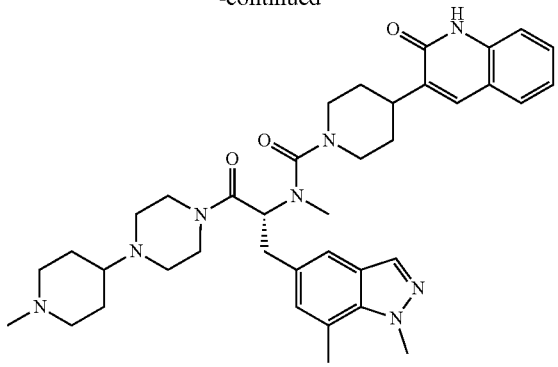

(R)—N-(3-(1,7-dimethyl-1H-indazol-5-yl)-1-(4-(1-methylpiperidin-4-yl)piperazin-1-yl)-1-oxopropan-2-yl)-N-methyl-4-(2-oxo-1,2-dihydroquinolin-3-yl)piperidine-1-carboxamide (132). To an ice cooled solution of (R)-methyl 3-(1,7-dimethyl-1H-indazol-5-yl)-2-(N-methyl-4-(2-oxo-1,2-dihydroquinolin-3-yl)piperidine-1-carboxamido)propanoate (170 mg, 0.33 mmol) in THF (1.5 mL) and MeOH (1.5 mL) was added LiOH (16 mg, 0.66 mmol). The reaction mixture was stirred at room temperature for 2 hours, diluted with ice water (10 mL) and acidified with 1N HCl (PH=2). The resulted precipitate was filtered and dried to get the acid as a white solid (100 mg, 60%).

To a solution of the above acid intermediate (50 mg, 0.1 mmol) and 1-(1-methylpiperidin-4-yl)piperazine (70 mg, 0.11 mmol) in DMF (0.5 mL) was added 2-(1H-benzotriazole-1-yl)-1,1,3,3-tetramethylaminium tetrafluoroborate, TBTU, (38.5 mg, 0.12 mmol) and triethyl amine (0.049 mL, 0.35 mmol). The reaction mixture was stirred at room temperature for 18 hours, concentrated and purified by RP-HPLC (Method B) as a white solid (50 mg, 75% yield). $^1$H NMR (DMSO-d$_6$) δ: 11.77 (s, 1H), 7.86 (s, 1H), 7.64 (m, 1H), 7.55 (s, 1H), 7.35-7.49 (m, 1H), 7.25 (d, J=8.2 Hz, 1H), 7.12-7.19 (m, 1H), 7.01 (s, 1H), 4.97 (m, 1H), 4.14 (s, 3H), 3.06-3.64 (m, 13H), 2.59-2.97 (m, 10H), 2.21 (br m, 4H), 1.88-2.15 (m, 4H), 1.39-1.77 (m, 6H). LC/MS method A: R$_t$=3.09 mins, (M+H)$^+$=667, purity >95%.

The compounds of the invention may be tested for biological activity as CGRP antagonists by methods known to those skilled in the art. In addition, methods such as, for example, a Caco-2 assay, may be used to test the bioavailability of the compounds of the invention. A description of a Caco-2 permeability assay is as follows:

Caco-2 Permeability Assay

The Caco-2 monolayer is widely used across the pharmaceutical industry as an in vitro model of the human small intestinal mucosa to predict the absorption of orally administered drugs.[1-4]

The Caco-2 cell model mimics processes such as transcellular transport, paracellular transport, and some aspects of efflux and active transport.

Readout: P$_{app}$ (A→B), P$_{app}$ (B→A), Efflux ratio, % Recovery

Controls: with and without Pgp inhibitor; Atenolol, Propanolol, Taxel-1

Assay Description:

The Caco-2 cells are cultured to confluency, trypsinized and seeded onto a filter transwell insert at a density of ~32,000 cells/well in DMEM cell culture medium. Cells are grown in a humidified atmosphere of 5% CO$_2$ at 37° C. Following an overnight attachment period (24 h after seeding), the cell medium is replaced with fresh medium in both the apical and basolateral compartments every other day. The cell monolayers are used for transport studies 21 days post seeding after measuring the TEER values (>600 Ohms/cm$^2$). The apical sides and basolateral sides are washed consecutively with HBSS 2.5% (v/v), HEPES (pH 7.4) or HBSS 2.5% (v/v), HEPES 10% (v/v), and Fetal Bovine Serum (pH 7.4) at 37° C. in an incubator under an atmosphere of 5% $CO_2$.

Donor working solution is prepared by dilution of DMSO stock of test article or positive control with transport media to 10 μM.

For A→B directional transport, the donor working solution (with test article or positive control, with or without Pgp inhibitor) is added to the apical (A) compartment and the transport media as receiver working solution is added to the basolateral (B) compartment. For B→A directional transport, the donor working solution (with positive control or test article, with or without Pgp inhibitor) is added to the basolateral (B) compartment and transport media as receiver working solution is added to the apical (A) compartment.

The cells are incubated in a humidified atmosphere of 5% $CO_2$ at 37° C. for 90 minutes.

At the end of the incubation, samples are taken from both donor and receiver compartments and transferred into 96-well assay plates containing internal standard solution (IS) in each well. After centrifugation, the supernatant solutions are transferred to clean 96 well plates and analyzed by LC-MS/MS. The MS detection is performed using a Sciex API 4000 instrument. Each compound is analyzed by reversed phase HPLC.

Data Analysis:

The parameters $P_{app}$ (apparent permeability) and efflux ratio are calculated as follows:

$$P_{app} = (dQ/dt) \times (1/C_0) \times (1/A)$$

$$\text{Efflux ratio} = P_{app}[B \to A]/P_{app}[A \to B]$$

where dQ/dt is the permeability rate, $C_0$ is the initial concentration in the donor compartment, and A is the surface area of the cell monolayer (0.33 cm$^2$). The $P_{app}$ value is a rate measured in cm/s. Calculated $P_{app}$ is ranked as low (<1×10$^6$ cm/s), moderate (1-10×10-6 cm/s), and high (>10×10$^6$ cm/s).

Comparing the efflux ratios generated in the presence and absence of a Pgp inhibitor identifies whether the test article is a Pgp substrate. A compound is considered to be a Pgp substrate when the efflux ratio in the absence of inhibitor is >1.99 and is significantly reduced 1) in the presence of an inhibitor.

Recovery is calculated as follows:

% Recovery=(Total compound mass in donor and receiver compartments at the end of the incubation/Initial compound mass in the donor compartment)×100.

The results of the Caco-2 testing of some of the prodrugs according to the present invention are summarized in Table 1 below:

TABLE 1

| Example No. | Compound Structure | $P_{app}$ A-B (nm/s) | $P_{app}$ B-A (nm/s) |
|---|---|---|---|
| BHV-3500 | 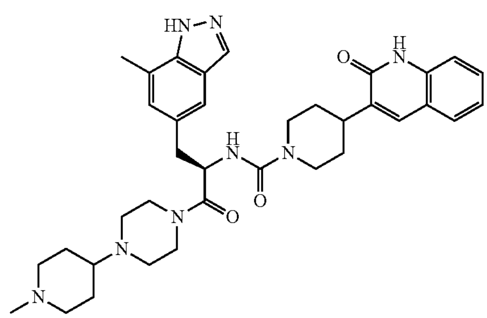 [SMILES: Cc1cc(C[C@@H](NC(=O)N2CCC(c3cc4ccccc4[nH]c3=O)CC2)C(=O)N2CCN(C3CCN(C)CC3)CC2)cc2cn[nH]c12] | <0.5 | ND |
| 4 | 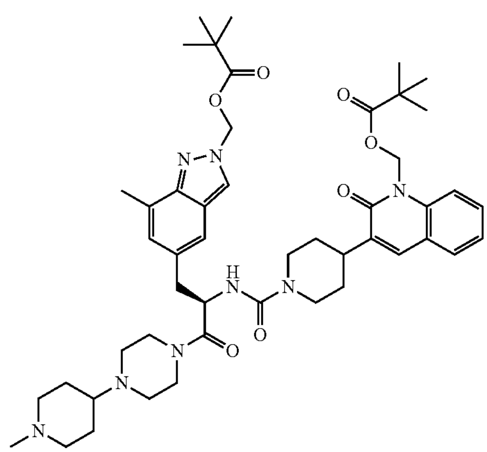 [SMILES: Cc1cc(C[C@@H](NC(=O)N2CCC(c3cc4ccccc4n(COC(=O)C(C)(C)C)c3=O)CC2)C(=O)N2CCN(C3CCN(C)CC3)CC2)cc2cn(COC(=O)C(C)(C)C)nc12] | 51 | 29 |

TABLE 1-continued
| Example No. | Compound Structure | $P_{app}$ A-B (nm/s) | $P_{app}$ B-A (nm/s) |
|---|---|---|---|
| 53 | 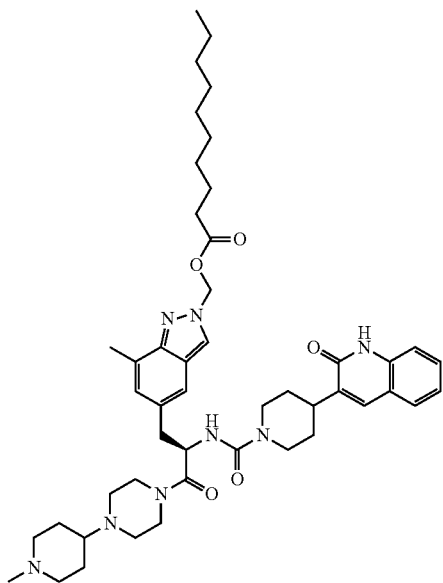 [SMILES: CCCCCCCCCC(=O)OCn1cc2cc(C[C@@H](NC(=O)N3CCC(c4cc5ccccc5[nH]c4=O)CC3)C(=O)N3CCN(C4CCN(C)CC4)CC3)cc(C)c2n1] | 3.1 | 41 |
| 59 | 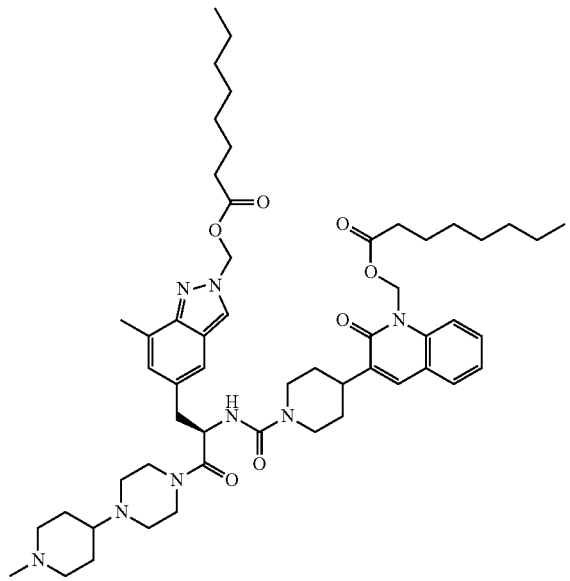 [SMILES: CCCCCCCC(=O)OCn1cc2cc(C[C@@H](NC(=O)N3CCC(c4cc5ccccc5n(COC(=O)CCCCCCC)c4=O)CC3)C(=O)N3CCN(C4CCN(C)CC4)CC3)cc(C)c2n1] | 22 | 76 |

TABLE 1-continued

| Example No. | Compound Structure | $P_{app}$ A-B (nm/s) | $P_{app}$ B-A (nm/s) |
|---|---|---|---|
| 61 | 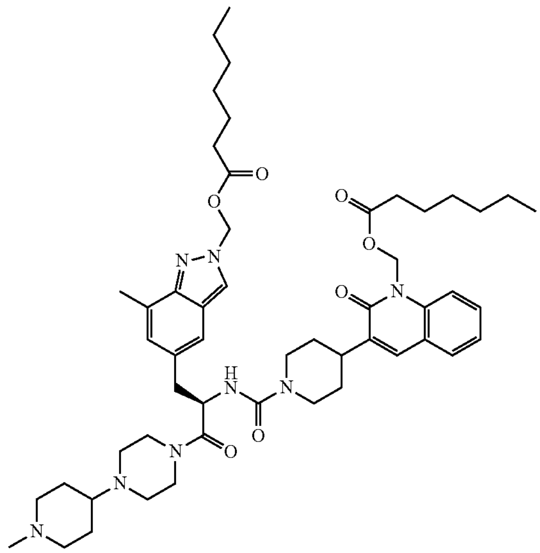 [SMILES: CCCCCCC(=O)OCn1cc2cc(C[C@@H](NC(=O)N3CCC(c4cc5ccccc5n(COC(=O)CCCCCC)c4=O)CC3)C(=O)N3CCN(C4CCN(C)CC4)CC3)cc(C)c2n1] | 25 | 19.6 |
| 10 | 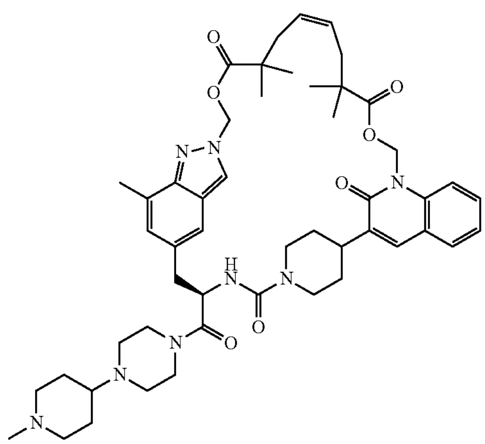 [SMILES: Cc1cc2cc3cn(nc13)COC(=O)C(C)(C)C/C=C\CC(C)(C)C(=O)OCn1c(=O)c(cc3ccccc31)C1CCN(CC1)C(=O)N[C@@H](C(=O)N1CCN(C3CCN(C)CC3)CC1)C2] | 3.1 | 289 |
| 93 | 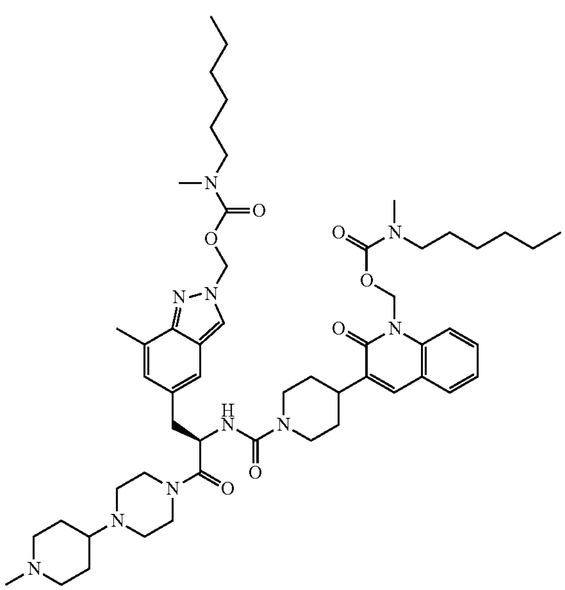 [SMILES: CCCCCCN(C)C(=O)OCn1cc2cc(C[C@@H](NC(=O)N3CCC(c4cc5ccccc5n(COC(=O)N(C)CCCCCC)c4=O)CC3)C(=O)N3CCN(C4CCN(C)CC4)CC3)cc(C)c2n1] | 11.3 | 107 |

TABLE 1-continued
| Example No. | Compound Structure | $P_{app}$ A-B (nm/s) | $P_{app}$ B-A (nm/s) |
|---|---|---|---|
| 13 | 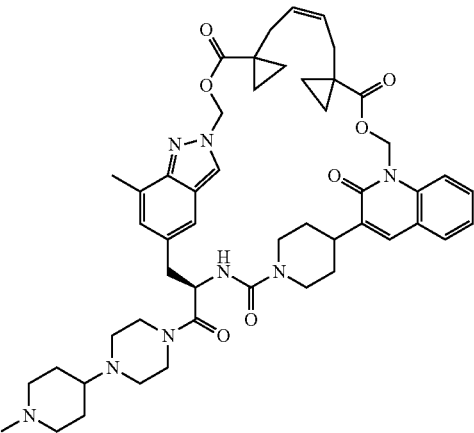 [SMILES: Cc1cc2cc3cn(nc13)COC(=O)C1(C/C=C\CC3(CC3)C(=O)OCn3c(=O)c(cc4ccccc43)C3CCN(CC3)C(=O)N[C@@H](C(=O)N3CCN(C4CCN(C)CC4)CC3)C2)CC1] | 8.39 | 200 |
| 47 | 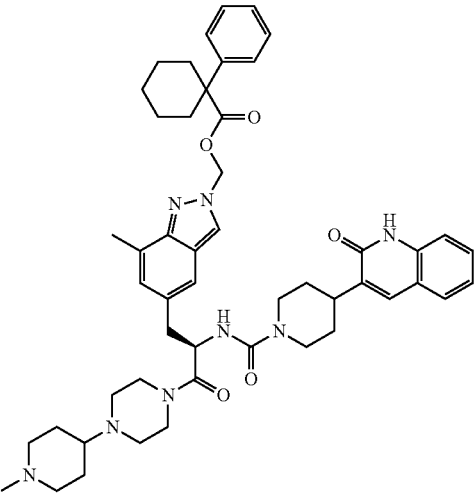 [SMILES: Cc1cc(C[C@@H](NC(=O)N2CCC(c3cc4ccccc4[nH]c3=O)CC2)C(=O)N2CCN(C3CCN(C)CC3)CC2)cc2cn(COC(=O)C3(c4ccccc4)CCCCC3)nc12] | 6.08 | 161 |
| 122 | 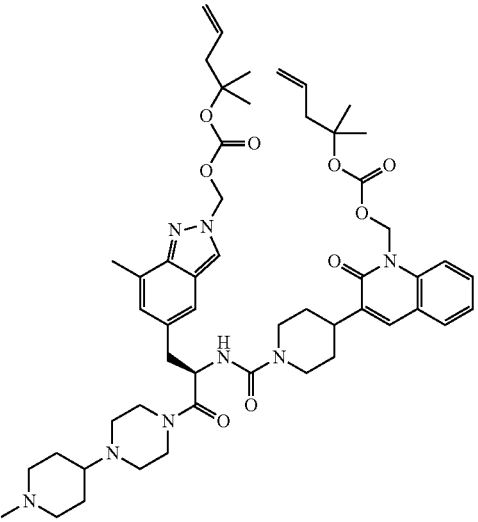 [SMILES: C=CCC(C)(C)OC(=O)OCn1cc2cc(C[C@@H](NC(=O)N3CCC(c4cc5ccccc5n(COC(=O)OC(C)(C)CC=C)c4=O)CC3)C(=O)N3CCN(C4CCN(C)CC4)CC3)cc(C)c2n1] | 7.36 | 90.3 |

TABLE 1-continued

| Example No. | Compound Structure | $P_{app}$ A-B (nm/s) | $P_{app}$ B-A (nm/s) |
|---|---|---|---|
| 125 | 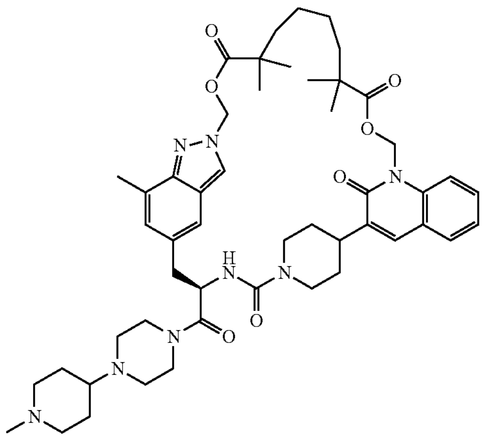 [SMILES: Cc1cc2cc3cn(nc13)COC(=O)C(C)(C)CCCCC(C)(C)C(=O)OCn1c(=O)c(cc3ccccc31)C1CCN(CC1)C(=O)N[C@@H](C(=O)N1CCN(C3CCN(C)CC3)CC1)C2] | 22 | 139 |

As can be seen from the data in Table 1, the prodrugs according to the present invention exhibit substantially higher Caco-2 values than BHV-3500.

| Abbreviations: | |
|---|---|
| ACN | Acetonitrile |
| CGRP | Calcitonin gene-related peptide |
| DCM | Dichloromethane |
| DIEA | Diisopropylethylamine |
| DMEM | Dulbecco's Modified Eagle Medium |
| DMF | Dimethylformamide |
| DMSO | Dimethylsulfoxide |
| DSC | N,N'-disuccinimidyl carbonate |
| EtOAc | Ethyl acetate |
| HBSS | Hank's Buffered Salt Solution |
| HEPES | 4-(2-Hydroxyethyl)-1-piperazineethanesulfonic acid |
| HPLC | High-performance liquid chromatography |
| IPA | Isopropyl alcohol |
| MeOH | Methanol |
| LC/MS | Liquid chromatography/mass spectrometry |
| Pgp | P-glycoprotein 1, also known as multidrug resistance protein 1 (MDR1) |
| LC | Liquid chromatography |
| LiHMDS | Lithium bis(trimethylsilyl)amide |
| MS | Mass spectrometry |
| NMR | Nuclear magnetic resonance |
| Pd-C | Palladium on carbon |
| RP-HPLC | Reversed phase high-performance liquid chromatography |
| TBTU | 2-(1H-benzotriazole-1-yl)-1,1,3,3-tetramethylaminium tetrafluoroborate |
| TEER | Transepithelial Resistance (in Ohm/cm$^2$) |
| TFA | Trifluoroacetic acid |
| THF | Tetrahydrofuran |
| TMS | Tetramethylsilane |

LITERATURE

1. Artursson, P.; Karlsson, J. "*Correlation between oral drug absorption in humans and apparent drug permeability coefficients in human intestinal epithelial (Caco-2) cells*"; Biochem. Biophys. Res. Commun. 175, 880, (1991).
2. Bohets, H.; Annaert, P.; Van Beijsterveldt, L.; Anciaux, K., Verboven, P.; Meuldermans, W., Lavrijsen, K. "*Strategies for absorption screening in drug discovery and development*"; 1, 367, (2001).
3. Artursson, P.; Palm, K.; Luthman, K. "*Caco-2 monolayers in experimental and theoretical predictions of drug transport*"; Adv. Drug Del. Rev. 64, 280, (2012).
4. Shah, P.; Jogani, V.; Bagchi, T.; Misra, A. "*Role of Caco-2 cell monolayers in prediction of intestinal drug absorption*"; Biotechnol. Progr. 22, 186, (2006).

Throughout this application, various publications are referenced by author name and date, or by patent number or patent publication number. The disclosures of these publications are hereby incorporated in their entireties by reference into this application in order to more fully describe the state of the art as known to those skilled therein as of the date of the invention described and claimed herein. However, the citation of a reference herein should not be construed as an acknowledgement that such reference is prior art to the present invention.

Those skilled in the art will recognize, or be able to ascertain using no more than routine experimentation, numerous equivalents to the specific procedures described herein. Such equivalents are considered to be within the scope of this invention and are covered by the following claims. For example, pharmaceutically acceptable salts other than those specifically disclosed in the description and Examples herein can be employed. Furthermore, it is intended that specific items within lists of items, or subset groups of items within larger groups of items, can be combined with other specific items, subset groups of items or larger groups of items whether or not there is a specific disclosure herein identifying such a combination.

What is claimed is:
1. A compound having General Formula 1, comprising a CGRP Parent Molecule having at least one functionalizable moiety Z:

General Formula (1)

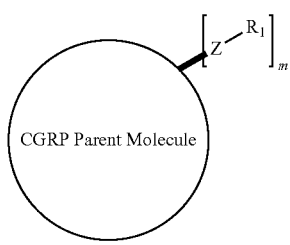

wherein:
the CGRP Parent Molecule having at least one functionalizable moiety Z is

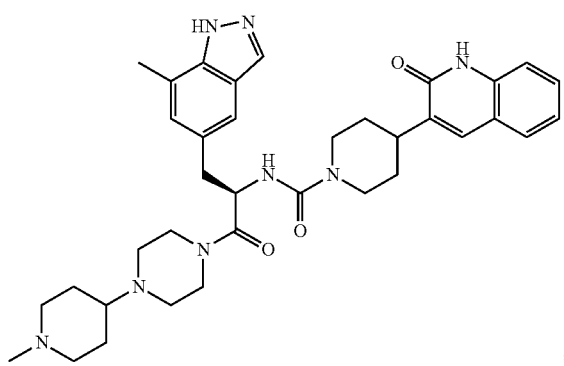

Z is a functionalizable moiety present on the CGRP Parent Molecule;
m is at least 1;
$R_1$ is

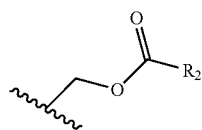

or —$CH_2OP(=O)(OH)_2$;
$R_2$ is —$[C(R_3)_2]_nR_4$, —$NR_3R_4$, or —$OR_4$, wherein each $R_3$ is independently hydrogen or C1-C10 alkyl wherein $R_3$ are optionally connected to form a ring, and $R_4$ is a substituted or unsubstituted C1-C20 alkyl group, a substituted or unsubstituted C2-C20 alkenyl group, a substituted or unsubstituted C2-C20 alkynyl group, a substituted or unsubstituted C1-C20 heteroalkyl group, a substituted or unsubstituted C2-C20 heteroalkenyl group, a substituted or unsubstituted C2-C20 heteroalkynyl group, a substituted or unsubstituted C3-C20 cycloalkyl group, a substituted or unsubstituted C3-C20 heterocycloalkyl group, a substituted or unsubstituted C6-C20 aryl group, or a substituted or unsubstituted C1-C20 heteroaryl group, and n is 0 or 1, wherein, when m is at least 2, $R_2$ are optionally connected to form a ring.

2. The compound according to claim 1, having one of Formulae (I) to (IV):

(I)

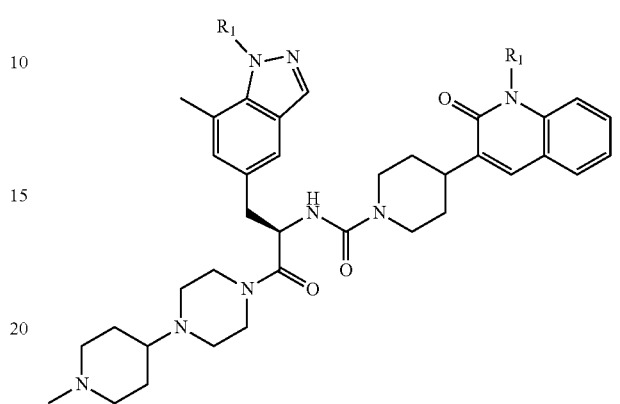

(II)

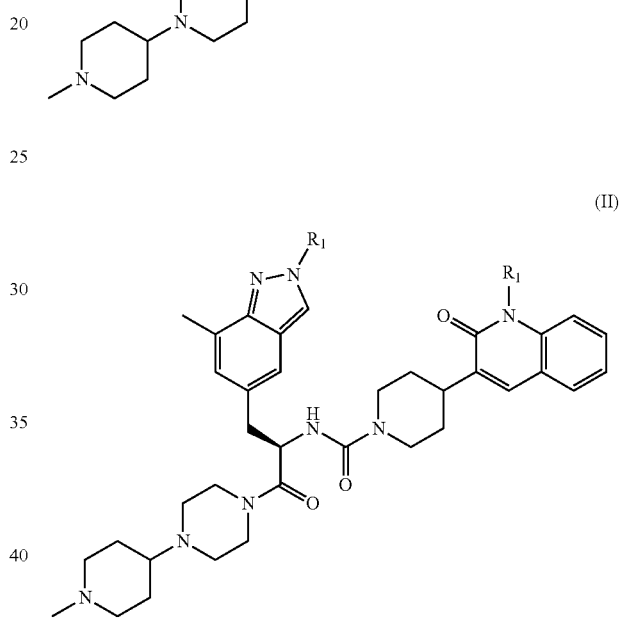

(III)

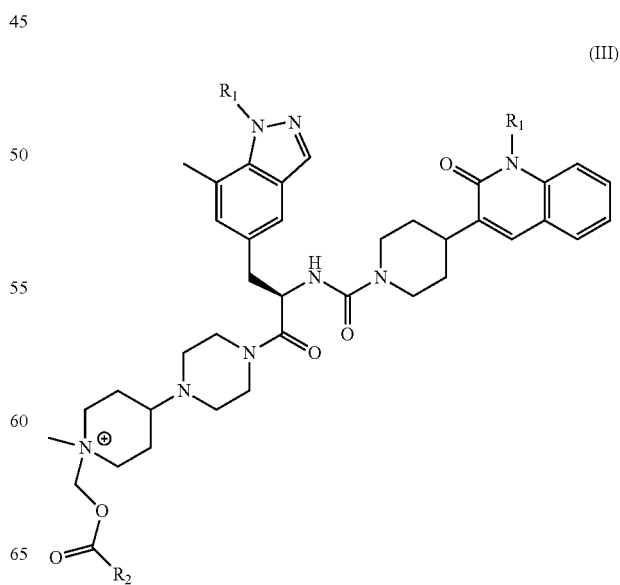

-continued (IV)

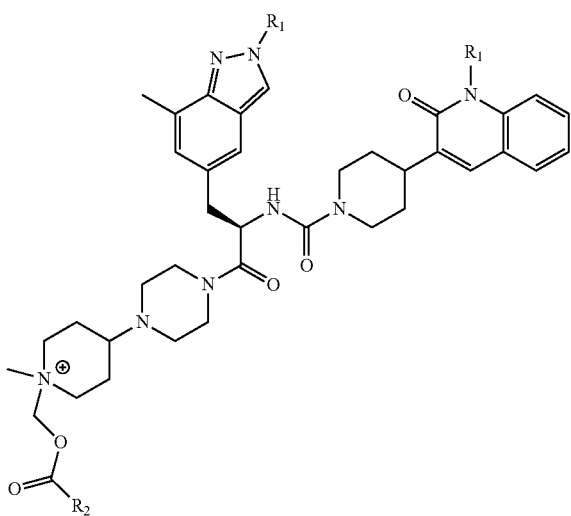

wherein, in Formulae (I) to (IV),
each $R_1$ is independently H,

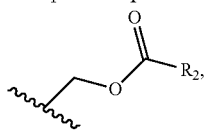

or —CH$_2$OP(=O)(OH)$_2$, provided that at least one $R_1$ is

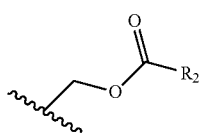

or —CH$_2$OP(=O)(OH)$_2$;

$R_2$ is —[C($R_3$)$_2$]$_n$$R_4$, —N$R_3$$R_4$, or —O$R_4$, wherein each $R_3$ is independently hydrogen or C1-C10 alkyl group, wherein $R_3$ are optionally connected to form a ring, and $R_4$ is a substituted or unsubstituted C1-C20 alkyl group, a substituted or unsubstituted C2-C20 alkenyl group, a substituted or unsubstituted C2-C20 alkynyl group, a substituted or unsubstituted C1-C20 heteroalkyl group, a substituted or unsubstituted C2-C20 heteroalkenyl group, a substituted or unsubstituted C2-C20 heteroalkynyl group, a substituted or unsubstituted C3-C20 cycloalkyl group, a substituted or unsubstituted C3-C20 heterocycloalkyl group, or a substituted or unsubstituted C6-C20 aryl group, or a substituted or unsubstituted C1-C20 heteroaryl group, and n is 0 or 1, wherein, when each $R_1$ is

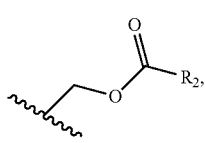

$R_2$ are optionally connected to form a ring.

3. The compound according to claim 2, wherein, in Formulae (I) and (II), each $R_1$ is

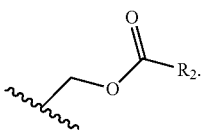

4. The compound according to claim 2, wherein at least one $R_3$ is not hydrogen.

5. The compound according to claim 2, wherein at least one $R_3$ is a methyl group.

6. The compound according to claim 2, wherein each $R_3$ is not hydrogen.

7. The compound according to claim 2, wherein each $R_3$ is a methyl group.

8. The compound according to claim 2, wherein $R_4$ is each independently a substituted or unsubstituted C1-C10 alkyl group, a substituted or unsubstituted C2-C10 alkenyl group, a substituted or unsubstituted C2-C10 alkynyl group, a substituted or unsubstituted C1-C10 heteroalkyl group, a substituted or unsubstituted C2-C10 heteroalkenyl group, a substituted or unsubstituted C2-C10 heteroalkynyl group, a substituted or unsubstituted C3-C10 cycloalkyl group, a substituted or unsubstituted C3-C10 heterocycloalkyl group, a substituted or unsubstituted C6-C10 aryl group, or a substituted or unsubstituted C1-C10 heteroaryl group.

9. The compound according to claim 2, wherein Formula (I) is represented by one of Formulae (Ia), (Ib), and (Ic), and wherein Formula (II) is represented by one of Formulae (IIa), (IIb), and (IIc):

(Ia)

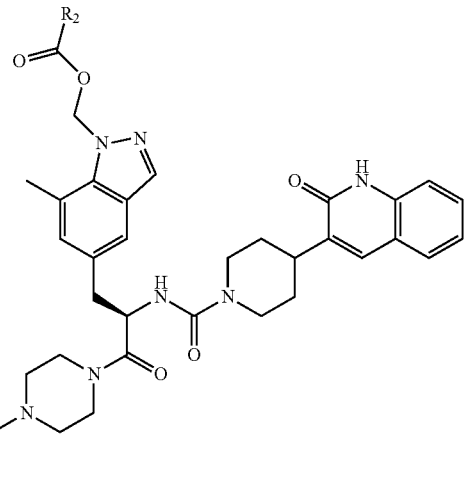

(Ib)
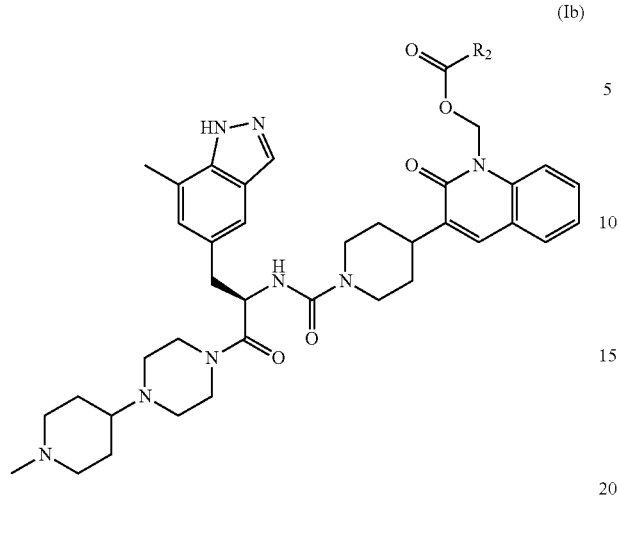
(Ic)
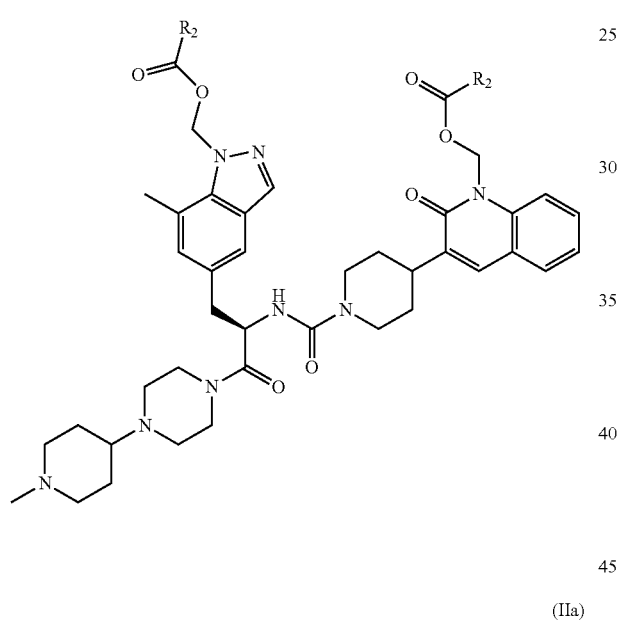
(IIa)
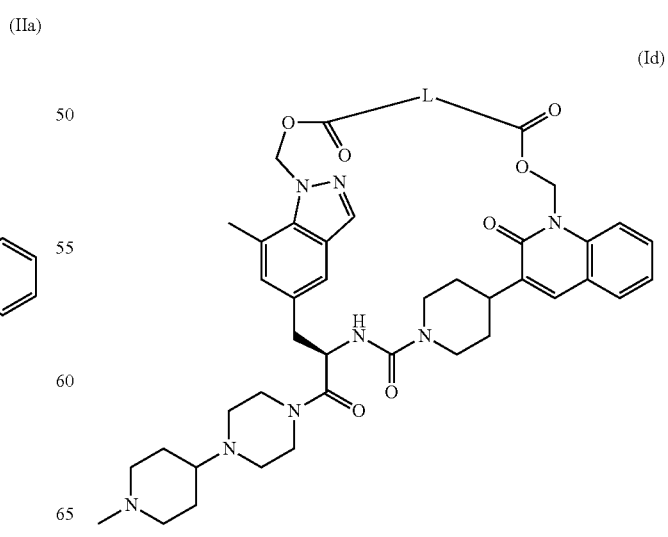
(IIb)
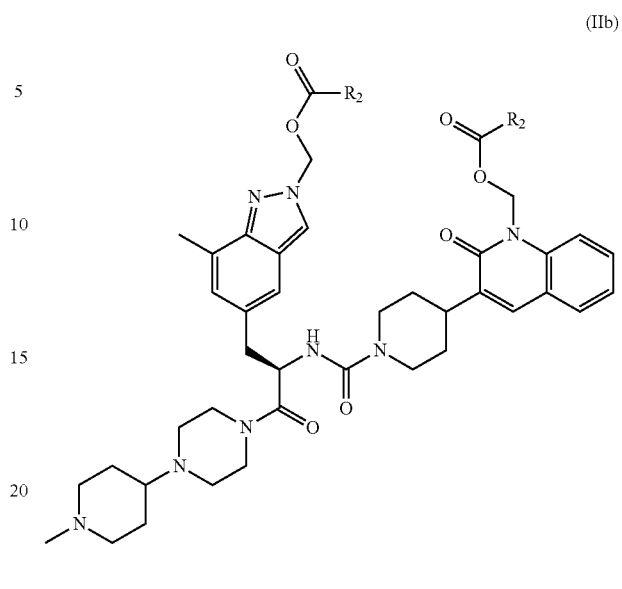
wherein, in Formulae (Ia), (Ib), (Ic), (IIa), and (IIb), $R_2$ is the same as that in claim 1.
10. The compound according to claim 9, wherein, in Formulae (Ic) and (IIb), $R_2$ are connected with a single bond to form a linking group L, as in Formulae (Id) and (IIc), respectively
(Id)

-continued (IIc)

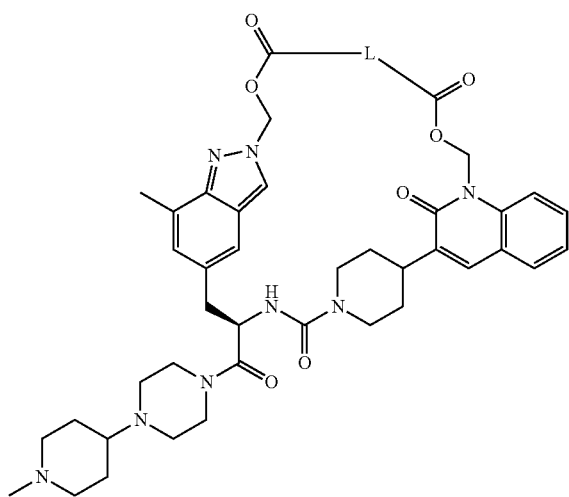

wherein, L is a substituted or unsubstituted C1-C10 alkylene group, a substituted or unsubstituted C2-C10 alkenylene group, a substituted or unsubstituted C2-C10 alkynylene group, a substituted or unsubstituted C1-C10 heteroalkylene group, a substituted or unsubstituted C2-C10 heteroalkenylene group, a substituted or unsubstituted C2-C10 heteroalkynylene group, a substituted or unsubstituted C3-C10 cycloalkylene group, a substituted or unsubstituted C3-C10 heterocycloalkylene group, a substituted or unsubstituted C6-C10 arylene group, or a substituted or unsubstituted C1-C10 heteroarylene group, or any combination thereof.

11. The compound according to claim 10, wherein the linking group L is:

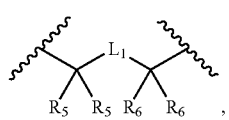

wherein
L$_1$ is a substituted or unsubstituted C1-C10 alkylene group, a substituted or unsubstituted C2-C10 alkenylene group, a substituted or unsubstituted C2-C10 alkynylene group, a substituted or unsubstituted C1-C10 heteroalkylene group, a substituted or unsubstituted C2-C10 heteroalkenylene group, a substituted or unsubstituted C2-C10 heteroalkynylene group, a substituted or unsubstituted C3-C10 cycloalkylene group, a substituted or unsubstituted C3-C10 heterocycloalkylene group, a substituted or unsubstituted C6-C10 arylene group, or a substituted or unsubstituted C1-C10 heteroarylene group, and
R$_5$ and R$_6$ are each independently hydrogen or C1-C10 alkyl, wherein two R$_5$ and two R$_6$ are optionally connected to form a ring.

12. The compound according to claim 11, wherein at least one R$_5$ is not hydrogen and at least one R$_6$ is not hydrogen.

13. The compound according to claim 11, wherein at least one R$_5$ is a methyl group and at least one R$_6$ is a methyl group.

14. The compound according to claim 11, wherein each R$_5$ is not hydrogen and each R$_6$ is not hydrogen.

15. The compound according to claim 11, wherein each R$_5$ is a methyl group and each R$_6$ is a methyl group.

16. The compound according to claim 2, wherein Formula (III) is represented by one of Formulae (IIIa), (IIIb), (IIIc), and (IIId), and wherein Formula (IV) is represented by one of Formulae (IVa) and (IVb):

(IIIa)

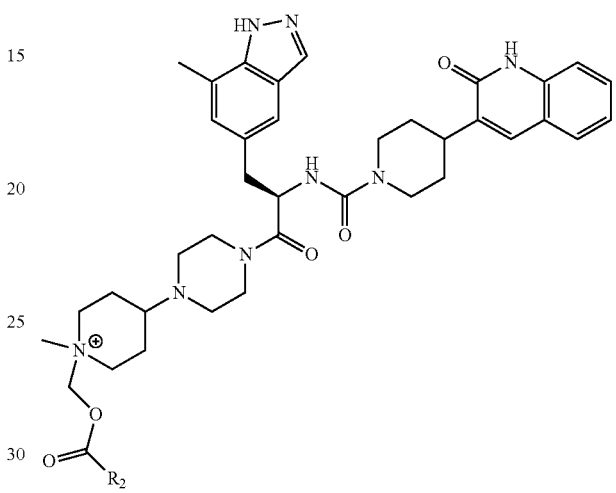

(IIIb)

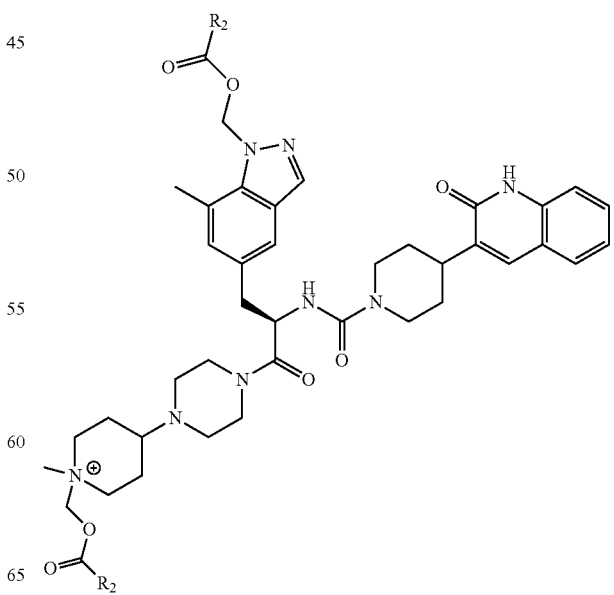

-continued
(IIIc)
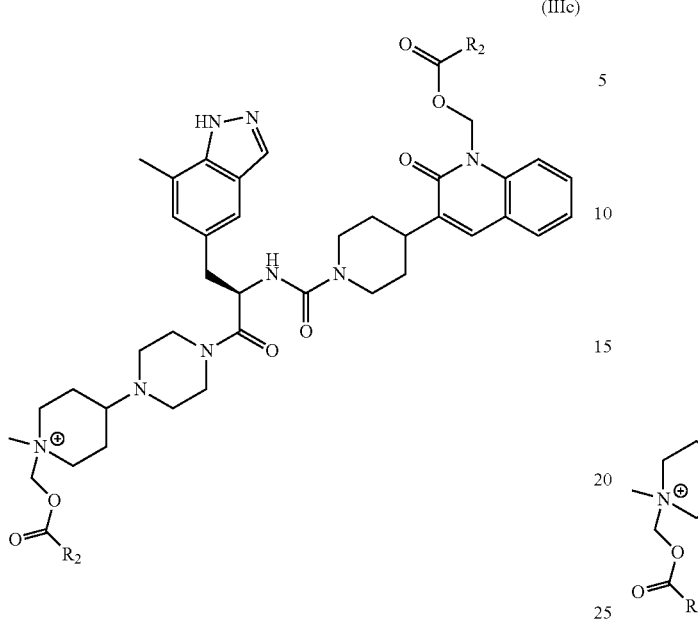
(IIId)
(IVa)
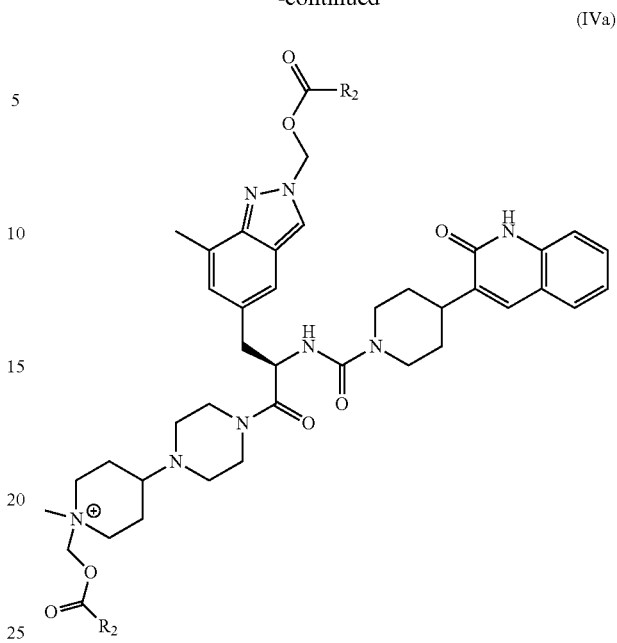
(IVb)
wherein, in Formulae (IIIa), (IIIb), (IIIc), (IIId), (IVa), and (IVb), $R_2$ is the same as that in claim 1.
17. The compound according to claim 16, wherein, in Formulae (IIId) and (IVb), $R_2$ are connected with a single bond to form a linking group L, as in Formulae (IIIe) and (IVc), respectively:

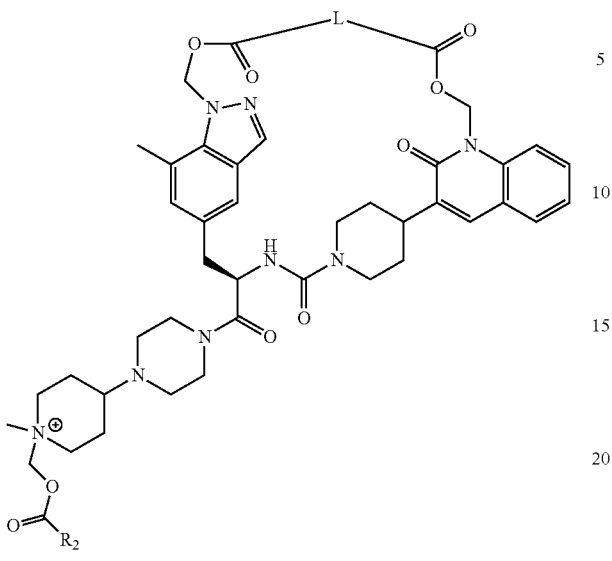

(IIIe)

(IVc)

wherein, in Formulae (IIIe) and (IVc), R₂ is the same as that in claim 1.

18. The compound according to claim 10, wherein the linking group is:

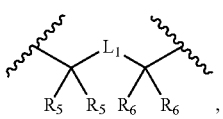

wherein

L₁ is a substituted or unsubstituted C1-C10 alkylene group, a substituted or unsubstituted C2-C10 alkenylene group, a substituted or unsubstituted C2-C10 alkynylene group, a substituted or unsubstituted C1-C10 heteroalkylene group, a substituted or unsubstituted C2-C10 heteroalkenylene group, a substituted or unsubstituted C2-C10 heteroalkynylene group, a substituted or unsubstituted C3-C10 cycloalkylene group, a substituted or unsubstituted C3-C10 heterocycloalkylene group, a substituted or unsubstituted C6-C10 arylene group, or a substituted or unsubstituted C1-C10 heteroarylene group, and R₅ and R₆ are each independently hydrogen or C1-C10 alkyl wherein R₃ are optionally connected to form a ring.

19. A pharmaceutical composition comprising a therapeutically effective amount of a compound in accordance with claim 1.

20. A kit for treating a condition associated with aberrant levels of CGRP in a patient, the kit comprising:

(a) a pharmaceutical composition comprising a therapeutically effective amount of a compound in accordance with claim 1; and (b) instructions for administering the pharmaceutical composition.

* * * * *